US007968567B2

(12) United States Patent
McGee et al.

(10) Patent No.: US 7,968,567 B2
(45) Date of Patent: *Jun. 28, 2011

(54) COMPOUNDS FOR THE MODULATION OF PPARγ ACTIVITY

(75) Inventors: Lawrence R. McGee, Pacifica, CA (US); Jonathan B. Houze, San Mateo, CA (US); Steven M. Rubenstein, Pacifica, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/578,498

(22) Filed: Oct. 13, 2009

(65) Prior Publication Data

US 2010/0113522 A1    May 6, 2010

Related U.S. Application Data

(63) Continuation of application No. 10/810,325, filed on Mar. 25, 2004, now Pat. No. 7,626,033, which is a continuation of application No. 10/209,205, filed on Jul. 30, 2002, now Pat. No. 6,770,648, which is a continuation of application No. 09/606,433, filed on Jun. 28, 2000, now Pat. No. 7,041,691.

(60) Provisional application No. 60/141,672, filed on Jun. 30, 1999.

(51) Int. Cl.
*C07D 215/38* (2006.01)
*A61K 31/04* (2006.01)

(52) U.S. Cl. ......................... 514/311; 514/314; 546/178

(58) Field of Classification Search ................... 546/178; 514/311, 314
See application file for complete search history.

(56) References Cited

U.S. PATENT DOCUMENTS

| | | | |
|---|---|---|---|
| 2,407,309 A | 9/1946 | Lott et al. |
| 3,033,870 A | 5/1962 | Druey et al. |
| 3,034,955 A | 5/1962 | Frick et al. |
| 3,174,901 A | 3/1965 | Sterne |
| 3,669,966 A | 6/1972 | Ambrogi et al. |
| 3,674,843 A | 7/1972 | Shen et al. |
| 3,686,192 A | 8/1972 | Moore et al. |
| 4,003,734 A | 1/1977 | Johnston |
| 4,013,621 A | 3/1977 | Knell |
| 4,061,642 A | 12/1977 | Fleckenstein et al. |
| 4,062,950 A | 12/1977 | Frommer et al. |
| 4,218,237 A | 8/1980 | Nishiyama et al. |
| 4,248,619 A | 2/1981 | Serban et al. |
| 4,289,876 A | 9/1981 | Algieri et al. |
| 4,499,304 A | 2/1985 | Gabrielsen et al. |
| 4,549,901 A | 10/1985 | James |
| 4,565,568 A | 1/1986 | Johnston et al. |
| 4,572,912 A | 2/1986 | Yoshioka et al. |
| 4,577,028 A | 3/1986 | Martin et al. |
| 4,670,045 A | 6/1987 | Ehr et al. |
| 4,731,090 A | 3/1988 | Boger et al. |
| 4,756,739 A | 7/1988 | Fuss et al. |
| 4,851,419 A | 7/1989 | Cox |
| 4,866,079 A | 9/1989 | Boger et al. |
| 4,900,751 A | 2/1990 | Cox |
| 4,946,854 A | 8/1990 | Maienfisch et al. |
| 4,952,235 A | 8/1990 | Andree et al. |
| 4,987,141 A | 1/1991 | Bushell et al. |
| 5,008,276 A | 4/1991 | Clough et al. |
| 5,070,096 A | 12/1991 | Mohrs et al. |
| 5,081,125 A | 1/1992 | Maienfisch et al. |
| 5,093,340 A | 3/1992 | Mohrs et al. |
| 5,143,937 A | 9/1992 | Lang et al. |
| 5,151,428 A | 9/1992 | Sakamoto et al. |
| 5,202,336 A | 4/1993 | Mohrs et al. |
| 5,204,354 A | 4/1993 | Chakravarty et al. |
| 5,250,549 A | 10/1993 | Yoshino et al. |
| 5,304,532 A | 4/1994 | Munro et al. |
| 5,360,810 A | 11/1994 | Hayase et al. |
| 5,444,036 A | 8/1995 | Iwasaki et al. |
| 5,514,696 A | 5/1996 | Murugesan et al. |
| 5,545,669 A | 8/1996 | Adams et al. |
| 5,610,320 A | 3/1997 | Yoshino et al. |
| 5,624,937 A | 4/1997 | Reel |
| 5,643,914 A | 7/1997 | Daines |
| 5,684,195 A | 11/1997 | Huang et al. |
| 5,716,993 A | 2/1998 | Ozaki et al. |
| 5,780,483 A | 7/1998 | Widdowson et al. |
| 5,814,646 A | 9/1998 | Heinz |
| 5,880,136 A | 3/1999 | Duggan et al. |
| 5,990,126 A | 11/1999 | Park et al. |
| 6,022,987 A | 2/2000 | Evans et al. |
| 6,028,052 A | 2/2000 | Heyman et al. |
| 6,200,995 B1 | 3/2001 | De la Brouse-Elwood |

(Continued)

FOREIGN PATENT DOCUMENTS

CH    592411    10/1977

(Continued)

OTHER PUBLICATIONS

Adams, B. et al., 1953, "Quinone Imides. XXV. Addition of Mercaptans to p-Quinonedibenzenesulfonimide," The Notes Chemical Laboratory, University of Illinois, Feb. 5, 1953, vol. 2:663-665.

Badilescu, I., "Sythesis of some N-aryl- and N,N-dialkyl-p-chlorobenzenesulfonamides" Rev.Chim., vol. 88. 17, No. 11, 1966, pp. 705-706 & Chemical Abstracts, vol. 67, No. 9, Aug. 28, 1967, Columbus, Ohio, United States; abstract No. 43516y, p. 4076; XP002099084.

Baguley et al., Database accession No. 108:179602, Database Chemabs 'Online!, RN 106831-10-1 Caplus, 134284-40-5 Caplus, Zh. Org. Khim, 26(9):1995-1998 (1990).

Bastin et al., "Salt Selection and Optimisation Procedures for Pharmaceutical New Chemical Entities," Organic Process Research and Development, Cambridge, GB, vol. 4, No. 5, Jan. 1, 2000, pp. 427-435.

Burmistrov et al., Database accession No. 122:132338, Database Chemabs Online!, RN 134284-40-5 Caplus, Zh. Org. Khim, 30(5):744-747 (1994).

Burmistrov et al., Database accession No. 115:8165, Database Chemabs Online!, RNS 98187-76-9 134284-40-5 &ZH. Org. Khim., vol. 26, No. 9, 1990, pp. 1995-1998.

(Continued)

*Primary Examiner* — D Seaman
(74) *Attorney, Agent, or Firm* — Jones Day

(57) ABSTRACT

Modulators of PPARγ activity are provided which are useful in pharmaceutical compositions and methods for the treatment of conditions such as type II diabetes and obesity.

4 Claims, No Drawings

U.S. PATENT DOCUMENTS

| | | | |
|---|---|---|---|
| 6,214,850 B1 | 4/2001 | Evans et al. | |
| 6,262,112 B1 | 7/2001 | Mittendorf et al. | |
| 6,294,559 B1 | 9/2001 | Smith | |
| 6,348,474 B1 | 2/2002 | Kayakiri et al. | |
| 6,353,011 B1 | 3/2002 | Pershadsingh et al. | |
| 6,369,075 B1 | 4/2002 | Rugged et al. | |
| 6,376,512 B1 | 4/2002 | Jayyosi et al. | |
| 6,403,607 B1 | 6/2002 | Hidaka et al. | |
| 6,469,054 B1 | 10/2002 | Mittendorf et al. | |
| 6,472,779 B2 | 10/2002 | Hwang et al. | |
| 6,545,050 B1 | 4/2003 | Mittendorf et al. | |
| 6,573,278 B2 | 6/2003 | Mittendorf et al. | |
| 6,583,157 B2 | 6/2003 | McGee et al. | |
| 6,586,475 B1 | 7/2003 | Kato et al. | |
| 6,620,827 B2 | 9/2003 | De la Brouse-Elwood et al. | |
| 6,653,309 B1 | 11/2003 | Saunders et al. | |
| 6,653,332 B2 | 11/2003 | Jaen et al. | |
| 6,677,488 B2 | 1/2004 | Reitz et al. | |
| 6,770,648 B2 * | 8/2004 | McGee et al. | 514/252.04 |
| 7,041,691 B1 | 5/2006 | McGee et al. | |
| 7,132,546 B2 | 11/2006 | Kato et al. | |
| 7,223,761 B2 | 5/2007 | Kruk et al. | |
| 7,439,242 B2 | 10/2008 | Houze et al. | |
| 7,601,841 B2 | 10/2009 | McGee et al. | |
| 7,626,033 B2 | 12/2009 | McGee et al. | |
| 2001/0028200 A1 | 10/2001 | Hwang et al. | |
| 2003/0088103 A1 | 5/2003 | Houze et al. | |
| 2003/0171399 A1 | 9/2003 | McGee et al. | |
| 2004/0048891 A1 | 3/2004 | Kato et al. | |
| 2004/0176409 A1 | 9/2004 | McGee et al. | |
| 2004/0259918 A1 | 12/2004 | Jaen et al. | |
| 2007/0293536 A1 | 12/2007 | Kruk et al. | |
| 2009/0221635 A1 | 9/2009 | McGee et al. | |

FOREIGN PATENT DOCUMENTS

| | | |
|---|---|---|
| DE | 3632329 A1 | 3/1988 |
| EP | 0 069 585 A1 | 1/1983 |
| EP | 0 148 730 A2 | 7/1985 |
| EP | 0 261 539 A2 | 9/1987 |
| EP | 0 306 222 A2 | 3/1989 |
| EP | 0 778 267 A1 | 11/1996 |
| EP | 0 749 751 A2 | 12/1996 |
| EP | 0 472 053 B1 | 6/1998 |
| EP | 0 855 391 A1 | 7/1998 |
| GB | 2373725 | 10/2002 |
| JP | 55-79369 A1 | 6/1980 |
| JP | 64-6245 A1 | 1/1989 |
| JP | 9-255656 A | 9/1997 |
| WO | WO 95/01326 A1 | 1/1995 |
| WO | WO 95/33462 | 12/1995 |
| WO | WO 96/09294 A1 | 3/1996 |
| WO | WO 96/15118 A1 | 5/1996 |
| WO | WO 97/00857 A1 | 1/1997 |
| WO | WO 97/30677 A1 | 8/1997 |
| WO | WO 97/31907 A1 | 9/1997 |
| WO | WO 97/36579 A1 | 10/1997 |
| WO | WO 98/02437 A1 | 1/1998 |
| WO | WO 98/16503 | 4/1998 |
| WO | WO 98/27081 | 6/1998 |
| WO | WO 98/37061 | 8/1998 |
| WO | WO 98/50029 | 11/1998 |
| WO | WO 98/50030 | 11/1998 |
| WO | WO 99/00372 | 1/1999 |
| WO | WO 99/06378 A1 | 2/1999 |
| WO | WO 99/10320 A1 | 3/1999 |
| WO | WO 99/20275 | 4/1999 |
| WO | WO 99/24404 | 5/1999 |
| WO | WO 99/32465 | 7/1999 |
| WO | WO 99/38845 A1 | 8/1999 |
| WO | WO 99/50237 A1 | 10/1999 |
| WO | WO 99/55663 | 11/1999 |
| WO | WO 00/10967 | 3/2000 |
| WO | WO 00/10968 | 3/2000 |
| WO | WO 00/12073 | 3/2000 |
| WO | WO 00/12623 A2 | 3/2000 |
| WO | WO 00/17202 | 3/2000 |
| WO | WO 00/31021 | 6/2000 |
| WO | WO 01/00579 A1 | 1/2001 |
| WO | WO 01/30343 | 5/2001 |
| WO | WO 01/60807 A1 | 8/2001 |
| WO | WO 01/70723 A1 | 9/2001 |
| WO | WO 01/82916 | 11/2001 |
| WO | WO 01/83427 A1 | 11/2001 |
| WO | WO 01/87860 A2 | 11/2001 |
| WO | WO 01/87861 A2 | 11/2001 |
| WO | WO 01/87862 A2 | 11/2001 |
| WO | WO 01/95906 A1 | 12/2001 |
| WO | WO 02/00611 | 1/2002 |
| WO | WO 02/00633 A1 | 1/2002 |
| WO | WO 02/08188 | 1/2002 |
| WO | WO 02/13812 | 2/2002 |
| WO | WO 02/13864 | 2/2002 |
| WO | WO 02/14291 | 2/2002 |
| WO | WO 02/17901 | 3/2002 |
| WO | WO 02/18355 | 3/2002 |
| WO | WO 02/26729 | 4/2002 |
| WO | WO 02/26737 | 4/2002 |
| WO | WO 02/28832 | 4/2002 |
| WO | WO 02/28857 | 4/2002 |
| WO | WO 02/30860 | 4/2002 |
| WO | WO 02/30863 | 4/2002 |
| WO | WO 02/30884 | 4/2002 |
| WO | WO 02/30895 | 4/2002 |
| WO | WO 02/40020 | 5/2002 |
| WO | WO 02/46161 | 6/2002 |
| WO | WO 02/49626 | 6/2002 |
| WO | WO 02/051397 | 7/2002 |
| WO | WO 02/051820 | 7/2002 |
| WO | WO 02/053546 | 7/2002 |
| WO | WO 02/059098 | 8/2002 |
| WO | WO 02/060434 | 8/2002 |
| WO | WO 02/062772 | 8/2002 |
| WO | WO 02/062774 | 8/2002 |
| WO | WO 02/062798 | 8/2002 |
| WO | WO 02/062799 | 8/2002 |
| WO | WO 02/064094 | 8/2002 |
| WO | WO 02/066028 | 8/2002 |
| WO | WO 02/072003 | 9/2002 |
| WO | WO 02/074291 | 9/2002 |
| WO | WO 02/080913 | 10/2002 |
| WO | WO 02/081454 | 10/2002 |
| WO | WO 02/092084 | 11/2002 |
| WO | WO 02/092590 | 11/2002 |
| WO | WO 2005/033074 A2 | 4/2005 |

OTHER PUBLICATIONS

Cain et al., "Potential antitumor agents. 14. Acridylmethanesulfonanilides," J. Med. Chem. 17(9):922-930 (1974).

Chaturvedi et al., "Antibacterial studies of 7-(α-substituted sulfonamido)methyl- and 7-(α-substituted sulfonamido)phenyl-8-hydroxyquinolines," Journal of the Indian Chemical Society 61(2):175-176 (1984) (Abstract. Chem. Abstract Accession No. 101:8731).

Collins, J. et al., "N-(2-Benzoylphenyl)-L-tyrosine PPARγ agonists. 2. Structure-activity relationship and optimization of the phenyl alkyl ether moiety," J. Med. Chem. 41(25):5037-5054 (1998).

Denny et al., Database accession No. 96:79437, Database Chemabs 'Online!, RNs 80260-24-8 Caplus, 80260-26-0 Caplus, J. Med. Chem., 25(3):276-315 (1982).

Dumas et al., "Synthesis and structure-activity relationships of novel small molecule cathepsin D inhibitors," Bioorg. Med. Chem. Lett. 9(17):2531-2536 (1999) (Abstract. Chem. Abstract Accession No. 131:336969).

Forman et al., "15-Deoxy-$\Delta^{12,14}$-Prostaglandin $J_2$ is a ligand for the adipocyte determination factor PPARγ," Cell, 83:803-812 (1995).

Jiang et al., "PPAR-γ agonists inhibit production of monocyte inflammatory cytokines," Nature, vol. 391, pp. 82-86, (Jan. 1998).

Lehmann et al., "Peroxisome Proliferator-activated Receptors a and V Arc Activated by Indomethacin and Other Non-steroidal Anti-inflammatory Drugs," The Journal of Biological Chemistry, 272(6):3406-3410 (1997).

Lehmann, J., et al., An Antidiabetic Thiazolidinedione is a High Affinity Ligand for Peroxisome Proliferator-activated Receptor γ (PPAR γ), J. Bio. Chem. 270(22): 12953-12956 (1995).

Misra, V., 1979, "Synthesis of New Substituted Quinolines & Study of Their Effect on the Tobacco Mosaic Virus," Indian Journal of Chemistry, vol. 18B(3):262-264.
Mysyk et al., Database accession No. 92:163637, Database Chemabs 'Online!, RN 73320-75-9 Caplus, Zh. Org. Khim, 15(12):2499-2502 (1979).
Pieper et al., Database accession No. 112:138679, Database Chemabs 'Online!, RN 101513-48-8 Caplus, Arzneim.-Forsch., 39(9):1073-1080 (1989).
Ricote et al., The peroxisome proliferators-activated receptor-γ is a negative regulator of macrophage activation, Nature, vol. 391, pp. 79-82, (Jan. 1998).
Sarul, et al., Database accession No. 103:123106, Database Chemabs 'Online!, RN 98187-77-0 Caplus, Latv. Psr Zinat. Akad. Vestis, Kim. Ser., 2:225-228 (1985).
Sebe et al., Database accession No. 117:214517, Database Chemabs 'Online!, RNs 144206-02-0 Caplus, 144232-65-5 Caplus, Rev. Chim, 43(5-6):222-225 (1992).
Shah, A.R., 1987, "Quinaldine Sulphonamide Derivatives," Journal of Institution of Chemists, vol. 59:257-258.
Spiegelman B.M., PPAR-γ: Adipogenic Regulator and Thiazolidinedione Receptor, Diabetes, vol. 47, pp. 507-514 (Apr. 1998).
Wilson et al., "The PPARs: from orphan receptors to drug discovery," J. Med. Chem. 43(4):527-550(2000).
Wilson et al., "The Structure-Activity Relationship between Peroxisome Proliferator-Activated Receptor γ Agonism and the Antihyperglycemic Activity of Thiazolidinediones," J. Med. Chem. 39:665-668 (1996).
Wollweber et al., Database accession No. 101:151540, Database Chemabs 'Online!, RN 92114-63-11 Caplus, Arzneim.-Forsch., 34(5):531-542 (1984).
Windholz et al. (Eds.), The Merck Index, 10th Ed., Merck & Co., Inc., Rahway, NJ., pp. 849-850, Abstract 5792 (1983).
Zaitseva et al., Database accession No. 86:43377, Database Chemabs 'Online!, RN 61381-98-4 Caplus, Zh. Org. Khim, 12(9):1987-1992 (1976).
http:/www.en.wikipedia.org/wiki/Biguanide (2007).
http:/www.en.wikipedia.org/wiki/Troglitazone (2007).
ISA, International Search Report dated Oct. 13, 2000 for PCT/US00/18178.
ISA, International Search Report dated Oct. 29, 2001 for PCT/US01/20756.
ISA, International Search Report and Written Opinion dated Apr. 6, 2005 for PCT/USO4/32552.
ISA, International Search Report dated May 16, 2002 for PCT/US01/14393.
ISA, International Search Report dated May 7, 1999 for PCT/US99/01147.
ISEA/EP, International Preliminary Examination Report dated Aug. 3, 2001 for PCT/US00/18178.
ISEA/EP, International Preliminary Examination Report dated Jun. 10, 2002 for PCT/US01/20756.
ISEA/EP, International Preliminary Report on Patentability dated Apr. 3, 2006 for PCT/US04/032552.
ISEA/EP, International Preliminary Report on Patentability dated Nov. 13, 2002 for PCT/US01/14393.
ISA, International Search Report, dated May 7, 1999, for International Application No. PCT/US99/01147, filed Jan. 20, 1999.
ISA, International Written Opinion, dated Oct. 8, 1999, for International Application No. PCT/US99/01147, filed Jan. 20, 1999.
EPO—Supplementary European Search Report dated Feb. 17, 2009 for European Patent Application No. EP 04 79 4053.1.
RU—Russian Office Action (with English translation) dated Feb. 26, 2009 for Russian Patent Application No. 200600701(2006050002).
AU—Australian Examiner's Report dated Apr. 6, 2009 for Australian Patent Application No. 2004278416.
EPO—European Communication Pursuant to Article 94(3) EPC dated Jul. 13, 2009 for European Patent Application No. EP 00 946 961.0.
CA—Canadian Office Action dated Aug. 18, 2009 for Canadian Patent Application No. 2,377,309.
CN—Intellectual Property Office of the People's Republic of China Decision of Rejection (with English translation) dated Sep. 25, 2009 for Chinese Patent Application No. 200480034669.7.
U.S.P.T.O. Non-Final Office Action, dated Apr. 19, 2007, for U.S. Appl. No. 10/123,298, filed Apr. 15, 2002.
U.S.P.T.O. Non-Final Office Action, dated Feb. 15, 2002, for U.S. Appl. No. 09/741,415, filed Dec. 19, 2000.
U.S.P.T.O. Non-Final Office Action, dated Jul. 29, 2002, for U.S. Appl. No. 09/741,415, filed Dec. 19, 2000.
U.S.P.T.O. Final Office action dated Mar. 11, 2009 for U.S. Appl. No. 10/810,325.
U.S.P.T.O. Non-final Office Action dated Apr. 15, 2009 for U.S. Appl. No. 11/258,817.
U.S.P.T.O. Non-final Office Action dated Dec. 16, 2009 for U.S. Appl. No. 11/258,817.
U.S.P.T.O. Issue Notification for U.S. Appl. No. 10/810,325.
U.S.P.T.O, Non-final Office action dated Jun. 6, 2002 for U.S. Appl. No. 09/847,887.
U.S.P.T.O, Non-final Office action dated Jan. 23, 2003 for U.S. Appl. No. 10/209,205.
U.S.P.T.O, Non-final Office action dated Jun. 15, 2005 for U.S. Appl. No. 10/956,251.
U.S.P.T.O, Non-final Office action dated Jun. 22, 2006 for U.S. Appl. No. 10/956,251.
U.S.P.T.O, Final Office action dated Jan. 4, 2006 for U.S. Appl. No. 10/956,251.
U.S.P.T.O, Non-final Office action dated Jul. 28, 2008 for U.S. Appl. No. 10/719,997.
U.S.P.T.O, Non-final Office action dated Jul. 23, 2007 for U.S. Appl. No. 10/719,997.
U.S.P.T.O, Non-final Office action dated Feb. 28, 2006 for U.S. Appl. No. 10/719,997.
U.S.P.T.O, Non-final Office action dated Jun. 15, 2005 for U.S. Appl. No. 10/719,997.
U.S.P.T.O, Non-final Office action dated Dec. 3, 2001 for U.S. Appl. No. 09/606,433.
Berger, J., "Novel Peroxisome Proliferator-activated Receptor (PPAR) γ and PPARδ Ligands Produce Distinct Biological Effects," J. Biol. Chem, 274(10):6718-6725 (1999).
Campbell, I. W., "The Clinical Significance of PPAR Gamma Agonism," Current Molecular Medicine, 5:349-363 (2005).
Clark, R. W., "The Role of PPARs in Inflammation and Immunity," J. Leukocyte Biology, 71:388-400 (2002).
EPO—Summons to attend oral proceedings pursuant to Rule 115(1) EPC dated Nov. 11, 2010 for European Patent Application No. EP 00 946 961.0.
U.S.P.T.O. Notice of Allowance and Fee(s) Due mailed Nov. 24, 2010 for U.S. Appl. No. 11/258,817.
U.S.P.T.O. Non-final Office Action mailed Feb. 23, 2010 for U.S. Appl. No. 12/372,699.
U.S.P.T.O. Final Office Action mailed Jul. 8, 2010 for U.S. Appl. No. 12/372,699.
U.S.P.T.O. Advisory Action mailed Oct. 27, 2010 for U.S. Appl. No. 12/372,699.
U.S.P.T.O. Non-final Office Action mailed Mar. 24, 2010 for U.S. Appl. No. 12/807,208.
U.S.P.T.O. Final Office Action mailed Sep. 7, 2010 for U.S. Appl. No. 12/807,208.

* cited by examiner

COMPOUNDS FOR THE MODULATION OF PPARγ ACTIVITY

CROSS-REFERENCES TO RELATED APPLICATIONS

This application is a continuation of U.S. patent application No. 10/810,325, filed Mar. 25, 2004, which is a continuation of U.S. patent application No. 10/209,205, filed Jul. 30, 2002, now U.S. Pat. No. 6,770,648, which is a continuation of U.S. patent application No. 09/606,433, filed Jun. 28, 2000, now U.S. Pat. No. 7,041,691, which claims the benefit of U.S. Provisional Application No. 60/141,672, filed Jun. 30, 1999, all of which applications are herein incorporated by reference in their entireties.

STATEMENT AS TO RIGHTS TO INVENTIONS MADE UNDER FEDERALLY SPONSORED RESEARCH AND DEVELOPMENT

The invention described herein was not made with the aid of any federally sponsored grants.

FIELD OF THE INVENTION

The present invention relates to compounds that modulate the PPARγ receptor and are useful in the diagnosis and treatment of type II diabetes (and complications thereof), hypercholesterolemia (and related disorders associated with abnormally high or low plasma lipoprotein or triglyceride levels) and inflammatory disorders.

BACKGROUND OF THE INVENTION

The peroxisome proliferator-activated receptors (PPARs) are transducer proteins belonging to the steroid/thyroid/retinoid receptor superfamily. The PPARs were originally identified as orphan receptors, without known ligands, but were named for their ability to mediate the pleiotropic effects of fatty acid peroxisome proliferators. These receptors function as ligand-regulated transcription factors that control the expression of target genes by binding to their responsive DNA sequence as heterodimers with RXR. The target genes encode enzymes involved in lipid metabolism and differentiation of adipocytes. Accordingly, the discovery of transcription factors involved in controlling lipid metabolism has provided insight into regulation of energy homeostasis in vertebrates, and further provided targets for the development of therapeutic agents for disorders such as obesity, diabetes and dyslipidemia.

PPARγ is one member of the nuclear receptor superfamily of ligand-activated transcription factors and has been shown to be expressed in an adipose tissue-specific manner. Its expression is induced early during the course of differentiation of several preadipocyte cell lines. Additional research has now demonstrated that PPARγ plays a pivotal role in the adipogenic signaling cascade. PPARγ also regulates the ob/leptin gene which is involved in regulating energy homeostasis, and adipocyte differentiation which has been shown to be a critical step to be targeted for anti-obesity and diabetic conditions.

In an effort to understand the role of PPARγ in adipocyte differentiation, several investigators have focused on the identification of PPARγ activators. One class of compounds, the thiazolidinediones, which were known to have adipogenic effects on preadipocyte and mesenchymal stem cells in vitro, and antidiabetic effects in animal models of non-insulin-dependent diabetes mellitus (NIDDM) were also demonstrated to be PPARγ-selective ligands. More recently, compounds that selectively activate murine PPARγ were shown to possess in vivo antidiabetic activity in mice.

Despite the advances made with the thiazolidinedione class of antidiabetes agents, unacceptable side effects have limited their clinical use. Accordingly, there remains a need for potent, selective activators of PPARγ which will be useful for the treatment of NIDDM and other disorders related to lipid metabolism and energy homeostasis. Still further, compounds that block PPARγ activity would be useful for interfering with the maturation of preadipocytes into adipocytes and thus would be useful for the treatment of obesity and related disorders associated with undesirable adipocyte maturation. Surprisingly, the present invention provides compounds that are useful as activators as well as antagonists of PPARγ activity and compositions containing them, along with methods for their use.

SUMMARY OF THE INVENTION

In one aspect, the present invention provides methods of modulating conditions which are mediated by PPARγ. The methods typically involve contacting the host with a PPARγ-modulating amount of a compound having the formula:

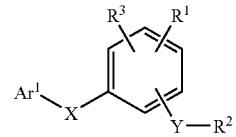

in which the symbol $Ar^1$ represents a substituted or unsubstituted aryl group; the letter X represents a divalent linkage selected from substituted or unsubstituted $(C_1-C_6)$alkylene, substituted or unsubstituted $(C_1-C_6)$alkylenoxy, substituted or unsubstituted $(C_1-C_6)$alkylenamino, substituted or unsubstituted $(C_1-C_6)$alkylene-S(O)$_k$, —O—, —C(O)—, —N($R^{11}$)—, —N($R^{11}$)C(O)—, —S(O)$_k$— and a single bond, in which $R^{11}$ is a member selected from hydrogen, $(C_1-C_8)$alkyl, $(C_2-C_8)$heteroalkyl and aryl$(C_1-C_4)$alkyl and the subscript k is an integer of from 0 to 2. The letter Y, in the above formula represents a divalent linkage selected from substituted or unsubstituted $(C_1-C_6)$alkylene, —O—, —C(O)—, —N($R^{12}$)—S(O)$_m$—, —N($R^{12}$)—S(O)$_m$—N($R^{13}$)—, —N($R^{12}$)C(O)—, —S(O)$_n$—, a single bond, and combinations thereof, in which $R^{12}$ and $R^{13}$ are members independently selected from hydrogen, substituted or unsubstituted $(C_1-C_8)$alkyl, substituted or unsubstituted $(C_2-C_8)$heteroalkyl and substituted or unsubstituted aryl$(C_1-C_4)$alkyl; and the subscripts m and n are independently integers of from 0 to 2.

The symbol $R^1$ represents a member selected from hydrogen, halogen, cyano, nitro, $(C_1-C_8)$alkyl, $(C_1-C_8)$alkoxy, —$CO_2R^{14}$, —C(O)NR$^{15}$R$^{16}$, —C(O)R$^{14}$, —S(O)$_p$—R$^{14}$, —S(O)$_q$—NR$^{15}$R$^{16}$, —O—C(O)—OR$^{17}$, —O—C(O)—R$^{17}$, —O—C(O)—NR$^{15}$R$^{16}$, —N(R$^{14}$)—C(O)—NR$^{15}$R$^{16}$, —N(R$^{14}$)—C(O)—R$^{17}$ and —N(R$^{14}$)—C(O)—OR$^{17}$, in which $R^{14}$ is a member selected from hydrogen, $(C_1-C_8)$alkyl, $(C_2-C_8)$heteroalkyl, aryl and aryl$(C_1-C_4)$alkyl; $R^{15}$ and $R^{16}$ are members independently selected from hydrogen, $(C_1-C_8)$alkyl, $(C_2-C_8)$heteroalkyl, aryl, and aryl$(C_1-C_4)$alkyl, or taken together with the nitrogen to which each is attached form a 5-, 6- or 7-membered ring; and $R^{17}$ is a member selected from hydrogen, $(C_1-C_8)$alkyl, $(C_2-C_8)$heteroalkyl, aryl and aryl($C_1$-$C_4$)alkyl. In each of the descriptions of, for example, alkyl, alkoxy and heteroalkyl, the groups can be substituted or unsubstituted.

The symbol $R^2$ represents a substituted or unsubstituted aryl group. Preferably, $R^2$ represents a phenyl, naphthyl, pyridazinyl or pyridyl group. More preferably, $R^2$ is a phenyl, naphthyl, pyridazinyl or pyridyl group substituted with from 0-3 substituents selected from halogen, —$OCF_3$, —OH, —O($C_1$-$C_8$)alkyl, —CN, —$CF_3$, —C(O)—($C_1$-$C_8$)alkyl, —($C_1$-$C_8$)alkyl and —$NH_2$.

The symbol $R^3$ represents a halogen, cyano, nitro or a substituted or unsubstituted ($C_1$-$C_8$)alkoxy group.

In another aspect, the present invention provides compounds of the formula above, as well as pharmaceutical compositions containing the compounds described above.

DETAILED DESCRIPTION OF THE INVENTION

Abbreviations and Definitions:

The following abbreviations are used herein: PPARγ: peroxisome proliferator-activated receptor γ; NIDDM: non-insulin-dependent diabetes mellitus; $Et_3N$: triethylamine; MeGH: methanol; and DMSO: dimethylsulfoxide.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include groups such as methyl, ethyl, n-propyl, isopropyl, n-butyl, t-butyl, isobutyl, sec-butyl, cyclohexyl, (cyclohexyl)ethyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below as "heteroalkyl," "cycloalkyl" and "alkylene." The term "alkylene" by itself or as part of another substituent means a divalent radical derived from an alkane, as exemplified by —$CH_2CH_2CH_2CH_2$—. Typically, an alkyl group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms are optionally oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Also included in the term "heteroalkyl" are those radicals described in more detail below as "heteroalkylene" and "heterocycloalkyl." The term "heteroalkylene" by itself or as part of another substituent means a divalent radical derived from heteroalkyl, as exemplified by —$CH_2$—$CH_2$—S—$CH_2CH_2$— and —$CH_2$—S—$CH_2$—$CH_2$—NH—$CH_2$—. For heteroalkylene groups, heteroatoms can also occupy either or both of the chain termini. Still further, for alkylene and heteroalkylene linking groups, as well as all other linking group provided in the present invention, no orientation of the linking group is implied.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "fluoroalkyl," are meant to include monofluoroalkyl and polyfluoroalkyl.

The term "aryl," employed alone or in combination with other terms (e.g., aryloxy, arylthioxy, arylalkyl) means, unless otherwise stated, an aromatic substituent which can be a single ring or multiple rings (up to three rings) which are fused together or linked covalently. The rings may each contain from zero to four heteroatoms selected from N, O, and S, wherein the nitrogen and sulfur atoms are optionally oxidized, and the nitrogen atom(s) are optionally quaternized. The aryl groups that contain heteroatoms may be referred to as "heteroaryl" and can be attached to the remainder of the molecule through a heteroatom Non-limiting examples of aryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 2-benzothiazolyl, 5-benzothiazolyl, 2-benzoxazolyl, 5-benzoxazolyl, purinyl, 2-benzimidazolyl, 5-indolyl, 1-isoquinolinyl, 5-isoquinolinyl, 2-quinoxalinyl, 5-quinoxalinyl, 3-quinolinyl, and 6-quinolinyl. Substituents for each of the above noted aryl ring systems are selected from the group of acceptable substituents described below. The term "arylalkyl" is meant to include those radicals in which an aryl group is attached to an alkyl group (e.g., benzyl, phenethyl, pyridylmethyl and the like) or a heteroalkyl group (e.g., phenoxymethyl, 2-pyridyloxymethyl, 3-(1-naphthyloxy)propyl, and the like).

Each of the above terms (e.g., "alkyl," "heteroalkyl" and "aryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups selected from: —OR', =O, =NR', =N—OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —CN and —NO$_2$ in a number ranging from zero to (2N+1), where N is the total number of carbon atoms in such radical. R', R" and R"' each independently refer to hydrogen, unsubstituted (C$_1$-C$_8$)alkyl and heteroalkyl, unsubstituted aryl, aryl substituted with 1-3 halogens, unsubstituted alkyl, alkoxy or thioalkoxy groups, or aryl-(C$_1$-C$_4$)alkyl groups. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl. From the above discussion of substituents, one of skill in the art will understand that the term "alkyl" is meant to include groups such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like). Preferably, the alkyl groups (and related alkoxy, heteroalkyl, etc.) are unsubstituted or have 1 to 3 substituents selected from halogen, —OR', =O, —NR'R", —SR', —OC(O)R', —C(O)R', —CO$_2$R', —CONR'R", —NR"C(O)R', —S(O)$_2$R', —S(O)$_2$NR'R", —CN and —NO$_2$. More preferably, the alkyl and related groups have 0, 1 or 2 substituents selected from halogen, —OR', =O, —NR'R", —SR', —CO$_2$R', —CONR'R", —NR"C(O)R', —CN and —NO$_2$.

Similarly, substituents for the aryl groups are varied and are selected from halogen, —OR', —OC(O)R', —NR'R", —SR', —R', —CN, —NO$_2$— —CO$_2$R', —CONR'R", —C(O)R', —OC(O)NR'R", —NR"C(O)R', —NR"C(O)$_2$R', —NR'—C(O)NR"R"', —NH—C(NH$_2$)=NH, —NR'C(NH$_2$)=NH, —NH—C(NH$_2$)=NR', —S(O)R', —S(O)$_2$R', —S(O)$_2$NR'R", —N$_3$, —CH(Ph)$_2$, perfluoro(C$_1$-C$_4$)alkoxy, and perfluoro(C$_1$-C$_4$)alkyl, in a number ranging from zero to the total number of open valences on the aromatic ring system; and where R', R" and R"' are independently selected from hydrogen, (C$_1$-C$_8$)alkyl and heteroalkyl, unsubstituted aryl, (unsubstituted aryl)-(C$_1$-C$_4$)alkyl, and (unsubstituted aryl)oxy-(C$_1$-C$_4$)alkyl. Preferably, the aryl groups are unsubstituted or have from 1 to 3 substituents selected from halogen, —OR', —OC(O)R', —NR'R", —SR', —R', —CN, —NO$_2$— —CO$_2$R', —CONR'R", —C(O)R', —NR"C(O)R', —S(O)$_2$R', —S(O)$_2$NR'R", perfluoro(C$_1$-C$_4$)alkoxy, and perfluoro(C$_1$-C$_4$)alkyl, Still more preferably, the aryl groups have 0, 1 or 2 substituents selected from halogen, —OR', —NR'R", —SR', —R', —CN, —NO$_2$— —CO$_2$R', —CONR'R", —NR"C(O)R', —S(O)$_2$R', —S(O)$_2$NR'R", perfluoro(C$_1$-C$_4$) alkoxy, and perfluoro(C$_1$-C$_4$)alkyl.

Two of the substituents on adjacent atoms of the aryl ring may optionally be replaced with a substituent of the formula wherein T and U are independently —NH—, —O—, —CH$_2$— or a single bond, and q is an integer of from 0 to 2. Alternatively, two of the substituents on adjacent atoms of the aryl ring may optionally be replaced with a substituent of the formula -A-(CH$_2$)$_r$—B—, wherein A and B are independently —CH$_2$—, —O—, —NH—, —S—, -S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted (C$_1$-C$_6$)alkyl.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, oxalic, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al., "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are all intended to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are intended to be encompassed within the scope of the present invention.

General:

A new class of compounds that interact with PPARγ has now been discovered. Depending on the biological environment (e.g., cell type, pathological condition of the host, etc.), these compounds can activate or block the actions of PPARγ. By activating the PPARγ receptor, the compounds will find use as therapeutic agents capable of modulating conditions mediated by the PPARγ receptor. As noted above, example of such conditions is NIDDM. Additionally, the compounds are useful for the prevention and treatment of complications of diabetes (e.g., neuropathy, retinopathy, glomerulosclerosis, and cardiovascular disorders), and treating hyperlipidemia. Still further, the compounds are useful for the modulation of inflammatory conditions which most recently have been found to be controlled by PPARγ (see, Ricote, et al., *Nature*, 391:79-82 (1998) and Jiang, et al., *Nature*, 391:82-86 (1998). Examples of inflammatory conditions include rheumatoid arthritis and atherosclerosis.

Compounds that act via antagonism of PPARγ are useful for treating obesity, hypertension, hyperlipidemia, hypercholesterolemia, hyperlipoproteinemia, and metabolic disorders.

EMBODIMENTS OF THE INVENTION

In one aspect, the present invention provides compounds which are represented by the formula:

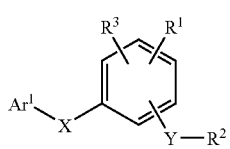

(I)

In formula (I), the symbol $Ar^1$ represents a substituted or unsubstituted aryl group. Preferably, $Ar^1$ is a monocyclic or fused bicyclic aryl group having from zero to four heteroatoms as ring members. More preferably, $Ar^1$ is a monocyclic or fused bicyclic aryl group comprising two fused six-membered rings, two fused five-membered rings, or a six-member ring having a fused five-membered ring. heteroaryl group containing from 1 to 3 nitrogen atoms in the ring or rings. Particularly preferred embodiments are those in which $Ar^1$ is phenyl, naphthyl, 2-pyridyl, 3-pyridyl, 4-pyridyl, 2-pyrimidyl, 4-pyrimidyl, 5-pyrimidyl, isoquinolinyl, benzothiazolyl, benzoxazolyl, and benzimidazolyl, with the proviso that when $Ar^1$ is substituted or unsubstituted 2-benzothiazolyl, then X is —S(O)$_k$— wherein the subscript k is 0, 1 or 2. As noted above, $Ar^1$ can be both unsubstituted and substituted. In preferred embodiments, $Ar^1$ is substituted with from 0 to 3 substituents selected from halogen, —OCF$_3$, —OH, —O—($C_1$-$C_6$)alkyl, —CF$_3$, ($C_1$-$C_6$)alkyl, or —NO$_2$. In one group of preferred embodiments, $Ar^1$ is a monocyclic heteroaryl group containing 1 to 2 nitrogen atoms in the ring and being monosubstituted by halogen, —OCF$_3$ or —CF$_3$. In another group of preferred embodiments, $Ar^1$ is a phenyl or naphthyl group having from 1 to 3 substituents selected from halogen, cyano, nitro, ($C_1$-$C_8$)alkyl or ($C_1$-$C_8$)alkoxy.

The letter X represents a divalent linkage selected from substituted or unsubstituted ($C_1$-$C_6$)alkylene, substituted or unsubstituted ($C_1$-$C_6$)alkylenoxy, substituted or unsubstituted ($C_1$-$C_6$)alkylenamino, substituted or unsubstituted ($C_1$-$C_6$)alkylene-S(O)$_k$, —O—, —C(O)—, —N($R^{11}$)—, —N($R^{11}$)C(O)—, —S(O)$_k$— and a single bond, in which $R^{11}$ is a member selected from hydrogen, ($C_1$-$C_8$)alkyl, ($C_2$-$C_8$) heteroalkyl and aryl($C_1$-$C_4$)alkyl and the subscript k is an integer of from 0 to 2. In preferred embodiments, X represents —O—, —C(O)—, substituted or unsubstituted ($C_1$-$C_6$)alkylene, —N($R^{11}$)—, or —S(O)$_k$—. Most preferably, X represents —O—, —CH$_2$—, —CH(CH$_3$)—, —CH(CH$_2$CH$_3$)—, —CH(isopropyl)-, —CH(CN)—, —C(O)—, —N($R^{11}$)—, or —S(O)$_k$—. Still further preferred are those embodiments in which X represents —O—, —CH$_2$—, —CH(CH$_3$)—, —C(O)—, —N($R^{11}$)—, or —S(O)$_k$—, wherein $R^{11}$ is hydrogen, methyl, ethyl, propyl and isopropyl.

The letter Y, in the above formula represents a divalent linkage selected from substituted or unsubstituted ($C_1$-$C_6$) alkylene, —O—, —C(O)—, —N($R^{12}$)—S(O)$_m$—, —N($R^{12}$)—S(O)$_m$—N($R^{13}$)—, —N($R^{12}$)C(O)—, —S(O)$_n$—, a single bond, and combinations thereof, in which $R^{12}$ and $R^{13}$ are members independently selected from hydrogen, substituted or unsubstituted ($C_1$-$C_8$)alkyl, substituted or unsubstituted ($C_2$-$C_8$)heteroalkyl and substituted or unsubstituted aryl($C_1$-$C_4$)alkyl; and the subscripts m and n are independently integers of from 0 to 2. In preferred embodiments, Y represents —N($R^{12}$)—S(O)$_2$— or —N($R^{12}$)—C(O)—. More preferably, Y represents —N($R^{12}$)—S(O)$_2$— in which $R^{12}$ is hydrogen or substituted or unsubstituted ($C_1$-$C_8$)alkyl. Most preferably, Y represents —NH—S(O)$_2$—. Additionally, the linkages provided herein (represented by X and Y) can be in either orientation. More particularly, for example, the nitrogen atom of —N($R^{12}$)—S(O)$_2$— can be attached to either the central benzene ring or to the $R^2$ group.

The symbol $R^1$ represents a member selected from hydrogen, halogen, cyano, nitro, ($C_1$-$C_8$)alkyl, ($C_1$-$C_8$)alkoxy, —CO$_2$$R^{14}$, —C(O)NR$^{15}$R$^{16}$, —C(O)R$^{14}$, —S(O)$_p$—R$^{14}$, —S(O)$_q$—NR$^{15}$R$^{16}$, —O—C(O)—OR$^{17}$, —O—C(O)—R$^{17}$, —O—C(O)—NR$^{15}$R$^{16}$, —N($R^{14}$)—C(O)—NR$^{15}$R$^{16}$, —N($R^{14}$)—C(O)—R$^{17}$ and —N($R^{14}$)—C(O)—OR$^{17}$, in which $R^{14}$ is a member selected from hydrogen, ($C_1$-$C_8$)alkyl, ($C_2$-$C_8$)heteroalkyl, aryl and aryl($C_1$-$C_4$)alkyl; $R^{15}$ and $R^{16}$ are members independently selected from hydrogen, ($C_1$-$C_8$) alkyl, ($C_2$-$C_8$)heteroalkyl, aryl, and aryl($C_1$-$C_4$)alkyl, or taken together with the nitrogen to which each is attached form a 5-, 6- or 7-membered ring; and $R^{17}$ is a member selected from hydrogen, ($C_1$-$C_8$)alkyl, ($C_2$-$C_8$)heteroalkyl, aryl and aryl($C_1$-$C_4$)alkyl. In each of the descriptions of, for example, alkyl, alkoxy and heteroalkyl, the groups can be substituted or unsubstituted. Preferably, when substituted the substituents are halogen (e.g., —CF$_3$, —OCF$_3$). In preferred embodiments, $R^1$ represents hydrogen, halogen, cyano, ($C_1$-$C_8$)alkyl, ($C_1$-$C_8$)alkoxy, —CO$_2$R$^{14}$ and —C(O)NR$^{15}$R$^{16}$. More preferably, $R^1$ represents hydrogen, halogen, cyano, ($C_1$-$C_8$)alkyl, ($C_1$-$C_8$)alkoxy, —CO$_2$R$^{14}$ and —C(O) NR$^{15}$R$^{16}$ in which $R^{14}$ is ($C_1$-$C_8$)alkyl, and $R^{15}$ and $R^{16}$ are independently hydrogen or ($C_1$-$C_8$)alkyl, or taken together with the nitrogen to which each is attached form a 5- or 6-membered ring. Other preferred $R^1$ groups are discussed below with reference to groupings of compounds wherein $Ar^1$ is phenyl, pyridyl, naphthyl, quinolinyl, isoquinolinyl, benzoxazolyl, benzothiazolyl and benzimidazolyl.

The symbol $R^2$ represents a substituted or unsubstituted aryl group. Preferably, $R^2$ represents a phenyl, naphthyl, pyridazinyl or pyridyl group. More preferably, $R^2$ is a phenyl, naphthyl, pyridazinyl or pyridyl group substituted with from 0-3 substituents selected from halogen, —$OCF_3$, —OH, —$O(C_1$-$C_8)$alkyl, —CN, —$CF_3$, —C(O)—$(C_1$-$C_8)$alkyl, —$(C_1$-$C_8)$alkyl and —$NH_2$. While certain preferred substituents have been provided (e.g., —$OCF_3$ and —$CF_3$), the terms alkyl and alkoxy are also meant to include substituted versions thereof, preferably halosubstituted versions including those specifically noted.

The symbol $R^3$ represents a halogen, cyano, nitro or a substituted or unsubstituted $(C_1$-$C_8)$alkoxy group, preferably a halogen, cyano or $(C_1$-$C_4)$alkoxy group. Most preferably, halogen, methoxy or trifluoromethoxy.

A number of preferred embodiments are provided herein. For example, in one preferred embodiment, X is a divalent linkage selected from —$CH_2$—, —$CH(CH_3)$—, —O—, —C(O)—, —$N(R^{11})$— and —S—; and Y is —$N(R^{12})$—S$(O)_2$—, wherein $R^{12}$ is a member selected from hydrogen and $(C_1$-$C_8)$alkyl. In another preferred embodiment, X is a divalent linkage selected from —$CH_2$—, —$CH(CH_3)$—, —O—, —C(O)—, —$N(R^{11})$— and —S—; Y is —$N(R^{12})$—S$(O)_2$—, wherein $R^{12}$ is a member selected from hydrogen and $(C_1$-$C_8)$alkyl; and $R^2$ is a substituted or unsubstituted aryl selected from phenyl, pyridyl, naphthyl and pyridazinyl. In yet another preferred embodiment, X is a divalent linkage selected from —$CH_2$—, —$CH(CH_3)$—, —O—, —C(O)—, —$N(R^{11})$— and —S—; Y is —$N(R^{12})$—S$(O)_2$—, wherein $R^{12}$ is a member selected from hydrogen and $(C_1$-$C_8)$alkyl; $R^2$ is a substituted or unsubstituted aryl selected from phenyl, pyridyl, naphthyl and pyridazinyl; and $Ar^1$ is a substituted or unsubstituted aryl selected from pyridyl, phenyl, naphthyl, quinolinyl, isoquinolinyl, benzoxazolyl, benzothiazolyl, and benzimidazolyl.

One of skill in the art will understand that a number of structural isomers are represented by formula I. In one group of embodiments, the isomers are those in which the groups on the phenyl ring occupy positions that are not contiguous. In other embodiments, the compounds are those having the structural orientations represented by the formulae:

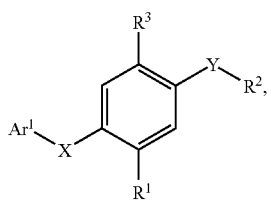
(Ia)

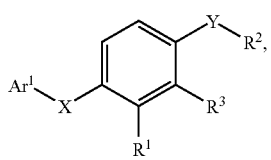
(Ib)

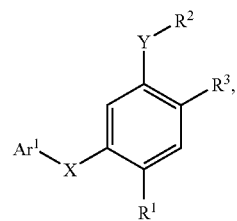
(Ic)

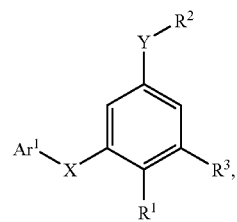
(Id)

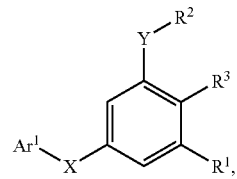
(Ie)

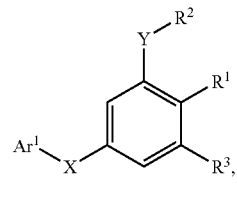
(If)

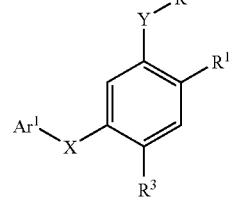
(Ig)

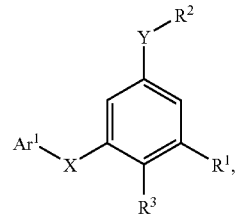
(Ih)

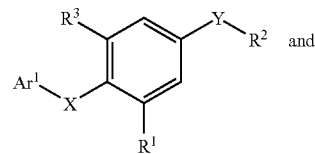
(Ii) and (Ij)

Still further preferred are those compounds having the structural orientation represented by formula Ia or Ib. Still other preferred compounds, are those of formula Ia or Ib in which the positions of $R^1$ and $R^3$ are switched (or reversed).

Yet other preferred compounds are those in which $Ar^1$—X— and —Y—$R^2$ occupy positions ortho to one another (exemplified by Ij).

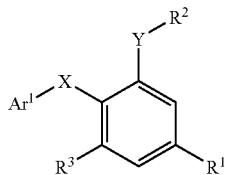
(Ij)

Still another group of preferred compounds are represented by the formula:

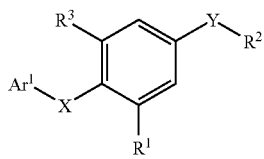
(Ii)

$Ar^1$ is Substituted or Unsubstituted Phenyl

In one group of particularly preferred embodiments, $Ar^1$ is a substituted or unsubstituted phenyl group. Further preferred are those embodiments in which the compound is represented by any of formulae Ia through Ij. Still further preferred are those embodiments in which X is —O—, —NH— or —S—; Y is —NH—$SO_2$—; $R^1$ is a member selected from hydrogen, halogen, ($C_1$-$C_8$)alkyl, ($C_2$-$C_8$)heteroalkyl, ($C_1$-$C_8$)alkoxy, —C(O)$R^{14}$, —$CO_2R^{14}$, —C(O)$NR^{15}R^{16}$, —S(O)$_p$—$R^{14}$ and —S(O)$_q$—$NR^{15}R^{16}$; $R^2$ is a phenyl group having from 0 to 3 substitutents selected from halogen, —$OCF_3$, —OH, —O($C_1$-$C_8$)alkyl, —C(O)—($C_1$-$C_8$)alkyl, —CN, —$CF_3$, ($C_1$-$C_8$)alkyl and —$NH_2$; and $R^3$ is selected from halogen, methoxy and trifluoromethoxy.

Other particularly preferred embodiments wherein $Ar^1$ is substituted or unsubstituted phenyl, are those that are represented by either of formulae Ii or Ij. In this group of embodiments, X is a divalent linkage selected from —$CH_2$—, —CH($CH_3$)—, —O—, —C(O)—, —N($R^{11}$)— and —S— wherein $R^{11}$ is a member selected from hydrogen and ($C_1$-$C_8$)alkyl; Y is a divalent linkage selected from —N($R^{12}$)—S(O)$_2$—, wherein $R^{12}$ is a member selected from hydrogen and ($C_1$-$C_8$)alkyl; $R^1$ is a member selected from hydrogen, halogen, ($C_1$-$C_8$)alkyl, ($C_2$-$C_8$)heteroalkyl, ($C_1$-$C_8$)alkoxy, —C(O)$R^{14}$, —$CO_2R^{14}$, —C(O)$NR^{15}R^{16}$, —S(O)$_p$—$R^{14}$, —S(O)$_q$—$NR^{15}R^{16}$, —O—C(O)—$R^{17}$, and —N($R^{14}$)—C(O)—$R^{17}$, wherein $R^{14}$ is a member selected from hydrogen, ($C_1$-$C_8$)alkyl, ($C_2$-$C_8$)heteroalkyl, aryl and aryl($C_1$-$C_4$)alkyl; $R^{15}$ and $R^{16}$ are members independently selected from hydrogen, ($C_1$-$C_8$)alkyl and ($C_2$-$C_8$)heteroalkyl, or taken together with the nitrogen to which each is attached form a 5-, 6- or 7-membered ring; $R^{17}$ is a member selected from hydrogen, ($C_1$-$C_8$)alkyl and ($C_2$-$C_8$)heteroalkyl; the subscript p is an integer of from 0 to 2; the subscript q is 2; $R^2$ is a substituted or unsubstituted phenyl; and $R^3$ is a halogen or ($C_1$-$C_8$)alkoxy.

In further preferred embodiments, X is —O—, —NH— or —S—; Y is —NH—$SO_2$—; $R^1$ is a member selected from hydrogen, halogen, ($C_1$-$C_8$)alkyl, ($C_2$-$C_8$)heteroalkyl, ($C_1$-$C_8$)alkoxy, —C(O)$R^{14}$, —$CO_2R^{14}$, —C(O)$NR^{15}R^{16}$, —S(O)$_p$—$R^{14}$ and —S(O)$_q$—$NR^{15}R^{16}$; $R^2$ is a phenyl group having from 0 to 3 substitutents selected from halogen, —$OCF_3$, —OH, —O($C_1$-$C_8$)alkyl, —C(O)—($C_1$-$C_8$)alkyl, —CN, —$CF_3$, ($C_1$-$C_8$)alkyl and —$NH_2$; and $R^3$ is selected from halogen, methoxy and trifluoromethoxy.

In still further preferred embodiments, $Ar^1$ is a phenyl group having from 1 to 3 substitutents selected from halogen, —$OCF_3$, —OH, —O($C_1$-$C_6$)alkyl, —$CF_3$, ($C_1$-$C_8$)alkyl and —$NO_2$; $R^1$ is a member selected from halogen, ($C_1$-$C_8$)alkyl, ($C_2$-$C_8$)heteroalkyl and ($C_1$-$C_8$)alkoxy; $R^2$ is a phenyl group having from 0 to 3 substitutents selected from halogen, —$OCF_3$, —OH, —O($C_1$-$C_8$)alkyl, —C(O)—($C_1$-$C_8$)alkyl, —CN, —$CF_3$, ($C_1$-$C_8$)alkyl and —$NH_2$, more preferably 1 to 3 substituents selected from halogen, —$OCF_3$ and —$CF_3$; and $R^3$ is selected from halogen, methoxy and trifluoromethoxy. Yet further preferred embodiments are those in which $R^1$ and $R^3$ are each independently a halogen, and $R^2$ is a phenyl group having from 1 to 3 substitutents selected from halogen, —$OCF_3$, and —$CF_3$.

$Ar^1$ is Substituted or Unsubstituted Pyridyl

In one group of particularly preferred embodiments, $Ar^1$ is a substituted or unsubstituted pyridyl group. Further preferred are those embodiments in which the compound is represented by any of formulae Ia through Ij. Still further preferred are those embodiments in which X is —O—, —NH— or —S—; Y is —NH—$SO_2$—; $R^1$ is a member selected from hydrogen, halogen, ($C_1$-$C_8$)alkyl, ($C_2$-$C_8$)heteroalkyl, ($C_1$-$C_8$)alkoxy, —C(O)$R^{14}$, —$CO_2R^{14}$, —C(O)$NR^{15}R^{16}$, —S(O)$_p$—$R^{14}$ and —S(O)$_q$—$NR^{15}R^{16}$; $R^2$ is a phenyl group having from 0 to 3 substitutents selected from halogen, —$OCF_3$, —OH, —O($C_1$-$C_8$)alkyl, —C(O)—($C_1$-$C_8$)alkyl, —CN, —$CF_3$, ($C_1$-$C_8$)alkyl and —$NH_2$; and $R^3$ is selected from halogen, methoxy and trifluoromethoxy.

Other particularly preferred embodiments wherein $Ar^1$ is substituted or unsubstituted pyridyl, are those that are represented by either of formulae Ii or Ij. In this group of embodiments, X is a divalent linkage selected from —$CH_2$—, —CH($CH_3$)—, —O—, —C(O)—, —N($R^{11}$)— and —S— wherein $R^{11}$ is a member selected from hydrogen and ($C_1$-$C_8$)alkyl; Y is a divalent linkage selected from —N($R^{12}$)—S(O)$_2$—, wherein $R^{12}$ is a member selected from hydrogen and ($C_1$-$C_8$)alkyl; $R^1$ is a member selected from hydrogen, halogen, ($C_1$-$C_8$)alkyl, ($C_2$-$C_8$)heteroalkyl, ($C_1$-$C_8$)alkoxy, —C(O)$R^{14}$, —$CO_2R^{14}$, —C(O)$NR^{15}R^{16}$, —S(O)$_p$—$R^{14}$, —S(O)$_q$—$NR^{15}R^{16}$, —O—C(O)—$R^{17}$, and —N($R^{14}$)—C(O)—$R^{17}$, wherein $R^{14}$ is a member selected from hydrogen, ($C_1$-$C_8$)alkyl, ($C_2$-$C_8$)heteroalkyl, aryl and aryl($C_1$-$C_4$)alkyl; $R^{15}$ and $R^{16}$ are members independently selected from hydrogen, ($C_1$-$C_8$)alkyl and ($C_2$-$C_8$)heteroalkyl, or taken together with the nitrogen to which each is attached form a 5-, 6- or 7-membered ring; $R^{17}$ is a member selected from hydrogen, ($C_1$-$C_8$)alkyl and ($C_2$-$C_8$)heteroalkyl; the subscript p is an integer of from 0 to 2; the subscript q is 2; $R^2$ is a substituted or unsubstituted phenyl; and $R^3$ is a halogen or ($C_1$-$C_8$) alkoxy.

In further preferred embodiments, X is —O—, —NH— or —S—; Y is —NH—$SO_2$—; $R^1$ is a member selected from hydrogen, halogen, ($C_1$-$C_8$)alkyl, ($C_2$-$C_8$)heteroalkyl, ($C_1$-$C_8$)alkoxy, —C(O)$R^{14}$, —$CO_2R^{14}$, —C(O)$NR^{15}R^{16}$, —S(O)$_p$—$R^{14}$ and —S(O)$_q$—$NR^{15}R^{16}$; $R^2$ is a phenyl group having from 0 to 3 substitutents selected from halogen, —$OCF_3$, —OH, —O($C_1$-$C_8$)alkyl, —C(O)—($C_1$-$C_8$)alkyl, —CN, —$CF_3$, ($C_1$-$C_8$)alkyl and —$NH_2$; and $R^3$ is selected from halogen, methoxy and trifluoromethoxy.

In still further preferred embodiments, $Ar^1$ is a pyridyl group having from 0 to 3 substituents selected from halogen, —$OCF_3$, —OH, —$O(C_1$-$C_6)$alkyl, —$CF_3$, $(C_1$-$C_8)$alkyl and —$NO_2$; $R^1$ is a member selected from halogen, $(C_1$-$C_8)$alkyl, $(C_2$-$C_8)$heteroalkyl and $(C_1$-$C_8)$alkoxy; $R^2$ is a phenyl group having from 0 to 3 substituents selected from halogen, —$OCF_3$, —OH, —$O(C_1$-$C_8)$alkyl, —$C(O)$—$(C_1$-$C_8)$alkyl, —CN, —$CF_3$, $(C_1$-$C_8)$alkyl and —$NH_2$, more preferably 1 to 3 substituents selected from halogen, —$OCF_3$ and —$CF_3$; and $R^3$ is selected from halogen, methoxy and trifluoromethoxy. Yet further preferred embodiments are those in which $R^1$ and $R^3$ are each independently a halogen, and $R^2$ is a phenyl group having from 1 to 3 substitutents selected from halogen, —$OCF_3$, and —$CF_3$. Most preferably, $Ar^1$ is a 3-pyridyl group having preferred substituents as indicated above.

In still other particularly preferred embodiments, the compounds are represented by formula I, in which $Ar^1$ is a pyridyl ring having a single substituent selected from halogen, —$OCF_3$ and —$CF_3$; X is a divalent linkage selected from the group of —O—, —C(O)—, —$CH_2$— and combinations thereof; Y is a divalent linkage selected from the group of —NH—$S(O)_2$— and —NH—C(O)—; $R^1$ is selected from hydrogen, halogen, cyano, $(C_1$-$C_8)$alkyl, $(C_1$-$C_8)$alkoxy and —$C(O)NR^{15}R^{16}$ in which $R^{15}$ and are selected from hydrogen, $(C_1$-$C_8)$alkyl, aryl and aryl$(C_1$-$C_4)$alkyl; $R^2$ is a phenyl or pyridyl ring, optionally substituted by 0-3 groups selected from halogen, $(C_1$-$C_8)$alkyl, —O—$(C_1$-$C_8)$alkyl and —CN; and $R^3$ is halogen, cyano or $(C_1$-$C_4)$alkoxy.

$Ar^1$ is Substituted or Unsubstituted Naphthyl

In one group of particularly preferred embodiments, $Ar^1$ is a substituted or unsubstituted naphthyl group. Further preferred are those embodiments in which the compound is represented by any of formulae Ia through Ij. Still further preferred are those embodiments in which X is —O—, —NH— or —S—; Y is —NH—$SO_2$—; $R^1$ is a member selected from hydrogen, halogen, $(C_1$-$C_8)$alkyl, $(C_2$-$C_8)$heteroalkyl, $(C_1$-$C_8)$alkoxy, —$C(O)R^{14}$, —$CO_2R^{14}$, —$C(O)NR^{15}R^{16}$, —$S(O)_p$—$R^{14}$ and and —$S(O)_q$—$NR^{15}R^{16}$; $R^2$ is a phenyl group having from 0 to 3 substituents selected from halogen, —$OCF_3$, —OH, —$O(C_1$-$C_8)$alkyl, —$C(O)$—$(C_1$-$C_8)$alkyl, —CN, —$CF_3$, $(C_1$-$C_8)$alkyl and —$NH_2$; and $R^3$ is selected from halogen, methoxy and trifluoromethoxy.

Other particularly preferred embodiments wherein $Ar^1$ is substituted or unsubstituted naphthyl, are those that are represented by either of formulae Ii or Ij. In this group of embodiments, X is a divalent linkage selected from —$CH_2$—, —$CH(CH_3)$—, —O—, —C(O)—, —$N(R^{11})$— and —S—, wherein $R^{11}$ is a member selected from hydrogen and $(C_1$-$C_8)$alkyl; Y is a divalent linkage selected from —$N(R^{12})$—$S(O)_2$—, wherein $R^{12}$ is a member selected from hydrogen and $(C_1$-$C_8)$alkyl; $R^1$ is a member selected from hydrogen, halogen, $(C_1$-$C_8)$alkyl, $(C_2$-$C_8)$heteroalkyl, $(C_1$-$C_8)$alkoxy, —$C(O)R^{14}$, —$CO_2R^{14}$, —$C(O)NR^{15}R^{16}$, —$S(O)_p$—$R^{14}$, —$S(O)_q$—$NR^{15}R^{16}$, —O—C(O)—$R^{17}$, and —$N(R^{14})$—C(O)—$R^{17}$, wherein $R^{14}$ is a member selected from hydrogen, $(C_1$-$C_8)$alkyl, $(C_2$-$C_8)$heteroalkyl, aryl and aryl$(C_1$-$C_4)$alkyl; $R^{15}$ and $R^{16}$ are members independently selected from hydrogen, $(C_1$-$C_8)$alkyl and $(C_2$-$C_8)$heteroalkyl, or taken together with the nitrogen to which each is attached form a 5-, 6- or 7-membered ring; $R^{17}$ is a member selected from hydrogen, $(C_1$-$C_8)$alkyl and $(C_2$-$C_8)$heteroalkyl; the subscript p is an integer of from 0 to 2; the subscript q is 2; $R^2$ is a substituted or unsubstituted phenyl; and $R^3$ is a halogen or $(C_1$-$C_8)$alkoxy.

In further preferred embodiments, X is —O—, —NH— or —S—; Y is —NH—$SO_2$—; $R^1$ is a member selected from hydrogen, halogen, $(C_1$-$C_8)$alkyl, $(C_2$-$C_8)$heteroalkyl, $(C_1$-$C_8)$alkoxy, —$C(O)R^{14}$, —$CO_2R^{14}$, —$C(O)NR^{15}R^{16}$, —$S(O)_p$—$R^{14}$ and —$S(O)_q$—$NR^{15}R^{16}$; $R^2$ is a phenyl group having from 0 to 3 substituents selected from halogen, —$OCF_3$, —OH, —$O(C_1$-$C_8)$alkyl, —$C(O)$—$(C_1$-$C_8)$alkyl, —CN, —$CF_3$, $(C_1$-$C_8)$alkyl and —$NH_2$; and $R^3$ is selected from halogen, methoxy and trifluoromethoxy.

In still further preferred embodiments, $Ar^1$ is a naphthyl group having from 0 to 3 substituents selected from halogen, —$OCF_3$, —OH, —$O(C_1$-$C_6)$alkyl, —$CF_3$, $(C_1$-$C_8)$alkyl and —$NO_2$; $R^1$ is a member selected from halogen, $(C_1$-$C_8)$alkyl, $(C_2$-$C_8)$heteroalkyl and $(C_1$-$C_8)$alkoxy; $R^2$ is a phenyl group having from 0 to 3 substituents selected from halogen, —$OCF_3$, —OH, —$O(C_1$-$C_8)$alkyl, —$C(O)$—$(C_1$-$C_8)$alkyl, —CN, —$CF_3$, $(C_1$-$C_8)$alkyl and —$NH_2$, more preferably 1 to 3 substituents selected from halogen, —$OCF_3$ and —$CF_3$; and $R^3$ is selected from halogen, methoxy and trifluoromethoxy. Yet further preferred embodiments are those in which $R^1$ and $R^3$ are each independently a halogen, and $R^2$ is a phenyl group having from 1 to 3 substitutents selected from halogen, —$OCF_3$, and —$CF_3$.

$Ar^1$ is Substituted or Unsubstituted Benzothiazolyl

In another group of particularly preferred embodiments, $Ar^1$ is a substituted or unsubstituted benzothiazolyl group, with the proviso that when $Ar^1$ is substituted or unsubstituted 2-benzothiazolyl, then X is —$S(O)_k$—. Further preferred are those embodiments in which the compound is represented by any of formulae Ia through Ij. Still further preferred are those embodiments in which X is —O—, —NH— or —S—; Y is —NH—$SO_2$—; $R^1$ is a member selected from hydrogen, halogen, $(C_1$-$C_8)$alkyl, $(C_2$-$C_8)$heteroalkyl, $(C_1$-$C_8)$alkoxy, —$C(O)R^{14}$, —$CO_2R^{14}$, —$C(O)NR^{15}R^{16}$, —$S(O)_p$—$R^{14}$ and —$S(O)_q$—$NR^{15}R^{16}$; $R^2$ is a phenyl group having from 0 to 3 substituents selected from halogen, —$OCF_3$, —OH, —$O(C_1$-$C_8)$alkyl, —$C(O)$—$(C_1$-$C_8)$alkyl, —CN, —$CF_3$, $(C_1$-$C_8)$alkyl and —$NH_2$; and $R^3$ is selected from halogen, methoxy and trifluoromethoxy.

Other particularly preferred embodiments wherein $Ar^1$ is substituted or unsubstituted benzothiazolyl, are those that are represented by either of formulae Ii or Ij. In this group of embodiments, X is a divalent linkage selected from —$CH_2$—, —$CH(CH_3)$—, —O—, —C(O)—, —$N(R^{11})$— and —S— wherein $R^{11}$ is a member selected from hydrogen and $(C_1$-$C_8)$alkyl; Y is a divalent linkage selected from —$N(R^{12})$—$S(O)_2$—, wherein $R^{12}$ is a member selected from hydrogen and $(C_1$-$C_8)$alkyl; $R^1$ is a member selected from hydrogen, halogen, $(C_1$-$C_8)$alkyl, $(C_2$-$C_8)$heteroalkyl, $(C_1$-$C_8)$alkoxy, —$C(O)R^{14}$, —$CO_2R^{14}$, —$C(O)NR^{15}R^{16}$, —$S(O)_p$—$R^{14}$, —$S(O)_q$—$NR^{15}R^{16}$, —O—C(O)—$R^{17}$, and —$N(R^{14})$—C(O)—$R^{17}$, wherein $R^{14}$ is a member selected from hydrogen, $(C_1$-$C_8)$alkyl, $(C_2$-$C_8)$heteroalkyl, aryl and aryl$(C_1$-$C_4)$alkyl; $R^{15}$ and $R^{16}$ are members independently selected from hydrogen, $(C_1$-$C_8)$alkyl and $(C_2$-$C_8)$heteroalkyl, or taken together with the nitrogen to which each is attached form a 5-, 6- or 7-membered ring; $R^{17}$ is a member selected from hydrogen, $(C_1$-$C_8)$alkyl and $(C_2$-$C_8)$heteroalkyl; the subscript p is an integer of from 0 to 2; the subscript q is 2; $R^2$ is a substituted or unsubstituted phenyl; and $R^3$ is a halogen or $(C_1$-$C_8)$ alkoxy.

In further preferred embodiments, X is —O—, —NH— or —S—; Y is —NH—$SO_2$—; $R^1$ is a member selected from hydrogen, halogen, $(C_1$-$C_8)$alkyl, $(C_2$-$C_8)$heteroalkyl, $(C_1$-$C_8)$alkoxy, —$C(O)R^{14}$, —$CO_2R^{14}$, —$C(O)NR^{15}R^{16}$, —$S(O)_p$—$R^{14}$ and —$S(O)_q$—$NR^{15}R^{16}$; $R^2$ is a phenyl group having from 0 to 3 substituents selected from halogen, —$OCF_3$, —OH, —$O(C_1$-$C_8)$alkyl, —$C(O)$—$(C_1$-$C_8)$alkyl, —CN, —$CF_3$, $(C_1$-$C_8)$alkyl and —$NH_2$; and $R^3$ is selected from halogen, methoxy and trifluoromethoxy.

In still further preferred embodiments, $Ar^1$ is a benzothiazolyl group having from 1 to 3 substituents selected from halogen, —$OCF_3$, —OH, —O($C_1$-$C_6$)alkyl, —$CF_3$, ($C_1$-$C_8$)alkyl and —$NO_2$; $R^1$ is selected from halogen, ($C_1$-$C_8$)alkyl, ($C_2$-$C_8$)heteroalkyl and ($C_1$-$C_8$)alkoxy; $R^2$ is a phenyl group having from 0 to 3 substitutents selected from halogen, —$OCF_3$, —OH, —O($C_1$-$C_8$)alkyl, —C(O)—($C_1$-$C_8$)alkyl, —CN, —$CF_3$, ($C_1$-$C_8$)alkyl and —$NH_2$, more preferably 1 to 3 substituents selected from halogen, —$OCF_3$ and —$CF_3$; and $R^3$ is selected from halogen, methoxy and trifluoromethoxy. Yet further preferred embodiments are those in which $R^1$ and $R^3$ are each independently a halogen, and $R^2$ is a phenyl group having from 1 to 3 substitutents selected from halogen, —$OCF_3$, and —$CF_3$. In particularly preferred embodiments, the benzothiazolyl group is a 2-benzothiazolyl group.

$Ar^1$ is Substituted or Unsubstituted Benzoxazolyl

In another group of particularly preferred embodiments, $Ar^1$ is a substituted or unsubstituted benzoxazolyl group. Further preferred are those embodiments in which the compound is represented by any of formulae Ia through Ij. Still further preferred are those embodiments in which X is —O—, —NH— or —S—; Y is —NH—$SO_2$—; $R^1$ is a member selected from hydrogen, halogen, ($C_1$-$C_8$)alkyl, ($C_2$-$C_8$)heteroalkyl, ($C_1$-$C_8$)alkoxy, —C(O)$R^{14}$, —$CO_2R^{14}$, —C(O)$NR^{15}R^{16}$, —S(O)$_p$—$R^{14}$ and —S(O)$_q$—$NR^{15}R^{16}$; $R^2$ is a phenyl group having from 0 to 3 substituents selected from halogen, —$OCF_3$, —OH, —O($C_1$-$C_8$)alkyl, —C(O)—($C_1$-$C_8$)alkyl, —CN, —$CF_3$, ($C_1$-$C_8$)alkyl and —$NH_2$; and $R^3$ is selected from halogen, methoxy and trifluoromethoxy.

Other particularly preferred embodiments wherein $Ar^1$ is substituted or unsubstituted benzoxazolyl, are those that are represented by either of formulae Ii or Ij. In this group of embodiments, X is a divalent linkage selected from —$CH_2$—, —CH($CH_3$)—, —O—, —C(O)—, —N($R^{11}$)— and —S—, wherein $R^{11}$ is a member selected from hydrogen and ($C_1$-$C_8$)alkyl; Y is a divalent linkage selected from —N($R^{12}$)—S(O)$_2$—, wherein $R^{12}$ is a member selected from hydrogen and ($C_1$-$C_8$)alkyl; $R^1$ is a member selected from hydrogen, halogen, ($C_1$-$C_8$)alkyl, ($C_2$-$C_8$)heteroalkyl, ($C_1$-$C_8$)alkoxy, —C(O)$R^{14}$, —$CO_2R^{14}$, —C(O)$NR^{15}R^{16}$, —S(O)$_p$—$R_{14}$, —S(O)$_q$—$NR^{15}R^{16}$, —O—C(O)—$R^{17}$, and —N($R^{14}$)—C(O)—$R^{17}$, wherein $R^{14}$ is a member selected from hydrogen, ($C_1$-$C_8$)alkyl, ($C_2$-$C_8$)heteroalkyl, aryl and aryl($C_1$-$C_4$)alkyl; $R^{15}$ and $R^{16}$ are members independently selected from hydrogen, ($C_1$-$C_8$)alkyl and ($C_2$-$C_8$)heteroalkyl, or taken together with the nitrogen to which each is attached form a 5-, 6- or 7-membered ring; $R^{17}$ is a member selected from hydrogen, ($C_1$-$C_8$)alkyl and ($C_2$-$C_8$)heteroalkyl; the subscript p is an integer of from 0 to 2; the subscript q is 2; $R^2$ is a substituted or unsubstituted phenyl; and $R^3$ is a halogen or ($C_1$-$C_8$) alkoxy.

In further preferred embodiments, X is —O—, —NH— or —S—; Y is —NH—$SO_2$—; $R^1$ is a member selected from hydrogen, halogen, ($C_1$-$C_8$)alkyl, ($C_2$-$C_8$)heteroalkyl, ($C_1$-$C_8$)alkoxy, —C(O)$R^{14}$, —$CO_2R^{14}$, —C(O)$NR^{15}R^{16}$, —S(O)$_p$—$R^{14}$ and —S(O)$_q$—$NR^{15}R^{16}$; $R^2$ is a phenyl group having from 0 to 3 substituents selected from halogen, —$OCF_3$, —OH, —O($C_1$-$C_8$)alkyl, —C(O)—($C_1$-$C_8$)alkyl, —CN, —$CF_3$, ($C_1$-$C_8$)alkyl and —$NH_2$; and $R^3$ is selected from halogen, methoxy and trifluoromethoxy.

In still further preferred embodiments, $Ar^1$ is a benzoxazolyl group having from 0 to 3 substituents selected from halogen, —$OCF_3$, —OH, —O($C_1$-$C_6$)alkyl, —$CF_3$, ($C_1$-$C_8$)alkyl and —$NO_2$; $R^1$ is selected from halogen, ($C_1$-$C_8$)alkyl, ($C_2$-$C_8$)heteroalkyl and ($C_1$-$C_8$)alkoxy; $R^2$ is a phenyl group having from 0 to 3 substitutents selected from halogen, —$OCF_3$, —OH, —O($C_1$-$C_8$)alkyl, —C(O)—($C_1$-$C_8$)alkyl, —CN, —$CF_3$, ($C_1$-$C_8$)alkyl and —$NH_2$, more preferably 1 to 3 substituents selected from halogen, —$OCF_3$ and —$CF_3$; and $R^3$ is selected from halogen, methoxy and trifluoromethoxy. Yet further preferred embodiments are those in which $R^1$ and $R^3$ are each independently a halogen, and $R^2$ is a phenyl group having from 1 to 3 substitutents selected from halogen, —$OCF_3$, and —$CF_3$. In particularly preferred embodiments, the benzoxazolyl group is a 2-benzoxazolyl group.

$Ar^1$ is Substituted or Unsubstituted Benzimidazolyl

In another group of particularly preferred embodiments, $Ar^1$ is a substituted or unsubstituted benzimidazolyl group. Further preferred are those embodiments in which the compound is represented by any of formulae Ia through Ij. Still further preferred are those embodiments in which X is or —O—, —NH— or —S—; Y is —NH—$SO_2$—; $R^1$ is a member selected from hydrogen, halogen, ($C_1$-$C_8$)alkyl, ($C_2$-$C_8$)heteroalkyl, ($C_1$-$C_8$)alkoxy, —C(O)$R^{14}$, —$CO_2R^{14}$, —C(O)$NR^{15}R^{16}$, —S(O)$_p$—$R^{14}$ and —S(O)$_q$—$NR^{15}R^{16}$; $R^2$ is a phenyl group having from 0 to 3 substituents selected from halogen, —$OCF_3$, —OH, —O($C_1$-$C_8$)alkyl, —C(O)—($C_1$-$C_8$)alkyl, —CN, —$CF_3$, ($C_1$-$C_8$)alkyl and —$NH_2$; and $R^3$ is selected from halogen, methoxy and trifluoromethoxy.

Other particularly preferred embodiments wherein $Ar^1$ is substituted or unsubstituted benzimidazolyl, are those that are represented by either of formulae Ii or Ij. In this group of embodiments, X is a divalent linkage selected from —$CH_2$—, —CH($CH_3$)—, —O—, —C(O)—, —N($R^{11}$)— and —S—, wherein $R^{11}$ is a member selected from hydrogen and ($C_1$-$C_8$)alkyl; Y is a divalent linkage selected from —N($R^{12}$)—S(O)$_2$—, wherein $R^{12}$ is a member selected from hydrogen and ($C_1$-$C_8$)alkyl; $R^1$ is a member selected from hydrogen, halogen, ($C_1$-$C_8$)alkyl, ($C_2$-$C_8$)heteroalkyl, ($C_1$-$C_8$)alkoxy, —C(O)$R^{14}$, —$CO_2R^{14}$, —C(O)$NR^{15}R^{16}$, —S(O)$_p$—$R^{14}$, —S(O)$_q$—$NR^{15}R^{16}$, —O—C(O)—$R^{17}$, and —N($R^{14}$)—C(O)—$R^{17}$, wherein $R^{14}$ is a member selected from hydrogen, ($C_1$-$C_8$)alkyl, ($C_2$-$C_8$)heteroalkyl, aryl and aryl($C_1$-$C_4$)alkyl; $R^{15}$ and $R^{16}$ are members independently selected from hydrogen, ($C_1$-$C_8$)alkyl and ($C_2$-$C_8$)heteroalkyl, or taken together with the nitrogen to which each is attached form a 5-, 6- or 7-membered ring; $R^{17}$ is a member selected from hydrogen, ($C_1$-$C_8$)alkyl and ($C_2$-$C_8$)heteroalkyl; the subscript p is an integer of from 0 to 2; the subscript q is 2; $R^2$ is a substituted or unsubstituted phenyl; and $R^3$ is a halogen or ($C_1$-$C_8$) alkoxy.

In further preferred embodiments, X is —O—, —NH— or —S—; Y is —NH—$SO_2$—; $R^1$ is a member selected from hydrogen, halogen, ($C_1$-$C_8$)alkyl, ($C_2$-$C_8$)heteroalkyl, ($C_1$-$C_8$)alkoxy, —C(O)$R^{14}$, —$CO_2R^{14}$, —C(O)$NR^{15}R^{16}$, —S(O)$_p$—$R^{14}$ and —S(O)$_q$—$NR^{15}R^{16}$; $R^2$ is a phenyl group having from 0 to 3 substitutents selected from halogen, —$OCF_3$, —OH, —O($C_1$-$C_8$)alkyl, —C(O)—($C_1$-$C_8$)alkyl, —CN, —$CF_3$, ($C_1$-$C_8$)alkyl and —$NH_2$; and $R^3$ is selected from halogen, methoxy and trifluoromethoxy.

In still further preferred embodiments, $Ar^1$ is a benzimidazolyl group having from 0 to 3 substituents selected from halogen, —$OCF_3$, —OH, —O($C_1$-$C_6$)alkyl, —$CF_3$, ($C_1$-$C_8$)alkyl and —$NO_2$; $R^1$ is selected from halogen, ($C_1$-$C_8$)alkyl, ($C_2$-$C_8$)heteroalkyl and ($C_1$-$C_8$)alkoxy; $R^2$ is a phenyl group having from 0 to 3 substitutents selected from halogen, —$OCF_3$, —OH, —O($C_1$-$C_8$)alkyl, —C(O)—($C_1$-$C_8$)alkyl, —CN, —$CF_3$, ($C_1$-$C_8$)alkyl and —$NH_2$, more preferably 1 to 3 substituents selected from halogen, —$OCF_3$ and —$CF_3$; and $R^3$ is selected from halogen, methoxy and trifluoromethoxy. Yet further preferred embodiments are those in which $R^1$ and $R^3$ are each independently a halogen, and $R^2$ is a phenyl group having from 1 to 3 substitutents selected from halogen, —OCF$_3$, and —CF$_3$. In particularly preferred embodiments, the benzimidazolyl group is a 2-benzimidazolyl group.

Ar$^1$ is Substituted or Unsubstituted Quinolinyl or Isoquinolinyl

In another group of particularly preferred embodiments, Ar$^1$ is a substituted or unsubstituted isoquinolinyl group. Further preferred are those embodiments in which the compound is represented by any of formulae Ia through Ij. Still further preferred are those embodiments in which X is —O—, —NH— or —S—; Y is —NH—SO$_2$—; R$^1$ is a member selected from hydrogen, halogen, (C$_1$-C$_8$)alkyl, (C$_2$-C$_8$)heteroalkyl, (C$_1$-C$_8$)alkoxy, —C(O)R$^{14}$, —CO$_2$R$^{14}$, —C(O)NR$^{15}$R$^{16}$, —S(O)$_p$—R$^{14}$ and —S(O)$_q$—NR$^{15}$R$^{16}$; R$^2$ is a phenyl group having from 0 to 3 substitutents selected from halogen, —OCF$_3$, —OH, —O(C$_1$-C$_8$)alkyl, —C(O)—(C$_1$-C$_8$)alkyl, —CN, —CF$_3$, (C$_1$-C$_8$)alkyl and —NH$_2$; and R$^3$ is selected from halogen, methoxy and trifluoromethoxy.

Other particularly preferred embodiments wherein Ar$^1$ is substituted or unsubstituted isoquinolinyl, are those that are represented by either of formulae Ii or Ij. In this group of embodiments, X is a divalent linkage selected from —CH$_2$—, —CH(CH$_3$)—, —O—, —C(O)—, —N(R$^{11}$)— and —S—, wherein R$^{11}$ is a member selected from hydrogen and (C$_1$-C$_8$)alkyl; Y is a divalent linkage selected from —N(R$^{12}$)—S(O)$_2$—, wherein R$^{12}$ is a member selected from hydrogen and (C$_1$-C$_8$)alkyl; R$^1$ is a member selected from hydrogen, halogen, (C$_1$-C$_8$)alkyl, (C$_2$-C$_8$)heteroalkyl, (C$_1$-C$_8$)alkoxy, —C(O)R$^{14}$, —CO$_2$R$^{14}$, —C(O)NR$^{15}$R$^{16}$, —S(O)$_p$—R$^{14}$, —S(O)$_q$—NR$^{15}$R$^{16}$, —O—C(O)—R$^{17}$, and —N(R$^{14}$)—C(O)—R$^{17}$, wherein R$^{14}$ is a member selected from hydrogen, (C$_1$-C$_8$)alkyl, (C$_2$-C$_8$)heteroalkyl, aryl and aryl(C$_1$-C$_4$)alkyl; R$^{15}$ and R$^{16}$ are members independently selected from hydrogen, (C$_1$-C$_8$)alkyl and (C$_2$-C$_8$)heteroalkyl, or taken together with the nitrogen to which each is attached form a 5-, 6- or 7-membered ring; R$^{17}$ is a member selected from hydrogen, (C$_1$-C$_8$)alkyl and (C$_2$-C$_8$)heteroalkyl; the subscript p is an integer of from 0 to 2; the subscript q is 2; R$^2$ is a substituted or unsubstituted phenyl; and R$^3$ is a halogen or (C$_1$-C$_8$)alkoxy.

In further preferred embodiments, X is —O—, —NH— or —S—; Y is —NH—SO$_2$—; R$^1$ is a member selected from hydrogen, halogen, (C$_1$-C$_8$)alkyl, (C$_2$-C$_8$)heteroalkyl, (C$_1$-C$_8$)alkoxy, —C(O)R$^{14}$, —CO$_2$R$^{14}$, —C(O)NR$^{15}$R$^{16}$, —S(O)$_p$—R$^{14}$ and —S(O)$_q$—NR$^{15}$R$^{16}$; R$^2$ is a phenyl group having from 0 to 3 substitutents selected from halogen, —OCF$_3$, —OH, —O(C$_1$-C$_8$)alkyl, —C(O)—(C$_1$-C$_8$)alkyl, —CN, —CF$_3$, (C$_1$-C$_8$)alkyl and —NH$_2$; and R$^3$ is selected from halogen, methoxy and trifluoromethoxy.

In still further preferred embodiments, Ar$^1$ is an isoquinolinyl group having from 0 to 3 substituents selected from halogen, —OCF$_3$, —OH, —O(C$_1$-C$_6$)alkyl, —CF$_3$, (C$_1$-C$_8$)alkyl and —NO$_2$; R$^1$ is selected from halogen, (C$_1$-C$_8$)alkyl, (C$_2$-C$_8$)heteroalkyl and (C$_1$-C$_8$)alkoxy; R$^2$ is a phenyl group having from 0 to 3 substitutents selected from halogen, —OCF$_3$, —OH, —O(C$_1$-C$_8$)alkyl, —C(O)—(C$_1$-C$_8$)alkyl, —CN, —CF$_3$, (C$_1$-C$_8$)alkyl and —NH$_2$, more preferably 1 to 3 substituents selected from halogen, —OCF$_3$ and —CF$_3$; and R$^3$ is selected from halogen, methoxy and trifluoromethoxy. Yet further preferred embodiments are those in which R$^1$ and R$^3$ are each independently a halogen, and R$^2$ is a phenyl group having from 1 to 3 substituents selected from halogen, —OCF$_3$, and —CF$_3$. In particularly preferred embodiments, the isoquinolinyl group is selected from 3-isoquinolinyl and 4-isoquinolinyl groups.

In another aspect, the present invention provides pharmaceutical compositions comprising at least one of the above compounds in admixture with a pharmaceutically acceptable excipient.

In yet another aspect, the present invention provides methods for modulating conditions mediated by PPARγ in a host. More particularly, the conditions are selected from non-insulin-dependent diabetes mellitus, obesity, conditions associated with abnormal plasma levels of lipoproteins or triglycerides, and inflammatory conditions such as, for example, rheumatoid arthritis and atherosclerosis.

Preparation of the Compounds

The compounds of the present invention can be prepared using standard synthetic methods. For exemplary purposes, Scheme 1 illustrates methods for the preparation of compounds of structural formula (Ia). One of skill in the art will understand that similar methods can be used for the synthesis of compounds in the other structural classes.

As shown in Scheme 1, compounds of the present invention can be prepared beginning with commercially available 2-chloro-5-nitrobenzonitrile (i). Treatment of J with a phenol, thiophenol, or optionally protected aniline in the presence of base and heat provides the adduct (ii). Reduction of the nitro group in ii with, for example, H$_2$ in the presence of Raney nickel catalyst provides an aniline derivative (iii). Sulfonylation of iii with an appropriate arylsulfonyl halide (Ar$^1$ 50$_2$C$_1$) in the presence of base (typically a tertiary amine) provides a target compound (iv). Compound iii can also be converted to a related compound of formula (vi) in which the orientation of the sulfonamide linkage is reversed. Thus, conversion of the aniline iii to the benzenesulfonyl chloride v can be accomplished using methods described in Hoffman, Organic Syntheses Collective Volume VII, p. 508-511. Subsequent treatment of v with an appropriate aniline provides the target compound vi.

Scheme 1

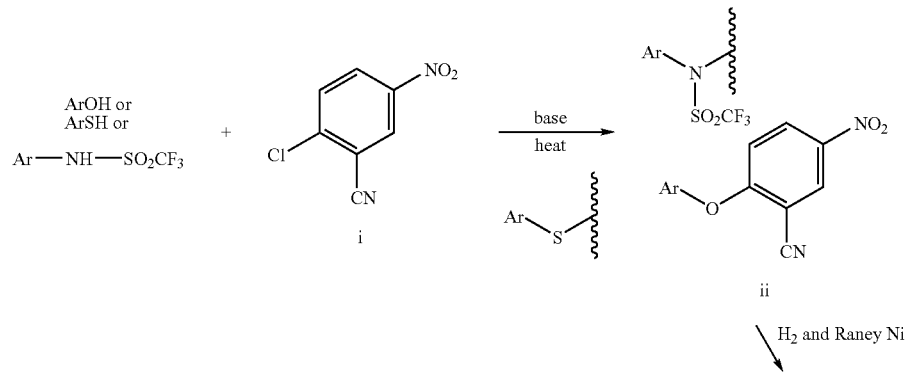

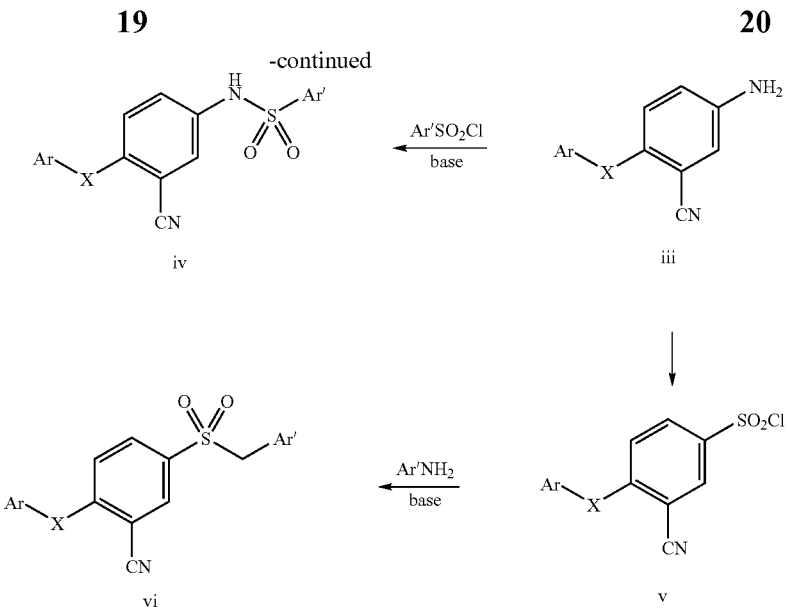

Other compounds of the present invention can be prepared beginning with, for example, 3,4-difluoronitrobenzene, 3-chloro-4-fluoronitrobenzene, 2-chloro-5-nitroanisole, 3-bromo-4-fluoronitrobenzene and the like.

Analysis of the Compounds

The compounds of the present invention can be evaluated for modulation of the PPARγ receptor using assays such as those described in Jiang, et al., Nature 391:82-86 (1998), Ricote, et al., Nature 391:79-82 (1998) and Lehmann, et al., J. Biol. Chem. 270(12): 12953-12956 (1995). Alternatively, the compounds can be evaluated for their ability to displace radiolabeled BRL 49653 from a PPARγ-GST fusion protein as follows:

Materials:

PPARγ-GST fusion protein (prepared according to standard procedures), [³H]-BRL 49653 having 50 Ci/mmol specific activity, Polyfiltronics Unifilter 350 filtration plate and glutathione-Sepharose® beads (from Pharmacia: washed twice with 10× binding buffer in which BSA and DTI can be left out).

Method:

Binding buffer (10 mM Tris-HCl, pH 8.0, 50 mM KCl, 10 mM DTT, 0.02% BSA and 0.01% NP-40) is added in 80 microliter amounts to the wells of the filtration plate. The test compound is then added in 10 microliters of DMSO. The PPARγ-GST fusion protein and radiolabeled BRL compound are premixed in binding buffer containing 10 mM DTT and added in 10 microliter amounts to the wells of the plate to provide final concentrations of 1 μg/well of PPARγ-GST fusion protein and 10 nM [³H]-BRL 49653 compound. The plate is incubated for 15 minutes. Glutathione-agarose bead is added in 50 μL of binding buffer, and the plate is vigorously shaken for one hour. The plate is washed four times with 200 μL/well of binding buffer (without BSA and DTT). The bottom of the plate is sealed and 200 μL/well of scintillation cocktail is added. The top of the plate is then sealed and the radioactivity is determined.

Formulation and Administration of the Compounds (Compositions)

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds described herein can be administered by inhalation, for example, intranasally. Additionally, the compounds of the present invention can be administered transdermally. Accordingly, the present invention also provides pharmaceutical compositions comprising a pharmaceutically acceptable carrier or excipient and either a compound of formula (I) or a pharmaceutically acceptable salt of a compound of formula (I).

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component. In tablets, the active component is mixed with the carrier having the necessary binding properties in suitable proportions and compacted in the shape and size desired.

The powders and tablets preferably contain from 5% or 10% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 1000 mg, preferably 1.0 mg to 100 mg according to the particular application and the potency of the active component. The composition can, if desired, also contain other compatible therapeutic agents.

In therapeutic use for the treatment of obesity, NIDDM, or inflammatory conditions, the compounds utilized in the pharmaceutical method of the invention are administered at the initial dosage of about 0.001 mg/kg to about 100 mg/kg daily. A daily dose range of about 0.1 mg/kg to about 10 mg/kg is preferred. The dosages, however, may be varied depending upon the requirements of the patient, the severity of the condition being treated, and the compound being employed. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. For convenience, the total daily dosage may be divided and administered in portions during the day, if desired.

The following examples are offered by way of illustration and are not intended to limit the scope of the invention.

EXAMPLES

Reagents and solvents used below can be obtained from commercial sources such as Aldrich Chemical Co. (Milwaukee, Wis., USA). $^1$H-NMR spectra were recorded on a Varian Gemini 400 MHz NMR spectrometer. Significant peaks are tabulated in the order: number of protons, multiplicity (s, singlet; d, doublet; t, triplet; q, quartet; m, multiplet; br s, broad singlet) and coupling constant(s) in Hertz. Electron Ionization (EI) mass spectra were recorded on a Hewlett Packard 5989A mass spectrometer. Mass spectrometry results are reported as the ratio of mass over charge, followed by the relative abundance of each ion (in parentheses). In tables, a single m/e value is reported for the M+H (or as noted M−H) ion containing the most common atomic isotopes.

Isotope patterns correspond to the expected formula in all cases. Electrospray ionization (ESI) mass spectrometry analysis was conducted on a Hewlett-Packard 1100 MSD electrospray mass spectrometer using the HP1 100 HPLC for sample delivery. Normally the analyte was dissolved in methanol at 0.1 mg/mL and 1 microliter was infused with the delivery solvent into the mass spectrometer which scanned from 100 to 1500 daltons. All compounds could be analyzed in the positive ESI mode, using 1:1 acetonitrile/water with 1% acetic acid as the delivery solvent. The compounds provided below could also be analyzed in the negative ESI mode, using 2 mM $NH_4OAc$ in acetonitrile/water as delivery solvent.

Abbreviations: N-hydroxybenzotriazole (HOBT), 2-(1H-benzotriazole-1-yl)-1,1,3,3-tetramethyluronium hexafluorophosphate (HBTU), N-methylmorpholine (NMM),:1-hydroxy-7-azabenzotriazole (HOAT), O-(7-azabenzotriazole-1-y1)-N,N,N',N'-tetramethyluronium hexafluorophosphate (HATU), 1-(3-dimethylaminopropyl)-3-ethylcarbodiimide hydrochloride (EDCI).

Example 1

This example illustrates the preparation of 5-nitro-2-(3-chloro-5-pyridyloxy)benzonitrile (1.1).

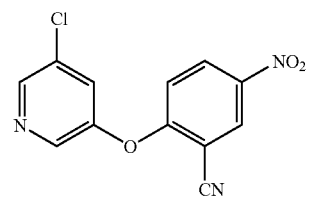

1.1

To a solution of 2-chloro-5-nitrobenzonitrile (18.3 g, 100 mmol) and 5-chloro 3-pyridinol (13 g, 100 mmol) in DMIF (100 mL) was added powdered K2C03 (13.9 g, 100 mmol). After heating at 60° C. for 12 hours, the suspension was poured into water (1 L). The resulting solid was collected by filtration, rinsed with water and dried under vacuum to afford 27.6 g (100%) of the title compound, mp 104-107° C.
$^1$H NMR (400 MHz) (DMSO-$d_6$) δ 8.755 (d, J=2.8 Hz, 1H); 8.734 (br s, 1H); 8.576 (br s, 1H); 8.542 (dd, J=9.2, 2.7 Hz, 1H); 7.689 (t, J=2.2 Hz, 1H); 7.122 (d, J=9.2 Hz, 1H).

Example 2

This example illustrates the preparation of 5-amino-2-(3-chloro-5-pyridyloxy)benzonitrile (2.1).

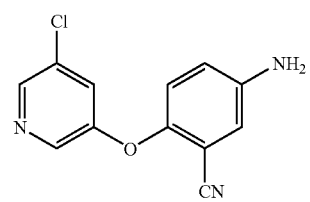

2.1

To a vigorously stirred solution of the intermediate from Example 1 (6.23 g) in ethanol and THF was added a slurry of Raney Nickel (~300 mg, Aldrich). The flask was filled with $H_2$ at atmospheric pressure and the reduction was monitored by TLC. Starting material disappeared rapidly, to form a nitroso intermediate which gradually was converted to the desired aniline over about 5 hours. Stirring was stopped and Raney Nickel was attracted to the magnetic stirbar. The remaining solution was filtered through Celite® which was then rinsed with ethanol and methylene chloride. The combined organic portions were concentrated to provide 5.75 g of the product aniline as an oil which was used without further purification.

$^1$H NMR (400 MHz) (CDCl$_3$) δ 8.456 (d, J=1.9 Hz, 1H); 8.3 89 (d, J=2.6 Hz, 1H); 7.38 (m, 1H); 7.03 (m, 3H); 4.06 (m 2H).

Example 3

This example illustrates the synthesis of 3.1.

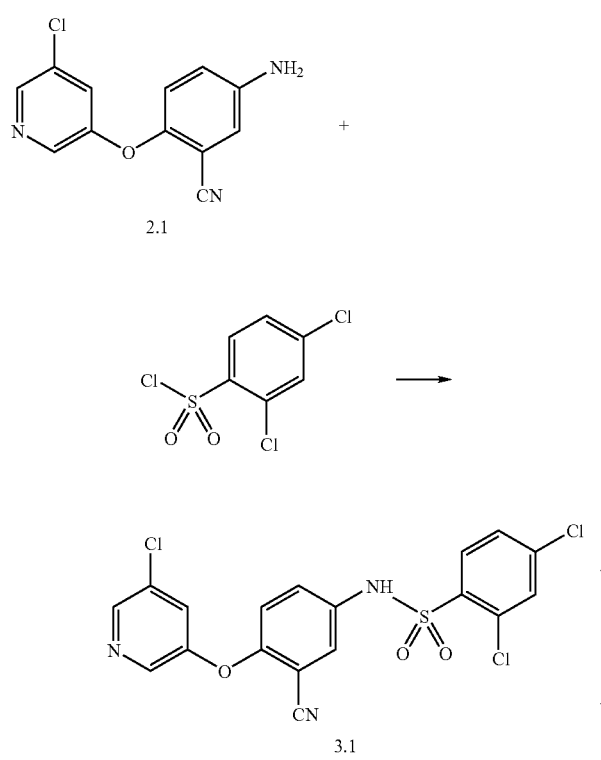

3.1

To a mixture of 5-amino-2-(3-chloro-5-pyridyloxy)benzonitrile from Example 2 (0.457 g) in methylene chloride was added 2,4-dichlorobenzenesulfonyl chloride (0.456 g, from Maybridge), followed by pyridine (150 μL). The reaction progress was monitored by TLC, and upon completion the solvent was removed under vacuum. The resulting residue was partitioned between methylene chloride and water. The organic layer was drawn off and concentrated. The residue was triturated with ether to provide 0.447 g of the title compound as a white solid, mp 154-156° C.

$^1$NMR (400 MHz) (CDCl$_3$) δ 8.59 (s, 1H); 8.42 (s, 1H) 8.08 (d, J=8.5 Hz, 1H); 7.72(t, J=1.8, 1H); 7.605 (d, J=2.7 Hz, 1H) 7.53 (dd, J=8.5, 2 Hz, 1H); 7.48 (dd, J=9.4 Hz, 1H); 7.22 (s, 1H); 7.0 (d, J=9.0 Hz, 1H). m/e (M−H) 456.

The title compound was oxidized to the corresponding pyridine N-oxide using 3-chloroperoxybenzoic acid in methylene chloride to provide 3.2 as a white solid. m/e 470 (M+H).

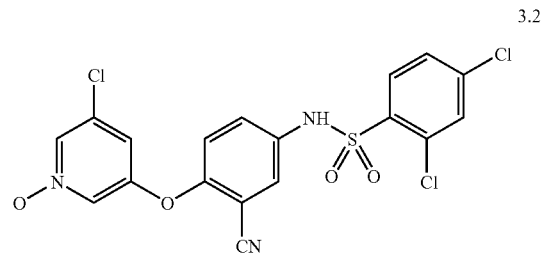

3.2

Example 4

This example illustrates the synthesis of 4.1.

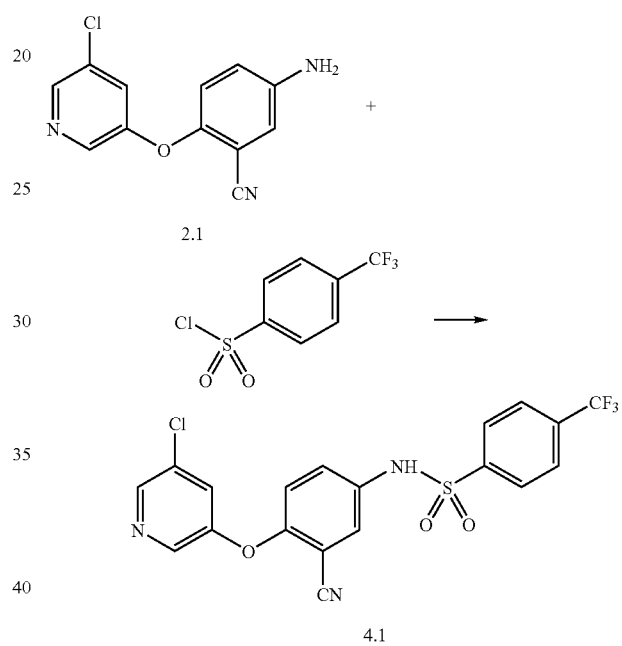

4.1

The title compound was prepared in a manner similar to Example 3, beginning with 1.6 g of the aniline of Example 2 and 1.6 g of 4-(trifluoromethyl)benzenesulfonyl chloride (from Maybridge). The crude product remaining after workup was purified by flash chromatography on silica eluting with 10% ethyl acetate/dichloromethane and then triturated in diethyl ether and collected as a white powder (1.04 g, 35% yield), mp 143-144° C.

Example 5

This example illustrates the synthesis of 5.1.

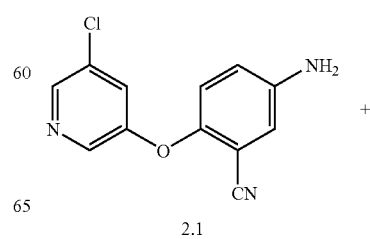

2.1

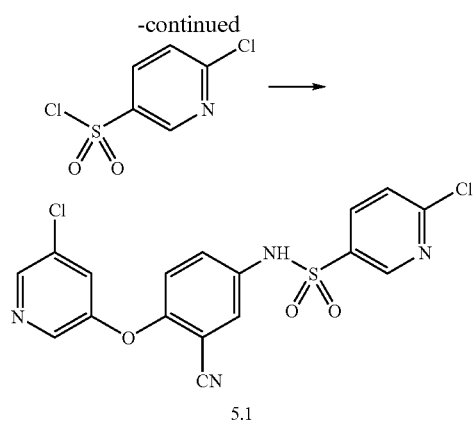

5.1

The title compound was prepared in a manner similar to Example 3, beginning with 397 mg of the aniline prepared as described in Example 2 and 345 mg of 2-chloropyridyl-5-sulfonyl chloride (prepared according to Hoffman, R. V., *Org Syn. Coll.* Vol. VII., p. 508-511). The crude product remaining after workup was purified by flash chromatography on silica eluting with 15% ethyl acetate/dichloromethane. The resulting solid was recrystallized from dichloromethane to provide the title compound (270 mg, 40%) as a white solid, m/e 419 (M–H).

Example 6

This example illustrates the synthesis of 6.1.

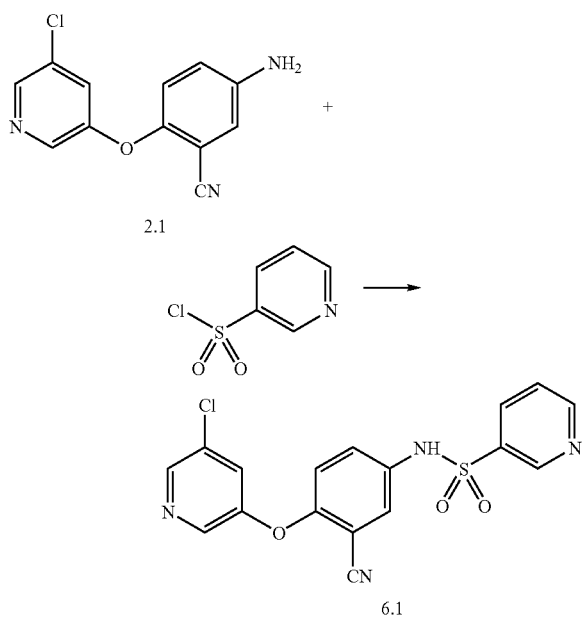

6.1

The title compound was prepared in a manner similar to Example 3, beginning with 400 mg of the aniline prepared as described in Example 2 and 349 mg of 3-pyridylsulfonyl chloride (prepared using methods similar to those described in *J. Med. Chem.* 40:1149 (1997)). The crude product remaining after workup was purified by flash chromatography on silica eluting with 1% ethanol/dichloromethane. The resulting solid was recrystallized from dichloromethane/diethyl ether and collected as a white solid (121 mg, 19%), mp 161-2° C.

In a similar manner, 6.2 was prepared from aniline 2.1 and 5-trifluoromethyl-2-pyridinesulfonyl chloride, mp 174-176° C.

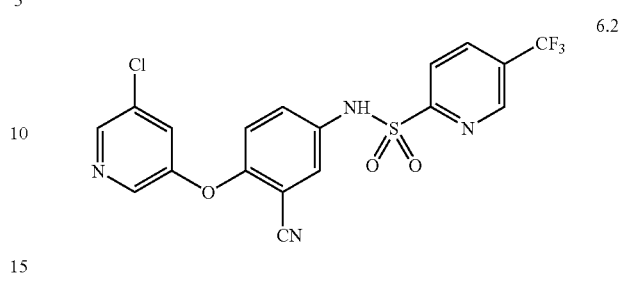

6.2

Example 7

This example illustrates the preparation of 7.1.

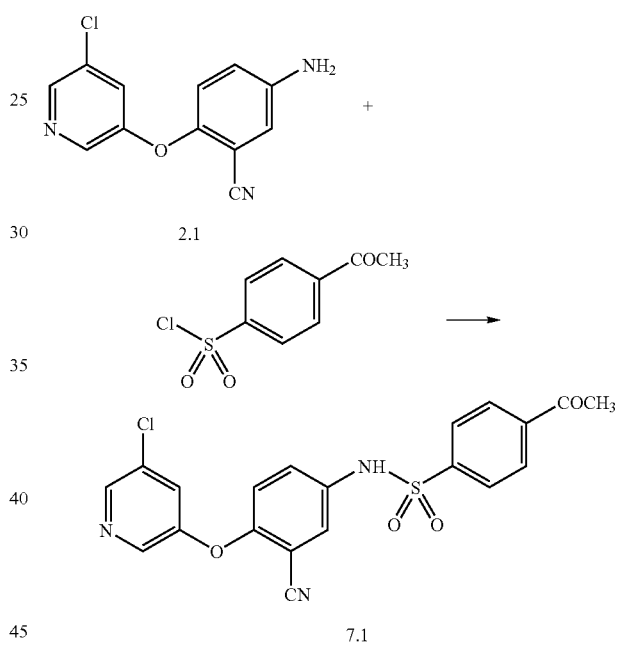

7.1

A round-bottomed flask was charged with the aniline prepared according to Example 2 (229 mg, 0.94 mmol), 4-acetylbenzenesulfonyl chloride (205 mg, 0.94 mmol, prepared according to Hoffman, R. V., Org. Syn. Coll. Vol. VII, p. 508-511), pyridine (75 mg, 0.94 mmol, Aldrich Chemical Co.), and a catalytic amount of DMAP (Aldrich Chemical Co.). Five mL of dichloromethane were added and the reaction was stirred at room temperature for eight hours. The reaction was then diluted with 25 mL of dichloromethane and washed successively with 10 mL of 1N HCl and brine. The organic portion was dried over $MgSO_4$ and passed through a plug of silica gel to remove baseline impurities. The resulting solid was triturated in hexanes to provide 362 mg (90%) of the title compound as a white solid.

$^1$H NMR (400 MHz) ($d_6$-DMSO) δ 10.81 (1H, s); 8.52 (1H, d, J=1.8 Hz); 8.43 (1H, d, J=2.3 Hz); 8.11 (2H, dd, J=6.8 Hz, 2.0 Hz); 7.90 (2H, dd, J=6.8 Hz, 2.0 Hz); 7.85 (1H, dd, J=4.4 Hz, 2.2 Hz); 7.53 (1H, d, J=2.7 Hz); 7.35 (1H, dd, J=9.1 Hz, 2.8 Hz); 7.35 (1H, d, J=9.1 Hz); 2.61 (3H, s). MS ESI m/e: 425.8 (M–H).

The compounds provided in Table 1 were prepared using the methods described in Examples 1-7.

TABLE 1

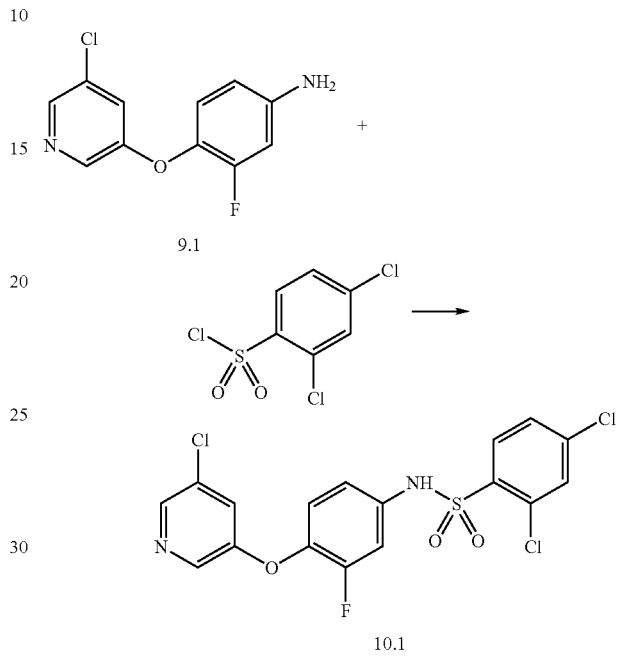

| | Ra | Rb | Rc | Rd | mp (°C.) |
|---|---|---|---|---|---|
| 7.2 | Cl | H | Cl | CH₃ | 181-182 |
| 7.3 | H | H | OCF₃ | H | 118-120 |
| 7.4 | H | H | CN | H | 160-163 |
| 7.5 | H | H | SO₂CH₃ | H | 174-175 |

Example 8

This example illustrates the preparation of 3-fluoro-4-(3-chloro-5-pyridyloxy)nitrobenzene (8.1).

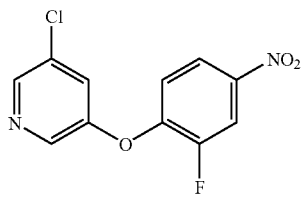

8.1

3,4-Difluoronitrobenzene (5.0 g, 32 mmol) and 5-chloro-3-pyridinol were combined using the procedure described in Example 1, to produce 8.2 g of the title compound.

$^1$H NMR (400 MHz) (DMSO-$d_6$) δ 8.562 (d, J=1.9 Hz, 1H); 8.537 (d, J=2.5 Hz, 1H); 8.384 (dd, J=10.8, 2.8 Hz, 1H); 8.117 (ddd, J=9.1, 2.7, 1.5 Hz, 1H); 7.967 (t, J=2.2 Hz, 1H); 7.418 (dd, J=9.2, 8.4 Hz, 1H).

Example 9

This example illustrates the preparation of 3-fluoro-4-(3-chloro-5-pyridyloxy)aniline (9.1).

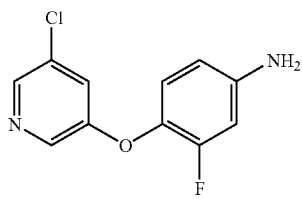

9.1

Using the method of Example 2, 3-fluoro-4-(3-chloro-5-pyridyloxy)nitrobenzene (8.1, 8.0 g) was converted to the title compound which was used directly in subsequent reactions.

MS (M+H) 239.1.

$^1$H NMR (400 MHz) (CDCl₃) δ 8.242 (br s, 2H); 7.142 (d, J=2.2 Hz, 1H); 6.937 (t, J=8.7 Hz, 1H); 6.512 (dd, J=12, 2.6 Hz, 1H); 6.444 (ddd, J=8.4, 2.7, 1.4 Hz, 1H); 3.62 (br s, 2H).

Example 10

This example illustrates the preparation of 10.1.

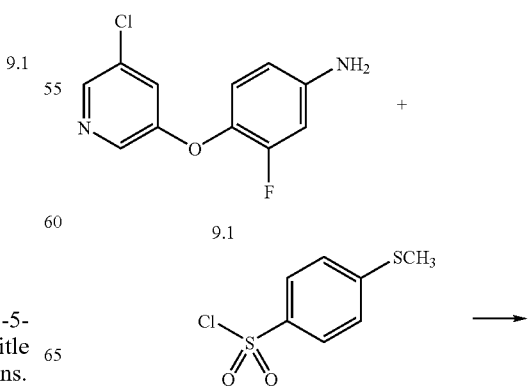

3-Fluoro-4-(3-chloro-5-pyridyloxy)aniline (239 mg, see Example 9) and 2,4-dichlorobenzenesulfonyl chloride (416 mg, Maybridge), were combined in a similar manner to that described in Example 3. The crude product was purified by flash chromatography on silica, eluting with 5% ethyl acetate/dichloromethane. The product fractions were concentrated and the solid was recrystallized from diethyl ether/hexanes to provide the title compound as a white solid (350 mg, 45%), mp 149-151° C.

Example 11

This example illustrates the preparation of 11.1.

-continued

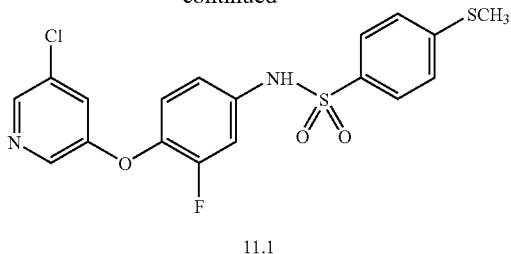

11.1

3-Fluoro-4-(3-chloro-5-pyridyloxy)aniline (310 mg, see Example 9) and 4-methylthiobenzenesulfonyl chloride (298 mg, prepared as described in Burton, et al., *J. Chem. Soc.,* 604-5 (1948)), were combined in a manner similar to that described in Example 3. The crude product was purified by flash chromatography on silica, eluting with ethyl acetate/hexanes/dichloromethane (1:5:4). The product fractions were concentrated and the solid was recrystallized from hexanes/diethyl ether to provide the title compound as a white solid (315 mg, 57%), mp 130-131° C.

The title compound was oxidized with mCPBA to the corresponding sulfoxide (11.2, mp 140-144° C.). The corresponding sulfone (11.3) was prepared using 4-(methylsulfonyl)benzenesulfonyl chloride (mp 165-168° C.).

Example 12

This example illustrates the preparation of 12.1.

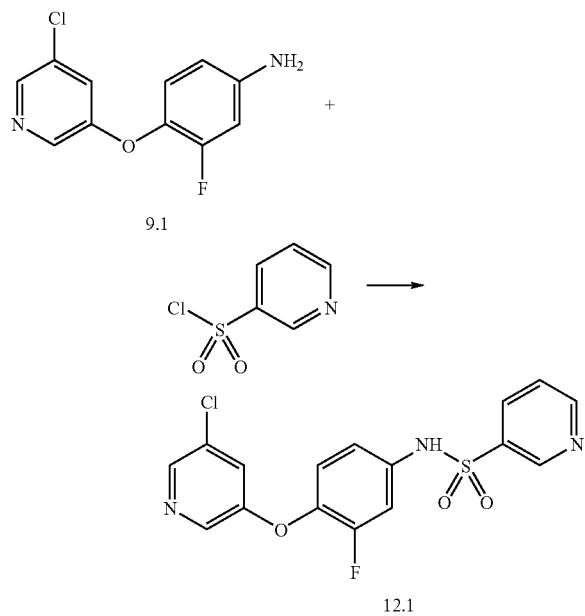

The title compound was prepared in a manner similar to Example 3, beginning with 3-pyridylsulfonyl chloride (335 mg, see Example 6) and 3-fluoro-4-(3-chloro-5-pyridyloxy)aniline (310 mg, see Example 9) with the addition of a catalytic amount of 4-dimethylaminopyridine. When reaction was complete by TLC, the mixture was filtered to remove amine salts. The filtrate was concentrated and the residue was purified by flash chromatography on silica, eluting with 5% methanol/dichloromethane. The product fractions were combined, concentrated, and the residue was triturated with diethyl ether to provide the title compound as a white solid (221 mg, 32%), mp 129° C.

Example 13

This illustrates the synthesis of 5-(4-acetylbenzenesulfonamido-2-fluorophenoxy)-3-chloropyridine (13.1).

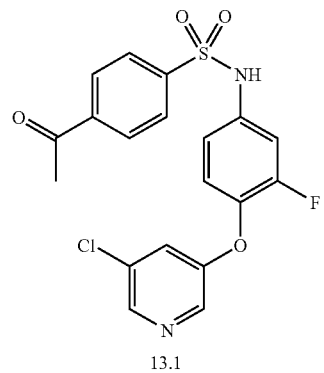

This was prepared using methods outlined in Examples 10-12, starting with 238 mg (1.0 mmol) of aniline 9.1, 218 mg (1.0 mmol) of 4-acetylbenzenesulfonyl chloride, 79 mg (1.0 mmol) of pyridine, catalytic DMAP, and 5 mL of methylene chloride. The title compound was obtained as a white solid (269 mg, 64%).

$^1$H NMR (400 MHz) (d$_6$-DMSO) δ 10.75 (1H, d, J=4.7 Hz); 8.38 (1H, dd, J$_1$=4.8 Hz J$_2$=2.1 Hz); 8.26 (1H, dd, J$_1$=5.0 Hz J$_2$=2.4 Hz) 8.09 (2H, m); 7.91 (2H, m); 7.52 (1H, dd, J$_1$=4.7 Hz J$_2$=2.6 Hz); 7.21 (1H, dt, J$_1$=5 Hz J$_2$=1.0 Hz); 7.12 (1H, dd, J$_1$=12.2 Hz J$_2$=1.0 Hz); 6.92 (1H, d, J=8.8 Hz); 2.59 (3H, t, J=2.1 Hz). MS ESI m/e: 418.7 (M–H).

Example 14

This example illustrates the synthesis of 3-chloro-4-(3-chloro-5-pyridyloxy)nitrobenzene (14.1).

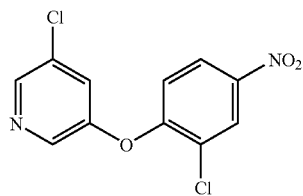

3-Chloro-4-fluoronitrobenzene (5.0 g, 28 mmol) and 5-chloro-3-pyridinol were combined using the procedure described in Example 1, to produce 7.9 g of the title compound.

$^1$H NMR (400 MHz) (DMSO-d$_6$) δ 8.571 (d, J=2.0 Hz, 1H); 8.509 (d, J=2.4 Hz, 1H); 8.499 (d, J=2.7 Hz, 1H); 8.208 (dd, J=9.0, 2.7 Hz, 1H); 7.949 (t, J=2.3 Hz, 1H); 7.335 (d, J=9.1 Hz, 1H).

Example 15

This example illustrates the preparation of 3-chloro-4-(3-chloro-5-pyridyloxy)aniline (15.1).

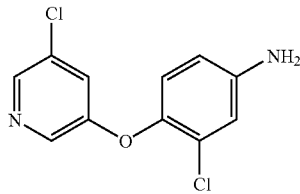

15.1

Using the method of Example 2, 3-chloro-4-(3-chloro-5-pyridyloxy)nitrobenzene (7.6 g) was converted to the title compound (7.2 g) and which was used directly in subsequent reactions.

$^1$H NMR (400 MHz) (CDCl$_3$) δ 8.244 (br s, 1H); 8.211 (br s, 1H); 7.096 (br 5, 1H); 6.929 (d, J=8.6 Hz, 1H); 6.785 (d, J=2.6 Hz, 1H); 6.592 (dd, J=8.6, 2.6 Hz, 1H); 3.577 (br s, 2H). MS (M+H) 255.1.

Example 16

This example illustrates the preparation of 16.1.

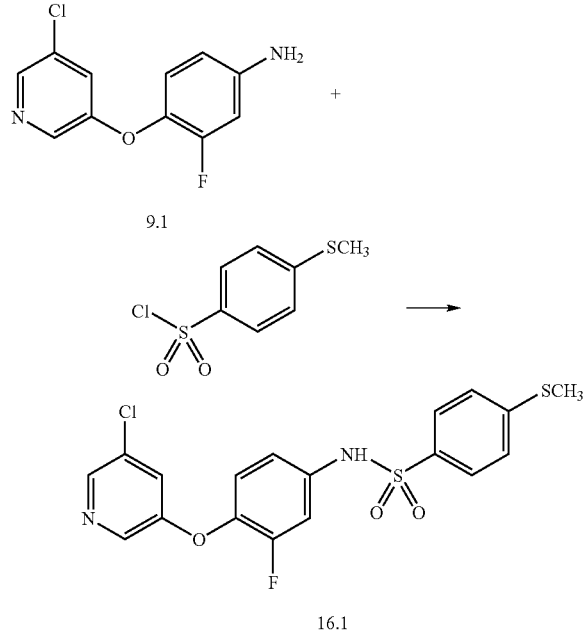

3-Chloro-4-(3-chloro-5-pyridyloxy)aniline (410 mg, 15.1) and 2,4-dichlorobenzenesulfonyl chloride (390 mg, Maybridge), were combined in a similar manner to that described in Example 3. The crude product was purified by flash chromatography on silica, eluting with 5% ethyl acetate/dichloromethane. The product fractions were concentrated and the residue was triturated in hexanes to provide the title compound as a white solid (538 mg, 73%), mp 128-130° C.

$^1$H NMR (400 MHz) (DMSO) δ 8.40 (d, J=1.8 Hz, 1H); 8.24 (d, J=2.4 Hz, 1H); 8.06 (d, J=8.5 Hz, 1H); 7.90 (d, J=2.0 Hz, 1H); 7.65 (dd, J=2, 8.5 Hz, 1H); 7.48 (t, J=2.2 Hz, 1H); 7.28 (d, J=2.5 Hz, 1H); 7.21 (d, J=8.84 Hz, 1H); 7.10 (dd, J=2.5, 7.1, 1H). MS m/e 465 (M+1).

Compound 16.1 was oxidized with 3-chloroperoxybenzoic acid to produce the corresponding pyridine N-oxide, 16.2, as a white solid after trituration in diethyl ether, mp 205-207° C.

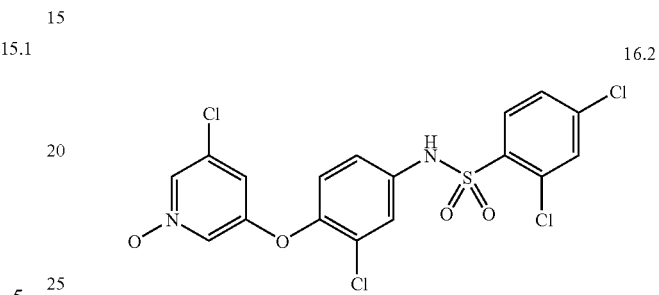

16.2

Example 17

This example illustrates the preparation of 17.1.

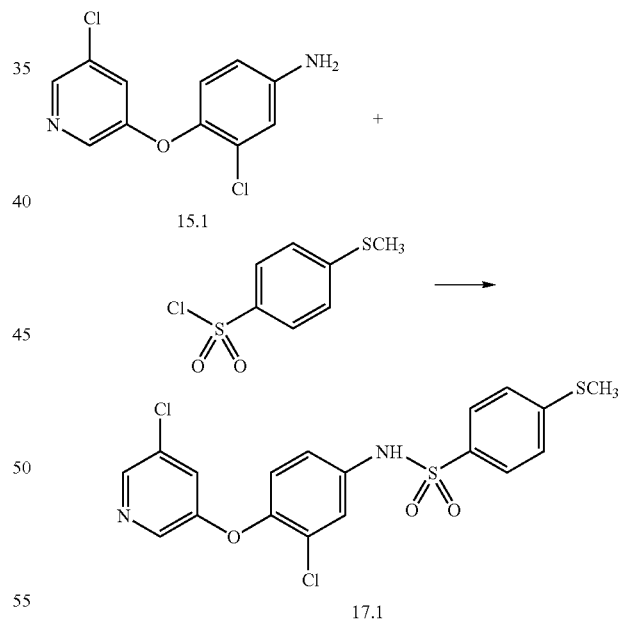

3-Chloro-4-(3-chloro-5-pyridyloxy)aniline (309 mg, 15.1) and 4-methylthiobenzenesulfonyl chloride (223 mg, prepared as described in Burton, et al., .1. *Chem. Soc.*, 604-5 (1948)), were combined in a manner similar to that described in Example 3. The crude product was purified by flash chromatography on silica, eluting with ethyl acetate/hexanes/dichloromethane (1:5:4). The product fractions were concentrated and the residue obtained was triturated in hexanes to provide the title compound as a white solid (200 mg, 37%), mp 96-98° C.

Oxidation of 17.1 to sulfoxide 17.2

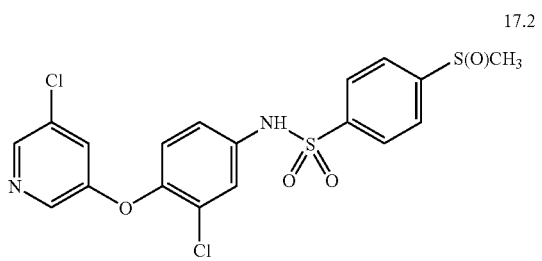

Compound 17.1 was oxidized to the corresponding sulfoxide using Oxidation to sulfoxide potassium peroxymonosulfate in methanol and acetone. The reaction was monitored by TLC. After the reaction was complete, the mixture was filtered and the filtrate was washed with water, dried over MgSO$_4$, filtered and concentrated. The residue was purified by chromatography on silica, eluting with 50% to 100% ethyl acetate/dichloromethane. Solvent was removed from the product fractions, and the residue was triturated in hexanes. The white solid product was collected by filtration to provide 121 mg of 17.2 (63%), mp 127-128° C.

Example 18

This example illustrates the preparation of 18.1.

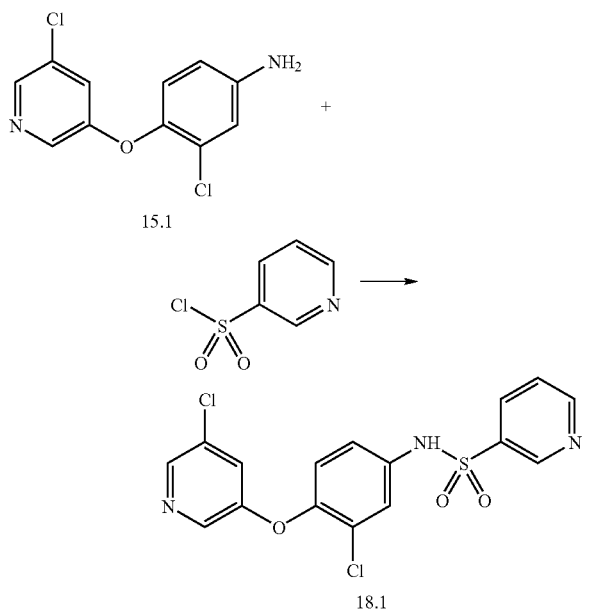

The title compound was prepared in a manner similar to Example 3, beginning with 3-pyridylsulfonyl chloride (335 mg, see Example 6) and 3-chloro-4-(3-chloro-5-pyridyloxy)aniline (411 mg, 15.1) with the addition of a catalytic amount of 4-dimethylaminopyridine. When the reaction was completed by TLC, the mixture was filtered to remove amine salts. The filtrate was concentrated and the residue was purified by flash chromatography on silica, eluting with 5% methanol/dichloromethane. The product fractions were combined, concentrated, and the residue was triturated dichloromethane to provide the title compound as a white solid (149 mg, 22%), mp 164-165° C.

In a similar manner, 18.2 (mp 174-175° C.) was prepared from aniline 15.1 and 5-trifluoromethyl-2-pyridinesulfonyl chloride.

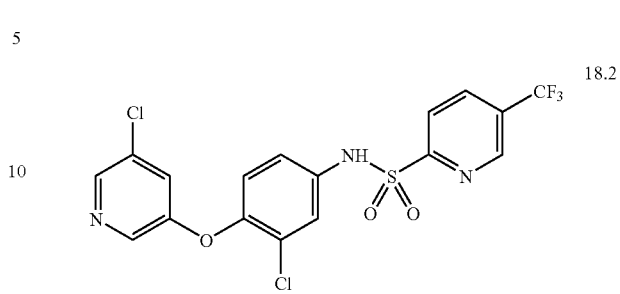

The compounds provided in Table 2 were prepared using commercially available intermediates and/or using the intermediates and methods described in the examples above.

TABLE 2

|      | Ra | Rb | Rc    | Rd | mp (° C.) or m/e |
|------|----|----|-------|----|------------------|
| 18.3 | H  | H  | CF$_3$ | H | 172-174° C. |
| 18.4 | Cl | H  | CF$_3$ | H | 111-113° C. |
| 18.5 | H  | H  | COCH$_3$ | H | 434.7 |
| 18.6 | H  | Cl | Cl    | H  | 460.9 |

Example 19

This example illustrates the preparation of 3-bromo-4-(3-chloro-5-pyridyloxy)nitrobenzene (19.1).

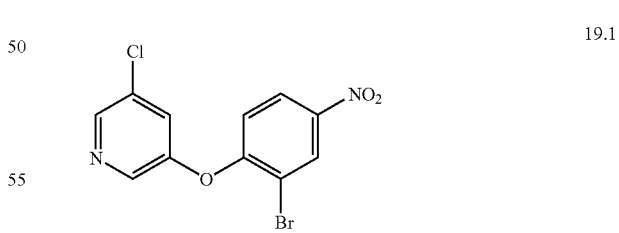

3-Bromo-4-fluoronitrobenzene (available from Reidel) and 5-chloro-3-pyridinol were combined using the procedure described in Example 1, to produce the title compound.

$^1$H NMR (400 MHz, DMSO-d$_6$) δ 8.61 (d, J=2.6 Hz, 1H), 8.57 (d, J=2.2 Hz, 1H), 8.49 (d, J=2.5 Hz, 1H), 8.24 (dd, J=9.3, 2.6 Hz, 1H), 7.94 (dd, J=2.4, 2.2 Hz, 1H), 7.3 (d, J=9.0 Hz, 2H). MS (EI): m/z 333 (25, M+H), 332 (15, M+H), 331 (100, M+H), 330 (10, M+H), 329 (76, M+H).

Example 20

This example illustrates the preparation of 3-bromo-4-(3-chloro-5-pyridyloxy)aniline (20.1).

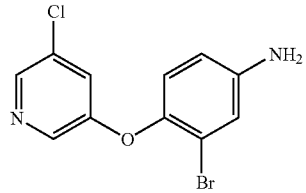

20.1

Using the method of Example 2, 3-bromo-4-(3-chloro-5-pyridyloxy)nitrobenzene (19.1) was converted to the title compound which was used directly in subsequent reactions.

$^1$H NMR (400 MHz, DMSO-$d_6$) δ 8.32 (d, J=2.1 Hz, 1H), 8.19 (d, J=2.5 Hz, 1H), 7.28 (dd, J=2.4, 2 Hz, 1H), 7.2 (d, J=8.7 Hz, 1H), 6.9 (d, J=2.6 Hz, 1H), 6.62 (dd, J=8.7, 2.6 Hz, 1H). MS (El): m/e 304 (5, M+H), 303 (35, M+H), 302 (20, M+H), 301 (100, M+H), 300 (15, M+H), 299 (90, M+H).

The compounds provided in Table 3 were prepared using 20.1 and commercially available intermediates and/or using the intermediates and methods described in the examples above.

TABLE 3

| | Ra | Rb | Rc | Rd | mp (°C.) |
|---|---|---|---|---|---|
| 20.2 | Cl | H | Cl | H | 114-115 |
| 20.3 | H | H | SCH$_3$ | H | 160-162 |
| 20.4 | H | H | S(O)CH$_3$ | H | 169-171 |

Similarly, 20.5 was prepared from aniline 20.1 and 5-trifluoromethyl-2-pyridinesulfonyl chloride, mp 202-204° C.

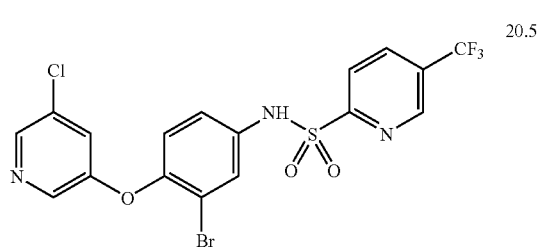

20.5

Example 21

This example illustrates the preparation of 5-(4-nitro-2-methoxyphenoxy)-3-chloropyridine (21.1).

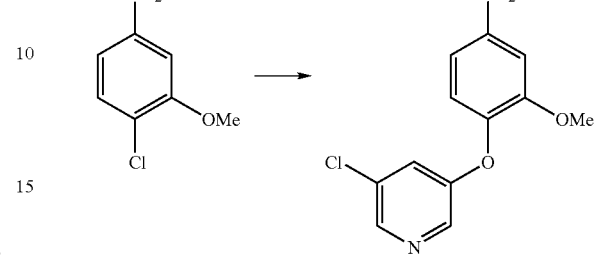

21.1

A round-bottomed flask was charged with 2-chloro-5-nitroanisole (1.03 g, 5.49 mmol, Avocado Chemical Co.), 5-chloro-3-pyridinol (750 mg, 5.76 mmol, Aldrich Chemical Co.), cesium carbonate (1.97 g, 6.04 mmol, Aldrich Chemical Co.), and anhydrous DMF (16 mL). The mixture was heated at 100° C. for 18 hours. The temperature was then increased to 130° C. for an additional two hours, after which the reaction was allowed to cool to room temperature. The reaction mixture was poured into 800 mL of distilled water, and extracted three times with 300 mL ethyl acetate. The combined extracts were dried over MgSO$_4$ and filtered. Solvent was removed from the filtrate under vacuum and the crude product was purified by flash chromatography on silica gel (5% hexanes in CH$_2$Cl$_2$ as eluant) to provide the title compound (1.42 g, 93%) as a yellow solid.

MS ESI m/e: 281.1 (M+H).

Example 22

This example illustrates the synthesis of 5-(4-amino-2-methoxyphenoxy)-3-chloropyridine (22.1).

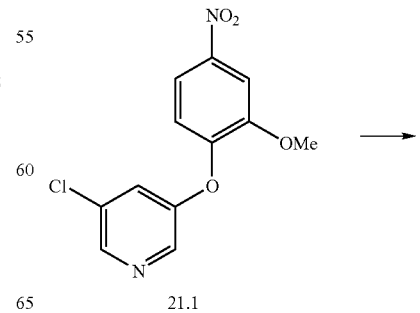

21.1

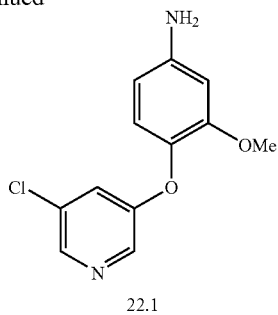

Using the method of Example 2, the nitro compound prepared in Example 21 (1.54 g, 6.56 mmol) was converted to 1.38 g (99%) of the title compound as an off-white solid. The product was used without further purification (upon standing several days in air the compound developed a very dark brown color).

MS ESI m/e: 251.1 (M+H).

Example 23

This example illustrates the synthesis of 5-(4-(2,4-dichlorobenzenesulfonamido)-2-methoxyphenoxy)-3-chloropyridine (23.1).

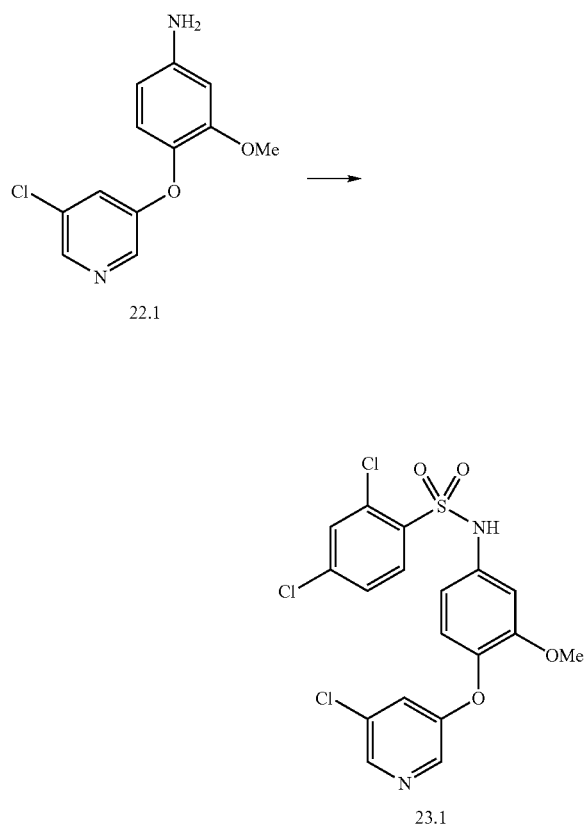

A round-bottomed flask was charged with aniline 22.1 (96 mg, 0.39 mmol), 2,4-dichlorobenzenesulfonyl chloride (104 mg, 0.42 mmol, Maybridge Chemical Co.), pyridine (28 mg, 0.39 mmol, Aldrich Chemical Co.), and a catalytic amount of DMAP (Aldrich Chemical Co.). Three mL of dichloromethane was added and the reaction mixture was stirred at room temperature for eight hours. The resulting mixture was then diluted with 15 mL of dichloromethane and washed successively with 10 mL of 1N HCl and brine. The combined organic portions were dried over $MgSO_4$ then passed through a plug of silica gel to remove baseline impurities. Solvent was removed from the filtrate and the resulting solid was triturated in hexanes to provide the title compound (69 mg, 40%) as a white powder.

$^1$HNMR (400 MHz) ($d_6$-DMSO) δ 10.81 (1H, s); 8.29 (1H, d, J=2.1 Hz); 8.11 (1H, d, J=2.4 Hz); 8.07 (1H, d, J=8.5 Hz); 7.88 (1H, d, J=2.0 Hz); 7.63 (1H, dd, J=8.7 Hz, 2.1 Hz); 7.20 (1H, dd, J=4.4 Hz, 2.1 Hz); 7.07 (1H, d, J=8.7 Hz); 6.91 (1H, d, J=2.4 Hz); 6.68 (1H, dd, J=8.7 Hz, 2.5 Hz); 3.65 (3H, s). MS ESI m/e: 459.0 (M+H).

Example 24

This example illustrates the synthesis of 5-(4-methylsulfonylbenzenesulfonamido-2-methoxyphenoxy)-3-chloropyridine (24.1).

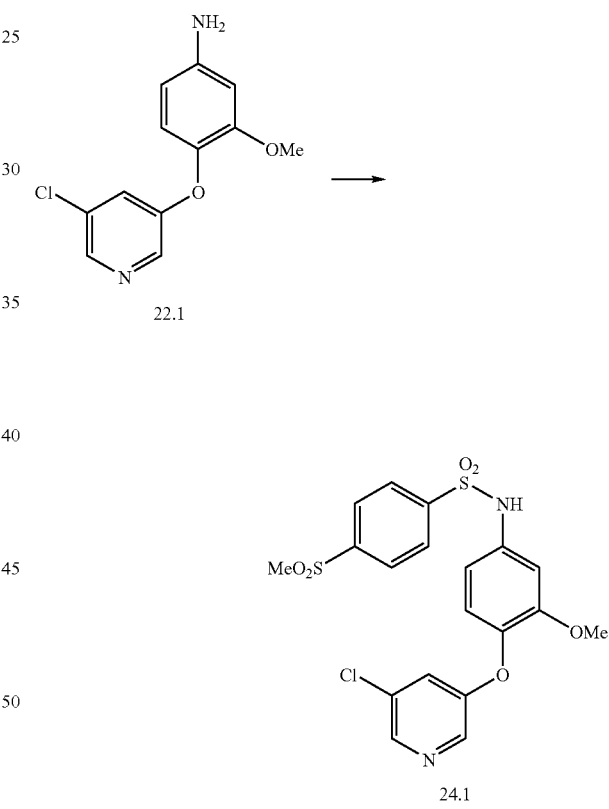

The title compound was prepared using the general procedure described in Example 22, starting with 150 mg (0.61 mmol) of the aniline, 155 mg (0.61 mmol, Aldrich Chemical Co.) of 4-methylsulfonebenzenesulfonyl chloride, 48 mg (0.61 mmol) of pyridine, catalytic DMAP, and 5 mL of methylene chloride. Following workup, the title compound was obtained (67 mg, 24%) as a white solid.

$^1$H NMR (400 MHz) ($d_6$-DMSO) δ 10.63 (1H, s); 8.30 (1H, d, J=2.0 Hz); 8.14 (2H, m); 8.04 (1H, dd, J=8.6 Hz, 1.9 Hz); 7.27 (1H, dd, J=4.5 Hz, 2.2 Hz); 7.08 (1H, d, J=8.6 Hz); 6.93 (1H, d, J=2.4 Hz); 6.70 (1H, dd, J=8.6 Hz, 2.4 Hz); 3.67 (3H s); 3.28 (3H, s). MS ESI m/e: 467.0 (M−H).

Example 25

This example illustrates the synthesis of 5-(4-acetylbenzenesulfonamido-2-methoxyphenoxy)-3-chloropyridine (25.1).

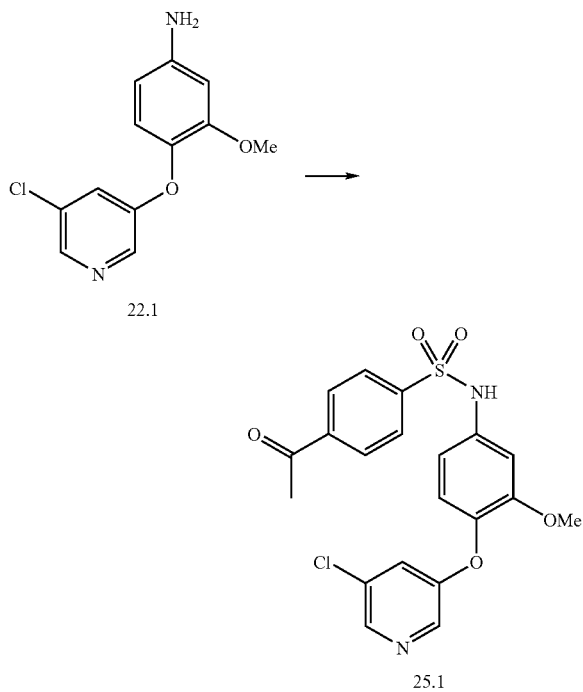

The title compound was prepared using the procedure described in Example 7, starting with 82 mg (0.33 mmol) of aniline 22.1, 72 mg (0.33 mmol) of 4-acetylbenzenesulfonyl chloride, 26 mg (0.33 mmol) of pyridine, catalytic DMAP, and 2 mL of methylene chloride. The title compound was produced (92 mg, 65%) as a white solid.

$^1$H NMR (400 MHz) ($d_6$-DMSO) δ 10.52 (1H, s); 8.29 (1H, d, J=1.9 Hz); 8.10 (3H, m); 7.92 (2H, dd, J=8.0 Hz, 2.3 Hz); 7.23 (1H, dd, J=4.5 Hz, 2.4 Hz); 7.06 (1H, d, J=8.6 Hz); 6.93 (1H, dd, J=8.6 Hz, 2.4 Hz); 6.70 (1H, dd, J=8.6 Hz, 2.4 Hz); 3.65 (3H, s); 2.60 (3H, s). MS ESI m/e: 431.1 (M−H).

In a similar manner, 25.2 and 25.3 were prepared from aniline 22.1 and the appropriate sulfonyl chloride.

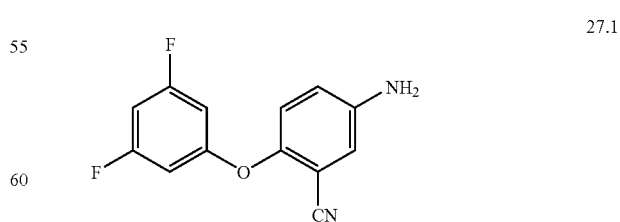

25.2 Z = N
25.3 Z = CH

Example 26

This example illustrates the preparation of 5-nitro-2-(3,5-difluorophenoxy)-benzonitrile (26.1).

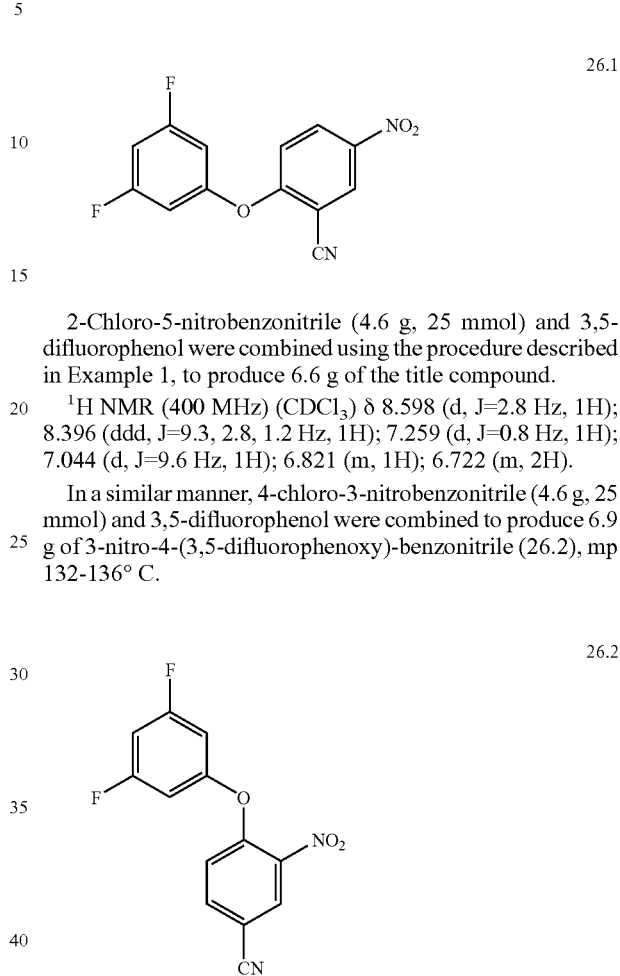

2-Chloro-5-nitrobenzonitrile (4.6 g, 25 mmol) and 3,5-difluorophenol were combined using the procedure described in Example 1, to produce 6.6 g of the title compound.

$^1$H NMR (400 MHz) (CDCl$_3$) δ 8.598 (d, J=2.8 Hz, 1H); 8.396 (ddd, J=9.3, 2.8, 1.2 Hz, 1H); 7.259 (d, J=0.8 Hz, 1H); 7.044 (d, J=9.6 Hz, 1H); 6.821 (m, 1H); 6.722 (m, 2H).

In a similar manner, 4-chloro-3-nitrobenzonitrile (4.6 g, 25 mmol) and 3,5-difluorophenol were combined to produce 6.9 g of 3-nitro-4-(3,5-difluorophenoxy)-benzonitrile (26.2), mp 132-136° C.

$^1$H NMR (400 MHz) (DMSO-d$_6$) δ 8.72 (d, J=2.0 Hz, 1H); 8.165 (dd, J=8.8, 1.9 Hz, 1H); 7.422 (d, J=8.8 Hz, 1H); 7.227 (m, 1H); 7.103 (m, 2H).

Example 27

This example illustrates the preparation of 5-amino-2-(3,5-difluorophenoxy)benzonitrile (27.1).

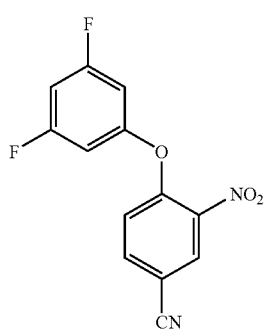

Using the method of Example 2, 5-nitro-2-(3,5-difluorophenoxy)-benzonitrile (26.1, 6.6 g) was converted to the title compound (5.47 g, mp 80-84° C.) which was used directly in subsequent reactions.

$^1$H NMR (400 MHz) (TFA/DMSO-d$_6$) δ 11.2 (br s, 2H); 7.083 (d, J=9.2 Hz, 1H); 7.077 (d, J=2.8 Hz, 1H); 7.033 (dd, J=9.2, 2.4 Hz, 1H); 6.998 (tt, J=9.2, 2.4 Hz, 1H); 6.727 (dd, J=8.4, 2.0 Hz, 2H).

Similarly, 3-amino-4-(3,5-difluorophenoxy)benzonitrile (27.2) was prepared from 26.2.

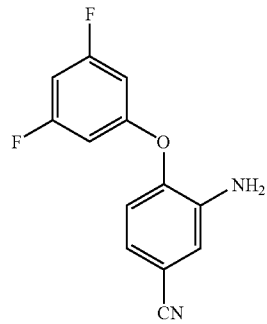

27.2

$^1$H NMR (400 MHz) (DMSO-d$_6$) δ 7.14 (d, J=2.0 Hz, 1H); 7.03-6.96 (m, 3H); 6.70 (dd, J=8.6, 2.3 Hz, 2H); 5.60 (s, 2H).

The compounds provided in Table 4 were prepared using 27.1 and commercially available substituted benzenesulfonyl chlorides and/or using the intermediates and methods described in the examples above.

TABLE 4

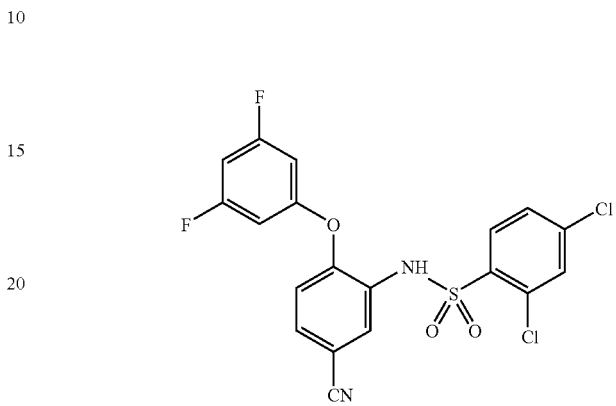

| | Ra | Rb | Rc | Rd | mp (°C.) or m/e |
|---|---|---|---|---|---|
| 27.3 | Cl | H | Cl | H | 452.7 |
| 27.4 | H | H | OCH$_3$ | H | 414.8 |
| 27.5 | H | H | I | H | 510.6 |
| 27.6 | H | H | C(O)CH$_3$ | H | 482.7 |
| 27.7 | H | H | CF$_3$ | H | 141-144° C. |

Example 28

This example illustrates the preparation of 28.1.

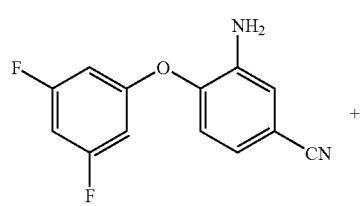

28.1

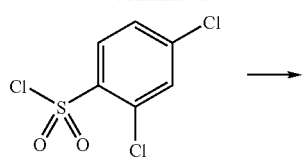

3-Amino-4-(3,5-difluorophenoxy)benzonitrile (201 mg, 27.2) and 2,4-dichlorobenzenesulfonyl chloride (302 mg, Maybridge), were combined in a similar manner to that described in Example 3, then heated to 40° C. The crude product obtained after workup was purified by flash chromatography on silica, eluting with dichloromethane. The product fractions were concentrated and the residue was triturated with diethyl ether to provide the title compound as a white solid (150 mg, 37%), mp 197-200° C.

Example 29

This example illustrates the preparation of 5-nitro-2-(3,5-dichlorophenoxy)-benzonitrile (29.1).

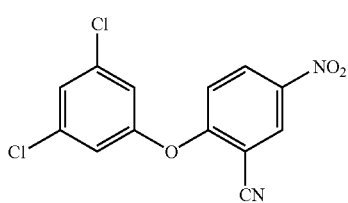

29.1

2-Chloro-5-nitrobenzonitrile (0.9 g, 5 mmol) and 3,5-dichlorophenol were combined using the procedure described in Example 1, to produce 1.5 g of the title compound, mp 188-190° C.

$^1$H NMR (400 MHz) (CDCl$_3$) δ 8.597 (d, J=2.4 Hz, 1H); 8.397 (ddd, J=9.2, 2.8, 0.8 Hz, 1H); 7.360 (dd, J=3.2, 2.0 Hz, 1H); 7.089 (dd, J=1.6, 0.8 Hz, 2H) 7.008 (d, J=9.6 Hz, 1H).

Example 30

This example illustrates the preparation of 5-amino-2-(3,5-dichlorophenoxy)benzonitrile (30.1).

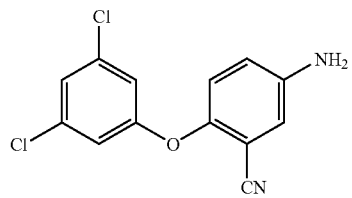

30.1

To a solution of 5-nitro-2-(3,5-dichlorophenoxy)benzonitrile (29.1, 1.5 g) in ethyl acetate (45 mL) was added stannous chloride dihydrate (5.47 g). The mixture was heated to 85° C. for 30 minutes during which time a thick white precipitate formed. The reaction vessel was cooled and the mixture was treated with 100 mL of 0.5 N NaGH. The resulting mixture was extracted twice with ethyl acetate. The combined organic extracts were dried over $MgSO_4$ and concentrated under vacuum to afford the title compound which was used without further purification. MS m/e 279 (M+H).

The compounds provided in Table 5 were prepared using 30.1 and commercially available substituted benzenesulfonyl chlorides and/or using the intermediates and methods described in the examples above.

TABLE 5

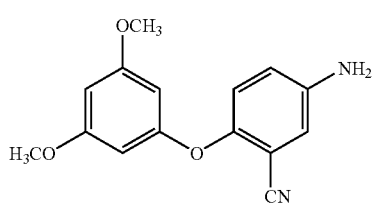

| | Ra | Rb | Rc | Rd | mp (°C.) |
|---|---|---|---|---|---|
| 30.2 | Cl | H | Cl | H | 143-144 |
| 30.3 | H | H | $CF_3$ | H | 148-149 |

Example 31

This example illustrates the preparation of 5-nitro-2-(3,5-dimethoxyphenoxy)benzonitrile (31.1).

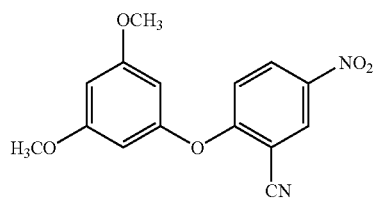

31.1

2-Chloro-5-nitrobenzonitrile (5.3 g) and 3,5-dimethoxyphenol (4.5 g, Aldrich) were combined using the procedure described in Example 1, to produce the title compound as a brown solid.

$^1$H NMR (400 MHz) (DMSO) δ 8.84 (d, J=2.8, 1H); 8.44 (dd, J=9.3, 2.8 Hz, 1H); 7.07 (d, J=9.3 Hz, 1H); 6.51 (s, 3H); 3.76 (s, 6H).

Example 32

This example illustrates the preparation of 5-amino-2-(3,5-dimethoxyphenoxy)benzonitrile (32.1).

32.1

To a solution of 5-nitro-2-(3,5-dichlorophenoxy)benzonitrile (31.1, 8.76 g) in ethyl acetate was added tin chloride (33 g). The mixture was heated to reflux for one hour. The resulting mixture was cooled and 0.5 N sodium hydroxide solution was added to induce the precipitation of tin salts which were removed by filtration. The filtrate was concentrated to provide 7.5 g of the title compound as an orange solid which was used in subsequent reactions without purification.

$^1$H NMR (400 MHz) (DMSO-$d_6$) δ 6.95-6.87 (m, 3H); 6.25 (t, J=2.2 Hz, 1H); 6.04 (d, J=2.2 Hz, 2H); 5.49 (s, 2H); 3.70 (s, 6H).

The compounds provided in Table 6 were prepared using 32.1 and commercially available substituted benzenesulfonyl chlorides and/or using the intermediates and methods described in the examples above.

TABLE 6

| | Ra | Rb | Rc | Rd | mp (°C.) or m/e |
|---|---|---|---|---|---|
| 32.2 | Cl | H | Cl | H | 477 |
| 32.3 | Cl | H | $CF_3$ | H | 101-105° C. |
| 32.4 | H | H | I | H | 439 |
| 32.5 | H | H | $OCH_3$ | H | 162-164° C. |

Example 33

This example illustrates the preparation of 3-methoxy-4-(3,5-difluorophenoxy)-nitrobenzene (33.1).

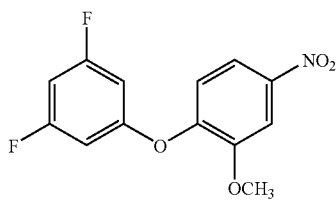

33.1

4-Chloro-3-methoxynitrobenzene (2.64 g) and 3,5-difluorophenol (Aldrich) were combined using the procedure described in Example 1 and heated to 125° C., to produce the title compound as a thick brown oil which solidified on trituration with hexane/methanol to yield 1.33 g of 33.1 as a red solid.

$^1$H NMR (400 MHz) (DMSO-$d_6$) δ 7.963 (d, J=2.6 Hz, 1H); 7.903 (dd, J=8.8, 2.7 Hz, 1H); 7.3 16 (d, J=8.8 Hz, 1H); 7.035 (m, 1H); 6.796 (m, 2H); 3.909 (s, 3H).

In a similar manner, 3-methoxy-4-(3,5-dichlorophenoxy)nitrobenzene (33.2) and 3-methoxy-4-(3,5-dimethoxyphenoxy)nitrobenzene (33.3) were prepared beginning with 3,5-dichlorophenol and 3,5-dimethoxyphenol, respectively.

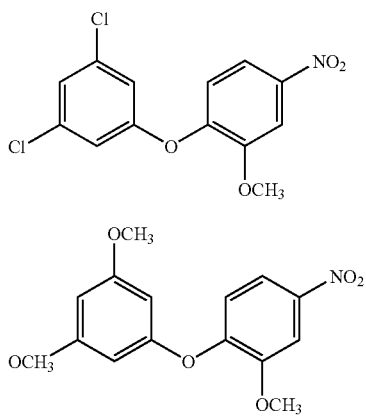

33.2
3-methoxy-4-(3,5-dichlorophenoxy)nitrobenzene $^1$H NMR (400 MHz) (DMSO-$d_6$) δ 7.960 (d, J=2.6 Hz, 1H); 7.900 (dd, J=8.9, 2.7 Hz, 1H); 7.394 (t, J=1.7 Hz, 1H); 7.3 10 (d, J=8.8 Hz, 1H); 7.107 (t, J=1.4 Hz, 2H); 3.907 (s, 3H).

33.3
3-methoxy-4-(3,5-dimethoxyphenoxy)nitrobenzene $^1$NMR (400 MHz) (DMSO-$d_6$) δ 7.910 (d, J=2.6 Hz, 1H); 7.862 (dd, J=8.8, 2.6 Hz, 1H); 7.064 (d, J=8.8 Hz, 1H); 6.353 (t, J=2.2 Hz, 1H); 6.207 (d, J=2.2 Hz, 2H); 3.927(s, 3H); 3.716 (s, 6H).

Each of the nitrobenzene derivatives (33.1, 33.2 and 33.3) were reduced to the corresponding aniline derivative using the Raney nickel procedure of Example 2. The aniline derivatives were then converted to the compounds shown in Table 7 using commercially available substituted benzenesulfonyl chlorides and/or using the intermediates and methods described in the examples above.

TABLE 7

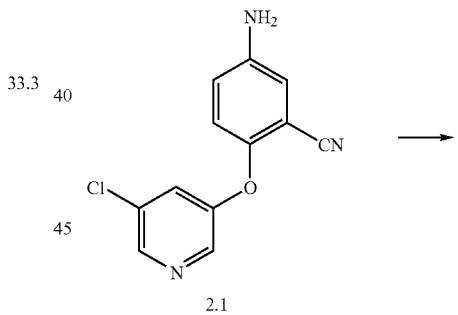

| | Ar | Ra | Rb | Rc | Rd | mp (°C.) |
|---|---|---|---|---|---|---|
| 33.4 | 3,5-dichlorophenyl | Cl | H | Cl | H | 128-131 |
| 33.5 | 3,5-difluorophenyl | H | H | CF$_3$ | H | 141-143 |
| 33.6 | 3,5-dichlorophenyl | H | H | CF$_3$ | H | 165-166 |
| 33.7 | 3,5-difluorophenyl | Cl | H | Cl | H | 120-124 |
| 33.8 | 3,5-difluorophenyl | H | H | OCH$_3$ | H | 129-133 |
| 33.9 | 3,5-dimethoxyphenyl | Cl | H | Cl | H | 100-103 |
| 33.10 | 3,5-dimethoxyphenyl | Cl | H | CF$_3$ | H | 72-79 |
| 33.11 | 3,5-dimethoxyphenyl | H | H | OCH$_3$ | H | 92-95 |

Example 34

This example illustrates the synthesis of 5-(4-chlorosulfonyl-2-cyanophenoxy)-3-chloropyridine (34.1).

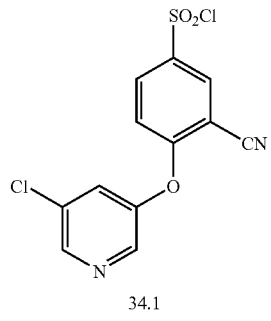

Aniline 2.1 (3.11 g, 12.69 mmol) was converted to the corresponding sulfonyl chloride according to the procedure of R. V. Hoffman (*Org. Syn. Coll.* Vol., VII, 508-511), yielding 770 mg (18%) of 34.1 as a white solid.

MS ESI m/e: 331.0 (M+H)

Example 35

This example illustrates the synthesis of compound 35.1.

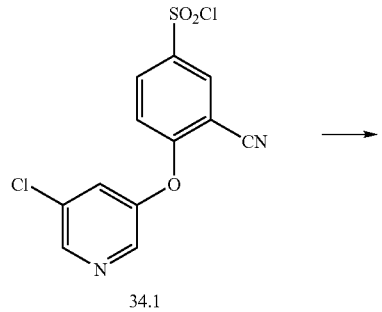
34.1

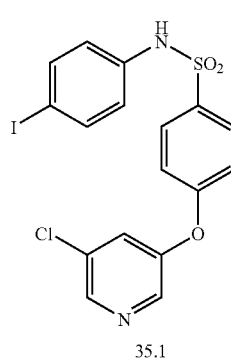
35.1

The title compound was prepared using the method described in Example 3, starting with 4-iodoaniline (136 mg, 0.6197 mmol, Aldrich Chemical Co.), 5-(4-chlorosulfonyl-2-cyanophenoxy)-3-chloropyridine (136 mg, 0.4131 mmol, 34.1), pyridine (49 mg, 0.6197 mmol), catalytic DMAP, and 3 mL of methylene chloride. The product was obtained as a white solid (187 mg, 89%).

$^1$H NMR (400 MHz) (d$_6$-DMSO) δ 10.57 (1H, s); 8.62 (1H, d, J=1.8 Hz); 8.60 (1H, d, J=2.2 Hz); 8.28 (1H, d, J=2.4 Hz); 8.12 (1H, d, J=2.2 Hz); 7.93 (1H, dd, J$_1$=8.9 Hz J$_2$=2.3 Hz); 7.61 (2H, dd, J$_1$=8.8 Hz J$_2$=2.0 Hz); 7.17 (1H, d, J=9.0); 6.93 (2H, dd, J$_1$=8.8 Hz J$_2$=2.0 Hz). MS ESI m/e: 509.9 (M−H).

Example 36

This example illustrates the synthesis of compound 36.1.

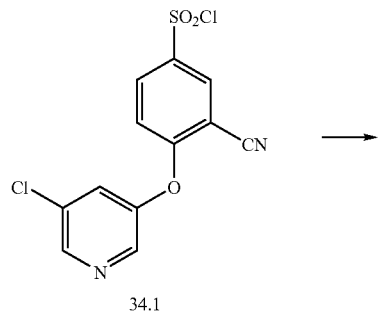
34.1

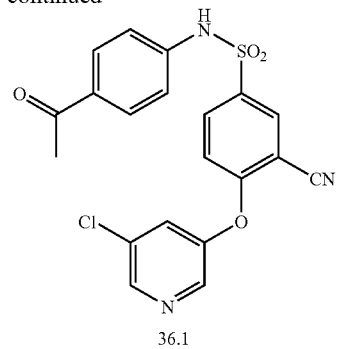
36.1

The title compound was prepared using the method described in Example 35, starting with 4-acetylaniline (100 mg, 0.31 mmol, Aldrich Chemical Co.), 5-(4-chlorosulfonyl-2-cyanophenoxy)-3-chloropyridine (62 mg, 0.46 mmol), pyridine (36 mg, 0.46 mmol), catalytic DMAP, and 3 mL of methylene chloride. The title compound 36.1 was obtained as a white solid (120 mg, 92%).

$^1$H NMR (400 MHz) (d$_6$-DMSO) δ 10.53 (1H, s); 8,58 (1H, d, J=1.9 Hz); 8.53 (1H, d, J=2.4 Hz); 8.15 (1H, d, J=2.5 Hz); 7.99 (1H, dd, J$_1$=4.4 Hz J$_2$=2.2 Hz); 7.86 (1H, dd, J$_1$=8.8 Hz J$_2$=2.5 Hz); 7.59 (2H, dd, J$_1$=8.8 Hz J$_2$=2.0 Hz); 7.13 (1H, d, J=8.7 Hz); 6.93 (2H, dd, J$_1$=8.8 Hz J$_2$=2.0 Hz); 2.61 (1H, s). MS ESI m/e: 425.9 (M−H).

Example 37

This example illustrates the synthesis of 5-(4-chlorosulfonyl-2-chlorophenoxy)-3-chloropyridine (37.1).

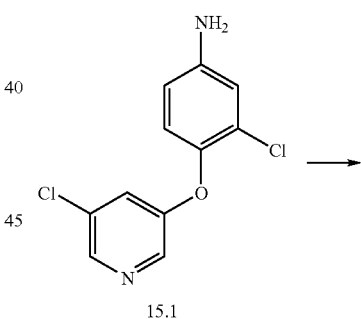
15.1

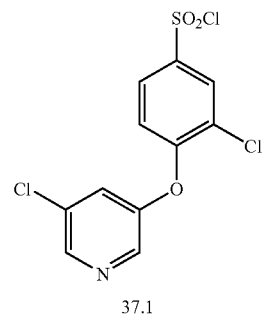
37.1

Aniline 15.1 (2.10 g, 8.24 mmol) was converted to the corresponding sulfonyl chloride 37.1, according to the procedure of R. V. Hoffman (Org. Syn. Coll. Vol., VII, 508-511). The title compound was obtained as a slightly yellow solid (1.65 g, 59%) MS ESI m/e: 338.0 (M+H).

Example 38

This example illustrates the synthesis of compound 38.1.

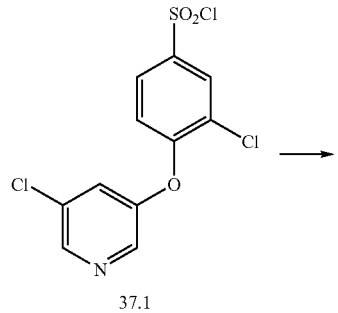

37.1

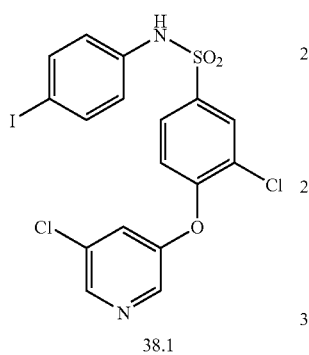

38.1

The title compound was prepared using the method described in Example 35, starting with 4-iodoaniline (101 mg, 0.46 mmol), S-(4-chlorosulfonyl-2-chlorophenoxyy3 chloropyridine (104 mg, 0.31 mmol), pyridine (35 mg, 0.46 mmol), catalytic DMAP, and 3 mL of methylene chloride. Compound 38.1 was obtained as a white solid (150 mg, 94%).

$^1$H NMR (400 MHz) ($d_6$-DMSO) δ 10.50 (1H, s); 8.55 (1H, d, J=2.1 Hz); 8.45 (1H, d, J=2.5 Hz); 7.93 (1H, d, J=2.2 Hz); 7.89(1H, dd, $J_1$=4.4 Hz $J_2$=2.2 Hz); 7.67 (1H, dd, $J_1$=8.7 Hz $J_2$=2.2 Hz); 7.61 (2H, dd, $J_1$=8.8 Hz $J_2$=2.0 Hz); 7.22 (1H, d, J=8.7 Hz); 6.94 (2H, dd, $J_1$=8.8 Hz $J_2$=2.0 Hz). MS ESI m/e: 518.9 (M−H).

Example 39

This example illustrates the synthesis of compound 39.1.

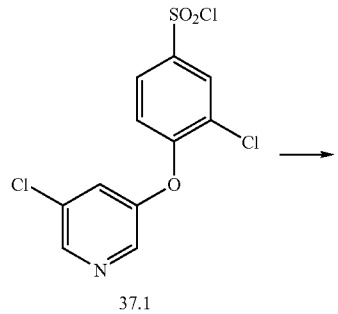

37.1

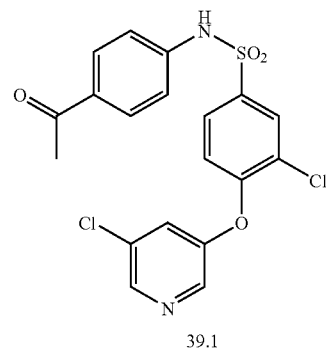

39.1

The title compound was prepared using the method of Example 38, starting with 4-acetylaniline (55 mg, 0.41 mmol), 5-(4-chlorosulfonyl-2-chlorophenoxy)-3-chloropyridine (92 mg, 0.27 mmol), pyridine (33 mg, 0.41 mmol), catalytic DMAP, and 3 mL of methylene chloride. After workup, 39.1 was obtained as a white solid (130 mg, 93%).

$^1$H NMR (400 MHz) ($d_6$-DMSO) δ 10.94 (1H, s); 8.54 (1H, d, J=2.0 Hz); 8.44 (1H, d, J=2.2 Hz); 8.01 (1H, d, J=2.1 Hz); 7.90 (1H, dd, $J_1$=4.4 Hz $J_2$=2.2 Hz); 7.86 (2H, dd, $J_1$=8.8 Hz $J_2$=1.6 Hz); 7.75 (1H, dd, $J_1$=8.7 Hz $J_2$=2.2 Hz); 7.23 (3H, m). MS ESI m/e: 435.0 (M−H).

Example 40

This example illustrates the preparation of 5-(4-amino-2,5-dibromophenoxy)3-chloropyridine (40.1), 5-(4-amino-2,3-dibromophenoxy)-3-chloropyridine (40.2), and 5-(4-amino-2,3,5-tribromophenoxy)-3-chloropyridine (40.3).

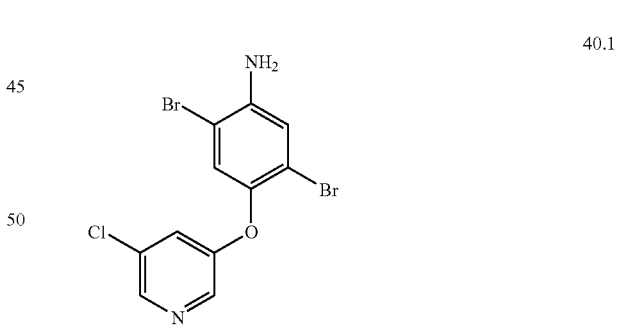

40.1

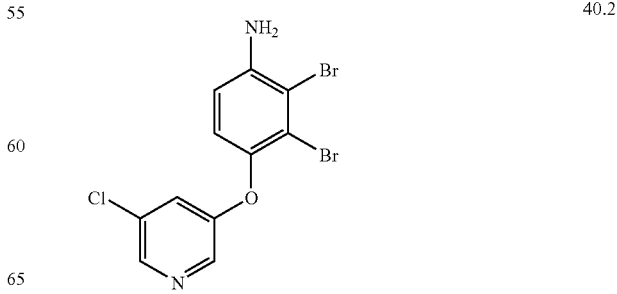

40.2

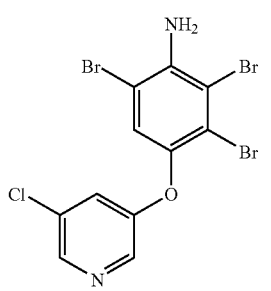

To a 0.1 M solution of 3-bromo-4-(3-chloro-5-pyridyloxy) aniline (20.1) in acetic acid was added bromine (Aldrich). The resulting solution was stirred for two days. Most of the acetic acid was removed azeotropically using hexanes and the residue was adjusted to pH 6 using 4 M aqueous NaGH. The aqueous layer was extracted with ethyl acetate and the combined organic portions were washed with brine (2×), dried over sodium sulfate, filtered and concentrated under reduced pressure. The products were separated by chromatography to provide 5-(4-amino-2,5-dibromophenoxy)-3-chloropyridine (40.1, 32%), 5-(4-amino-2,3-dibromophenoxy)-3-chloropyridine (40.2, 15%), and 5-(4-amino-2,3,5-tribromophenoxy)-3-chloropyridine (40.3, 13%).

40.1: $^1$H NMR (400 MHz, DMSO-$d_6$) δ 8.35 (d, J=1.5 Hz, 1H), 8.22 (d, J=2.5 Hz, 1H), 7.46 (d, J=1.0 Hz, 1H), 7.39 (dd, J=2.8, 2.6 Hz, 1H), 7.14 (s, 1H), 5.6 (s, 2H). MS (EI): m/z 383 (18, M+H), 382 (10, M+H), 381 (75, M+H), 380 (15, M+H), 379 (100, M+H), 378 (7, M+H), 377 (50, M+H).

40.2: $^1$H NMR (400 MHz, DMSO-$d_6$) δ 8.34 (d, J=2 Hz, 1H), 8.21 (d, J=2.6 Hz, 1H), 7.36 (dd, J=2.4, 2.2 Hz, 1H), 7.32 (dd, J=8.8 Hz, 1H), 6.49 (d, J=8.8 Hz, 1H), 5.7 (s, 2H). MS (EI): m/z 383 (18, M+H), 382 (10, M+H), 381 (75, M+H), 380 (15, M+H), 379 (100, M+H), 378 (7, M+H), 377 (50, M+H).

40.3: $^1$H NMR (400 MHz, DMSO-$d_6$) δ 8.36 (d, J=2.2 Hz, 1H), 8.26 (d, J=2.4 Hz, 1H), 7.63 (s, 1H), 7.48 (dd, J=2.4, 1.9 Hz, 1H), 5.65 (s, 2H). MS (EI): m/z 463 (10, M+H), 462 (5, M+H), 461 (50, M+H), 460 (12, M+H), 459 (100, M+H), 458 (12, M+H), 457 (85, M+H), 456 (5, M+H), 455 (25, M+H).

Example 41

This example illustrates the preparation of 5-(4-(2,4-dichlorobenzene-sulfonamido)-2,5-dibromophenoxy)-3-chloropyridine (41.1).

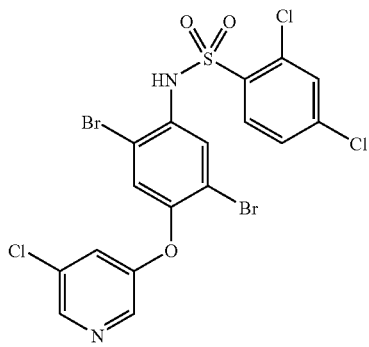

5-(4-(2,4-dichlorobenzenesulfonamido)-2,5-dibrOi-nOphenOxy)-3-chloropyridine was prepared in 39% yield from 40.1 and 2,4-dichlorobenzenesulfonyl chloride using the method of Example 3.

$^1$H NMR (400 MHz, DMSO-$d_6$) δ 10.6 (s, 1H), 8.47 (bs, 1H), 8.33 (bs, 1H), 7.9 (s, 1H), 7.88 (d, J=8.8 Hz, 1H), 7.68 (bs, 1H), 7.61 (d, J=8.8 Hz, 1H), 7.57 (s, 1H 7.52 (s, 1H). MS (EI): m/z 593 (6, M+H), 592 (4, M+H), 591 (27, M+H), 590 (10, M+H) 589 (50, M+H), 588 (10, M+H), 587 (45, M+H), 586 (3, M+H), 585 (17, M+H).

Example 42

This example illustrates the preparation of 5-(4-amino-2-cyano-3-bromophenoxy))-3-chloropyridine (42.1).

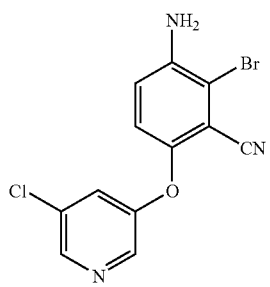

3-Cyano-4-(3-chloro-5-pyridyloxy)aniline (see Example 2) was combined with bromine in acetic acid in a manner similar to that described in Example 40 to produce 5-(4-amino-2-cyano-3-bromophenoxy)-3-chloropyridine (37%) after chromatography.

$^1$H NMR (400 MHz, DMSO-$d_6$) δ 8.44 (d, J=1.8 Hz, 1H), 8.37 (d, J=2.2 Hz, 1H), 7.7 (dd, J=2.2, 1.8 Hz, 1H), 7.13 (½ABq, J=9.1 Hz, 1H), 7.11 (½ABq, J=9.1 Hz, 1H), 5.83 (s, 2H). MS (EI): m/z 328 (30, M+H), 327 (13, M+H), 326 (100, M+H), 325 (10, M+H), 324 (75, M+H).

Example 43

This example illustrates the synthesis of 5-(4-(2,4-dichlorobenzene-sulfonamido)-2-cyano-3-bromophenoxy)-3-chloropyridine (43.1).

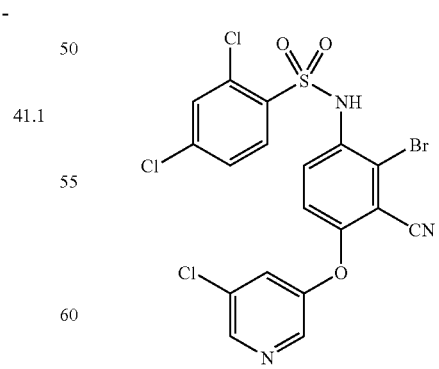

5-(4-(2,4-dichlorobenzenesulfonamido)-2-cyano-3-bromophenoxy)-3-chloropyridine was prepared in 28% yield from 42.1 and 2,4-dichlorobenzenesulfonyl chloride using the method of Example 3.

¹H NMR (400 MHz, DMSO-d₆) δ 10.7 (s, 1H), 8.59 (d, J=1.6 Hz, 1H), 8.53 (d, J=2 Hz, 1H), 8.05 (bs, 1H), 7.9 (s, 1H), 7.84 (d, J=8.4 Hz, 1H), 7.6 (dd, J=8.4, 1.6 Hz, 1H), 7.41 (d, J=8.8 Hz, 1H), 7.01 (d, J=9.2 Hz, 1H). MS (EI): m/z 537 (20, M+H), 535 (73, M+H), 533 (100, M+H), 531 (52, M+H).

Example 44

This example illustrates the preparation of 5-(4-amino-5-bromo-2-methoxyphenoxy))-3-chloropyridine (44.1).

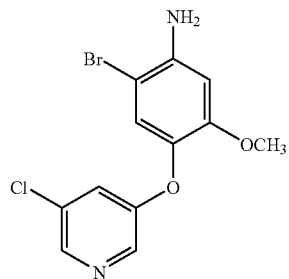

44.1

To a 0.2M solution of 5-(4-amino-2-methoxyphenoxy)-3-chloropyridine (200 mg, 0.8 mmol, 22.1) in CH₂Cl₂ at 0° C. was added 2,4,4,6-tetrabromo-2,5-cyclohexadieneone (334 mg, 0.82 mmol, Lancaster). The resulting solution was stirred for 21 hours at ambient temperature. The reaction mixture was diluted with CH₂Cl₂ (50 mL), washed twice with a 2M solution of aqueous sodium hydroxide (50 mL), once with brine (50 mL), dried over Na₂SO₄, and concentrated under vacuum. The crude solid was purified by column chromatography (0-2% MeOH in CH₂Cl₂) to furnish 133 mg (50%) of the title compound as a brown solid.

¹NMR (400 MHz, DMSO-d₆) δ 8.27 (d, J=2.2 Hz, 1H), 8.17 (d, J=2.6 Hz, 1H), 7.26 (dd, J=2.3, 1.9 Hz, 1H), 7.24 (s, 1H), 6.64 (s, 1H), 5.38 (s, 2H), 3.65 (s, 3H). MS (EI): m/z 329 (80, M+H), 330 (12, M+H), 331 (100, M+H), 332 (16, M+H), 333 (28, M+H), 334 (4, M+H).

Example 45

This example illustrates the preparation of 5-(4-(2,4-dichlorobenzene-sulfonamido)-5-bromo-2-methoxyphenoxy)-3-chloropyridine (45.1).

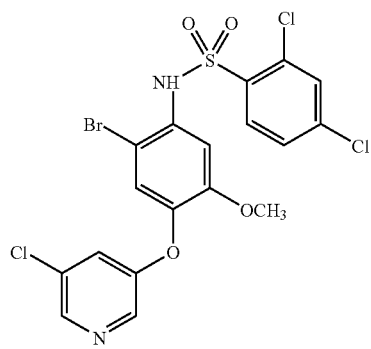

45.1

5-(4-(2,4-dichlorobenzenessulfonamido)-5-bromo-2-methoxyphenoxy)-3-chloropyridine was prepared in 25% yield from 44.1 and 2,4-dichlorobenzenesulfonyl chloride using the method of Example 3.

¹H NMR (400 MHz, DMSO-d₆) δ 10.4 (s, 1H), 8.36 (d, J=1.8 Hz, 1H), 8.2 (d, J=2.5 Hz, 1H), 7.9 (d, J=8.6 Hz, 1H), 7.9-7.65 (m, 1H), 7.68 (bs, 1H), 7.59 (dd, J=8.6, 2.2 Hz, 1H), 7.45 (s, 1H), 7.42 (dd, J=2.4, 1.9 Hz, 1H), 6.99 (s, 1H), 3.65 (s, 3H). MS (EI): m/z 537 (58, M+H), 538 (10, M+H), 539 (100, M+H), 540 (20, M+H), 541 (70, M+H), 542 (15, M+H), 543 (25, M+H).

Example 46

This example illustrates the preparation of 5-(4-amino-5-bromo-2-chlorophenoxy))-3-chloropyridine (46.1).

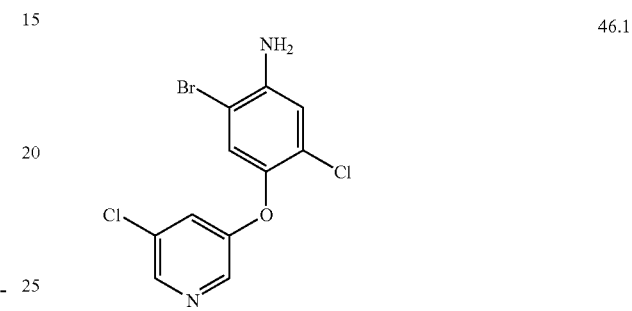

46.1

5-(4-Amino-5-bromo-2-chlorophenoxy)-3-chloropyridine was synthesized (43%) in a similar manner as described by Example 44 using 3-chloro-4-(3-chloro-5-pyridyloxy) aniline (15.1).

¹NMR (400 MHz, DMSO-d₆) δ 8.35 (d, J=1.9 Hz, 1H), 8.23 (d, J=2.5 Hz, 1H), 7.48 (s, 1H), 7.41 (dd, J=2.4, 2.2 Hz, 1H), 6.98 (s, 1H), 5.62 (s, 2H). MS (EI): m/z 333 (55, M+H), 334 (12, M+H), 335 (90, M+H), 336 (12, M+H), 337 (40, M+H), 338 (5, M+H).

Example 47

This example illustrates the preparation of 5-(4-(2,4-dichlorobenzene-sulfonamido)-5-bromo-2-chlorophenoxy)-3-chloropyridine (47.1).

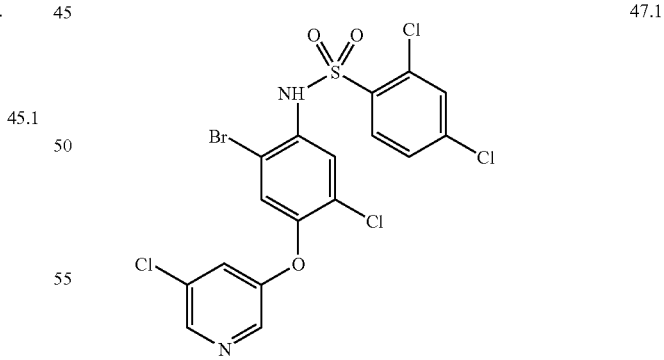

47.1

5-(4-(2,4-dichlorobenzenesulfonamido)-5-bromo-2-chlorophenoxy)-3-chloropyridine was prepared in 17% yield from 46.1 and 2,4-dichlorobenzenesulfonyl chloride using the method of Example 3.

¹H NMR (400 MHz, DMSO-d₆) δ 10.6 (s, 1H), 8.47 (d, J=2.2 Hz, 1H), 8.34 (d, J=2.6 Hz, 1H), 7.89 (d, J=2.1 Hz, 1H), 7.88 (d, J=8.6 Hz, 1H), 7.7 (dd, J=2.3, 2.2 Hz, 1H), 7.6 (dd, J=8.5, 2.0 Hz, 1H), 7.55 (s, 1H), 7.47 (s, 1H). MS (EI): m/z 539 (40, M–H), 540 (10, M–H), 541 (100, M–H), 542 (20, M–H), 543 (80, M–H), 544 (25, M–H), 545 (35, M–H), 546 (5, M–H).

Example 48

This example illustrates the preparation of 5-(3-chloro-4-amino-2-(N-ethylcarboxamidophenoxy))-3-chloropyridine (48.1) and 5-(5-chloro-4-amino-2-(N-ethylcarboxamidophenoxy))-3-chloropyridine (48.2).

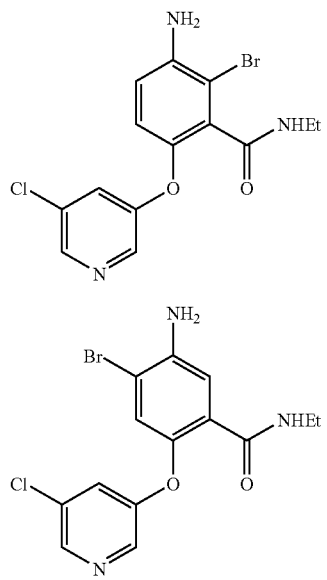

To a 0.1M solution of 5-(4-amino-2-(N-ethylcarboxamidophenoxy))-3-chloropyridine, (1 g, 3.6 mmol, prepared as described in Ser. No. 09/234,327) in AcOH was added bromine (194 µL, 3.8 mmol) and the resulting solution was stirred for 2 days. Most of the AcOH was azeotropically removed using hexanes and the resulting solution was adjusted to ph 6 using a 4M aqueous solution of NaOH. The aqueous layer was extracted three times with EtOAc (50 mL) and the combined organic layers were washed twice with an aqueous brine solution (100 mL), dried over $Na_2SO_4$, and concentrated under vacuum. The crude solid was purified by chromatography (50-100% EtOAc in hexanes) to separate the products 48.1 and 48.2 from the starting materials and dibrominated materials. The desired products were then rechromatographed (1-3% MeOH in $CH_2Cl_2$) to furnish 478 mg (36%) of 48.1 and 198 mg (15%) of 48.2 as white solids.

48.1: $^1$H NMR (400 MHz, DM50-d$_6$) δ 8.37 (t, J=5.2 Hz, 1H), 8.3 (bs, 1H), 8.24 (d, J=2.2 Hz, 1H), 7.38 (m, 1H), 6.94 (d, J=8.8 Hz, 1H), 6.84 (d, J=8.8 Hz, 1H), 3.1 (pentet, J=7.0 Hz, 2H), 0.91 (t, J=7.1 Hz, 3H). MS (EI): m/z 370 (80, M+H), 371 (15, M+H), 372 (100, M+H), 373 (18, M+H), 374 (25, M+H).

48.2: $^1$H NMR (400 MHz, DMSO-d$_6$) δ 8.3 (d, J=1.75 Hz, 1H), 8.23 (t, J=5.4 Hz, 1H), 8.2 (d, J=2.0 Hz, 1H), 7.34-7.28 (m, 2H), 6.99 (d, J=1.6 Hz, 1H), 3.08 (pentet, J=7.2 Hz, 2H), 0.88 (t, J=7.3 Hz, 3H). MS (EI): m/z 370 (80, M+H), 371 (15, M+H), 372 (100, M+H), 373 (18, M+H), 374 (25, M+H).

Example 49

This example illustrates the preparation of 5-(5-bromo-4-(2,4-dichloro-5-methylbenzenesulfonamido)-2-(N-ethylcarboxamido)phenoxy)-3-chloropyridine (49.1).

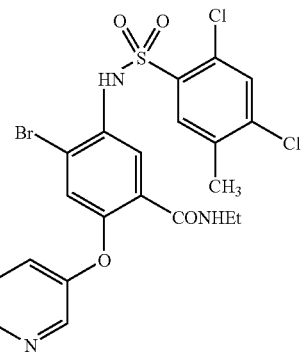

The title compound was prepared in 67% yield from 48.1 and 2,4-dichloro-5-methylbenzenesulfonyl chloride using the method of Example 3.

$^1$H NMR (400 MHz, DMSO-d$_6$) δ 10.41 (s, 1H), 8.48 (d, J=2.1 Hz, 1H), 8.35 (t, J=5.4 Hz, 1H), 8.31 (d, J=2.5 Hz, 1H), 7.85 (bs, 2H), 7.6 (dd, J=2.3, 2.2 Hz, 1H), 7.41 (s, 1H), 7.39 (s, 1H), 3.14 (pentet, J=7.2 Hz, 2H), 2.34 (s, 3H), 0.94 (t, J=7.2 Hz, 3H). MS (EI): m/z 597 (8, M–H), 596 (25, M–H), 595 (20, M–H), 594 (70, M–H), 593 (30, M–H), 592 (100, M–H), 591 (12, M–H), 590 (50, M–H).

Example 50

This example illustrates the preparation of 5-(5-bromo-4-(2,4-dichlorobenzenesulfonamido)-2-(N-ethylcarboxamido)phenoxy)-3-chloropyridine (50.1).

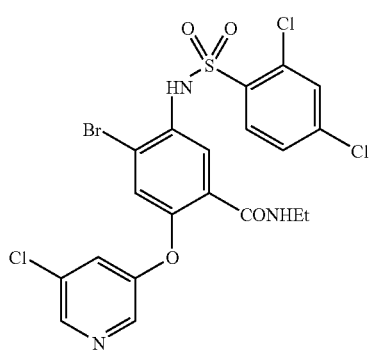

The title compound was prepared in 28% yield from 48.1 and 2,4-dichloro-benzenesulfonyl chloride using the method of Example 3.

$^1$H NMR (400 MHz, DMSO-d$_6$) δ 10.5 (s, 1H), 8.44 (d, J=2.1 Hz, 1H), 8.34 (t, J=5.6 Hz, 1H), 8.31 (d, J=2.3 Hz, 1H), 7.9 (d, J=2.0 Hz, 1H), 7.85 (d, J=8.6 Hz, 1H), 7.62 (dd, J=2.4, 2.1 Hz, 1H), 7.59 (dd, J=8.6, 2.2 Hz, 1H), 7.41 (s, 1H), 7.38 (s, 1H), 3.14 (pentet, J=7.0 Hz, 2H), 0.94 (t, J=7.3 Hz, 3H). MS (EI): m/z 585 (8, M+H), 584 (25, M+H), 583 (18, M+H), 582 (70, M+H), 581 (25, M+H), 580 (100, M–H), 579 (12, M+H), 578 (50, M+H).

Example 51

This example illustrates the preparation of 5-(3-bromo-4-(2,4-dichloro-5-methylbenzenesulfonamido)-2-(N-ethylcarboxamido)phenoxy)-3chloropyridine (51.1).

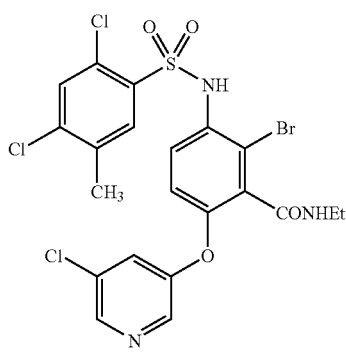

51.1

The title compound was prepared in 37% yield from 48.2 and 2,4-dichloro-5-methylbenzenesulfonyl chloride using the method of Example 3.

$^1$H NMR (400 MHz, DMSO-$d_6$) δ 10.39 (s, 1H), 8.55 (t, 1H), 8.42 (d, 1H), 8.31 (d, 1H), 7.89 (s, 1H), 7.88 (s, 1H), 7.6 (dd, 1H), 7.12 (d, 1H), 7.02 (d, 1H), 3.14 (pentet, 2H), 2.35 (s, 3H), 0.94 (t, 3H). MS (EI): m/z 599 (8, M+H), 598 (25, M+H), 597 (18, M+H), 596 (70, M+H), 595 (25, M+H), 594 (100, M−H), 593 (12, M+H), 592 (50, M+H).

Example 52

This example illustrates the synthesis of 5-(5-bromo-4-chlorosulfonyl-2-methoxyphenoxy)-3-chloropyridine (52.1).

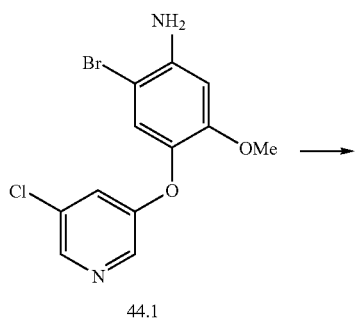

44.1

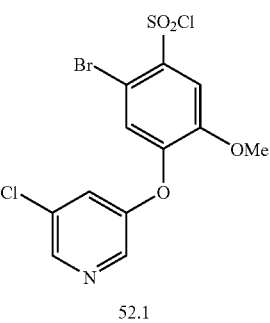

52.1

Compound 44.1 (1.20 g, 3.66 mmol) was converted to the title compound using the general procedure of R. V. Hoffman (Org. Syn. Coll. Vol., VII, 508-511), to provide 1.26 g (84%) of 52.1 as a clear oil which was carried on without purification.

MS ESI m/e: 412.0(M+H).

Example 53

This example illustrates the preparation of 53.1.

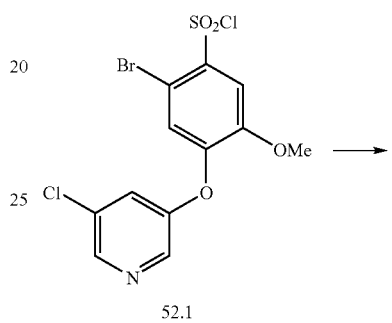

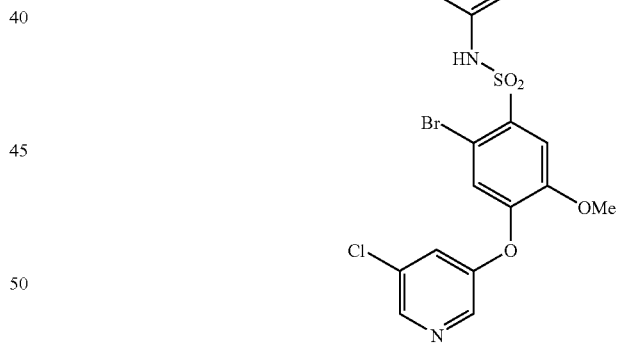

53.1

4-Chloroaniline (73 mg, 0.57 mmol, Aldrich Chemical Co.), 5-(5-bromo-4-chlorosulfonyl-2-methoxyphenoxy)-3-chloropyridine (236 mg, 0.57 mmol), pyridine (45 mg, 0.57 mmol), catalytic DMAP, and 2 mL of methylene chloride were combined using the general method of Example 35. The title compound was obtained (245 mg, 85%) as a white solid.

$^1$H NMR (400 MHz) ($d_6$-DMSO) δ 10.80 (1H, s); 8.43 (1H, d, J=2.0 Hz); 8.30 (1H, d, J=2.4 Hz); 7.74 (1H, s); 7.64 (1H, dd, J=4.4 Hz, 2.2 Hz); 7.52 (1H, s); 7.31 (2H, dd, J=8.8 Hz, 2.1 Hz); 7.14 (1H, dd, J=8.8 Hz, 2.1 Hz); 3.83 (3H, s). MS ESI m/e: 435.0 (M−H).

Example 54

This example illustrates the preparation of 54.1.

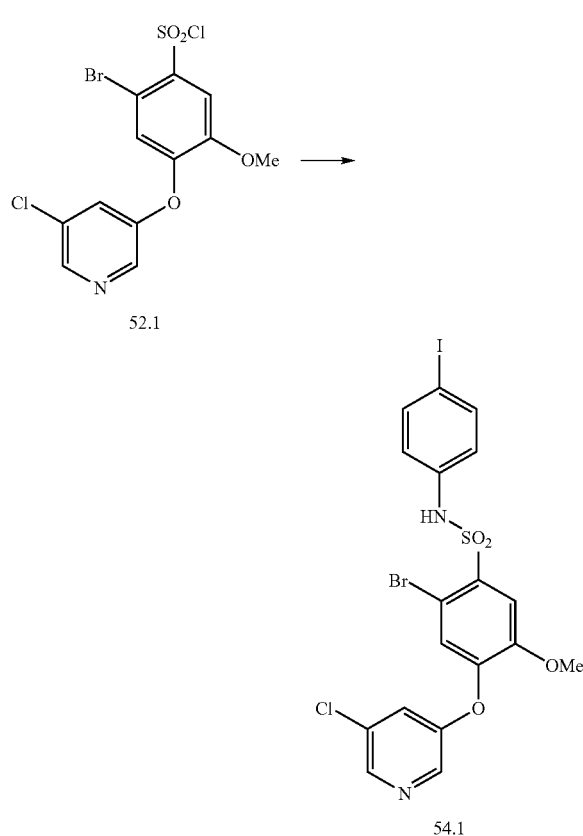

In a manner similar to that described in Example 53, 4-iodoaniline (83 mg, 0.38 mmol), 5-(5-bromo-4-chlorosulfonyl-2-methoxyphenoxy)-3-chloropyridine (155 mg, 0.38 mmol), pyridine (30 mg, 0.38 mmol), catalytic DMAP, and 2 mL of methylene chloride were combined and stirred. After workup, the title compound was obtained (162 mg, 73%) as a white solid.

$^1$H NMR (400 MHz) (d$_6$-DMSO) δ 10.80 (1H, s); 8.43 (1H, d, J=2.0 Hz); 8.31 (1H, d, J=2.4 Hz); 7.75 (1H, s); 7.64 (1H, dd, J=4.4 Hz, 2.2 Hz); 7.58 (2H, m); 7.51 (1H, s) 6.95 (1H, dd, J=8.6 Hz, 2.2 Hz); 3.84 (3H, s). MS ESI m/e: 592.8 (M−H).

Example 55

This example illustrates the preparation of 55.1.

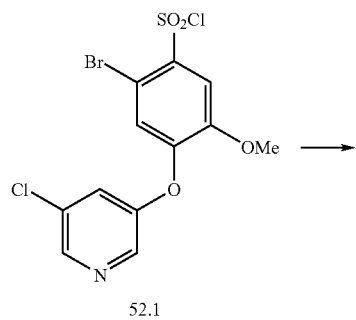

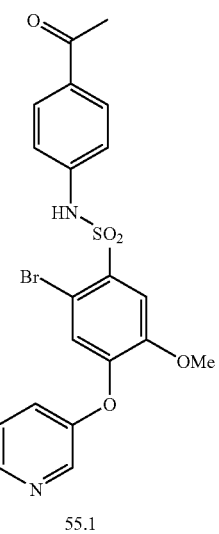

In a manner similar to that described in Example 53, 4-acetylaniline (69 mg, 0.51 mmol), 5-(5-bromo-4-chlorosulfonyl-2-methoxyphenoxy)-3-chloropyridine (210 mg, 0.51 mmol), pyridine (40 mg, 0.51 mmol), catalytic DMAP, and 2 mL of methylene chloride were combined and stirred. After workup, the title compound was obtained (192 mg, 74%) as a white solid.

$^1$NMR (400 MHz) (d$_6$-DMSO) δ 10.80 (1H, s); 8.43 (1H, d, J=2.0 Hz); 8.31 (1H, d, J=2.4 Hz); 7.75 (1H, s); 7.64 (1H, dd, J=4.4 Hz, 2.2 Hz); 7.58 (2H, m); 7.51 (1H, s) 6.95 (1H, dd, J=8.6 Hz, 2.2 Hz); 3.84 (3H, s). MS ESI m/e: 509.0 (M−H).

Example 56

This example illustrates the preparation of 3-chloro-4-(2-naphthylxoy)nitrobenzene (56.1).

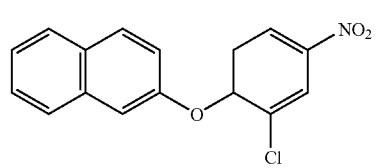

To a 250 mL flask, were added 3-chloro-4-fluoro-nitrobenzene (Aldrich) (5.0 g, 28 mmol), 2-naphtol (Aldrich) (4.Sg, 31 mmol), Cs$_2$CO$_3$ (Aldrich) (9.7 g, 30 mmol) and DME (80 mL). The mixture was heated at 100° C. overnight. After removal of DMF under vacuum, the mixture was poured into water and extracted with dichloromethane. The organic solution was then washed with brine, dried over magnesium sulfate. After filtration, the filtrate was concentrated under vacuum to give a crude product, which was then chromatographed with eluent (30% dichloromethane/hexanes) to give the title compound (6.8 g, 24 mmol, 86%).

Example 57

This example illustrates the preparation of compounds 57.1, 57.2, 57.3 and 57.4.

Compound 56.1 was reduced to the corresponding aniline derivative (57.1) using the procedure of Example 2, and converted to the compounds in Table 8 using commercially available substituted benzenesulfonyl chlorides and/or using the intermediates and methods described in the examples above.

TABLE 8

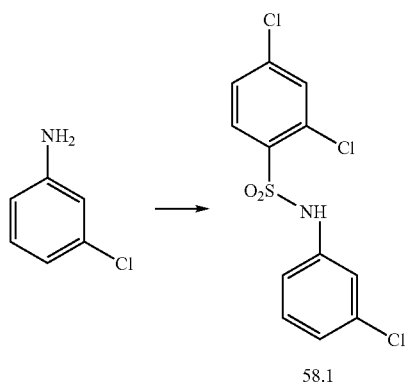

| | Ra | Rb | Rc | Rd | m/e |
|---|---|---|---|---|---|
| 57.2 | Cl | H | Cl | H | 476 |
| 57.3 | Cl | H | I | H | 534 |
| 57.4 | H | H | OCH$_3$ | H | 438 |

Example 58

This illustrates the synthesis of 3-chloro-(2,4-dichlorobenzene-sulfonamido)benzene (58.1).

The title compound was prepared using the method described in Example 3, starting with 800 mg (6.29 mmol) of 3-chloroaniline, 1.53 g (6.29 mmol) of 2,4-dichlorosulfonylchloride, 497 mg (6.29 mmol) of pyridine, catalytic DMAP, and 10 mL of methylene chloride. The title compound was obtained as a white foam (928 mg, 44%).

MS ESI m/e: 334.0 (M−H).

Example 59

This example illustrates the synthesis of compound 59.1.

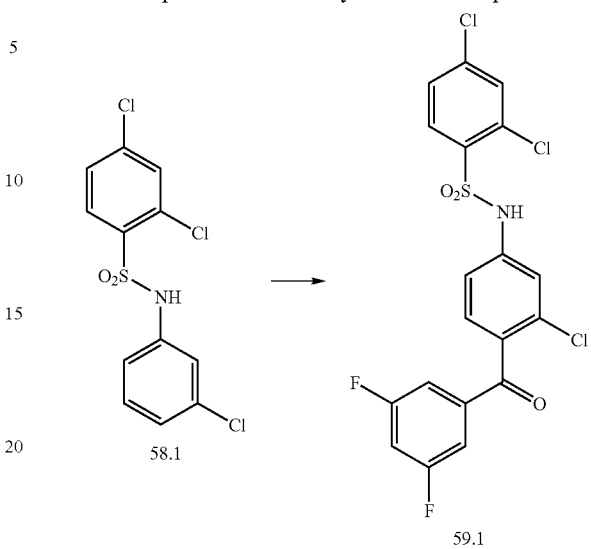

A round-bottomed flask was charged with 330 mg (0.99 mmol) of 3-chloro-(2,4-dichlorobenzenesulfonamido)benzene (58.1), 397 mg (2.97 mmol, Aldrich Chemical Co.) of anhydrous aluminum trichloride, and 2 mL of dry dichloroethane. Then 210 mg (1.19 mmol, Aldrich Chemical Co.) of 3,5-difluorobenzoyl chloride was added dropwise and the deep red solution was allowed to stir at room temperature overnight. The reaction was then diluted with 30 mL of methylene chloride, washed consecutively with 2N HCl and brine, dried over MgSO$_4$, and concentrated to a dark oil. This was further purified by silica gel flash chromatography (eluting with 1:24 ethyl acetate:methylene chloride). The resulting clear glaze was recrystallized from ether/hexanes to yield 273 mg (58%) of a white solid.

$^1$H NMR (400 MHz) (d$_6$-DMSO) δ 8.15 (1H, d, J=8.5 Hz); 7.91 (1H, d, J=2.1 Hz); 7.68 (1H, dd, J=8.6 Hz, 2.1 Hz); 7.63 (1H, t, J=8.6 Hz); 7.46 (1H, d, J=8.4 Hz); 7.31 (2H, dd, J=7.8 Hz, 2.1 Hz); 7.23 (1H, d, J=1.9 Hz); 7.17 (1H, dd, J=8.4 Hz, 2.2 Hz). MS ESI m/e: 473.9 (M−H).

Example 60

This illustrates the synthesis of compound 60.1.

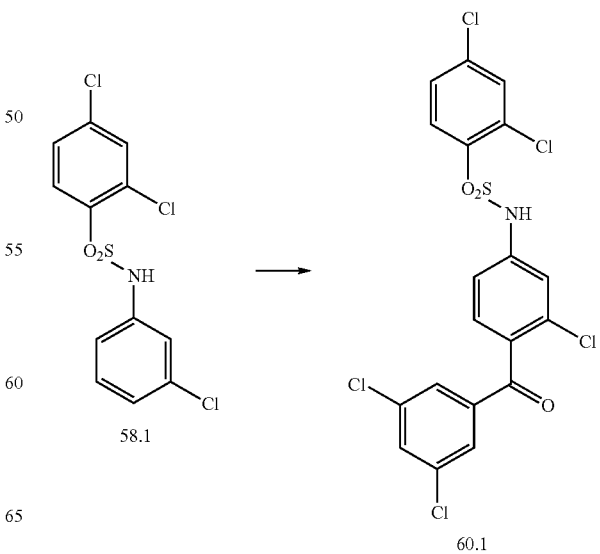

The title compound was prepared using the method of Example 59, starting with 286 mg (0.85 mmol) of 3-chloro-(2,4-dichlorobenzenesulfonamido)benzene (58.1), 341 mg (1.02 mmol) of anhydrous aluminum trichloride, 214 mg (1.02 mmol, Aldrich Chemical Co.) of 3,5-dichlorobenzoyl chloride, and 2 mL of dry dichloroethane. The title compound was obtained as a white solid (139 mg, 32%).

$^1$H NMR (400 MHz) (d$_6$-DMSO) δ 11.49 (1H, s) 8.15 (1H, d, J=8.6 Hz); 7.97 (1H, d, J=3.8 Hz); 7.91 (1H, d, J=2.1 Hz); 7.69 (1H, dd, J=8.5 Hz, 2.0 Hz); 7.58 (2H, d, J=1.9 Hz); 7.47 (1H, d, J=8.4 Hz); 7.24 (1H, d, J=2.0 Hz); 7.17 (1H, dd, J=8.4 Hz, 2.1 Hz). MS ESI m/e: 505.9 (M−H).

Example 61

This illustrates the synthesis of compound 61.1.

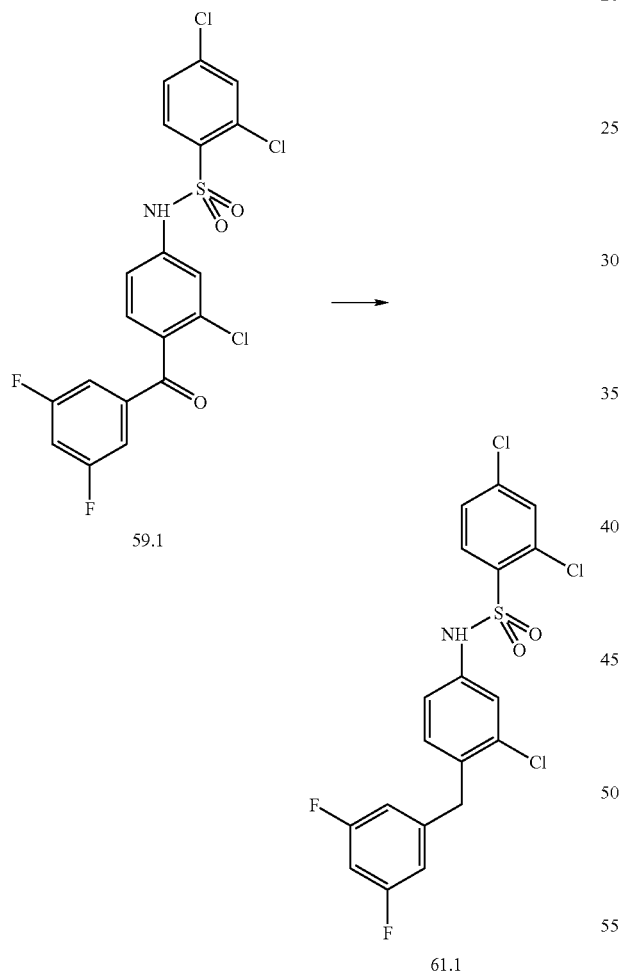

Biaryl ketone 59.1 (103 mg, 0.22 mmol) was reduced to the methylene compound 61.1 according to the procedure of West, et. al., *J. Org. Chem.*, 38(15):2675-2681 (1973). The title compound was obtained as a white solid (86 mg, 86%).

$^1$H NMR (400 MHz) (d$_6$-DMSO) δ 10.96 (1H, s) 8.05 (1H, d, J=8.6 Hz); 7.87 (1H, d, J=2.0 Hz); 7.63 (1H, dd, J=8.5 Hz, 2.1 Hz); 7.23 (1H, d, J=8.5 Hz); 7.14 (1H, d, J=2.2 Hz); 7.02 (2H, m); 7.17 (2H, m). MS ESI m/e: 460.0 (M−H).

Example 62

This example illustrates the preparation of 2-chloro-4-(3-chloro-5-pyridyloxy)-nitrobenzene 62.1.

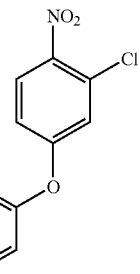

62.1

5-Chloro-3-pyridinol (5 g, Aldrich) and 2,4-dichloronitrobenzene (7.4 g, Aldrich) were combined as described in Example 1. The title compound was isolated as the minor product using gravity chromatography on silica eluting with 10% ethyl acetate/hexanes.

$^1$NMR (400 MHz) (DMSO-d$_6$) δ 8.53 (s, 1H); 8A (s, 1H); 8.0 (d, J=8.9 Hz, 1H); 7.44 (t, J=1.9 Hz, 1H); 7.26 (d, J=1.5 Hz, 1H); 7.14 (d, J=2.7 Hz, 1H); 6.99 (dd, J=9.0, 2.6 Hz, 1H) 1.6 (impurity).

Example 63

This example illustrates the preparation of 2-chloro-4-(3-chloro-5-pyridyloxy)-aniline 63.1.

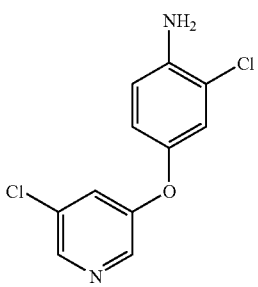

63.1

Compound 62.1 was reduced using the method of Example 2 to provide the title compound as a yellow solid.

$^1$H NMR (400 MHz) (DMSO) δ 8.33 (d, J=2.1 Hz, 1H); 8.25 (d, J=2.4 Hz, 1H); 7.41 (t, J=2.2 Hz, 1H); 7.12 (d, J=2.6 Hz, 1H); 6.91 (dd, J=2.6, 8.8 Hz, 1H); 6.84 (d, J=8.8 Hz, 1H); 5.35 (s, 2H).

Example 64

This example illustrates the preparation of 64.1.

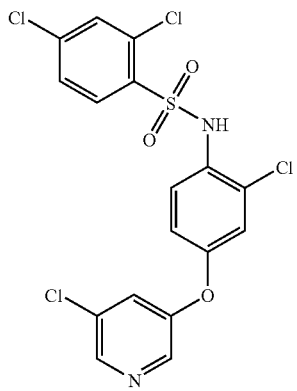

64.1

Compound 63.1 and 2,4-dichlorobenzenesulfonyl chloride were combined with pyridine and DMAP using the method described in Example 3. The crude product was purified by flash chromatography on silica eluting with dichloromethane. The resulting product was then triturated in diethyl ether/hexanes to furnish the title compound as a white solid. MS ESI m/e: 461 (M−H).

Example 65

This example illustrates the preparation of 65.1.

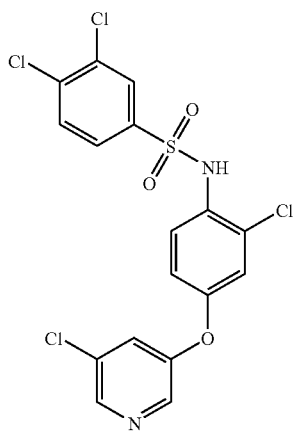

65.1

Compound 63.1 and 3,4-dichlorobenzenesulfonyl chloride were combined with pyridine and DMAP using the method described in Example 3. The crude product was purified by flash chromatography on silica eluting with 5% ethyl acetate/dichloromethane. The resulting product was then triturated in hexanes to furnish the title compound as a white solid. MS ESI m/e: 461 (M−H).

Example 66

This example illustrates the preparation of 66.1.

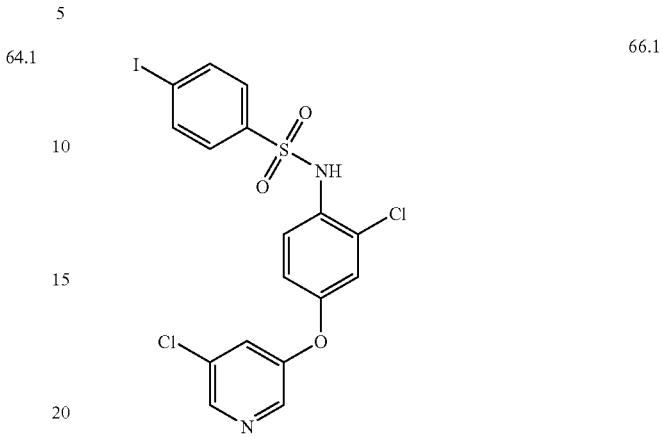

66.1

Compound 63.1 and 4-iodobenzenesulfonyl chloride were combined with pyridine and DMAP using the method described in Example 3. The crude product was purified by flash chromatography on silica eluting with dichloromethane. The resulting product was then triturated in hexanes to furnish the title compound as a white solid. MS ESI m/e: 519 (M−H).

Example 67

This example illustrates the preparation of 67.1.

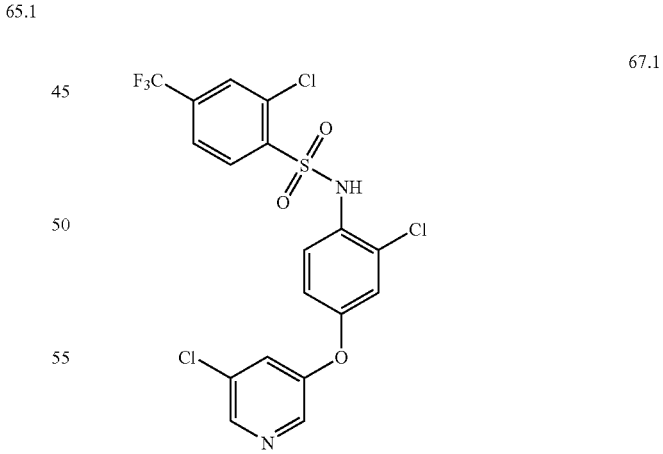

67.1

Compound 63.1 and 2-chloro-4-tri fluoromethylbenzenesulfonyl chloride were combined with pyridine and DMAP using the method described in Example 3. The crude product was purified by flash chromatography on silica eluting with 5% ethyl acetate/dichloromethane. The resulting product was then triturated in hexanes to furnish the title compound as a white solid. MS ESI m/e: 495 (M−H).

Example 68

This example illustrates the preparation of 2-chloro-4-(3-pyridyloxy)nitrobenzene (68.1).

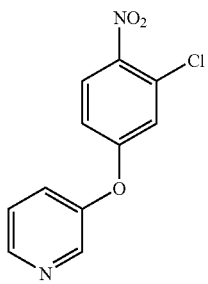

68.1

2,4-Dichloronitrobenzene (10.2 g, Aldrich) and 3-hydroxypyridine (5 g, Aldrich) were combined using the method of Example 1, to provide the 0.82 g of the title compound as a yellow solid.

$^1$H NMR (400 MHz) (CDCl$_3$) δ 8.58 (s, 1H); 8.52 (s, 1H); 8.0 (d, J=9.0 Hz, 1H); 7.44 (s, 2H); 7.10 (d, J=2.6 Hz, 1 H) 6.96 (dd, J=9.0, 6.65 Hz).

Example 69

This example illustrates the preparation of 2-chloro-4-(3-pyridyloxy)aniline.

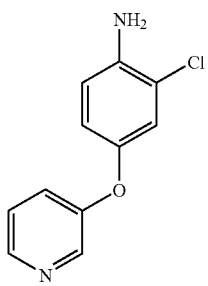

Compound 68.1 was reduced using the method of Example 2 to provide the title compound as a brown oil, which was used without further purification.

$^1$H NMR (400 MHz) (DMSO) δ 8.29-8.26 (m, 2H); 7.35 (dd, J=4.6, 8.4 Hz, 1H); 7.29-7.26 (m, 1H); 7.04 (d, J=2.0 Hz, 1H); 6.85-6.84 (m, 2H); 5.29 (s, 2H).

Example 70

This example illustrates the preparation of 70.1.

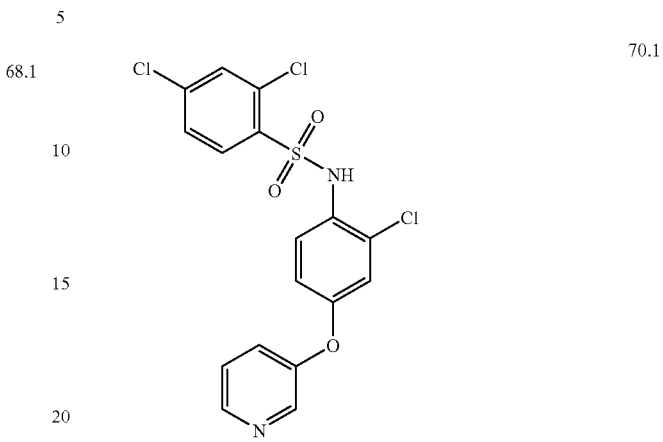

70.1

Compound 69.1 and 2,4-dichlorobenzenesulfonyl chloride were combined with pyridine and DMAP using the method described in Example 3. The crude product was purified by flash chromatography on silica eluting with 5% ethyl acetate/dichloromethane. The resulting product was then triturated in diethyl ether to furnish the title compound as a white solid. MS ESI m/e: 429 (M−H).

Example 71

This example illustrates the preparation of 71.1.

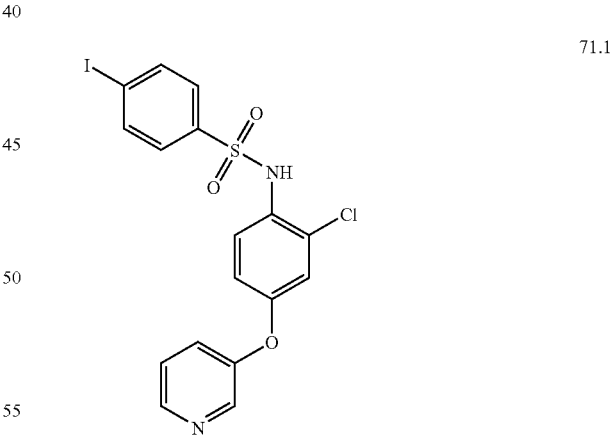

71.1

Compound 69.1 and 4-iodobenzenesulfonyl chloride were combined with pyridine and DMAP using the method described in Example 3. The crude product was purified using flash chromatography on silica eluting with 5-20% ethyl acetate/dichloromethane. The resulting product was then triturated in diethyl ether to furnish the title compound as a white solid. MS ESI m/e: 485 (M−H).

Example 72

This example illustrates the preparation of 72.1.

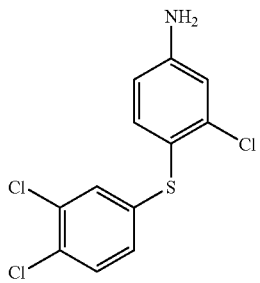

To a solution of 3,4-dichlorothiophenol (0.87 mL) and 4-fluoro-3-chloronitrobenzene (1.2 g) in THF (12 mL) was added a solution of potassium t-butoxide in THF (1 M, 3.7 mL). Ethanol was added to form a precipitate and the mixture was heated to dissolve the solid. The mixture was then cooled to ambient temperature and water was added. The resulting solids were collected by filtration and washed with water. The product was dissolved in methylene chloride, dried over magnesium sulfate, filtered and concentrated to provide a yellow nitro intermediate (2.08 g).

SnCl$_2$ hexahydrate (7 g) was added to a solution of the intermediate nitro compound in ethyl acetate (40 mL) at 85° C. After 12 hr, the reaction was treated with 420 mL of 0.5 N NaOH solution and diluted with EtOAc (100 mL). The milky suspension was filtered through Celite and rinsed with additional EtOAc. The layers were separated and the water layer was extracted with additional EtOAc. The combined organic portions were dried over MgSO$_4$, filtered and concentrated under vacuum to provide the aniline derivative 72.1, which was used without purification.

The compounds provided in Table 9 were prepared using 72.1 and commercially available substituted benzenesulfonyl chlorides and/or using the intermediates and methods described in the examples above.

TABLE 9

| | Ra | Rb | Rc | Rd | m/e (M − H) |
|---|---|---|---|---|---|
| 72.2 | H | Cl | Cl | H | 510 |
| 72.3 | Cl | H | Cl | H | 510 |
| 72.4 | H | H | I | H | 568 |

Compound 72.3 was converted to the corresponding biaryl sulfoxide (72.5, m/e 526) and biaryl sulfone (72.6, m/e 542) using an oxone procedure (see, for example, Trost, et al., *Tetrahedron Lett.*, 22:1287 (1981) and Webb, *Tetrahedron Lett.*, 35:3457-3460 (1994)). Similarly, compound 72.2 was converted to the biaryl sulfoxide (72.7, m/e 526) using a routine oxidation with mCPBA.

Example 73

This example illustrates the preparation of 73.4 through 73.9.

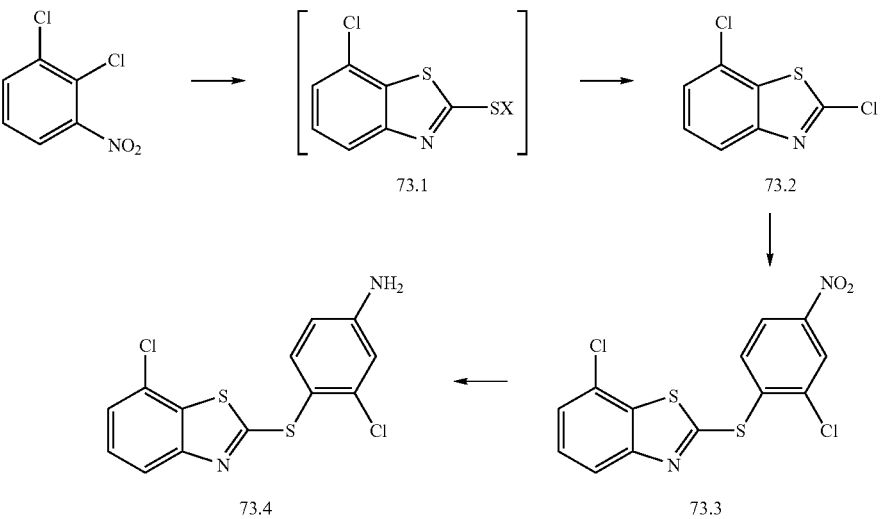

2,3 dichloronitrobenzene (19.04 g) was suspended in 40% Na$_2$CS$_3$ solution in water (66 ml) with 5 ml of ethanol and heated at 130° C. bath temperature for 3 days. After cooling, the residue was diluted in water and acidified with 5N HCl (caution: foaming gas evolution). The tan solids were collected by filtration, rinsed with water and dried under vacuum to give 19.9 g of an intermediate complex (73.1). The crude 73.1 (6.03 g) was added to neat sulfuryl chloride (20 ml) cautiously over about 5 minutes. The mixture was then heated at 50° C. The character of the solid changed but did not dissolve. The reaction was quenched by pouring onto ice. The ice mixture was stirred until the initial heavy dark oil solidified. The solids were collected by filtration, dissolved in ethyl ether and washed with water. The product was purified by flash chromatography using hexane, then 20% methylene chloride/hexane to afford 3.2 g of a 2,7-dichlorobenzothiazole (73.2) as a low melting solid.

$^1$H NMR (CDCl$_3$) δ 7.823 (d, J=8.4 Hz), 7.417 (t, J=8.4 Hz), 7.371 (d, J=8.4 Hz). Anal. calc: 41.20% C, 1.48% H, 6.86% N; found: 41.06% C, 1.46% H, 6.75% N 3-Chloro-4-mercapto nitrobenzene (prepared by the method of Price and Stacy, *J. Amer. Chem. Soc.* 68, 498-500 (1946)) (1.33 g) and 2,7-dichlorobenzothiazole (73.2) (1.43 g) were dissolved in ethanol (20 ml) with heating. Pyridine (1.1 g, 2 eq) was added. After a solid formed, additional ethanol (20 ml) was added and the mixture maintained at 50° C. overnight. The solid was collected by filtration and rinsed with water. The solids were dried as a solution in methylene chloride and concentrated to afford the nitro compound 73.3 (2.22 g) as an off-white solid. (mp 210-212° C.)

$^1$H NMR (DMSO) δ 8.544 (d, J=2.4 Hz, 1H), 8.273 (dd, J=8.8, 2.5 Hz, 1H) 8.081 (d, J=8.6 Hz, 1H) 7.961 (dd, J=6.3, 2.4 Hz, 1H), 7.60 (m, 2H).

Using the method of example 32, the nitro derivative 73.3 was converted to the corresponding aniline (73.4). Flash chromatography gave a white solid. (mp 165-167° C.).

$^1$NMR (DMSO) δ 7.775 (d, J=8.4 Hz, 1H), 7.606 (d, J=8.0 Hz, 1H), 7.367 (t, J=8.0 Hz, 1H), 7.265 (d, J=8.0 Hz, 1H), 6.931 (d, J=2.0 Hz, 1H), 6.672 (dd, J=8.4, 2.4 Hz, 1H), 4.15 (br s, 2H). ESI MS 327 (M+H). Anal. calcd. 47.71% C, 2.46% H, 8.56% N; found: 47.93%C, 2.48% H, 8.47% N Reaction of 2-chloro-4-trifluoromethylbenzene sulfonyl chloride with aniline 73.4 according to the method of Example 3 gave sulfonamide 73.5 (see Table 10).

$^1$H NMR (DMSO) δ 11.712 (br s, 1H) 8.377 (d, J=8.4 Hz, 1H), 8.187 (d, J=2 Hz, 1H), 7.995 (dd, J=8.4, 1.2 Hz, 1H), 7.880 (d, J=8.4 Hz, 1H), 7.822 (dd, 7.2, 2.0 Hz, 1H), 7.509 (t, J=8.0 Hz, 1H), 7.474 (dd, J=7.6, 2.0 Hz, 1H), 7.443 (d, J=2.4 Hz, 1H), 7.256 (dd, J=8.8, 2.4 Hz, 1H). MS (M+H) 569; MS (M−H) 567. Anal. calcd. 42.15% C, 1.77% H, 4.92% N; found: 42.30% C, 1.76% H, 4.94% N.

The additional compounds provide in Table 10 were prepared similarly using aniline 73.4 and the corresponding sulfonyl chlorides using the method of Example 3.

TABLE 10

| | Ra | Rb | Rc | Rd | m/e (M − H) |
|---|---|---|---|---|---|
| 73.5 | Cl | H | CF$_3$ | H | 567 |
| 73.6 | H | Cl | Cl | H | 533 |
| 73.7 | Cl | H | Cl | H | 533 |
| 73.8 | H | H | I | H | 591 |
| 73.9 | Cl | H | Cl | Me | 547 |

Example 74

The following benzenesulfonyl chlorides were prepared by the procedure of R. V. Hoffman (Org. Syn. Coll. Vol. VII, 508-511) from the corresponding commercially available anilines and used to make the indicated examples.

74a 2-chloro-4-t-butylbenzenesulfonyl chloride. yield 34% for examples 76.8 and 79.9

$^1$H NMR (CDCl$_3$) δ 8.06 (1H, d, J=8.4 Hz), 7.62 (1H, s), 7.48 (1H, d, J=8.4 Hz), 1.37 (9H, s)

m.p. 68.8° C.

74b 2-trifluoromethyl-4-chlorobenzenesulfonyl chloride. yield 76% as a solid.

for examples 176 and 347

$^1$H NMR (CDCl$_3$) δ 8.325 (d, J=8.4 Hz, 1H), 7.966 (br s, 1H), 7.829 (br d, J=8.4 Hz, 1H)

m.p. 37.0° C.

74c 2-chloro-4-methylbenzenesulfonyl chloride. yield 47% as an oil.

for examples 76.9, 79.8 and 351.

$^1$H NMR (CDCl$_3$) δ 8.02 (1H, d, J=8.8 Hz), 7.46 (1H, s), 7.28 (1H, d, J=8.8 Hz), 2.47 (3H, s)

Example 75

This illustrates the synthesis of compound 75.

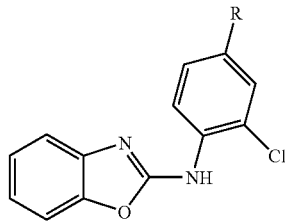

75.1 R = NO2
75 R = NH2

By the method of example 201, 2-chlorobenzoxazole (5 g) and 2-chloro-4-nitroaniline (6.1 g) were coupled to provide nitro compound 75.1 (2.6 g) as a yellow solid.

$^1$H NMR (d6-acetone) δ 9.514 (s, 1H), 9.01 (d, J=9 Hz, 1H), 8.4 (s, 1H), 8.37 (dd, J=8.4, 2 Hz, 1H), 7.58 (d, J=8.4 Hz, 1H), 7.52 (d, J=8 Hz, 1H), 7.34 (t, J=7.6 Hz, 1H), 7.28 (t, J=7.6 Hz, 1H). MS (M−H) 288; (2M−2H+Na) 599

Reduction by the method of example 32 gave the aniline 75 (93%) as a grey solid.

$^1$HNMR (d6-acetone) δ 8.45 (br s, 1H), 7.796 (d, J=8.4 Hz, 1H), 7.353 (d, J=7.6 Hz, 1H), 7.335)d, J=7.6 Hz, 1H), 7.191 (t, J=7.6 Hz, 1H), 7.088 (t, J=8 Hz, 1H), 6.846 (d, J=2.4 Hz, 1H), 6.673 (dd, J=8.8, 2.4 Hz, 1H), 4.912 (br s, 2H). MS (M+H) 260.1

Example 76

This example illustrates the preparation of 76.2 and sulfonamides derived from it.

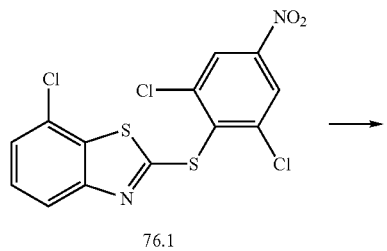

3,5-dichloro-4-mercapto nitrobenzene (prepared by the method of Price and Stacy, *J. Amer. Chem. Soc.* 68, 498-500 (1946)) (0.65 g) and 2,7-dichlorobenzothiazole (73.2) were combined by the method of Example 73, to afford the nitro derivative (76.1) as a yellow solid (0.95 g).

$^1$H NMR (DMSO) δ 8.587 (s, 2H), 7.852 (m, 1H), 7.54 (m 2H). Anal. calcd: 39.87% C, 1.29% H, 7.15 N; found 39.62% C, 1.21% H, 7.00% N.

Reduction of the nitro derivative (76.1) (0.92 g) by the method of example 32 gave the aniline (76.2) (0.76 g) after flash chromatography.

$^1$H NMR (DMSO) δ 7.822 (d, J=8 Hz, 1H) 7.509 (t, J=8Hz, 1H), 7.465 (d, J=6.8 Hz, 1H) 6.882 (s, 2H), 6.529 (br s, 2H). MS (M+H) 361. Anal. calcd: 43.177% C, 1.95 H, 7.74% N; found: 43.10% C, 2.05% H, 7.65% N.

Reaction of the aniline 76.2 according to the method of example 3 with various sulfonyl chlorides gave the sulfonamides of Table 11.

TABLE 11

| | Ra | Rb | Rc | Rd | m/e (M − H) |
|---|---|---|---|---|---|
| 76.3 | Cl | H | CF₃ | H | 601 |
| 76.4 | H | H | t-Bu | H | |
| 76.5 | Cl | H | Cl | H | 567 |
| 76.6 | Cl | H | H | H | 535 (M + H) |
| 76.7 | H | H | H | H | |
| 76.8 | Cl | H | t-Bu | H | 589 |
| 76.9 | Cl | H | Me | H | 547 |

Example 76.3

$^1$H NMR (DMSO) δ 11.96 (br s, 1H) 8.417 (d, J=8.4 Hz, 1H), 8.209 (s, 2H), 8.013 (d, J=8 Hz, 1H), 7.819 (d, J=6.8 Hz, 1H), 7.514 (m, 2 H), 7.411 (s, 2H). Anal. calcd: 39.75% C, 1.50% H, 4.64% N; found: 39.48% C, 1.73% H, 4.37% N. MS (M−H) 601.

Example 76.4

Anal. calcd. for M+0.5 H₂O: 48.72% C, 3.56% H, 4.94% N; found: 48.80% C, 3.68% H, 4.78% N.

Example 76.5

$^1$H NMR (DMSO) δ 11.83 (br s, 1H) 8.212 (d, J=8.4 Hz, 1H), 7.962 (d, J=2H, 1H), 7.827 (dd, J=6.8, 2 Hz, 1H), 7.723 (dd, J=8.5, 2.1 Hz, 1H), 7.518 (t, J=7.9 Hz, 1H), 7.492 (dd, J=7.8, 2.0 Hz, 1H), 7.385 (s, 2H). MS (M−H) 567. mp 216° C. Anal. calcd: 39.98% C, 1.59% H, 4.91% N; found: 39.81% C, 1.59% H, 4.85% N.

Example 76.6

$^1$H NMR (DMSO) δ 11.72 (br s, 1H), 8.222 (d, J=8 Hz, 1H), 7.822 (dd, J=7.2, 2.0 Hz, 1H), 7.730 (d, J=4 Hz, 2H), 7.636 (m, 1H), 7.516 (t, J=8 Hz, 1H), 7.490 (d, J=8 Hz, 1H), 7.379 (s, 2H). MS (M+H) 535.

Example 76.7

$^1$H NMR (DMSO) δ 11.38 (br s, 1H), 8.906 (d, J=8 Hz, 2H), 7.827 (dd, J=7.2, 2.0 Hz, 1H), 7.721 (t, J=6.8 Hz, 1H), 7.655 (t, J=8 Hz, 2H), 7.519 (t, J=8 Hz, 1H), 7.493 (d, J=6.8 Hz, 1H), 7.412 (s, 2H).

Example 76.8

$^1$H NMR (DMSO) δ 11.70 (1H, s), 8.13 (1H, d, 8.4), 7.80-7.87 (1H, m), 7.63-7.71 (2H, m), 7.48-7.55 (2H, m), 7.39 (2H, s). MS (M−H) 589. mp 131.3° C. Anal. calcd: C, 46.63; H, 3.06; N, 4.73; found C, 48.09; H, 3.65; N, 4.35

Example 76.9

$^1$H NMR (DMSO) δ 11.70 (1H, s), 8.07-8.20 (1H, m), 7.80-7.93 (1H, m), 7.35-7.65 (6H, m). MS (M−H) 546.8. mp 220.9° C.

Example 77

This example illustrates the preparation of anilines 77.7, 77.8 and 77.9

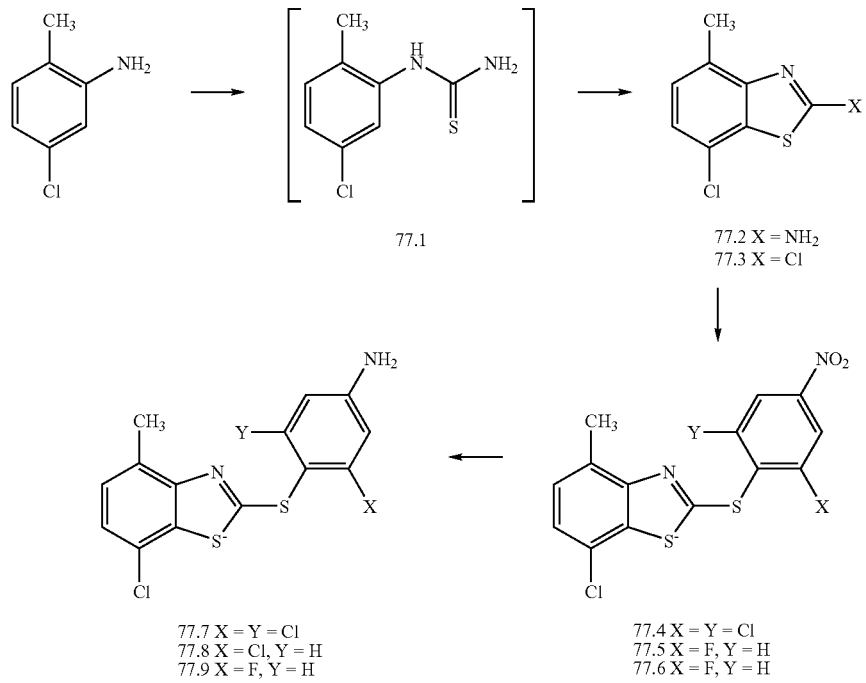

77.7 X = Y = Cl
77.8 X = Cl, Y = H
77.9 X = F, Y = H 77.4 X = Y = Cl
77.5 X = F, Y = H
77.6 X = F, Y = H

In analogy to the procedures of Weinstock et. al (*J. Med. Chem.* 30:1166-1176 (1987), conc. sulfuric acid (8.74 g) was added slowly to a solution of 5-chloro-2-methylaniline (25 g) in chlorobenzene (120 mL) to form a thick slurry. Powdered NaSCN (18.6 g) was added. The mixture was heated at 110° C. for one hour then maintained at 50° C. overnight. After dilution with hexane (300 mL), the solid was collected by filtration, washed with hot water and rinsed with ethyl ether to afford 15.65 g of intermediate thiourea 77.1 which was used directly in the next step.

Preparation of 2-amino-4-methyl-7-chlorobenzothiazole (77.2)

Bromine (25.44 g) was added to a suspension of 77.1 (15 g) in chloroform (110 mL) maintained below +10° C. After the addition was complete, the reaction was allowed to warm to RT then heated at reflux for 30 minutes. After cooling, the orange solid was collected by filtration and suspended in acetone (100 mL) which discharges the remaining color. Solids were collected by filtration and rinsed with ethyl ether to afford the HBr salt.

$^1$H NMR (DMSO) δ 7.182 (d, J=8 Hz, 1H), 7.137 (d, J=8 Hz, 1H), 2.40 (s, 3H).

The salt was suspended in water at 95° C. The pH of the suspension was adjusted to pH 9 with 0.5 N NaOH. After cooling, the solids were collected by filtration, rinsed with water and dissolved in ethylether/methylene chloride. The organic layer was dried over magnesium sulfate. After concentration, 2-amino-4-methyl-7-chlorobenzothiazole (77.2) (7.47 g) was obtained as a white solid.

MS (M+H) 199. Anal. calcd.: 48.36% C, 3.55% H, 14.10% N; found: 48.29% C, 3.55% H, 14.01% N.

Preparation of 2-7-dichloro-4-methyl-benzothiazole (77.3)

To a slurry of 2-amino-4-methyl-7-chlorobenzothiazole (77.2) (6.37 g) in H3PO4 (85%, 213 ml) in a 500 ml 3-necked flask with mechanical stirring and an internal temperature of <−10° C., was added dropwise a solution of NaNO$_2$ (6.87 g) in water (11 ml). The mixture was warmed to 0° for 30 minutes and then recooled. The slurry was then slowly added to a cold (~5° C.) solution of CuSO4.5H$_2$O (32 g) and NaCl (40 g) in water (128 ml) with vigorous mechanical stirring. After the foaming subsides and warming to RT, the solids were collected by filtration and rinsed with water. The solids were dissolved in ether leaving some insoluble residue. The ether solution was washed with water, and sodium bicarbonate solution. After the organic layer was concentrated, the residue was purified by flash chromatography with 10% methylene chloride in hexane to afford 2-chloro-4-methyl-7-chlorobenzothiazole (77.3) (4.48 g).

$^1$H NMR (CDCl$_3$) δ 7.288 (d, J=8 Hz, 1H), 7.231 (dq, J=8.0.8 Hz, 1H), 2.651 (d, J=0.8 Hz, 3H). Anal. calcd.: 44.06% C, 2.31% H, 6.42% N; found: 44.16% C, 2.34% H, 6.32% N.

Coupling of 77.3 (0.65 g) with 3,5-dichloro-4-mercapto nitrobenzene by the method of example 73 gave after flash chromatography the nitro derivative 77.4 (0.97 g) as a yellow solid.

$^1$NMR (DMSO) δ 8.394 (s, 2H), 7.237 (d, J=8 Hz, 1H), 7.209 (d, J=8 Hz, 1H), 2.621 (s, 3H). MS (M+H) 405

Coupling of 77.3 (0.7 g) with 3-chloro-4-mercapto nitrobenzene by the method of example 73 gave the nitro derivative 77.5 (1.02 g) as a yellow solid.

$^1$NMR (DMSO) δ 8.535 (br s, 1H), 8.261 (dd, J=8.4, 2 Hz, 1H), 8.040 (d, J=8.4 Hz, 1H), 7.496 (d, J=8.4 Hz, 1H), 7.419

(d, J=8.4 Hz, 1H), 2.601 (s, 3H). MS (M+H) 371. Anal. calcd.: 45.40% C, 2.18% H, 7.57% N; found: 45.25% C, 2.23% H, 7.49% N.

Coupling of 77.3 (1.12 g) with 3-fluoro-4-mercapto nitrobenzene by the method of example 73 gave after flash chromatography the nitro derivative 77.6 (SY1904-2) (1.8 g)
$^1$H NMR Reduction of 77.4 (0.96 g) with tin dichloride by the method of example 32 gave the aniline (77.7) (0.84 g) used directly in later reactions:
$^1$NMR (DMSO) δ 7.352 (d, J=8 Hz, 1H), 7.322 (d, J=8 Hz, 1H), 6.884 (s, 2H), 6.533 (br s, 2H), 2.565 (s, 3H).

Reduction of 77.5 (1.13 g) with tin dichloride by the method of example 32 gave the aniline (77.8) (1.04 g) used directly in later reactions:
$^1$NMR (DMSO) δ 7.543 (d, J=8.4 Hz, 1H), 7.329 (d, J=8 Hz, 1H), 7.301 (d, J=8 Hz, 1H), 6.889 (d, J=2 Hz, 1H), 6.663 (dd, J=8.4, 2.4Hz, 1H), 6.231 (br s, 2H), 2.557 (s, 3H). MS (M+H) 341. Anal. calcd. for M+0.25 H$_2$O: 48.63% C, 3.06% H, 8.10% N; found: 48.67% C, 3.06% H, 7.96% N.

Reduction of 77.6 (1.75 g) with tin dichloride by the method of example 32 gave after chromatography the aniline (77.9) (1.2 g)
$^1$H NMR: δ 7.43 (1H, t, 8.3), 7.30-7.37 (2H, m), 6.53-6.58 (2H, m), 6.28 (2H, s).

Example 78

Treatment of the anilines 77.7, 77.8 or 77.9 by the method of example 3 with various sulfonyl chlorides gave the sulfonamides of Table 12.

TABLE 12

| | X | Y | Ra | Rb | Rc | Rd | m/e (M − H) |
|---|---|---|---|---|---|---|---|
| 78.1 | Cl | Cl | Cl | H | Cl | H | 581 |
| 78.2 | Cl | Cl | Cl | H | CF$_3$ | H | 615 |
| 78.3 | Cl | Cl | Cl | H | Cl | Me | 595 |
| 78.4 | Cl | H | Cl | H | CF$_3$ | H | 581 |
| 78.5 | Cl | H | Cl | H | Cl | H | 565 |
| 78.6 | F | H | Cl | H | CF$_3$ | H | 565 |
| 78.7 | F | H | Cl | H | Cl | H | 531 |

Example 78.1

$^1$H NMR (DMSO) δ 11.813 (br s, 1H), 8.208 (d, J=8.8 Hz, 1H), 7.951 (d, J=2 Hz, 1H), 7.716 (dd, J=8.4, 2 Hz, 1H), 7.396 (s, 2H), 7.377 (d, J=8.4 Hz, 1H), 7.334 (d, J=8 Hz, 1H), 2.516 (s, 3H). MS (M−H) 581. Anal. calcd. for M+H$_2$O: 39.85% C, 2.17% H, 4.65% N; found: 40.10% C, 1.89% H, 4.57% N.

Example 78.2

$^1$H NMR (DMSO) δ 11.975 (br s, 1H), 8.416 (d, J=8.4 Hz, 1H), 8.205 (br s, 1H), 8.012 (d, J=8 Hz, 1H), 7.423 (s, 2H), 7.376 (d, J=8 Hz, 1H), 7.332 (d, J=8 Hz, 1H), 2.512 (s, 3H). MS (M−H) 615. Anal. calcd.: 40.79% C, 1.79% H, 4.53% N; found: 41.05% C, 1.86% H, 4.57% N.

Example 78.3

$^1$H NMR (DMSO) δ 11.748 (s, 1H), 8.233 (s, 1H), 7.880 (s, 1H), 7.407 (s, 2H), 7.370 (d, J=8 HZ, 1H), 7.330 (d, J=8 Hz, 1H), 2.408 (s, 3H). MS (M−H) 595. Anal. calcd.: 42.12% C, 2.19% H, 4.68% N; found: 41.84% C, 2.23% H, 4.51% N.

Example 78.4

$^1$H NMR (DMSO) δ 11.73 (1H, s), 8.38 (1H, d, J=8.3 Hz), 8.19 (1H, s), 7.99 (1H, d, J=8.3 Hz), 7.88 (1H, d, J=8.6 Hz), 7.45 (1H, d, J=2.3 Hz), 7.23-7.40 (3H, m). MS (M−H) 580.8 (M−H). mp 189.0° C.

Example 78.5

$^1$H NMR (DMSO) δ 11.57 (1H, s), 8.17 (1H, d, J=8.6 Hz), 7.92 (1H, d, J=2.1 Hz), 7.78 (1H, d, J=8.5 Hz), 7.69 (1H, dd, J=8.6, 2.1 Hz), 7.43 (1H, d, J=2.3 Hz), 7.30-7.38 (2H, m), 7.25 (1H, dd, J=8.6, 2.4 Hz). MS (M−H) 546.9. mp 218.1° C.

Example 78.6

$^1$NMR: δ 8.04 (1H, d, 8.3), 8.18 (1H, s), 7.99 (1H, d, 8.3), 7.80 (1H, t, 8.3), 7.30-7.40 (2H, m), 7.10-7.22 (2H, m). MS (M−H) 565.0. mp 221.2° C. Anal. calcd.: C, 44.45; H, 2.13; N, 4.94; found C, 44.01; H, 2.18; N, 4.67.

Example 78.7

$^1$H NMR (DMSO) δ 11.60 (1H, s), 8.18 (1H, d, 8.6), 7.91 (1H, d, 2.0), 7.79 (1H, t, 8.4), 7.69 (1H, dd, 8.6, 2.1), 7.30-7.40 (2H, m), 7.10-7.20 (2H, m). MS (M−H) 530.9. mp 230.4° C. Anal. calcd.: C, 44.99; H, 2.27; N, 5.25; found C, 44.49; H, 2.26; N, 5.08.

Example 79

This example illustrates the preparation of compounds 79.1 to 79.7.

To a solution of 5-chloro-2-mercaptobenzothiazole (Acros) (2 g), KOH (630 mg) in water (8 mL) at 100° C. was added a solution of 3,4-dichloronitrobenzene (1.88 g) in n-propanol (24 mL). The mixture was heated at reflux for 72 hrs. After cooling, the solids were collected by filtration and rinsed with water. The solids were dried under vacuum to afford the nitro derivative 79.1 (2.25 g) as a yellow solid used directly in the next step.

$^1$H NMR (DMSO) δ 8.54 (d, J=2.4 Hz, 1H), 8.26 (dd, J=8.6, 2.4 Hz, 1H), 8.123 (d, J=8.6 Hz1, 1H), 8.08 (d, J=1.9 Hz, 1H), 8.03 (d, J=8.7 Hz, 1H), 7.533 (dd, J=8.6, 2.1).

Reduction of 79.1 (2.2 g) with tin dichloride by the method of example 32 gave after work-up the aniline (79.2) (1.2 g) which was used directly in later reactions.

$^1$H NMR (DMSO) δ 7.94 (d, J=8.4 Hz, 1H), 7.891 (d, J=1.6 Hz, 1H), 7.537 (d, J=8.4 Hz, 1H), 7.371 (dd, J=8.4, 2.1 Hz, 1H), 6.877 (d, J=2.4 Hz, 1H), 6.651 (dd, J=8.4, 2.4 Hz, 1H), 6.203 (s, 2H). MS (M+H) 327

Treatment of the aniline 79.2 by the method of example 3 with various sulfonyl chlorides gave the sulfonamides of Table 13.

TABLE 13

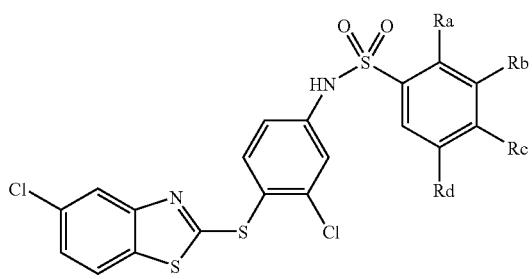

| | Ra | Rb | Rc | Rd | m/e (M − H) |
|---|---|---|---|---|---|
| 79.3 | Cl | H | Cl | Me | 547 |
| 79.4 | Cl | H | Cl | H | 533 (M + H) |
| 79.5 | Cl | H | CF$_3$ | H | 567 |
| 79.6 | H | Cl | Cl | H | 533 |
| 79.7 | Me | H | Cl | Me | 527 |

Example 79.3

$^1$H NMR(DMSO) δ 11.52 (1H, s), 8.20 (1H, s), 7.84-8.00 (4H, m), 7.35-7.43 (2H, m), 7.22 (1H, d, J=8.5 Hz), 2.41 (3H, s). MS (M−H) 546.8. mp 203.7° C.

Example 79.4

$^1$H NMR(DMSO) δ 11.57 (1H, s), 8.18 (1H, d, J=8.5 Hz), 7.90-7.98 (2H, m), 7.86 (1H, d, J=8.5 Hz), 7.72 (1H, d, J=8.7 Hz), 7.37-7.43 (2H, m), 7.22(1H, d, J=8.8 Hz). MS (M+H) 532.8. mp 174.7° C.

Example 79.5

$^1$H NMR(DMSO) δ 8.38 (1H, d, 8.4 Hz), 8.21 (1H, s), 8.01 (1H, d, J=8.2 Hz), 7.90-7.96 (2H, m), 7.86 (1H, d, J=7.7 Hz), 7.42 (2H, s), 7.23 (1H, d, J=8.6 Hz). MS (M−H) 566.9. mp 158.8° C.

Example 79.6

$^1$H NMR(DMSO) δ 11.25 (1H, s), 8.06 (1H, d, J=1.5 Hz), 7.80-7.96 (5H, m), 7.40-7.46 (2H, m), 7.27-7.32 (1H, m). MS (M−H) 532.8. mp 201.2° C.

Example 79.7

$^1$H NMR(DMSO) δ 11.30 (1H, s), 8.00 (1H, s), 7.90-7.98 (2H, m), 7.84 (1H, d, J=8.6 Hz), 7.57 (1H, s), 7.35-7.44 (2H, m), 7.18-7.23 (1H, m), 2.57 (3H, s), 2.37 (3H, s). mp 205.1° C.

TABLE 14

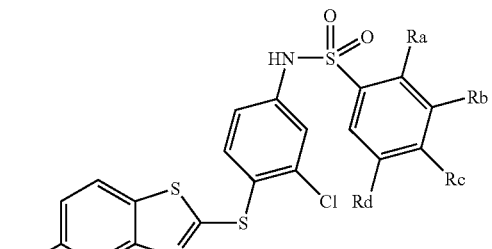

| | Ra | Rb | Rc | Rd | m/e (M − H) |
|---|---|---|---|---|---|
| 79.3 | Cl | H | Cl | Me | 547 |
| 79.4 | Cl | H | Cl | H | 533 (M + H) |
| 79.5 | Cl | H | CF$_3$ | H | 567 |
| 79.6 | H | Cl | Cl | H | 533 |
| 79.7 | Me | H | Cl | Me | 527 |
| 79.8 | Cl | H | Me | H | 513 |
| 79.9 | Cl | H | t-Bu | H | 555 |

Example 79.8

$^1$H NMR (d$_6$-DMSO) δ 11.43 (1H, s), 8.08 (1H, d, J=8.0 Hz), 7.90-8.00 (2H, m), 7.85 (1H, d, J=8.5 Hz), 7.57 (1H, s), 7.37-7.47 (3H, m), 7.21 (1H, d, J=8.4 Hz), 2.38 (3H, s). MS (M−H) 512.9. mp 201.0° C. Anal. calcd.; C, 46.56; H, 2.54; N, 5.43; found C, 46.93; H, 2.58; N, 5.40.

Example 79.9

$^1$H NMR (d$_6$-DMSO) δ 11.44 (1H, s), 8.10 (1H, d, J=8.3 Hz), 7.90-7.97 (2H, m), 7.86 (1H, d, J=8.6 Hz), 7.60-7.68 (2H, m), 7.37-7.43 (2H, m), 7.23 (1H, dd, J=8.5, 2.4 Hz), 1.29 (9H, s). MS (M−H) 554.9. mp 177.8° C. Anal. calcd.; C 49.51, H 3.43, N 5.02; found C 49.67, H 3.44, N 4.97.

Example 80

This illustrates the synthesis of compound 80.4.

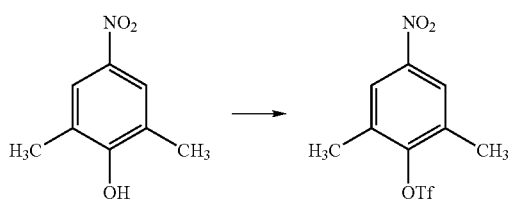

80.1

2,6-dimethyl-4-nitro-phenol (4.93 g, 29.5 mmol) was suspended in anhydrous CH$_2$Cl$_2$ (30 mL). Hünig's base (12.4 mL, 70 mmol) was added to give a homogeneous, dark red solution. The reaction mixture was cooled to −15° C. and triflic anhydride (10 g, 35 mmol) was slowly added. The very dark reaction mixture was stirred at −15° C. for 15 minutes, then poured into 3N HCl (100 mL). The layers were separated and the aqueous layer was extracted 1×150 mL CH$_2$Cl$_2$. The combined organic layers were washed 1×50 mL sat. brine, dried over MgSO$_4$, and concentrated to a dark red oil. This oil was filtered through a 2 cm plug of silica gel (eluting with 3:1 hexanes:ethyl acetate) and concentrated to an orange oil which was diluted with 10 mL of hexanes and allowed to stand at room temperature until crystallization of the product took place. The crystals were collected and dried under vacuum. The mother liquor was concentrated, then diluted with 5 mL of CH$_2$Cl$_2$ and 25 mL of hexanes and again allowed to stand until crystallization was complete. The second crop was collected by filtration and dried under vacuum. Combined yield of the two crops was 7.87 g of triflate 80.1.

$^1$H NMR (CDCl$_3$) δ 8.03 (s, 2H); 2.50 (s, 6H).

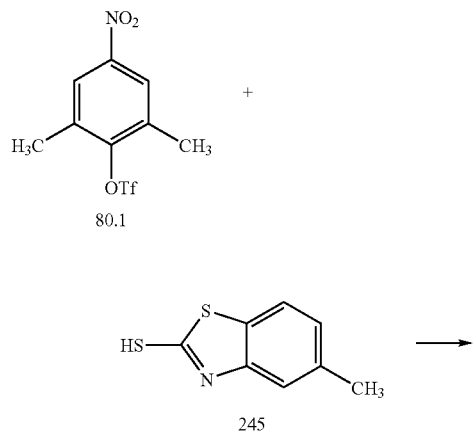

Triflate 80.1 (2 g, 6.7 mmol) was dissolved in DMF (1 mL) and added to the reaction mixture which was then heated to 50° C. for 16 h. The reaction mixture was poured into 100 mL DI water and extracted 2×50 mL of ethyl acetate. The combined organic layers were washed with sat. brine, dried over MgSO$_4$, filtered, concentrated, and the residue purified by flash chromatography (silica gel, 19:1 to 4:1 hexanes:ethyl acetate). Fractions containing the desired product were concentrated and the residue recrystallized from hot hexanes:ethyl acetetate. Filtration and drying provided the S-arylated compound 80.2 as bright yellow crystals (0.90 g).

$^1$H NMR (CD$_3$CN) δ 8.12 (s, 2H); 7.68 (d, 1H); 7.61 (s, 1H); 7.17 (d, 1H); 2.60 (s, 6H); 2.42 (s, 3H). MS (M+H) 331.1

Reduction of 80.2 (0.88 g) by the method of Example 32 gave aniline 80.3 (0.4 g) as a solid.

$^1$H NMR (CDCl$_3$) δ 7.723 (m, 1H), 7.598 (s, 1H), 7.122 (d, J=8.4 Hz, 1H), 6.706 (s, 2H), 5.304 (br, 2H), 2.399 (s, 3H), 2.338 (s, 6H)

Sulfonylation of 80.3 (400 mg) by the method of example 3 gave 80.4 (Table 15) (0.36 g).

$^1$H NMR (DMSO) δ 11.284 (s, 1H), 8.369 (d, J=8.2Hz, 1H), 8.170 (s, 1H), 7.969 (d, J=8.2 Hz, 1H), 7.676 (d, J=8.2 Hz, 1H), 7.591 (s, 1H), 7.126 (d, J=8.2 Hz, 1H), 7.056 (s, 2H), 2.372 (s, 3H), 2.326 (s, 6H). MS (M+H) 543

Example 81

This illustrates the synthesis of compound 81.4.

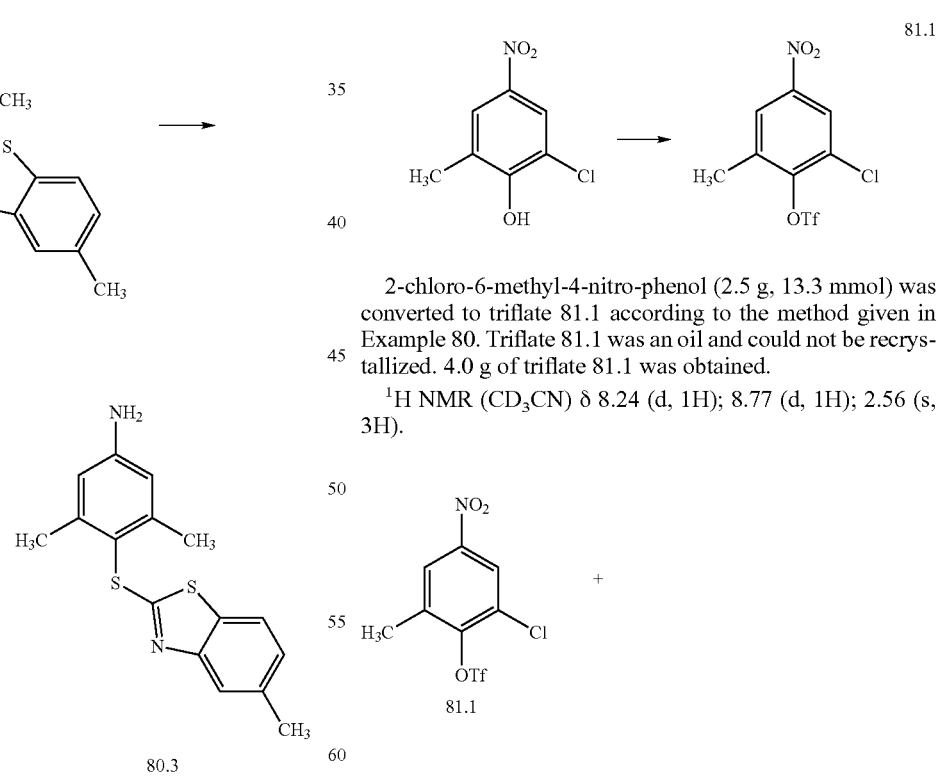

2-chloro-6-methyl-4-nitro-phenol (2.5 g, 13.3 mmol) was converted to triflate 81.1 according to the method given in Example 80. Triflate 81.1 was an oil and could not be recrystallized. 4.0 g of triflate 81.1 was obtained.

$^1$H NMR (CD$_3$CN) δ 8.24 (d, 1H); 8.77 (d, 1H); 2.56 (s, 3H).

5-methyl-2-mercaptobenzothiazole (1.45 g, 8 mmol) was suspended in anhydrous THF (3.5 mL). A solution of potassium tert-butoxide (7.35 mL, 1.0 N in THF) was added in one portion. The very thick precipitate of the mercaptobenzothiazole potassium salt was dissolved by addition of DMF (1 mL).

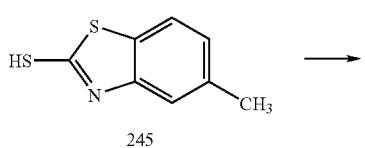

83

-continued

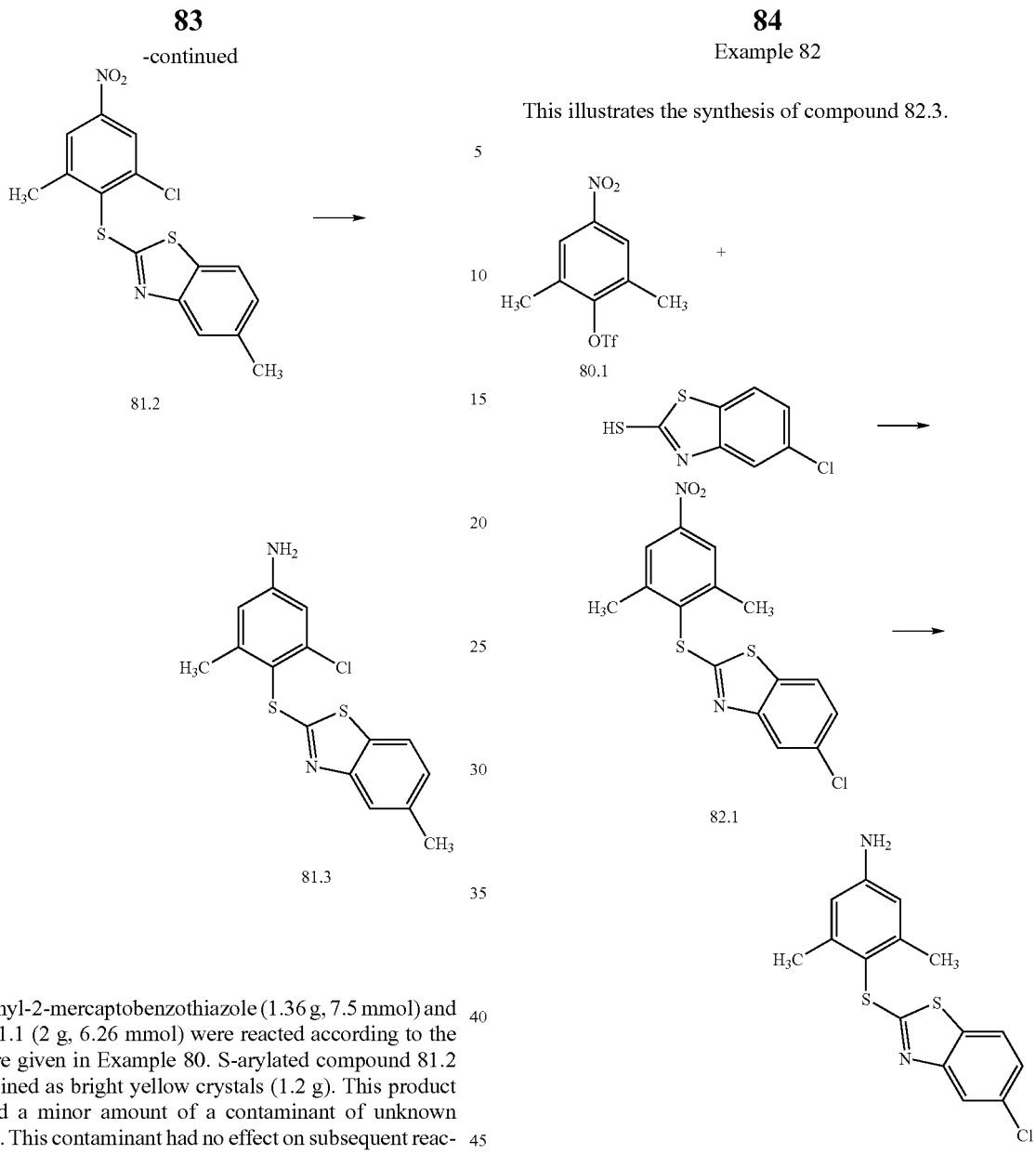

5-methyl-2-mercaptobenzothiazole (1.36 g, 7.5 mmol) and triflate 81.1 (2 g, 6.26 mmol) were reacted according to the procedure given in Example 80. S-arylated compound 81.2 was obtained as bright yellow crystals (1.2 g). This product contained a minor amount of a contaminant of unknown structure. This contaminant had no effect on subsequent reactions, nor was it found in subsequent products.

$^1$H NMR (CD$_3$CN) δ 8.28 (d, 1H); 8.14 (d, 1H); 7.67 (s, 1H); 7.56 (d, 1H); 7.14 (d, 1H); 2.68 (s, 3H); 2.45 (s, 3H). MS (M+H) 351.

Reduction of 81.2 (0.88 g) by the method of Example 32 gave aniline 81.3 (0.4 g) as a solid.

$^1$H NMR (DMSO) δ 7.740 (d, J=8 Hz, 1H), 7.608 (s, 1H), 7.131 (d, J=8 Hz, 1H), 6.732 (d, J=2.6 Hz, 1H), 6.588 (d, J=2.6 Hz, 1H), 6.048 (s, 2H), 2.403 (s, 3H), 2.334 (s, 3H).

Sulfonylation of 81.3 by the method of example 3 gave 81.4 (see Table 15).

$^1$H NMR (DMSO) δ 11.610 (s, 1H), 8.398 (d, J=8.4 Hz, 1H), 8.210 (s, 1H), 8.005 (d, J=8.4 Hz, 1H), 7.730 (d, J=8 Hz 1H), 7.621 (s, 1H), 7.7.276 (d, J=2.8 Hz, 1H), 7.167 (m, 2H), 2.409 (s, 3H), 2.397 (s, 3H).

84

Example 82

This illustrates the synthesis of compound 82.3.

5-chloro-2-mercaptobenzothiazole (202 mg, 1 mmol) and triflate 80.1 (270 mg, 0.9 mmol) were reacted according to the procedure given in Example 80. S-arylated compound 82.1 was obtained as a light yellow solid (203 mg).

$^1$H NMR (CDCl$_3$) δ 8.09 (s, 2H); 7.83 (d, 1H); 7.56 (d, 1H); 7.26 (dd, 1H); 2.63 (s, 3H). MS (M+H) 351.0

Reduction of 82.1 (0.7 g) by the method of example 32 gave aniline 82.2 (0.62 g).

$^1$H NMR (DMSO) δ 7.884 (d, J=8.4 Hz, 1H), 7.846 (d, J=2 Hz, 1H), 7.329 (dd, J=8.4, 2 Hz, 1H), 6.495 (s, 2H), 5.669 (s, 2H), 2.283 (s, 3H). MS (M+H) 321

Sulfonylation of 82.2 by the method of example 3 gave 82.3 (see Table 15).

$^1$H NMR (DMSO) δ 11.304 (s, 1H), 8.377 (d, J=8 Hz, 1H), 8.180 (d, J=1.2 Hz, 1H), 7.980 (br d, J=8.4, 1H), 7.874 (d, J=2.4 Hz, 1H), 7.866 (d, J=8 Hz, 1H), 7.365 (dd, J=8.4, 2 Hz, 1H), 7.068 (br s, 2H), 2.341 (s, 3H). MS (M−H) 561

Example 83

This illustrates the synthesis of compound 83.3.

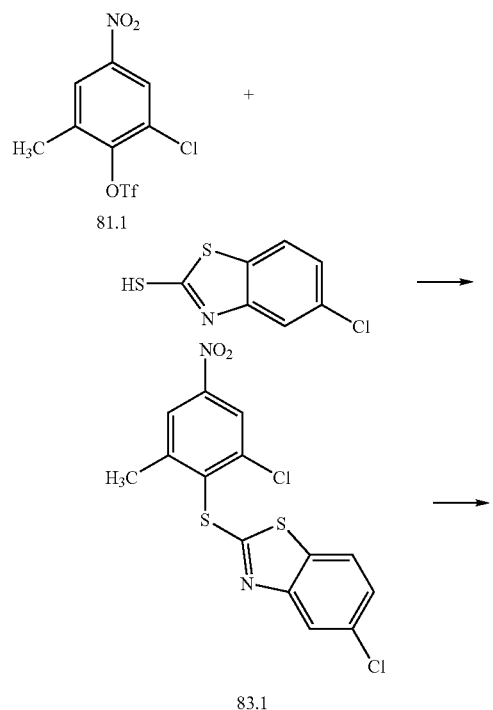

5-chloro-2-mercaptobenzothiazole (0.76 g, 3.75 mmol) and triflate 81.1 (1.0 g, 3.44 mmol) were reacted according to the procedure given in Example 80. S-arylated compound 83.1 was obtained as a light yellow solid (0.83 g).

$^1$H NMR (CDCl$_3$) δ 8.30 (s, 1H); 8.17 (s, 1H); 7.85 (s, 1H); 7.61 (d, 1H); 7.30 (d, 1H); 2.71 (s, 3H). MS (M+H) 371

Reduction of 83.1 (0.8 g) by the method of Example 32 gave aniline 83.2 (0.47 g).

$^1$H NMR (DMSO) δ 7.918 (d, J=8.8 Hz, 1H), 7.874 (d, J=2 Hz, 1H), 7.356 (dd, J=8.4, 2 Hz, 1H), 6.745 (d, J=2.4 Hz, 1H), 6.600 (d, J=2 Hz, 1H), 6.089 (br s, 2H), 2.336 (s, 3H). MS (M+H) 341.

Sulfonylation of 83.2 by the method of example 3 gave 83.3 (see Table 15).

$^1$H NMR (DMSO) δ 11.647 (s, 1H), 8.407 (d, J=8.4 Hz, 1H), 8.213 (br s, 1H), 8.008 (br d, J=8.4, 1H), 7.910 (d, J=8 Hz, 1H), 7.90 (s, 1H), 7.396 (d, J=8.8 H, 1H), 7.290 (br s, 1H), 7.188 (br s, 1H), 2.416 (s, 3H). MS (M−H) 581.

TABLE 15

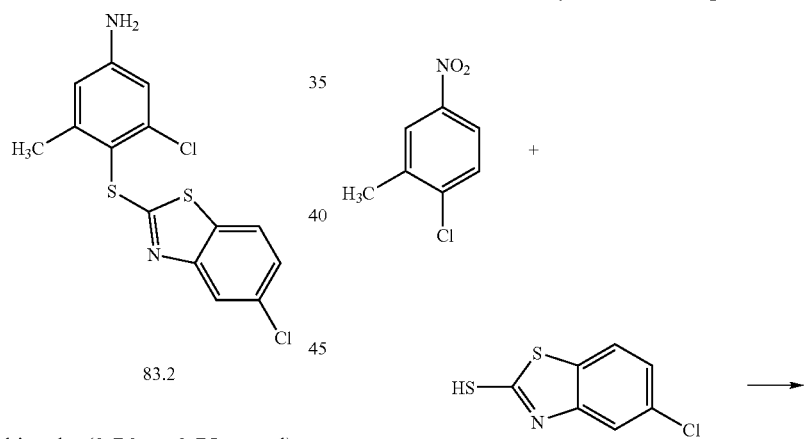

| | X | V | W | m/e (M − H) |
|---|---|---|---|---|
| 80.4 | Me | Me | Me | 543 (M + H) |
| 81.4 | Me | Me | Cl | |
| 82.3 | Cl | Me | Me | 561 |
| 83.3 | Cl | Me | Cl | 581 |
| 84.3 | Cl | H | Me | 547 |

Example 84

This illustrates the synthesis of compound 84.3

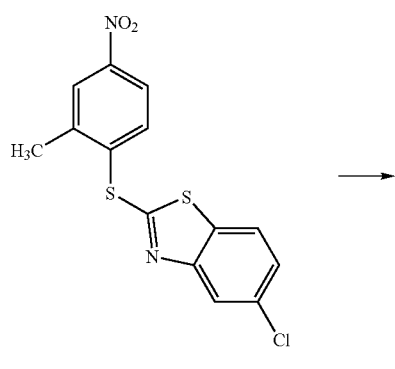

-continued

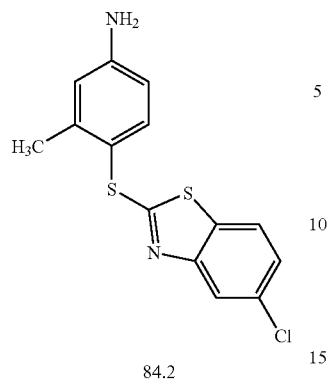
84.2

Sodium hydride (1 g, 60% in oil) was added to a solution of 5-chloro-2-mercaptobenzothiazole (5.4 g) in DMF (50 mL). After gas evolution had subsided a solution of 2-chloro-5-nitrotoluene in DMF was added and the mixture heated at 60° C. for 2 days. After cooling, the solution was filtered. The filtrate was diluted with water and extracted into ethyl ether. The organic layer was concentrated to a brown oil which was treated with hexane to form a solid precipitate which was collected by filtration as 84.1 (0.624 g).

$^1$H NMR (DMSO) δ 8.372 (d, J=2.4 Hz, 1H), 8.171 (dd, J=8.8, 2.4 Hz, 1H), 8.027 (d, J=8.8 Hz, 1H), 8.003 (d, J=8 Hz, 1H), 7.988 (d, J=2 Hz, 1H), 7.454 (dd, J=8.4, 1.6 Hz, 1H), 2.553 (s, 3H).

Reduction of 84.1 (0.6 g) with SnCl2 by the method of example 32 gave after chromatography 84.2 (0.48 g) as a solid.

$^1$NMR (DMSO) δ 7.899 (d, J=8.8 Hz, 1H), 7.853 (d, J=2 Hz, 1H), 7.345 (d, J=8.4 Hz, 1H), 7.336 (dd, J=8.4, 2 Hz, 1H), 6.631 (d, J=2 Hz, 1H), 6.531 Hz, 1H), 5.766 (br s, 2H). MS (M+Na) 329

Sulfonylation of 84.2 (0.4 g) by the method of example 3 gave 84.3 (Table 15) (0.66 g) as a foam.

$^1$H NMR (DMSO) δ 11.376 (s, 1H), 8.355 (d, J=8 Hz, 1H), 8.180 (d, J=1.2 Hz, 1H), 7.983 (dd, J=8.4, 2 Hz, 1H), 7.893 (d, J=9.2 Hz, 1H), 7.88 (s, 1H), 7.656 (d, J=8.4 H, 1H), 7.377 (dd, J=8.8, 1.6 Hz, 1H), 7.211 (d, J=2.8 Hz, 1H), 7.108 (dd, J=8.4, 2 Hz, 1H), 2.334 (s, 3H). MS (M−H) 547

Example 85

This illustrates the synthesis of compound 85.3

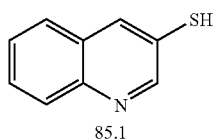
85.1

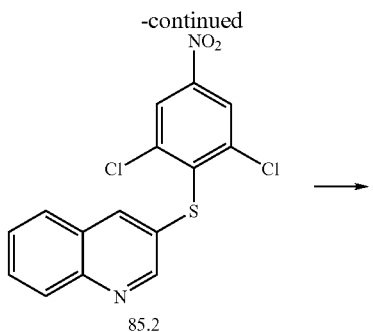
85.2

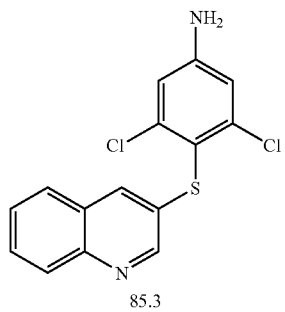
85.3

Compound 85.1 was prepared by a modification of the published procedure of Albert and Barlin (J. Chem. Soc. 2384-2396 (1959). 3-Aminoquinoline (15.0 g, 105 mmol) was suspended in a mixture of 10N HCl (40 mL), ice (21 g) and water (100 mL) at 0-5° C., before sodium nitrite (7.6 g, 110 mmol) was added slowly. The mixture was then added portionwise to another solution of potassium ethyl xanthate_ (20.8 g, 125 mmol) in water (60 mL) at 45° C. The mixture was heated for 1 hr before cooling off. The mixture was then extracted with ether. The ethereal solution was washed with 2N NaOH solution, water, and brine before drying over magnesium sulfate. After filtration, the removal of the solvent gave a brown oil (15 g), which was then dissolved in ethanol (150 mL) and refluxed with KOH (25 g) under nitrogen overnight. The ethanol solvent was then removed under vacuum, and the residue was separated between water and ether. The ethereal solution was discarded. The aqueous solution was acidified to pH=~4, before it was extracted with ether. Then ethereal solution was washed with brine, dried over magnesium sulfate, filtered and concentrated under vacuum to give crude product (7.5 g) as a brown oil. Subsequent flash chromatography with eluent (0%-5%-10% ethyl acetate/dichloromethane) produced 3-mercaptoquinoline (85.1) (5.35 g, 32% yield) as a solid.

$^1$H NMR (DMSO) δ 9.02 (1H, d, J=2.3 Hz), 8.63 (1H, d, J=2.2 Hz), 7.95-8.05 (2H, m), 7.75-8.02 (1H, m), 7.60-7.67 (1H, m).

To a mixture of 3-mercaptoquinoline (85.1)(1.18 g, 7.33 mmol) and 1,2,3-chloro-5-nitrobenzene (1.66 g, 7.33 mmol) dissolved in ethanol (100 mL), was added a THF solution of t-BuOK (7.5 mL, 1M). The mixture was then heated at 80° C. overnight before cooling off. After the removal of ethanol solvent, the mixture was separated between ethyl acetate and water. The organic solution was washed with brine, dried over magnesium sulfate and filtered. The filtrate was then concentrated to give a crude product, which was then flash chromatographed with eluent (10% hexanes/dichloromethane) to afford 85.2 (1.80 g, 70% yield) as a yellow oil.

$^1$H NMR (DMSO) δ 8.75 (1H, d, J=2.3), 8.51 (1H, s), 8.22 (1H, s), 8.01 (1H, d, J=8.4 Hz), 7.92 (1H, d, J=7.6 Hz), 7.74-7.80 (1H, m), 7.60-7.66 (1H, m).

An ethyl acetate solution (100 mL) of 85.2 (1.80 g, 5.1 mmol) and tin chloride(II)dihydrate (6.88 g, 30 mmol) was heated at reflux overnight before cooling off. The solution was then poured into 1N NaOH solution (400 mL). After stirring for 30 min, the mixture was separated, and the organic solution was washed with water, saturated sodium bicarbonate and brine. After drying over magnesium sulfate, the solution was filtered and concentrated under vacuum. The residue was mixed with dichloromethane (10 mL) and sonicated. Subsequent vacuum filtration provided the aniline 85.3 (1.35 g, 82% yield) as an off-white solid.

$^1$H NMR (DMSO) δ 8.61 (1H, d, J=2.4), 7.96 (1H, d, J=8.4 Hz), 7.88 (1H, d, J=8.2 Hz), 7.83 (1H, d, J=2.2 Hz), 7.67-7.72 (1H, m), 7.54-7.60 (1H, m). mp 213.2° C.

Example 86

This illustrates the synthesis of compound 86 (see Table 16).

The aniline 85.3 (250 mg, 0.78 mmol) and 2-chlorobenzenesufonyl chloride (339 mg, 1.60 mmol) were dissolved in a mixed solvent of THF (5 mL) and dichloromethane (5 mL). To the solution was added pyridine (0.185 mL, 2.34 mmol) and catalytic amount of DMAP. The solution was heated at 50° C. to distill off dichloromethane, and then THF with assistance of vacuum. The residue was flash chromatographed with eluent (2.5% ethyl acetate/dichloromethane) to give sulfonamide 86 (302 mg, 78%) as an off-white solid.

$^1$H NMR(DMSO) δ 11.58 (1H, s), 8.61 (1H, d, J=2.4 Hz), 8.19 (1H, d, J=7.6 Hz), 7.83-8.00 (3H, m), 7.67-7.75 (3H, m), 7.56-7.65 (2H, m), 7.31 (2H, s). MS (M+H) 494.9. mp: 219.6° C. Anal. calcd: C, 50.87; H, 2.64; N, 5.65; found C, 50.86; H, 2.62; N, 5.52.

The compounds of Table 16 were prepared by the method of example 86 from compound 84.3 and the corresponding arylsulfonyl chloride.

TABLE 16

| | k | $R_a$ | $R_b$ | $R_c$ | $R_d$ | m/e (M + H) |
|---|---|---|---|---|---|---|
| 86 | 0 | Cl | H | H | H | 495 |
| 87.1 | 0 | Cl | H | Cl | H | 529 |
| 87.2 | 0 | H | H | H | H | 461 |
| 87.3 | 0 | Cl | H | CF$_3$ | H | 561 (M−H) |
| 88.1 | 1 | Cl | H | H | H | 511 |
| 88.2 | 1 | Cl | H | Cl | H | 543 (M−H) |
| 88.3 | 1 | H | H | H | H | 477 |

Example 87

Example 87.1

$^1$H NMR(DMSO) δ 11.66 (1H, broad), 8.63 (1H, d, J=2.3 Hz), 8.18 (1H, d, J=8.6 Hz), 7.85-8.00 (4H, m), 7.70-7.75 (2H, m), 7.57-7.62 (1H, m), 7.32 (2H, s). MS (M+H) 529.0. mp 214.0° C. Elemental Analysis: theory C, 47.56; H, 2.28; N, 5.28; Found C, 47.30; H, 2.36; N, 5.37.

Example 87.2

$^1$H NMR(DMSO): δ 11.22 (1H, s), 8.61 (1H, d, J=2.3 Hz), 7.82-7.98 (5H, m), 7.57-7.75 (5H, m), 7.34 (2H, s). MS (M+H) 461.0. mp 246.8° C. Elemental Analysis theory C, 54.67; H, 3.06; N, 6.07; found C, 54.71; H, 3.05; N, 5.94.

Example 87.3

$^1$H NMR (DMSO) δ 11.70-12.00 (1H, broad), 8.60-8.67 (1H, m), 8.35-8.43 (1H, m), 8.20-8.25 (1H, m), 7.56-8.06 (6H, m), 7.32-7.38 (2H, m). MS (M−H) 560.9. mp: 225.1° C. Elemental Analysis: theory C, 46.86; H, 2.15; N, 4.97; found C, 47.01; H, 2.26; N, 4.98.

Example 88

General Procedure for Sulfur Oxidation to the Sulfoxide:

A naphthylthioether of examples 86 or 87 (0.2 mmol) was dissolved in a mixed solvent of dichloromethane (10 mL) and methanol (5 mL). To the solution was added mCPBA (120 mg, 0.7 mmol, 77% pure) in six batches over 20 minute intervals. Then the solution was washed with 5% sodium thiosulfate solution, 1% sodium bicarbonate solution and brine and then dried over magnesium sulfate. After filtering, the filtrate was concentrated to give a crude product, which was then flash chromatographed with eluent (5%-30% ethyl acetate/dichloromethane) to afford the corresponding sulfoxide.

Example 88.1

$^1$H NMR (DMSO): δ 11.75 (1H, s), 8.82 (1H, s), 8.68 (1H, s), 8.15-8.20 (2H, m), 8.09 (1H, d, J=8.5 Hz), 7.85-7.91 (1H, m), 7.67-7.75 (3H, m), 7.57-7.64 (1H, m), 7.17 (2H, s). MS (M+H) 511. mp 239.5° C. with decomposition. Elemental Analysis: theory C, 49.28; H, 2.56; N, 5.47; found C, 49.30; H, 2.63; N, 5.37.

Example 88.2

$^1$H NMR(DMSO): δ 11.5-12.0 (broad), 8.83 (1H, s), 8.68 (1H, s), 8.15-8.20 (2H, m), 8.09 (1H, d, J=8.5 Hz), 7.85-7.92 (2H, m), 7.55-7.75 (2H, m), 7.17 (2H, s). MS (M−H) 542.9. mp: 234.4. Elemental Analysis: theory C, 46.17; H, 2.21; N, 5.13; found C, 45.97; H, 2.26; N, 4.92.

Example 88.3

$^1$H NMR(DMSO) δ 11.43 (1H, s), 8.81 (1H, s), 8.68 (1H, s), 8.18 (1H, d, J=8.2 Hz), 8.09 (1H, d, J=8.5 Hz), 7.82-7.90 (3H, m), 7.58-7.74 (4H, m), 7.21 (2H, s). MS (M+H) 476.9. mp 261.8° C. with decomposition. Elemental Analysis: theory C, 52.83; H, 2.96; N, 5.87; found C, 52.71; H, 3.05; N, 5.71.

Example 89

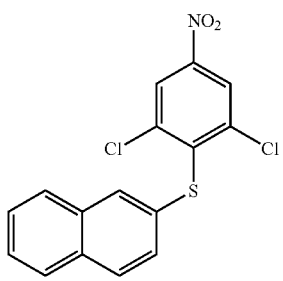

2-(2,6-Dichloro-4-nitro-phenylsulfanyl)-napthalene (89)

2-(2,6-Dichloro-4-nitro-phenylsulfanyl)-napthalene was synthesized (100%) from 3,4,5-trichloronitrobenzene (Acros) and napthalene-2-thiol (Avocado) in a similar manner as described in example 1 using DMSO as solvent instead of DMF.

$^1$H NMR (DMSO-d$_6$) δ 8.48 (s, 2H), 7.95-7.85 (m, 1H), 7.88 (d, J=8.6 Hz, 1H), 7.85-7.8 (m, 1H), 7.75 (d, J=1.8 Hz, 1H), 7.55-7.45 (m, 2H), 7.25 (dd, J=8.7, 2.0 Hz, 1H).

Example 90

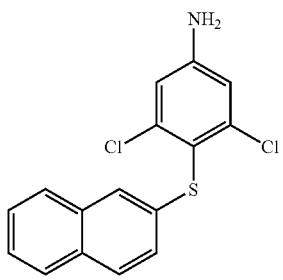

3,5-dichloro-4-(napthalen-2-ylsulfanyl)-phenylamine (90)

To a 0.1M solution 2-(2,6-Dichloro-4-nitro-phenylsulfanyl)-napthalene (89) (774 mg, 2.2 mmol), in EtOAc was added tin(II)chloride dihydrate, obtained from Aldrich, (2.49 g, 11.05 mmol). The resulting mixture was refluxed for 2 hour. The crude reaction mixture was cooled to ambient temperature and excess 2M aqueous NaOH was added and allowed to stir for 15 minutes. Solid tin salts precipitated from the solution, were filtered off through a pad of celite and washed with EtOAc (200 mL). The organic layer was washed twice with brine (200 mL), dried over Na$_2$SO$_4$, and concentrated under vacuum to yield 592 mg (84%) of (90) which was used without further purification.

$^1$H NMR (DMSO-d$_6$) δ 7.88-7.82 (m, 1H), 7.83 (d, J=8.7 Hz, 1H), 7.75 (d, J=7.7 Hz, 1H), 7.5-7.4 (m, 3H), 7.13 (dd, J=8.7, 1.9 Hz, 1H), 6.83 (s, 2H), 6.21 (s, 2H). MS (M−H) 318.

Example 91

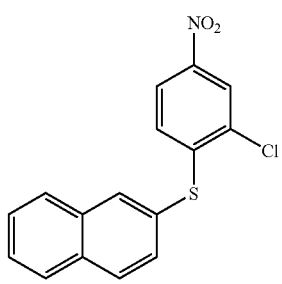

2-(2-Chloro-4-nitro-phenylsulfanyl)-napthalene (91)

2-(2-Chloro-4-nitro-phenylsulfanyl)-napthalene was synthesized (100%) from 3-chloro-4-fluoro-nitrobenzene (Aldrich) and napthalene-2-thiol (Avocado) in a similar manner as described in example 89.

$^1$H NMR (DMSO-d$_6$) δ 8.4-8.34 (m, 2H), 8.14 (d, J=8.6 Hz, 1H), 8.09-8.0 (m, 3H), 7.72-7.6 (m, 3H), 6.88 (d, J=8.9 Hz, 1H).

Example 92

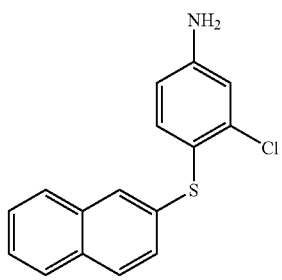

3-chloro-4-(napthalen-2-ylsulfanyl)-phenylamine 3-chloro-4-(napthalen-2-ylsulfanyl)-phenylamine (92) was synthesized (97%) from 2-(2-Chloro-4-nitro-phenylsulfanyl)-napthalene (91) in a similar manner as described in example 90.

$^1$H NMR (DMSO-d$_6$) δ 7.88-7.8 (m, 2H), 7.75 (d, J=7.5 Hz, 1H), 7.5-7.42 (m, 3H), 7.35 (d, J=8.4 Hz, 1H), 7.18 (dd, J=8.6, 1.8 Hz, 1H), 6.82 (d, J=2.4 Hz, 1H), 6.6 (dd, J=8.4, 2.4 Hz, 1H). MS (M+H) 286

Example 93

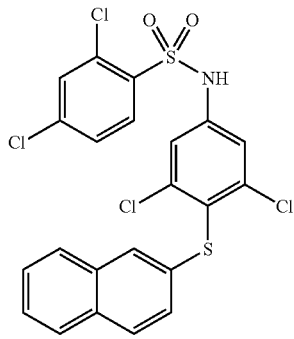

2,4-Dichloro-N-[3,5-dichloro-4-(napthalen-2-ylsulfanyl)-phenyl]-benzenesulfonamide (93)

To a 0.4M solution of 3,5-dichloro-4-(napthalen-2-ylsulfanyl)-phenylamine (90) (153 mg, 0.48 mmol) in THF was added pyridine, obtained from aldrich, (0.19 mL, 2.4 mmol) followed by 2,4-dichlorobenzenesulfonyl chloride, obtained from Maybridge, (129 mg, 0.53 mmol). The resulting mixture was stirred for 6 days. A 1M aqueous solution of HCl (20 mL) was added and the crude reaction mixture was extracted 3× with EtOAc (20 mL). The organic layers were combined and washed once with a brine solution (20 mL), dried over $Na_2SO_4$, and concentrated under vacuum. The crude solid was chromatographed (5-15% EtOAc in hexane) to yield 125 mg (49%) of 93 as an off white solid.

$^1$H NMR (DMSO-$d_6$) δ 11.6 (s, 1H), 8.17 (d, J=8.6 Hz, 1H), 7.96 (d, J=2.1 Hz, 1H), 7.88-7.83 (m, 1H), 7.83 (d, J=8.7 Hz, 1H), 7.76-7.73 (m, 1H), 7.1 (dd, J=8.6, 2.1 Hz, 1H), 7.52-7.44 (m, 3H), 7.32 (s, 2H), 7.21 (s, 2H), 7.1 (dd, J=8.6, 2.0 Hz, 1H). MS (M−H) 526

Example 94

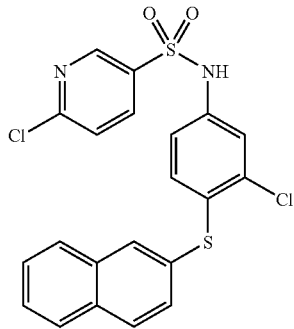

6-Chloro-pyridine-3-sulfonic acid[3-chloro-4-(naphthalen-2-ylsulfanyl)-phenyl]-amide (94)

To a 0.35M solution of 3-chloro-4-(naphthalen-2-ylsulfanyl)-phenylamine (90) (150 mg, 0.53 mmol) in THF was added pyridine (Aldrich, 0.21 mL, 2.63 mmol) followed by 6-chloro-pyridine-3-sulfonyl chloride (Qorpark, 122 mg, 0.58 mmol). The resulting mixture was stirred for 15 hours. A 1M aqueous solution of HCl (20 mL) was added and the crude reaction mixture was extracted 3× with EtOAc (50 mL). The organic layers were combined and washed twice with a brine solution (100 mL), dried over $Na_2SO_4$, and concentrated under vacuum. The crude solid was chromatographed (5-15% EtOAc in hexane) to yield 140 mg (58%) of 94 as a pale yellow solid.

$^1$H NMR (DMSO-$d_6$) δ 10.93 (s, 1H), 8.77 (d, J=2.0 Hz, 1H), 8.19 (dd, J=8.4, 2.6 Hz, 1H), 7.97-7.90 (m, 2H), 7.90-7.84 (m, 2H), 7.78 (d, J=8.4 Hz, 1H), 7.59-7.52 (m, 2H), 7.36 (dd, J=8.6, 1.9 Hz, 1H), 7.29 (d, J=2.1 Hz, 1H), 7.12-7.04 (m, 2H). MS (M−H)

Example 95

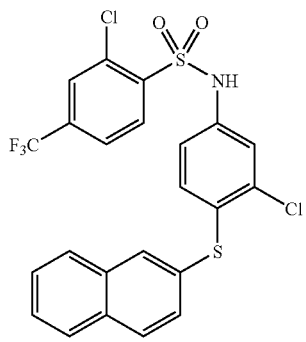

2-Chloro-N-[3-chloro-4-(naphthalen-2-ylsulfanyl)-phenyl]-4-trifluoromethyl-benzenesulfonamide (95)

The title compound was prepared using the method of example 94, starting with 3-chloro-4-(naphthalen-2-ylsulfanyl)-phenylamine (150 mg, 0.53 mmol), pyridine (Aldrich, 0.21 mL, 2.63 mmol) and 2-chloro-4-trifluoromethylbenzenesulfonyl chloride (Maybridge, 162 mg, 0.58 mmol) in THF. 250 mg (90%) of title compound (95) was obtained as a pale yellow solid.

$^1$H NMR (DMSO-$d_6$) δ 11.30 (s, 1H), 8.23 (d, J=8.3 Hz, 1H), 8.18 (d, J=1.6 Hz, 1H), 7.97-7.84 (m, 3H), 7.84-7.80 (m, 2H), 7.58-7.50 (m, 2H), 7.32 (dd, J=8.6, 1.9 Hz, 1H), 7.28 (d, J=2.3 Hz, 1H), 7.11 (d, J=8.6 Hz, 1H), 7.04 (dd, J=8.6, 2.3 Hz, 1H). MS (M−H) 526

Example 96

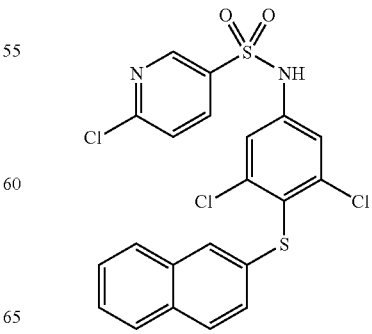

6-Chloro-pyridine-3-sulfonic acid[3,5-dichloro-4-(naphthalen-2-ylsulfanyl)-phenyl]-amide (96)

The title compound was prepared using the method of example 94, starting with 3,5-dichloro-4-(naphthalen-2-yl-sulfanyl)-phenylamine (90) (150 mg, 0.47 mmol), pyridine (Aldrich, 0.19 mL, 2.34 mmol) and 6-chloro-pyridine-3-sulfonyl chloride (Qorpark, 109 mg, 0.52 mmol) in THF. 130 mg (56%) of 96 was obtained as a pale yellow solid.

$^1$H NMR (DMSO-$d_6$) δ 11.40 (br s, 1H), 8.88 (d, J=1.9 Hz, 1H), 8.28 (dd, J=8.4, 1.6 Hz, 1H), 7.88-7.80 (m, 3H), 7.76 (d, J=9.1, 1.8 Hz, 1H), 7.52-7.42 (m, 3H), 7.38 (s, 2H), 7.14 (dd, J=8.7, 2.0 Hz, 1H). MS (M–H) 493

Example 97

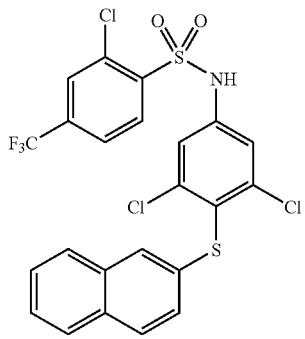

2-Chloro-N-[3,5-dichloro-4-(naphthalen-2-ylsulfa-nyl)-phenyl]-4-trifluoromethyl-benzenesulfonamide (97)

The title compound was prepared using the method of example 94, starting with 3,5-dichloro-4-(naphthalen-2-yl-sulfanyl)-phenylamine (90) (150 mg, 0.47 mmol), pyridine (Aldrich, 0.19 mL, 2.34 mmol) and 2-chloro-4-trifluorom-ethylbenzenesulfonyl chloride (Maybridge, 144 mg, 0.52 mmol) in THF. 137 mg (52%) of 97 was obtained as a pale yellow solid.

$^1$H NMR (DMSO-$d_6$) δ 8.38 (d, J=8.0 Hz, 1H), 8.21 (d, J=1.4 Hz, 1H), 8.01 (dd, J=8.4, 1.1 Hz, 1H), 7.88-7.80 (m, 2H), 7.76-7.71 (m, 1H), 7.51-7.42 (m, 2H), 7.34 (s, 2H), 7.12 (dd, J=8.6, 2.0 Hz, 1H). MS (M–H) 560

Example 98

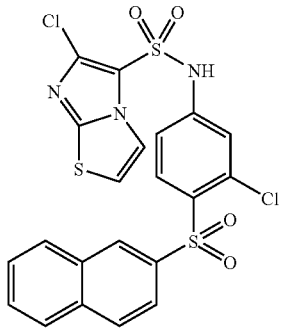

6-Chloro-imidazo[2,1-b]thiazole-5-sulfonic acid[3-chloro-4-(naphthalen-2-ylsulfanyl)-phenyl]-amide (98)

The title compound was prepared using the method of example 94, starting with 3-chloro-4-(naphthalen-2-ylsulfa-nyl)-phenylamine (92) (150 mg, 0.53 mmol), pyridine (Aldrich, 0.21 mL, 2.63 mmol) and 6-chloro-imidazo[2,1-b]thia-zole-5-sulfonyl chloride (Maybridge, 149 mg, 0.58 mmol) in THF. 172 mg (65%) of 98 was obtained as a pale yellow solid.

$^1$H NMR (DMSO-$d_6$) δ 11.26 (s, 1H), 7.98 (d, J=4.4 Hz, 1H), 7.96-7.88 (m, 2H), 7.88-7.84 (m, 2H), 7.68 (d, J=2.4 Hz, 1H), 7.58-7.52 (m, 2H), 7.33-7.28 (m, 2H), 7.14 (d, J=8.5 Hz, 1H), 7.01 (dd, J=8.5, 2.4 Hz, 1H), 7.04 (dd, J=8.6, 2.3 Hz, 1H). MS (M–H) 504

Example 99

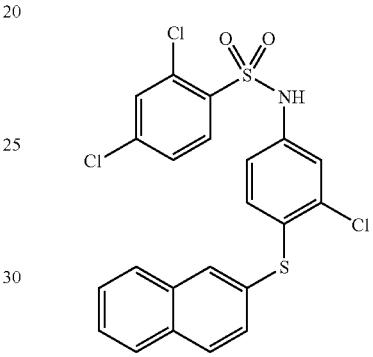

2,4-Dichloro-N-[3-chloro-4-(napthalen-2-ylsulfa-nyl)-phenyl]-benzene sulfonamide (99)

2,4-Dichloro-N-[3-chloro-4-(naphthalen-2-ylsulfanyl)-phenyl]-benzene sulfonamide was synthesized (67%) from 3-chloro-4-(naphthalen-2-ylsulfanyl)-phenylamine (92) and 2,4-dichlorobenzenesulfonyl chloride, obtained from Maybridge, in a similar manner as described in example 93.

$^1$H NMR (DMSO-$d_6$) δ 11.1 (s, 1H), 8.06 (d, J=8.6 Hz, 1H), 7.95-7.88(m, 3H), 7.86-7.81 (m, 2H), 7.65 (dd, J=8.4 Hz, 1H), 7.57-7.51 (m, 2H), 7.31 (dd, J=8.6, 1.9 Hz, 1H), 7.26 (d, J=2.2 Hz, 1H), 7.12 (d, J=8.7 Hz, 1H), 7.03 (dd, J=8.6, 2.3 Hz, 1H). MS (M–H) 492

Example 100

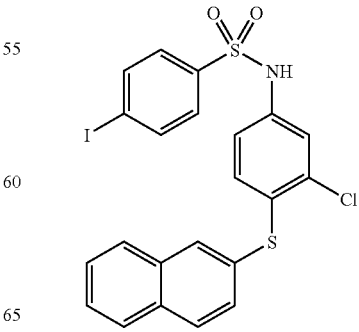

N-[3-Chloro-4-(naphthalen-2-ylsulfanyl)-phenyl]-4-iodo-benzenesulfonamide (100)

The title compound was prepared using the method of example 94, starting with 3-chloro-4-(naphthalen-2-ylsulfanyl)-phenylamine (92) (150 mg, 0.53 mmol), pyridine (Aldrich, 0.21 mL, 2.63 mmol) and 4-iodobenzenesulfonyl chloride (Acros, 175 mg, 0.58 mmol) in THF. 153 mg (53%) of 100 was obtained as a pale yellow solid.

$^1$H NMR (DMSO-d$_6$) δ 10.75 (s, 1H), 8.01-7.95 (m, 2H), 7.95-7.89 (m, 2H), 7.87-7.82 (m, 2H), 7.59-7.50 (m, 4H), 7.32 (dd, J=8.6, 1.9 Hz, 1H), 7.26 (d, J=2.3 Hz, 1H), 7.13 (d, J=8.6 Hz, 1H), 7.04 (dd, J=8.5, 2.2 Hz, 1H). MS (M−H) 550

Example 101

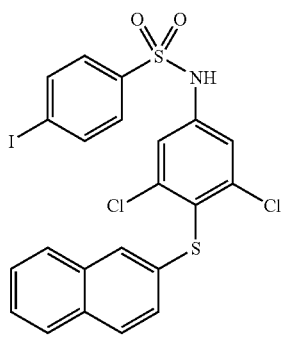

N-[3,5-Dichloro-4-(naphthalen-2-ylsulfanyl)-phenyl]-4-iodo-benzenesulfonamide (101)

The title compound was prepared using the method of example 94, starting with 3,5-dichloro-4-(naphthalen-2-ylsulfanyl)-phenylamine (90) (150 mg, 0.47 mmol), pyridine (Aldrich, 0.19 mL, 2.34 mmol) and 4-iodobenzenesulfonyl chloride (Acros, 155 mg, 0.52 mmol) in THF. 254 mg (93%) of 101 was obtained as a pale yellow solid.

$^1$H NMR (DMSO-d$_6$) δ 11.22 (s, 1H), 8.08-8.02 (m, 2H), 7.88-7.82 (m, 2H), 7.74 (d, J=7.7 Hz, 1H), 7.65-7.58 (m, 2H), 7.52-7.40 (m, 3H), 7.35 (s, 2H), 7.12 (dd, J=8.7, 1.9 Hz, 1H). MS (M−H) 584

Example 102

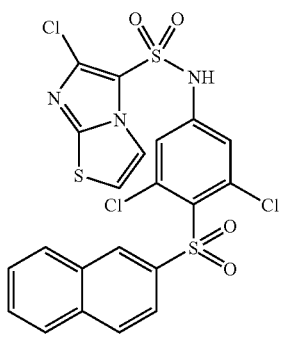

6-Chloro-imidazo[2,1-b]thiazole-5-sulfonic acid[3,5-dichloro-4-(naphthalen-2-ylsulfanyl)-phenyl]-amide (102)

The title compound was prepared using the method of example 94, starting with 3,5-dichloro-4-(naphthalen-2-ylsulfanyl)-phenylamine (90) (150 mg, 0.47 mmol), pyridine (Aldrich, 0.19 mL, 2.34 mmol) and 6-chloro-imidazo[2,1-b]thiazole-5-sulfonyl chloride (Maybridge, 132 mg, 0.52 mmol) in THF. 172 mg (65%) of 102 was obtained as a pale yellow solid.

$^1$H NMR (DMSO-d$_6$) δ 11.71 (br s, 1H), 8.02 (d, J=4.4 Hz, 1H), 7.89-7.82 (m, 2H), 7.77 (m, 1H), 7.72 (d, J=4.4 Hz, 1H), 7.52-7.432 (m, 3H), 7.35 (s, 2H), 7.11 (dd, J=8.7, 2.0 Hz, 1H). MS (M−H) 504

Example 103

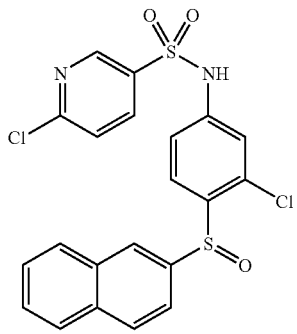

6-Chloro-pyridine-3-sulfonic acid[3-chloro-4-(naphthalene-2-sulfinyl)-phenyl]-amide (103)

To a solution of 6-Chloro-pyridine-3-sulfonic acid[3-chloro-4-(naphthalen-2-ylsulfanyl)-phenyl]-amide (94, 55 mg, 0.12 mmol) in CH$_2$Cl$_2$ (2 mL), was added dropwise a solution of m-chloroperoxybenzoic acid (mCPBA, Aldrich, 36 mg, 0.12 mmol) in CH$_2$Cl$_2$ (1 mL). The resulting mixture was stirred at ambient temperature for 1 hour and diluted with EtOAc (60 mL). The organic layer was washed with saturated aqueous NaHCO$_3$ solution (50 mL), twice with brine solution (50 mL), dried over Na$_2$SO$_4$, and concentrated under vacuum. The crude solid was chromatographed (10-25% EtOAc in hexane) to yield 17 mg (30%) of 103 as an off white solid.

$^1$H NMR (DMSO-d$_6$) δ 11.25 (s, 1H), 8.82 (d, J=2.6 Hz, 1H), 8.43 (d, J=1.5 Hz, 1H), 8.19 (dd, J=8.4, 2.6 Hz, 1H), 8.10 (m, 1H), 8.04 (d, J=8.5 Hz, 1H), 7.98 (m, 1H), 7.88 (d, J=8.7 Hz, 1H), 7.74 (d, J=8.5 Hz, 1H), 7.70-7.60 (m, 2H), 7.53 (dd, J=8.7, 1.8 Hz, 1H), 7.40 (dd, J=8.5, 2.2 Hz, 1H), 7.19 (d, J=2.1 Hz, 1H). MS (M−H) 475

Example 104

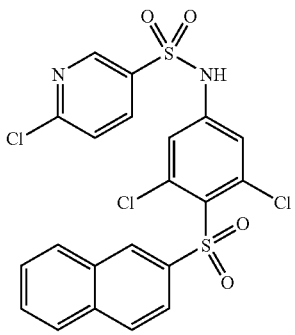

6-Chloro-pyridine-3-sulfonic acid[3,5-dichloro-4-(naphthalene-2-sulfonyl)-phenyl]-amide (104)

To a solution of 6-Chloro-pyridine-3-sulfonic acid[3,5-dichloro-4-(naphthalen-2-ylsulfanyl)-phenyl]-amide (96, 20 mg, 0.04 mmol) in $CH_2Cl_2$ (1 mL), was added dropwise a solution of mCPBA (Aldrich, 36 mg, 0.12 mmol) in $CH_2Cl_2$ (1 mL). The resulting mixture was stirred at ambient temperature overnight and diluted with EtOAc (60 mL). The organic layer was washed twice with 5% aqueous Na2S2O3 solution (20 mL), twice with 1% aqueous $NaHCO_3$ solution (20 mL), and brine solution (20 mL), dried over $Na_2SO_4$. Removal of the solvent under vacuum gave 21 mg (99%) of 104 as an off white solid.

$^1$H NMR (DMSO-$d_6$) δ 8.68 (d, J=2.5 Hz, 1H), 8.58 (d, J=1.8 Hz, 1H), 8.22 (d, J=8.1 Hz, 1H), 8.12-8.05 (m, 2H), 8.02 (d, J=8.0 Hz, 1H), 7.79 (dd, J=8.7, 2.0 Hz, 1H), 7.76-7.64 (m, 2H), 7.58 (d, J=8.4 Hz, 1H), 6.93 (s, 2H). MS (M−H) 525

Example 105

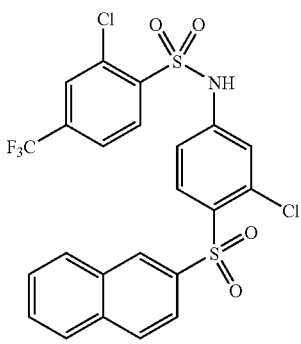

2-Chloro-N-[3-chloro-4-(naphthalene-2-sulfonyl)-phenyl]-4-trifluoromethyl-benzenesulfonamide (105)

The title compound was prepared using the method of example 104, starting with 2-Chloro-N-[3-chloro-4-(naphthalen-2ylsulfanyl)-phenyl]-4-trifluoromethylbenzene-sulfonamide (95, 35 mg, 0.066 mmol), mCPBA (Aldrich, 100 mg, 0.33 mmol) in $CH_2Cl_2$. 38 mg (100%) of 105 was obtained as an off white solid.

$^1$H NMR (DMSO-$d_6$) δ 11.90 (br s, 1H), 8.62 (d, J=1.8 Hz, 1H), 8.28 (d, J=8.1 Hz, 1H), 8.20 (d, J=8.1 Hz 1H), 8.16-8.00 (m, 4H), 7.90 (d, J=8.5 Hz, 1H), 7.77-7.64 (m, 3H), 7.20 (d, J=9.0 Hz, 1H), 7.09 (s, 1H). MS (M−H) 558

Example 106

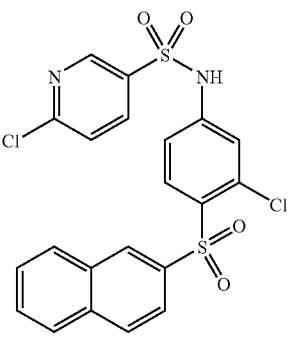

6-Chloro-pyridine-3-sulfonic acid[3-chloro-4-(naphthalene-2-sulfonyl)-phenyl]-amide (106)

The title compound was prepared using the method of example 104, starting with 6-Chloro-pyridine-3-sulfonic acid [3-chloro-4-(naphthalen-2-ylsulfanyl)-phenyl]-amide (94, 15 mg, 0.03 mmol), mCPBA (Aldrich, 50 mg, 0.15 mmol) in $CH_2Cl_2$. 16 mg (100%) of 106 was obtained as an off white solid.

$^1$H NMR (DMSO-$d_6$) δ 11.60 (br s, 1H), 8.82 (d, J=2.5 Hz, 1H), 8.62 (d, J=1.8 Hz, 1H), 8.24-8.16 (m, 2H), 8.14 (d, J=8.8 Hz, 1H), 8.08 (d, J=8.8 Hz, 1H), 8.03 (d, J=8.4 Hz, 1H), 7.76-7.64 (m, 4H), 7.27 (dd, J=8.8, 2.0 Hz, 1H), 7.10 (d, J=2.1 Hz, 1H). MS (M−H) 491

Example 107

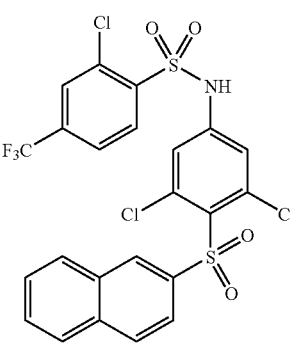

2-Chloro-N-[3,5-dichloro-4-(naphthalene-2-sulfonyl)-phenyl]-4-trifluoromethyl-benzenesulfonamide (107)

The title compound was prepared using the method of example 104, starting with 2-Chloro-N-[3,5-dichloro-4-(naphthalen-2-ylsulfanyl)-phenyl]-4-trifluoromethylbenzene-sulfonamide (97, 30 mg, 0.05 mmol), mCPBA (Aldrich, 80 mg, 0.26 mmol) in CH$_2$Cl$_2$. 32 mg (100%) of 107 was obtained as an off white solid.

$^1$H NMR (DMSO-d$_6$) δ 8.59 (d, J=1.1 Hz, 1H), 8.22 (d, J=8.1 Hz, 1H), 8.15 (d, J=8.1 Hz, 1H), 8.10 (d, J=8.6 Hz, 1H), 8.03 (d, J=8.1 Hz, 1H), 7.90 (s, 1H), 7.84-7.77 (m, 2H), 7.75-7.64 (m, 2H), 6.92 (s, 2H). MS (M−H) 592

Example 108

This example illustrates the preparation of 108.1 through 108.6.

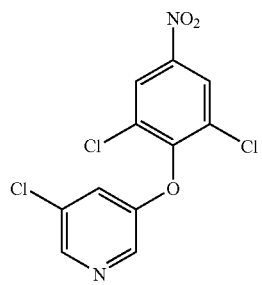

108.1

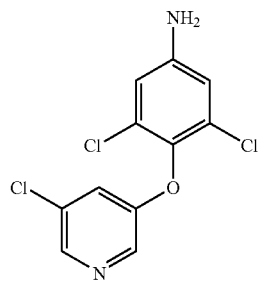

108.2

A solution of potassium t-butoxide (1 M in THF; 26.5 mL) was added to a solution of 3,4,5-trichloronitrobenzene (3 g) and 5-chloro-3-hydroxypyridine (1.7 g) in THF (15 mL). The deep red solution was heated at 50° C. overnight, then poured into water. The precipitate was collected by filtration and purified by chromatography on silica (10% ethyl acetate/hexanes as eluant) to provide 108.1.

$^1$H NMR (400 MHz) (DMSO-d$_6$) δ 8.58 (s, 2H); 8.47 (d, J=2 Hz, 1H); 8.41 (d, J=2.6 Hz, 1H); 7.72 (dd, J=2.6, 2 Hz, 1H).

Using the method of Example 2, 108.1 (2.2 g) was converted to the aniline 108.2.

$^1$H NMR (400 MHz) (DMSO-d$_6$) δ 8.35 (d, J=2 Hz, 1H); 8.21 (d, J=2.5 Hz, 1H); 7.37 (dd, J=2.5, 2 Hz, 1H); 6.73 (s, 2H); 5.78 (br s, 2H).

The compounds provided in Table 17 were prepared using 108.2 and commercially available substituted benzenesulfonyl chlorides and/or using the intermediates and methods described in the examples above.

TABLE 17

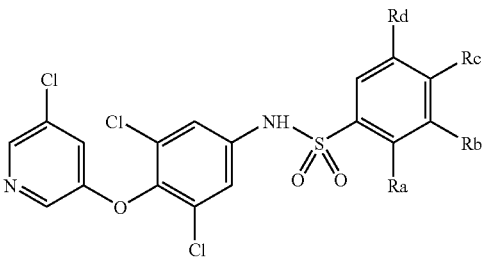

| | Ra | Rb | Rc | Rd | mp (° C.) |
|---|---|---|---|---|---|
| 108.3 | H | Cl | Cl | H | 199-200 |
| 108.4 | Cl | H | Cl | H | 166-169 |
| 108.5 | H | H | I | H | 211-214 |
| 108.6 | Cl | H | CF$_3$ | H | 185-189 |

Example 109

This example illustrates the synthesis of 109.1.

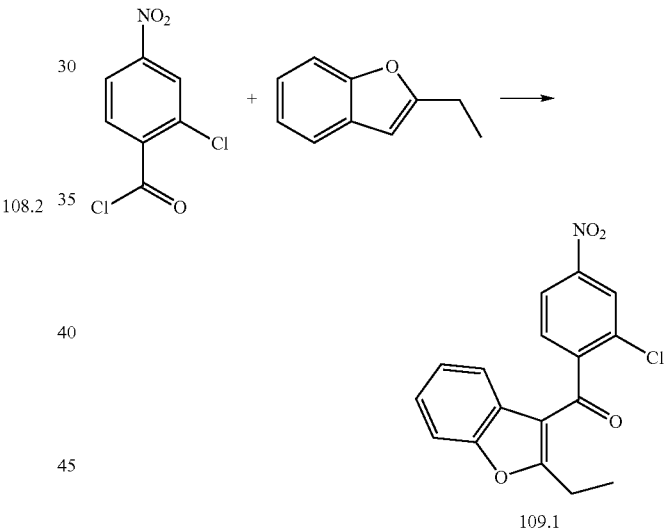

A round-bottomed flask was charged with 2-chloro-4-nitrobenzoyl chloride (3.50 g, 15.9 mmol), 2-ethylbenzofuran (2.11 g, 14.4 mmol), and anhydrous methylene chloride (20 mL). This was cooled in an ice/water bath and titanium tetrachloride (5.49 g, 28.9 mmol) was added in a dropwise fashion with vigorous stirring. After addition was complete, the reaction was stirred at 0° C. for 20 minutes and then was warmed to room temperature for an additional four hours. The reaction was then diluted with 80 mL of methylene chloride and washed twice with 50 mL volumes of 2N HCl and then once with 50 mL of brine. The organics were dried over Na$_2$SO$_4$ and concentrated to a yellow oil. This oil was further purified using silica gel flash chromatography (eluting with 20% hexanes in methylene chloride). The desired fractions were concentrated to give 2.9 g (61%) of ketone 109.1 as an off-white solid.

MS ESI m/e: 330.0 (M+H).

Example 110

(2,6-Dichloro-4-nitro-phenyl)-acetic acid (110)

To a solution of diethyl malonate (Aldrich, 13.8 mL, 90 mmol) in DMF (60 mL) was added cesium carbonate (Aldrich, 48.9 g, 150 mmol). The mixture was heated to 70° C. and then was added 1,2,3-trichloro-5-nitrobenzene (Aldrich, 13.56 g, 60 mmol). The mixture was stirred at 70° C. for 3 hours and cooled to room temperature. A 2M aqueous solution of HCl (50 mL) was added and the crude reaction mixture was extracted 3× with EtOAc (150 mL). The organic layers were combined and washed twice with a brine solution (150 mL), dried over $Na_2SO_4$, and concentrated under vacuum. The light yellow oil was used for the next reaction without further purification.

The light yellow oil was suspended in 90 mL of 6 N aqueous HCl. The mixture was refluxed overnight (15 hours). The mixture was cooled in the ice bath for 2 hours and filtered. The crude solid product was triturated with $CH_2Cl_2$/Hexanes to give compound 110 (11.5 g, 77%) as pale brown solid.

$^1$H NMR (DMSO-$d_6$) δ 13.00 (br s, 1H), 8.23 (s, 2H), 4.16 (s, 2H).

Example 111

(2-Chloro-4-nitro-phenyl)-acetic acid (111)

The title compound was prepared using the method of example 110, starting with diethyl malonate (Aldrich, 30.5 mL, 200 mmol), 3,4-dichloronitrobenzene (Aldrich, 19.2 g, 100 mmol), cesium carbonate (Aldrich, 81.5 g, 250 mmol) and 150 mL of aqueous 6N HCl solution. 18.8 g (87%) of compound 111 was obtained as pale yellow solid.

$^1$H NMR (DMSO-$d_6$) δ 12.80 (br s, 1H), 8.29 (d, J=2.4 Hz, 1H), 8.18 (dd, J=8.4, 2.4 Hz, 1H), 7.73 (d, J=8.4 Hz, 1H), 3.90 (s, 2H).

Example 112

2-Amino-4-chloro-benzenethiol hydrochloride (112)

By the procedure of R. L. Danley and D. A. Zazaris (Can. J. Chem. 43, 2610-2612 (1965) sodium tetrasulfide was obtained by dissolving sulfur (Aldrich, 9.6 g, 300 mmol) in molten sodium sulfide nonahydrate (Aldrich, 24.0 g, 100 mmol). This hot liquid was added to a solution of 2,5-dichloronitrobenzene (Aldrich, 38.4 g, 200 mmol) in 95% ethanol (140 mL). After the exothermic reaction had ceased, the mixture was refluxed for 2 hours and filtered while hot. The precipitate was washed with water (50 mL) and ethanol (50 mL) to give 37.7 g of intermediate trisulfide as a yellow solid.

$^1$H NMR (CDCl$_3$) δ 8.83 (d, J=2.3 Hz, 1H), 7.76 (d, J=8.6 Hz, 1H), 7.55 (dd, J=8.6, 2.3 Hz, 1H).

Concentrated hydrochloric acid (125 mL) was slowly (overnight, 15 hours) added to a well-stirred suspension of the trisulfide (37.7 g) described above and tin (Aldrich, 88 g, 737 mmol) in 95% ethanol (200 mL). After filtration of the hot solution, the filtrate was allowed to stand at room temperature overnight to precipitate the crude product. The precipitate was collected by filtration, washed with 1:1 ethanol/concentrated HCl. Recrystalization from 1:1 MeOH/concentrated HCl gave compound 112 (13.8 g) as white needles.

$^1$H NMR (DMSO-$d_6$) δ 6.96 (d, J=8.3 Hz, 1H), 6.86 (d, J=2.3 Hz, 1H), 6.50 (dd, J=8.3, 2.3 Hz, 1H).

Example 113

2-Amino-4-methyl-benzenethiol hydrochloride (113)

bis-(4-Methyl-2-nitrophenyl)-trisulfide was prepared using the method in example 112, starting from 4-chloro-3-nitro-toluene (Aldrich, 34.3 g, 200 mmol), sulfur (Aldrich, 9.6 g, 300 mmol) and sodium sulfide nonahydrate (Aldrich, 24.0 g, 100 mmol) in 95% EtOH (150 mL). 27.7 g of the trisulfide was obtained as a yellow solid.

$^1$H NMR (400 MHz, CDCl$_3$) δ 8.21 (d, J=8.3 Hz, 1H), 8.07 (br s, 1H), 7.58 (dd, J=8.3, 1.3 Hz, 1H), 2.48 (s, 3H).

Reduction of the bis-(4-Methyl-2-nitrophenyl)trisulfide as in example 112 gave compound 113 (11.3 g) as a mixture after recrystalization, but which was used directly in subsequent reactions.

Example 114

5-Chloro-2-(2,6-dichloro-4-nitro-benzyl)-benzothiazole (114)

By a modification of the procedure of D. L. Boger (J. Org. Chem. 43, 2296-2297 (1978) a solution of $P_2O_5$/MeSO$_3$H (Aldrich, 7.5 g, 1:10, w:w) was treated with 2-amino-4-chloro-benzenethiol hydrochloride (example 112, 1.96 g, 10.0 mmol) and (2,6-dichloro-4-nitro-phenyl)-acetic acid (example 110, 2.50 g, 10.0 mmol). The resulting mixture was stirred at room temperature for 1 hour, then heated at 90° C. overnight (15 hours). After cooled to room temperature, the reaction mixture was poured to ice and the resulting mixture was extracted 3× with EtOAc (50 mL). The organic layers were combined and washed twice with a brine solution (100 mL), dried over $Na_2SO_4$, and concentrated under vacuum. The crude solid was chromatographed (CH$_2$Cl$_2$) to yield 3.7 g (99%) of compound 114 as a pale yellow solid.

$^1$H NMR (CDCl$_3$) δ 8.28 (s, 2H), 7.98 (d, J=1.9 Hz, 1H), 7.76 (d, J=8.5 Hz, 1H), 7.38 (dd, J=8.5, 1.9 Hz, 1H), 4.87 (s, 2H). MS (M+H) 373

The compounds of Table 18 were prepared using the method of example 114.

TABLE 18

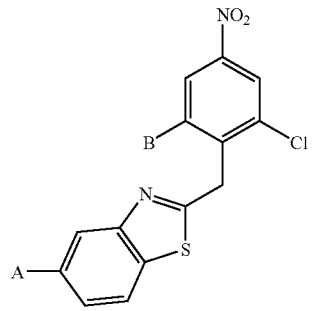

| Example | A | B | yield |
|---------|-----|-----|------|
| 114 | Cl | Cl | 99% |
| 115 | Cl | H | 98% |
| 116 | CF$_3$ | Cl | 96% |
| 117 | CF$_3$ | H | 89% |
| 118 | H | Cl | 92% |
| 119 | H | H | 77% |
| 120 | Me | Cl | 20% |
| 121 | Me | H | 28% |

Example 115

5-Chloro-2-(2-chloro-4-nitro-benzyl)-benzothiazole

¹H NMR (400 MHz, DMSO-d₆) δ 8.35 (d, J=2.3 Hz, 1H), 8.25 (dd, J=8.5, 2.4 Hz, 1H), 8.10 (d, J=8.6 Hz, 1H), 8.02 (d, J=2.0 Hz, 1H), 7.89 (d, J=8.5 Hz, 1H), 7.48 (dd, J=8.6, 2.0 Hz, 1H), 4.77 (s, 2H). MS (M+H) 339

Example 116

2-(2,6-Dichloro-4-nitro-benzyl)-5-trifluoromethyl-benzothiazole

¹H NMR (DMSO-d₆) δ 8.42 (s, 2H), 8.34 (d, J=8.4 Hz, 1H), 8.28 (br s, 1H), 7.76 (d, J=8.4 Hz, 1H), 4.94 (s, 2H). MS (M+H) 407

Example 117

2-(2-Chloro-4-nitro-benzyl)-5-trifluoromethyl-benzothiazole

¹H NMR (CDCl₃) δ 8.33 (d, J=2.3 Hz, 1H), 8.27 (br s, 1H), 8.14 (dd, J=8.5, 2.3 Hz, 1H), 7.96 (br d, J=8.3 Hz, 1H), 7.63 (d, J=8.5 Hz, 2H) 4.70 (s, 2H). MS (M+H) 371

Example 118

2-(2,6-Dichloro-4-nitro-benzyl)-benzothiazole

¹H NMR (DMSO-d₆) δ 8.41 (s, 2H), 8.06 (d, J=8.0 Hz, 1H), 7.90 (d, J=7.9 Hz, 1H), 7.50-7.38 (m, 2H), 4.94 (s, 2H). MS (M−H) 337

Example 119

2-(2-Chloro-4-nitro-benzyl)-benzothiazole

¹H NMR (CDCl₃) δ 8.35 (d, J=2.2 Hz, 1H), 8.25 (dd, J=8.4, 2.2 Hz, 1H), 8.05 (d, J=7.9 Hz, 1H), 7.93 (d, J=8.1 Hz, 1H), 7.86 (d, J=8.5 Hz, 1H), 7.49 (t, J=7.9 Hz, 1H), 7.42 (t, J=7.6 Hz, 1H), 4.76 (s, 2H). MS (M+H) 305

Example 120

2-(2,6-Dichloro-4-nitro-benzyl)-5-methyl-benzothiazole

¹H NMR (DMSO-d₆) δ 8.41 (s, 2H), 7.91 (d, J=8.2 Hz, 1H), 7.71 (br s, 1H), 7.25 (d, J=8.2 Hz, 1H), 4.85 (s, 2H), 2.41 (s, 3H). MS (M+H) 353.

Example 121

2-(2-Chloro-4-nitro-benzyl)-5-methyl-benzothiazole

¹H NMR (DMSO-d₆) δ 8.35 (d, J=2.3 Hz, 1H), 8.24 (dd, J=8.5, 2.3 Hz, 1H), 7.91 (d, J=8.2 Hz, 1H), 7.85 (d, J=8.5 Hz, 1H), 7.74 (br s, 1H), 7.25 (dd, J=8.2, 1.0 Hz, 1H), 4.73 (s, 2H), 2.42 (s, 3H). MS (M−H) 317

Reduction of the compounds of Table 18 gave the anilines of Table 19.

TABLE 19

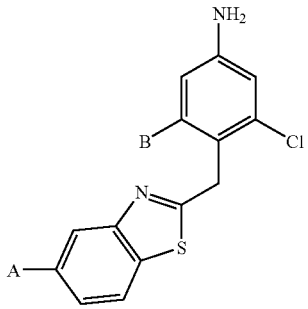

| Example | A | B | Method | yield |
|---|---|---|---|---|
| 122 | Cl | Cl | A | 100% |
| 123 | Cl | H | B | 88% |
| 124 | CF₃ | Cl | A | 90% |
| 125 | CF₃ | H | B | 89% |
| 126 | H | Cl | B | 97% |
| 127 | H | H | B | 90% |
| 128 | Me | Cl | B | 97% |
| 129 | Me | H | B | 97% |

Method A: see example 90
Method B: see example 181

Example 122

3,5-Dichloro-4-(5-chloro-benzothiazol-2-ylmethyl)-phenylamine

¹H NMR (DMSO-d₆) δ 8.03 (d, J=8.4 Hz, 1H), 8.01 (d, J=2.1 Hz, 1H), 7.45 (dd, J=8.5, 2.2 Hz, 1H), 6.70 (s, 2H), 5.79 (s, 2H), 4.52 (s, 2H). MS (M+H) 343

Example 123

3-Chloro-4-(5-chloro-benzothiazol-2-ylmethyl)-phenylamine

¹H NMR (DMSO-d₆) δ 8.05-7.95 (m, 2H), 7.43 (dd, J=8.5, 2.1 Hz, 1H), 7.17 (d, J=8.2 Hz, 1H), 6.66 (d, J=2.2 Hz, 1H), 6.53 (dd, J=8.2, 2.2 Hz, 1H), 5.44 (s, 2H), 4.36 (s, 2H). MS (M+H) 309.

Example 124

3,5-Dichloro-4-(5-trifluoromethyl-benzothiazol-2-ylmethyl)-phenylamine

¹H NMR (DMSO-d₆) δ 8.29 (br s, 1H), 8.26 (d, J=8.4 Hz, 1H), 7.72 (d, J=8.4 Hz, 1H), 6.70 (s, 2H), 5.81 (s, 2H), 4.56 (s, 2H). MS (M+H) 377

Example 125

3-Chloro-4-(5-trifluoromethyl-benzothiazol-2-ylmethyl)-phenylamine

¹H NMR (DMSO-d₆) δ 8.25 (br s, 1H), 8.26 (d, J=8.4 Hz, 1H), 7.72 (dd, J=8.4, 1.3 Hz, 1H), 7.19 (d, J=8.2 Hz, 1H), 6.67 (d, J=2.2 Hz, 1H), 6.54 (dd, J=8.2, 2.2 Hz, 1H), 5.46 (s, 2H), 4.40 (s, 2H). MS (M+H) 343

Example 126

4-Benzothiazol-2-ylmethyl-3,5-dichloro-phenylamine $^1$H NMR (DMSO-d$_6$) δ 7.99 (dd, J=8.0, 0.6 Hz, 1H), 7.92 (d, J=8.1 Hz, 1H), 7.45 (td, J=8.2, 1.2 Hz, 1H), 7.38 (td, J=8.0, 1.0 Hz, 1H), 6.70 (s, 2H), 5.78(s, 2H), 4.51 (s, 2H). MS (M+H) 309.

Example 127

4-Benzothiazol-2-ylmethyl-3-chloro-phenylamine $^1$H NMR (DMSO-d$_6$) δ 7.98 (d, J=8.0 Hz, 1H), 7.92 (d, J=8.0 Hz, 1H), 7.47 (td, J=7.9, 1.2 Hz, 1H), 7.38 (td, J=7.9, 1.0 Hz, 1H), 7.17 (d, J=8.3 Hz, 1H), 6.66 (d, J=2.2 Hz, 1H), 6.54 (dd, J=8.2, 2.2 Hz, 1H), 5.44 (s, 2H), 4.35 (s, 2H). MS (M+H) 275

Example 128

3,5-Dichloro-4-(5-methyl-benzothiazol-2-ylmethyl)-phenylamine $^1$H NMR (DMSO-d$_6$) δ 7.84 (d, J=8.2 Hz, 1H), 7.73 (br s, 1H), 7.21 (dd, J=8.2, 1.0 Hz, 1H), 6.69 (s, 2H), 5.77 (s, 2H), 4.48 (s, 2H), 2.43 (s, 3H). MS (M+H) 323.

Example 129

3-Chloro-4-(5-methyl-benzothiazol-2-ylmethyl)-phenylamine $^1$H NMR (DMSO-d$_6$) δ 7.84 (d, J=8.2 Hz, 1H), 7.73 (s, 1H), 7.21 (d, J=8.2 Hz, 1H), 7.15 (d, J=8.2 Hz, 1H), 6.65 (d, J=2.1 Hz, 1H), 6.52 (dd, J=8.2, 2.1 Hz, 1H), 5.41 (s, 2H), 4.32 (s, 2H), 2.43 (s, 3H). MS (M+H) 289.

The compounds of Table 20 were prepared using the method of example 94 from compounds in Table 19 and corresponding arylsulfonyl chloride.

TABLE 20

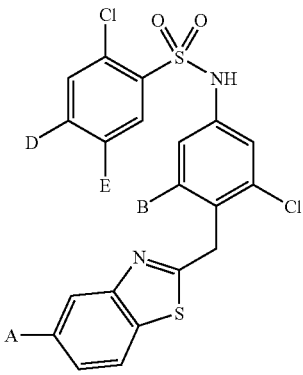

| Example | A | B | D | E | yield |
|---|---|---|---|---|---|
| 130 | Cl | Cl | CF$_3$ | H | 83% |
| 131 | Cl | Cl | Cl | H | 63% |
| 132 | Cl | Cl | Cl | Me | 73% |
| 133 | Cl | H | CF$_3$ | H | 78% |
| 134 | CF$_3$ | Cl | CF$_3$ | H | 74% |
| 135 | CF$_3$ | Cl | Cl | H | 82% |
| 136 | CF$_3$ | H | CF$_3$ | H | 55% |
| 137 | CF$_3$ | H | Cl | H | 26% |
| 138 | H | Cl | CF$_3$ | H | 67% |
| 139 | H | Cl | Cl | H | 55% |
| 140 | H | Cl | Cl | Me | 85% |
| 141 | H | H | CF$_3$ | H | 64% |
| 142 | Me | Cl | CF$_3$ | H | 84% |
| 143 | Me | H | CF$_3$ | H | 88% |

Example 130

2-Chloro-N-[3,5-dichloro-4-(5-chloro-benzothiazol-2-ylmethyl)-phenyl]-4-trifluoromethyl-benzenesulfonamide $^1$H NMR (DMSO-d$_6$) δ 11.56 (br s, 1H), 8.35 (d, J=8.2 Hz, 1H), 8.20 (d, J=1.1 Hz, 1H), 8.03 (d, J=8.6 Hz, 1H), 8.00-7.95 (m, 2H), 7.45 (dd, J=8.6, 2.1 Hz, 1H), 7.23 (s, 2H), 4.62 (s, 2H). MS (M−H) 583

Example 131

2,4-Dichloro-N-[3,5-dichloro-4-(5-chloro-benzothiazol-2-ylmethyl)-phenyl]-benzenesulfonamide $^1$H NMR (DMSO-d$_6$) δ 11.40 (br s, 1H), 8.14 (d, J=8.6 Hz, 1H), 8.05 (d, J=8.6 Hz, 1H), 8.02 (d, J=2.0 Hz, 1H), 7.94 (d, J=2.1 Hz, 1H), 7.70 (dd, J=8.6, 2.1 Hz, 1H), 7.46 (dd, J=8.6, 2.0 Hz, 1H), 7.20 (s, 2H), 4.62 (s, 2H). MS (M−H) 549

Example 132

2,4-Dichloro-N-[3,5-dichloro-4-(5-chloro-benzothiazol-2-ylmethyl)-phenyl]-5-methyl-benzenesulfonamide $^1$H NMR (DMSO-d$_6$) δ 11.33 (br s, 1H), 8.28 (s, 1H), 8.17 (s, 1H), 8.04 (d, J=8.6 Hz, 1H), 8.01 (d, J=1.9 Hz, 1H), 7.87 (s, 1H), 7.45 (dd, J=8.6, 1.9 Hz, 1H), 7.22 (s, 2H), 4.61 (s, 2H), 2.40 (s, 3H). MS (M−H) 563

Example 133

2-Chloro-N-[3-chloro-4-(5-chloro-benzothiazol-2-ylmethyl)-phenyl]-4-trifluoromethyl-benzenesulfonamide $^1$H NMR (DMSO-d$_6$) δ 11.24 (br s, 1H), 8.29 (d, J=8.3 Hz, 1H), 8.16 (br s, 1H), 8.02 (d, J=8.6 Hz, 1H), 8.00 (d, J=1.8 Hz, 1H), 7.96 (d, J=8.3 Hz, 1H), 7.45 (d, J=8.3 Hz, 2H), 7.20 (d, J=2.0 Hz, 1H), 7.10 (dd, J=8.4, 2.0 Hz, 1H), 4.47 (s, 2H). MS (M−H)z 549

Example 134

2-Chloro-N-[3,5-dichloro-4-(5-trifluoromethyl-benzothiazol-2-ylmethyl)-phenyl]-4-trifluoromethyl-benzenesulfonamide $^1$H NMR (DMSO-d$_6$) δ 11.56 (s, 1H), 8.35 (d, J=8.2 Hz, 1H), 8.27 (d, J=8.3 Hz, 1H), 8.26 (br s, 1H), 8.20 (br s, 1H), 7.99 (dd, J=8.3, 1.0 Hz, 1H), 7.73 (dd, J=8.2, 1.2 Hz, 1H), 7.24 (s, 2H), 4.67 (s, 2H). MS (M–H) 617

Example 135

2,4-Dichloro-N-[3,5-dichloro-4-(5-trifluoromethyl-benzothiazol-2-ylmethyl)-phenyl]-benzenesulfonamide $^1$H NMR (DMSO-d$_6$) δ 11.41 (s, 1H), 8.29 (br s, 1H), 8.27 (d, J=8.6 Hz, 1H), 8.15 (d, J=8.6 Hz, 1H), 7.94 (d, J=2.0 Hz, 1H), 7.73 (dd, J=8.4, 1.4 Hz, 1H), 7.70 (dd, J=8.6, 2.0 Hz, 1H), 7.21 (s, 2H), 4.67 (s, 2H). MS (M–H)

Example 136

2-Chloro-N-[3-chloro-4-(5-trifluoromethyl-benzothiazol-2-ylmethyl)-phenyl]-4-trifluoromethyl-benzenesulfonamide $^1$H NMR (DMSO-d$_6$) δ 11.25 (br s, 1H), 8.32-8.22 (m, 3H), 8.16 (br s, 1H), 7.96 (d, J=8.4 Hz, 1H), 7.72 (d, J=8.4 Hz, 1H), 7.46 (d, J=8.3 Hz, 1H), 7.21 (s, 1H), 7.11 (d, J=8.4 Hz, 1H), 4.52 (s, 2H). MS (M–H) 583

Example 137

2,4-Dichloro-N-[3-chloro-4-(5-trifluoromethyl-benzothiazol-2-ylmethyl)-phenyl]-benzenesulfonamide $^1$H NMR (DMSO-$_6$) δ 11.10 (br s, 1H), 8.28 (br s, 1H), 8.26 (d, J=8.5 Hz, 1H), 8.08 (d, J=8.5 Hz, 1H), 7.89 (d, J=2.0 Hz, 1H), 7.72 (dd, J=8.4, 1.4 Hz, 1H), 7.65 (dd, J=8.6, 2.1 Hz, 1H), 7.46 (d, J=8.4 Hz, 1H), 7.18 (d, J=2.2 Hz, 1H), 7.10 (dd, J=8.3, 2.2 Hz, 1H), 4.52 (s, 2H). MS (M–H) 549

Example 138

N-(4-Benzothiazol-2-ylmethyl-3,5-dichloro-phenyl)-2-chloro-4-trifluoromethyl-benzenesulfonamide $^1$H NMR (DMSO-d$_6$) δ 11.54 (s, 1H), 8.35 (d, J=8.3 Hz, 1H), 8.20 (br s, 1H), 7.99 (d, J=8.3 Hz, 2H), 7.88 (d, J=7.8 Hz, 1H), 7.46 (td, J=8.0, 1.0 Hz, 1H), 7.40 (td, J=7.8, 0.9 Hz, 1H), 7.23 (s, 2H), 4.61 (s, 2H). MS (M–H) 549

Example 139

N-(4-Benzothiazol-2-ylmethyl-3,5-dichloro-phenyl)-2,4-dichloro-benzenesulfonamide $^1$H NMR (DMSO-d$_6$) δ 11.38 (s, 1H), 8.14 (d, J=8.6 Hz, 1H), 8.00 (d, J=7.9 Hz, 1H), 7.94 (d, J=2.0 Hz, 1H), 7.90 (d, J=8.0 Hz, 1H), 7.70 (dd, J=8.6, 2.0 Hz, 1H), 7.46 (m, 1H), 7.40 (m, 1H), 7.20 (s, 2H), 4.60 (s, 2H). MS (M–H) 515

Example 140

N-(4-Benzothiazol-2-ylmethyl-3,5-dichloro-phenyl)-2,4-dichloro-5-methyl-benzenesulfonamide $^1$H NMR (DMSO-d$_6$) δ 11.32 (s, 1H), 8.17 (s, 1H), 8.00 (d, J=7.9 Hz, 1H), 7.90 (d, J=8.1 Hz, 1H), 7.88 (s, 1H), 7.46 (t, J=7.3 Hz, 1H), 7.39 (t, J=7.4 Hz, 1H), 7.16 (s, 2H), 4.60 (s, 2H), 2.40 (s, 3H). MS (M–H) 531

Example 141

N-(4-Benzothiazol-2-ylmethyl-3-chloro-phenyl)-2-chloro-4-trifluoromethyl-benzenesulfonamide $^1$H NMR (DMSO-d$_6$) δ 11.23 (br s, 1H), 8.29 (d, J=8.3 Hz, 1H), 8.15 (br s, 1H), 7.98 (d, J=7.9 Hz, 1H), 7.96 (d, J=8.4 Hz, 1H), 7.90 (d, J=8.1 Hz, 1H), 7.46 (td, J=7.9, 1.0 Hz, 1H), 7.44 (d, J=7.8 Hz, 1H), 7.38 (t, J=7.7 Hz, 1H), 7.20 (d, J=2.1 Hz, 1H), 7.11 (dd, J=8.3, 2.1 Hz, 1H), 4.46 (s, 2H). MS (M–H) 517

Example 142

2-Chloro-N-[3,5-dichloro-4-(5-methyl-benzothiazol-2-ylmethyl)-phenyl]-4-trifluoromethyl-benzenesulfonamide $^1$H NMR (DMSO-d$_6$) δ 11.54 (s, 1H), 8.36 (d, J=8.2 Hz, 1H), 8.19 (br s, 1H), 8.00 (dd, J=8.2, 1.0 Hz, 1H), 7.84 (d, J=8.2 Hz, 1H), 7.70 (br s, 1H), 7.26-7.18 (m, 3H), 4.58 (s, 2H), 2.40 (s, 3H). MS (M–H) 563

Example 143

2-Chloro-N-[3-chloro-4-(5-methyl-benzothiazol-2-ylmethyl)-phenyl]-4-trifluoromethyl-benzenesulfonamide $^1$H NMR (DMSO-d$_6$) δ 11.22 (br s, 1H), 8.19 (d, J=8.2 Hz, 1H), 8.15 (br s, 1H), 7.45 (dd, J=8.3, 1.1 Hz, 1H), 7.83 (d, J=8.2 Hz, 1H), 7.71 (br s, 1H), 7.43 (d, J=8.4 Hz, 1H), 7.24-7.19 (m, 2H), 7.05 (dd, J=8.5, 2.2 Hz, 1H), 4.43 (s, 2H), 2.41 (s, 3H). MS (M–H) 529

Example 144

This example illustrates the synthesis of 144.1.

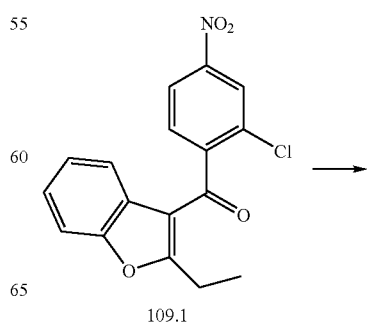

109.1

Example 145

This example illustrates the synthesis of 145.1.

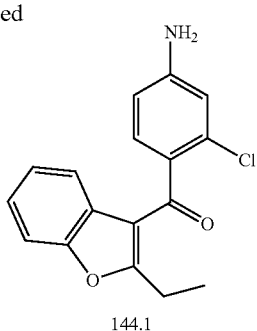

144.1

Nitro compound 109.1 (1.91 g, 5.8 mmol) was reduced to the corresponding aniline using $SnCl_2 \cdot 2H_2O$ (6.54 g, 29.0 mmol) in EtOAc (40 mL) according to the procedure previously described in Example 30. This yielded 692 mg (40%) of compound 144.1 as a white powder.

MS ESI m/e: 300.0 (M+H).

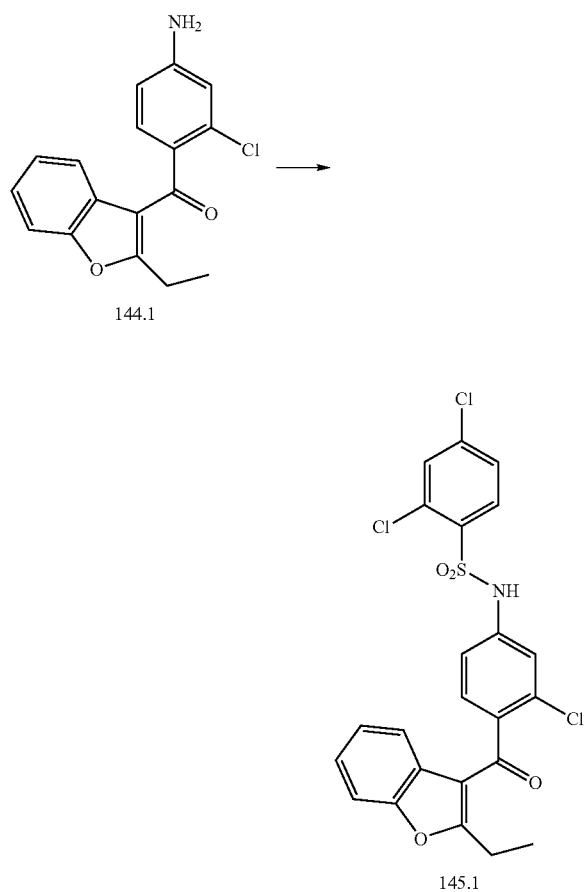

145.1

A round-bottomed flask was charged with aniline 144.1 (110 mg, 0.37 mmol), 2,4-dichlorobenzenesulfonyl chloride (108 mg, 0.44 mmol), 2,6-lutidine (47 mg, 0.44 mmol), catalytic DMAP, and methylene chloride (2.0 mL). The reaction was allowed to stir overnight. The reaction was then diluted with 20 mL of methylene chloride and washed with 10 mL of 1N HCl and 10 mL of brine. The organics were dried over $Na_2SO_4$ and concentrated to a yellow oil. This oil was further purified using silica gel flash chromatography. The desired fractions were combined and concentrated to yield 60 mg (32%) of compound 145.1 as a white foam.

$^1$H NMR (400 MHz) ($d_6$-DMSO) δ 11.36 (1H, s); 8.12 (1H, d, J=8.6 Hz); 7.94 (1H, d, J=2.1 Hz); 7.68 (1H, dd, J=8.6, 2.1 Hz); 8.63 (1H, d, J=8.4 Hz); 7.47 (1H, d, J=8.4 Hz); 7.36-7.32 (1H, m); 7.27-7.19 (4H, m); 2.54 (2H, q, J=7.6 Hz); 1.08 (3H, t, J=7.6 Hz). MS ESI m/e: 506.0 (M–H).

Example 146

This example illustrates the synthesis of 146.1.

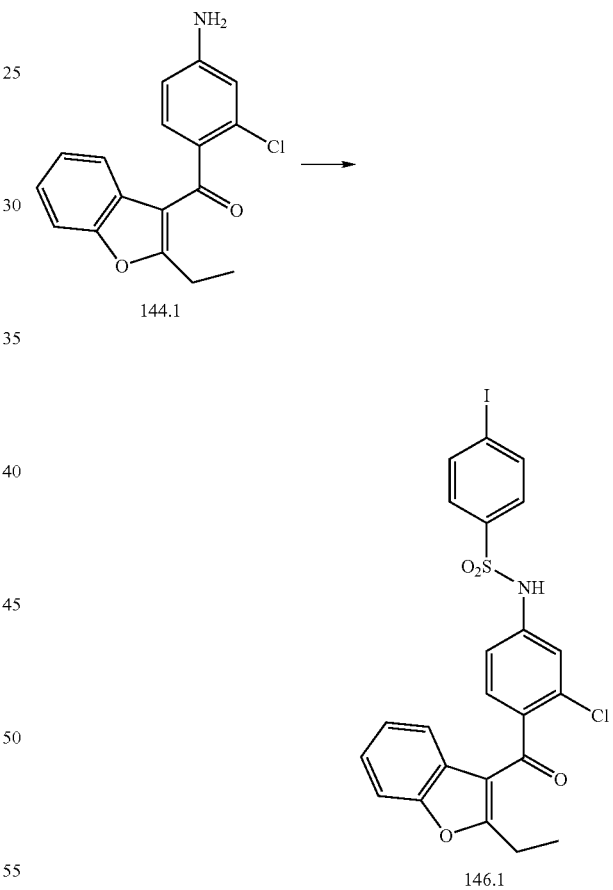

Aniline 144.1 (111 mg, 0.37 mmol), pipsyl chloride (135 mg, 0.45 mmol), 2,6-lutidine (48 mg, 0.45 mmol), and catalytic DMAP were combined in methylene chloride (2.0 mL) according to the procedure described in Example 77. This yielded 140 mg (67%) of compound 146.1 as a white foam.

$^1$H NMR (400 MHz) ($d_6$-DMSO) δ 10.97 (1H, s); 8.01 (2H, d, J=8.4 Hz); 7.63 (1H, d, J=8.4 Hz); 7.58 (2H, d, J=8.4 Hz); 7.46 (1H, d, J=8.4 Hz); 7.34 (1H, m); 7.46-7.20 (4H, m); 2.54 (2H, q, J=7.5 Hz); 1.09 (3H, t, J=7.5 Hz). MS ESI m/e: 563.9 (M–H).

Example 147

This example illustrates the synthesis of 147.1.

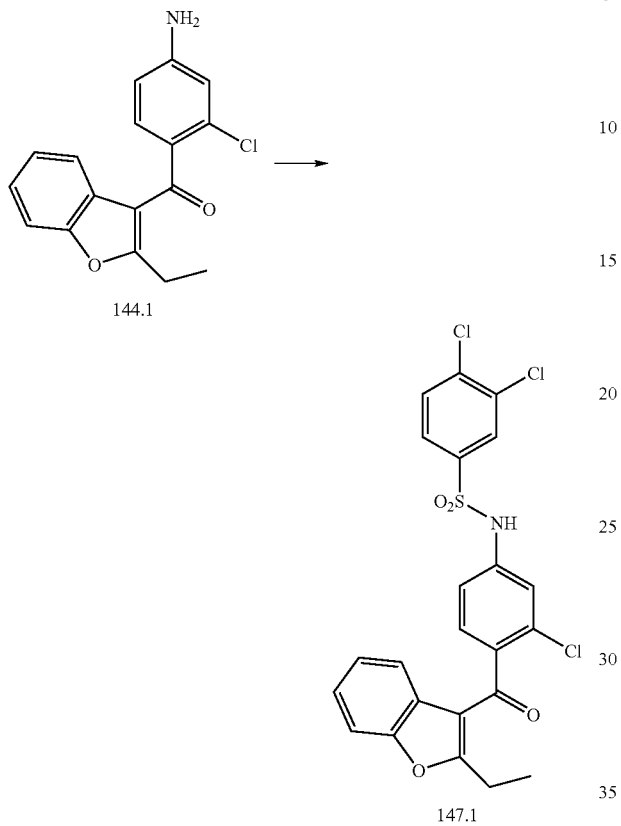

Aniline 144.1 (108 mg, 0.36 mmol), 3,4-dichlorobenzene-sulfonyl chloride (106 mg, 0.43 mmol), 2,6-lutidine (46 mg, 0.43 mmol), and catalytic DMAP were combined in methylene chloride (2.0 mL) according to the procedure described in Example 77. This yielded 113 mg (62%) of compound 147.1 as a white foam.

$^1$H NMR (400 MHz) (CDCl$_3$) δ 7.96 (1H, d, J=2.2 Hz); 7.66 (1H, dd, J=8.4, 2.2 Hz); 7.57 (1H, d, J=8.4 Hz); 7.46 (1H, d, J=8.3 Hz); 7.34 (1H, d, J=8.3 Hz); 7.31-7.26 (3H, m); 7.20-7.15 (2H, m); 2.79 (2H, q, J=7.6 Hz); 1.27 (3H, t, J=7.6 Hz). MS ESI m/e: 506.0 (M−H).

Example 148

This illustrates the synthesis of (2-fluoro-4-nitro-phenyl)acetic acid 148.

A round-bottomed flask was charged with diethyl malonate (8.6 g, 54 mmol), cesium carbonate (29.3 g, 90 mmol), and anhydrous DMF (36 mL). The mixture was warmed to 70° C. and 2,4-difluoronitrobenzene (5.75 g, 36 mmol) was added in a dropwise fashion with vigorous stirring. The reaction medium immediately turned dark purple. After the addition was complete, the reaction was stirred at 70° C. for 30 minutes. After cooling to room temperature, the reaction was quenched with 4 mL of acetic acid and then poured into 300 mL of 0.3 N HCl$_{(aq)}$. The purple color discharged completely upon addition to the acid. The mixture was then neutralized by adding solid NaHCO$_3$ until no gas evolution took place. The mixture was extracted 2×150 mL 1:1 diethyl ether:hexanes. The combined organic layers were washed 2×100 mL DI water and 1×50 mL sat. brine. The organic layer was dried over MgSO$_4$ and concentrated to a yellow oil. This oil was suspended in 40 mL of 6N HCl$_{(aq)}$ and the mixture heated to reflux for 16 h. Upon cooling, crystals separated and were collected by filtration. The crystals were dried under vacuum to yield 2-fluoro-4-nitro-phenylacetic acid (148) as off-white crystals (5.42 g).

$^1$H NMR (400 MHz) (d$_4$-MeOH) δ 8.06 (1H, d); 8.04 (1H, d); 7.60 (1H, t); 3.81 (2H, s).

Example 149

This illustrates the synthesis of 7-chloro-2-(2-fluoro-4-nitro-benzyl)-benzoxazole 149.

The benzoxazole 149 was formed according to the method of Terashima and Ishi (*Synthesis* 1982, 484-85.). Phenylacetic acid 148 (387 mg, 1.95 mmol), 2-amino-6-chloro-phenol (233 mg, 1.67 mmol, described in *J. Med. Chem.* 1996, 39, 3435-3450), and boric acid (120 mg, 1.95 mmol) were combined in xylenes (24 mL) and the mixture heated to reflux in a flask equipped with a Dean-Stark trap. After 8 h, the reaction mixture was filtered, concentrated, and the residue purified by flash chromatography (silica gel, 3:1 hexanes:ethyl acetate). Fractions containing benzoxazole 149 were concentrated to a yellow solid (419 mg).

$^1$H NMR (CDCl$_3$) δ 8.05 (d, 1H); 8.00 (dd, 1H); 7.61 (d, 1H); 7.57 (d, 1H); 7.33 (d, 1H); 7.27 (d, 1H) 4.38 (s, 2H). MS (M+H) 307.0

Example 150

This illustrates the synthesis of compound 150.

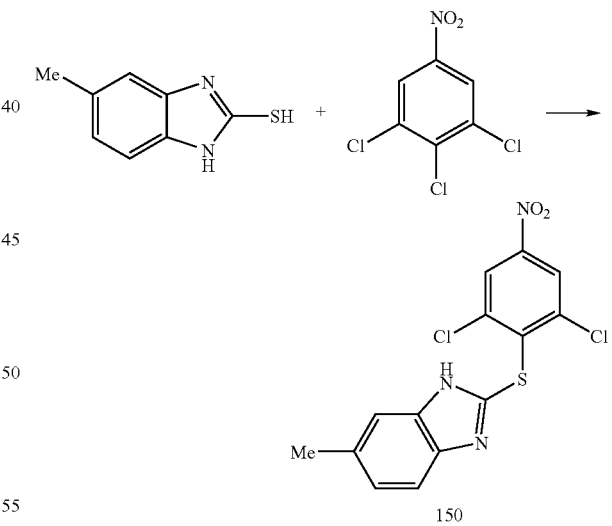

A round-bottomed flask was charged with 2-mercapto-5-methylbenzimidazole (4.84 g, 29.5 mmol), potassium hydroxide (1.66 g, 29.5 mmol), and water (18 mL). This suspension was heated to 120° C. for 3.0 hours. Then 3,4,5-trichloronitrobenzene (6.68 g, 29.5 mmol) dissolved in 53 mL of n-butanol was added dropwise while the reaction stirred at 120° C. All the white solids went into solution and the solution proceeded to turn a deep red color. The reaction was left stirring for five days, at which point a yellow precipitate was seen. The reaction was then cooled to room temperature and the precipitate was filtered and washed with distilled water to yield 8.10 g (78%) of compound 150 as canary yellow crystals which were a 50/50 mixture of both possible tautomers.

$^1$H NMR (400 MHz) (d$_6$-DMSO) δ 12.64 (1H, s); 8.48 (2H, d, J=2.2 Hz); 7.34 and 7.27 (1H, 2 tautomeric doublets, J=8.3 Hz); 7.26 and 7.19 (1H, 2 tautomeric singlets); 6.99 and 6.95 (1H, 2 tautomeric doublets, J=8.1 Hz); 2.38 and 2.35 (3H, 2 tautomeric singlets).

Example 151

This illustrates the synthesis of compound 151.

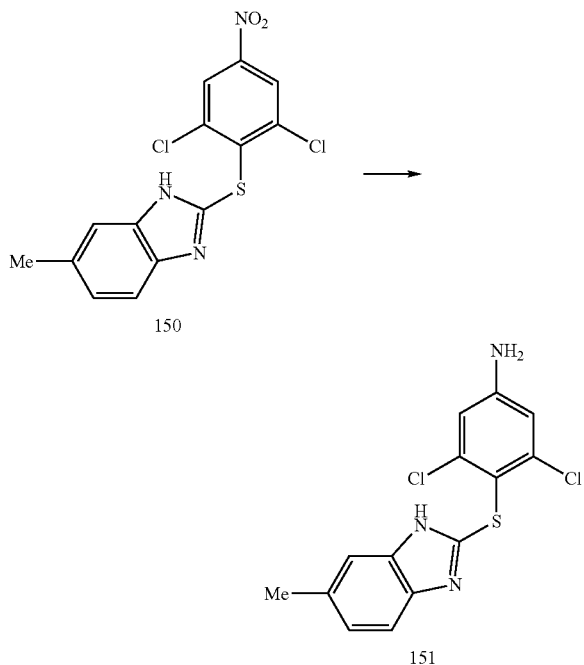

A round-bottomed flask was charged with 8.1 g (22.8 mmol) of compound 150, 20.6 g (91.4 mmol) of tin dichloride dihydrate, and 150 mL of EtOAc. This was heated to 75° C. for 3.0 hours. The reaction was cooled to room temperature, diluted with 300 mL of EtOAc and washed with 250 mL of 2N aqueous KOH solution followed by 200 mL of brine. The organics were dried over sodium sulfate and concentrated to 7.4 g (94%) of 151 as a pale yellow solid that was used without further purification. MS (M+H) 324

Example 152

This illustrates the synthesis of compound 152.

A round-bottomed flask was charged with compound 151 (749 mg, 2.31 mmol), 4-acetylbenzenesulfonyl chloride (1.01 g, 4.62 mmol), 2,6-lutidine (496 mg, 4.62 mmol), acetone (4.0 mL), and a catalytic amount of DMAP. This was stirred at room temperature for 12 hours, after which 2,6-lutidine hydrochloride was seen as a white precipitate. The reaction was diluted with 40 mL of EtOAc and washed with 30 mL of 1N aqueous HCl followed by 30 mL of brine. The organics were dried over magnesium sulfate and concentrated to a clear oil that was dissolved in 30 mL of THF. To this was added 30 mL of 0.5N aqueous KOH. This was stirred at room temperature for 12 hours, and the reaction color progressed from a light yellow to a deep orange. Next, the pH was brought to 7.0 with 1.0N HCl and the THF was removed in vacuo. The remaining aqueous phase was extracted with 100 mL of Et$_2$O. The organic layer was dried over sodium sulfate and concentrated to a yellow oil that was further purified with silica gel flash chromatography (3:2 hexanes:EtOAc). The desired fractions were combined and concentrated to an oil which was recrystallized from hot EtOAc/hexanes to yield 312 mg (27%) of 152 as an off-white solid. MS (M–H) 504.

$^1$H NMR (d$_6$-DMSO) δ 12.36 (1H, broad s); 11.39 (1H, broad s); 8.18 (2H, t); 8.03 (2H, t); 7.32 (2H, s); 7.32-7.04 (2H, m); 6.96 (1H, m); 2.62 (3H, s); 2.35 (3H, s).

Example 153

This illustrates the synthesis of compound 153.

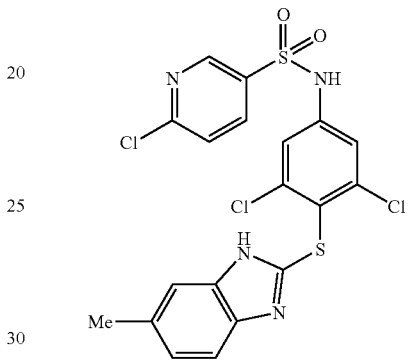

Compound 153 was prepared according to Example 152. In this case, 353 mg (1.1 mmol) of compound 151 was used to give 76 mg (14%) of 153 as white crystals.

$^1$H NMR (d$_6$-DMSO) δ 12.31 (1H, broad s); 11.42 (1H, broad s); 8.90 (1H, d); 8.29 (1H, dd); 7.81 (1H, d); 7.34 (2H, s); 7.26 (1H, broad s); 7.17 (1H, broad s); 6.92 (1H, d); 2.35 (3H, s). MS (M–H) 497.0.

The additional examples of Table 21 were prepared according to the method of Example 152.

TABLE 21

|  | V | A | B | C | D | m/e (M – H) |
|---|---|---|---|---|---|---|
| 152 | Cl | H | H | —C(=O)Me | H | 504 |
| 153 | Cl | [2-chloro-5-pyridyl] | | | | 497 |
| 154 | Cl | Me | H | Cl | Me | 524 |
| 155 | Cl | Cl | H | Cl | H | 530 |
| 156 | Cl | Cl | H | CF$_3$ | H | 564 |
| 157 | Cl | Cl | H | Cl | Me | 544 |
| 158 | H | Cl | H | Cl | H | 496 |

TABLE 21-continued

| | | | | | | |
|---|---|---|---|---|---|---|
| 159 | H | H | Cl | Cl | H | 496 |
| 160 | H | Cl | H | CF$_3$ | H | 530 |
| 161 | H | Cl | H | Cl | Me | 510 |
| 162 | H | H | H | I | H | 554 |
| 163 | H | | [2-chloro-5-pyridyl] | | | 463 |
| 164 | H | Me | H | Cl | Me | 490 |

Example 154

$^1$H NMR (d$_6$-DMSO) δ 12.29 (1H, broad s); 11.37 (1H, broad s); 8.01 (1H, s); 7.57 (1H, s); 7.19-7.33 (4H, m); 6.91 (1H, s); 2.57 (3H, s); 2.38 (3H, s); 1.24 (3H, s). MS (M–H) 524.

Example 155

MS (M–H) 529.8. $^1$H NMR (d$_6$-DMSO) δ 12.31 (1H, broad s); 11.64 (1H, broad s); 8.18 (1H, d); 7.94 (1H, d); 7.71 (1H, dd); 7.34-7.09 (4H, m); 6.93 (1H, d); 2.33 (3H, s).

Example 156

MS (M–H) 564. $^1$H NMR (d$_6$-DMSO) δ 12.28 (1H, broad s); 11.80 (1H, broad s); 8.38 (1H, d); 8.19 (1H, s); 8.00 (1H, d); 7.29 (2H, s); 7.24 (1H, broad s); 7.15 (1H, broad s); 6.91 (1H, d); 2.34 (3H, s).

Example 157

MS (M–H) 544. $^1$H NMR (d$_6$-DMSO) δ 12.29 (1H, broad s); 11.58 (1H, s); 8.22 (1H, s); 7.89 (1H, s); 7.29 (2H, s); 7.24 (1H, broad s); 7.16 (1H, broad s); 6.91 (1H, d); 2.41 (3H, s); 2.34 (3H, s).

The examples of Table 22 were prepared by analogy to the methods of Examples 150-152.

TABLE 22

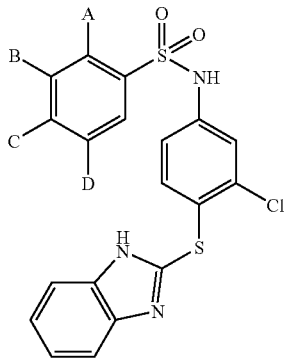

| | A | B | C | D | m/e (M − H) |
|---|---|---|---|---|---|
| 165 | Cl | H | Cl | Me | 496 |
| 166 | Cl | H | Cl | H | 482 |
| 167 | H | H | I | H | 540 |
| 168 | H | Cl | Cl | H | 482 |
| 169 | Cl | H | CF$_3$ | H | 516 |
| 170 | Me | H | Cl | Me | 476 |

The examples of Table 23 were prepared by analogy to the methods of Examples 150-152.

TABLE 23

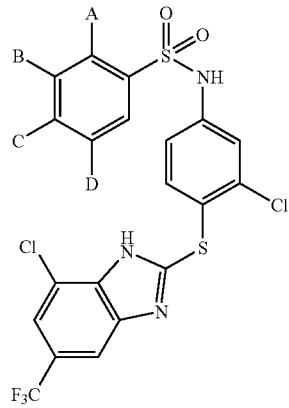

| | A | B | C | D | m/e (M − H) |
|---|---|---|---|---|---|
| 171 | Cl | H | Cl | H | 584 |
| 172 | Cl | H | CF$_3$ | H | 618 |
| 173 | Me | H | Cl | Me | 578 |

Example 174

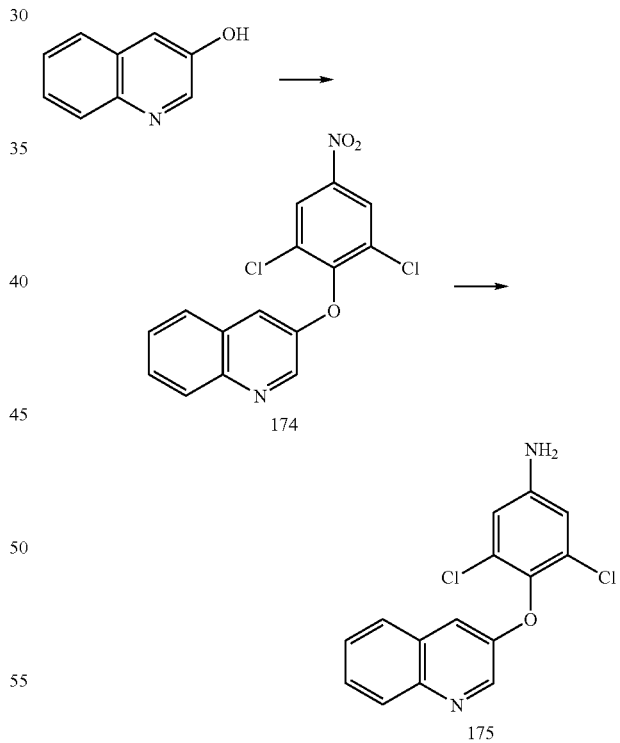

3-Hydroxyquinoline (prepared according to the procedure of Naumann, et. al., *Synthesis,* 1990, 4, 279-281)) (3 g) and 1,2,3-trichloro-5-nitrobenzene (4.7 g) were dissolved in DMF (80 mL) and heated with cesium carbonate (7.4 g) for 2 hr at 60° C. The reaction was poured into ice/water (500 ml). The resulting off-white precipitate was collected by filtration and rinsed with hexane to afford compound 174 as a solid (6.9 g) suitable for use in the next reaction.

¹H NMR in CDCl₃ 8.863 (d, J=2.2 Hz, 1H), 8.360 (s, 2H), 8.106 (d, J=8.6 Hz, 1H), 7.646 (m, 2H), 7.529 (d, J=8.6 Hz, 1H), 7.160 (d, J=2.2 Hz, 1H)

Example 175

To a solution of compound 180 (6.9 g) in ethanol/THF/water (ratio 40:20:10) was added ammonium chloride (3.3 g) and powdered iron (3.4 g). This mixture was heated to reflux for 5 hr. The hot mixture was then filtered through Celite and concentrated. The residue was dissolved in ethyl acetate and washed with saturated NaHCO₃ solution followed by water and then brine. The solution was dried over magnesium sulfate and concentrated to afford compound 175 as an off-white solid (5.6 g).

¹H NMR in (DMSO) δ 8.846 (d, J=2.9 Hz, 1H), 8.010 (m, 1H), 7.915 (m, 1H), 7.645 (m, 1H), 7.560 (m, 1H), 7.401 (d, J=2.9 Hz, 1H), 6.778 (s, 2H), 5.762 (s, 2H).

Treatment of the aniline 175 with various sulfonyl chlorides according to conventional methods gave the sulfonamides of Table 24.

TABLE 24

| Example | X | Y | V | A | B | C | D |
|---------|------|-------|----|-----|---|-----|----|
| 176 | H | H | Cl | CF₃ | H | Cl | H |
| 177 | H | H | Cl | Cl | H | CF₃ | H |
| 178 | H | H | Cl | Cl | H | Cl | H |
| 179 | H | H | Cl | Cl | H | Cl | Me |
| 180 | H | H | H | Cl | H | Cl | H |
| 181 | —CO₂Me | H | Cl | Cl | H | Cl | H |
| 182 | H | —CO₂Me | Cl | Cl | H | Cl | H |
| 183 | —CO₂H | H | Cl | Cl | H | Cl | H |
| 184 | H | —CO₂H | Cl | Cl | H | Cl | H |
| 185 | Me | H | Cl | Cl | H | Cl | Me |
| 186 | H | H | F | Cl | H | Cl | Me |

Example 176

¹H NMR (DMSO) δ 11.4-11.6 (1H, broad), 8.87 (1H, d, J=2.9 Hz), 8.15-8.22 (2H, m), 8.00-8.08 (2H, m), 7.87 (1H, d, J=8.0 Hz), 7.55-7.68 (2H, m), 7.47 (1H, d, J=2.9 Hz), 7.35 (2H, s). MS (M−H) 545. mp 98.8° C.

Example 177

¹H NMR(DMSO) δ 11.58 (1H, s), 8.86 (1H, d, J=2.9 Hz), 8.38 (1H, d, J=8.4 Hz), 8.23 (1H, s), 8.01 (1H, d, J=8.4 Hz), 7.86 (1H, d, J=8.1 Hz), 7.53-7.68 (2H, m), 7.46 (1H, d, J=2.9 Hz), 7.34 (2H, s). MS (M−H) 545.0

Example 178

¹H NMR(d₆-acetone) 9.9 (1H, br s), 8.794 (1H, d, J=2.9 Hz), 8.23 (1H, d, J=8.4 Hz), 8.035 (1H, br d, J=8.4 Hz), 7.793 (1H, d, J=1.5 Hz), 7.78 (1H, m), 7.62-7.70 (2H, m), 7.57 (1H, td, J=6.8, 1.2 Hz), 7.476 (2H, s), 7.364 (1H, d, J=2.6 Hz). MS (M−H) 511.0.

Example 179

¹H NMR(300 MHz/CDCl₃) δ 2.43(3H, s), 7.10(1H, d, J=3 Hz), 7.26(2H, s) 7.48-7.64(4H, m), 7.96(1H, s), 8.09(1H, d, J=8.7 Hz), 8.78(1H, d, J=3 Hz). MS(M+H) 527. mp 233-235°

Example 180

¹H NMR(300 MHz/CDCl₃) δ 7.14(1H, dd, J=2.6 Hz, J=8.9 Hz), 7.26(1H, d, J=8.9 Hz), 7.33(1H, d, J=2.6 Hz), 7.56-7.58 (2H, m), 7.66-7.69(2H,m), 7.87(1H, m), 7.93(1H, d, J=2.0 Hz), 8.00(1H, m), 8.09(1H, d, J=8.5 Hz), 8.80(1H, d, J=2.9 Hz), 11.06(1H, brs). MS(M+H)) 479 mp 122° C.

Example 181

3-[2,6-Dichloro-4-(2,4-dichloro-benzenesulfonylamino)-phenoxy]-quinoline-6-carboxylic acid methyl ester (181)

A solution of 3-(4-Amino-2,6-dichloro-phenoxy)-quinoline-6-carboxylic acid methyl ester (312) (0.93 mmol) and 2,4-dichlorobenzenesulfonyl chloride (250 mg, 1.02 mmol) in Pyridine (0.13 ml, 1.53 mmol)-CH₂Cl₂ (3.7 ml) was stirred at room temperature for 12 hr. Sat NaHCO₃ was added to the reaction mixture, which was then extracted twice with AcOEt. Organic layer was washed by brine, dried over anhydrous MgSO₄, and concentrated. Crude residue was purified by column chromatography (Hexane/AcOEt=2/1, 80 g of silica gel) to afford compound 181 (237 mg, 41%, in 3 steps).

¹H NMR (300 MHz,DMSO-d₆) δ 3.90 (3H, s), 7.31(2H, s), 7.72 (1H, dd, J=1.8, 7.8 Hz), 7.79 (1H, d, J=3.0 Hz), 7.96 (1H, d, J=1.8 Hz), 8.11 (2H, s), 8.18 (1H, d, J=7.8 Hz), 8.64 (1H, s), 8.99 (1H, d, J=3.0 Hz), 11.42 (1H, br s). MS (M+H) 571

Example 182

3-[2,6-Dichloro-4-(2,4-dichloro-benzenesulfonylamino)-phenoxy]-quinoline-8-carboxylic acid methyl ester (182)

To a solution of 3-(4-Amino-2,6-dichloro-phenoxy)-quinoline-8-carboxylic acid methyl ester (315) (1.26 mmol) in Pyridine (0.15 ml, 1.80 mmol) and CH₂Cl₂ (5 ml), was added 2,4-Dichlorobenzenesulfonyl chloride (381 mg, 1.55 mmol). The mixture was stirred at room temperature for 12 hr. Sat NaHCO₃ was added to the reaction mixture, which was then extracted twice with AcOEt. Organic layer was washed by Brine, dried over MgSO₄, and concentrated. The crude residue was purified by column chromatography (Hexane/AcOEt=2/1, 80 g of silica gel) to afford compound 182 (506 mg, 70%) as a white solid.

¹H NMR (300 MHz, DMSO-d₆) δ 3.91 (3H, s), 7.31(2H, s), 7.57-7.65 (2H, m), 7.72 (1H, dd, J=2.1, 8.6 Hz), 7.83(1H, d, J=8.6 Hz), 7.96 (2H, d, J=2.1 Hz), 8.03 (1H, d, J=8.6 Hz), 8.18 (1H, d, J=8.6 Hz), 8.94 (1H, d, J=2.1 Hz), 11.4 (1H, br s), MS(M+H) 571

Example 183

3-[2,6-Dichloro-4-(2,4-dichloro-benzenesulfonylamino)-phenoxy]-quinoline-6-carboxylic acid (183)

To a solution of 3-[2,6-Dichloro-4-(2,4-dichloro-benzenesulfonylamino)-phenoxy]-quinoline-6-carboxylic acid methyl ester (181) (200 mg, 0.35 mmol) in THF/MeOH(2 ml/2 ml) was added 4N NaOH (0.1 ml, 0.4 mmol). This mixture was refluxed for 2.5 hr. The reaction mixture was cooled to room temperature and was neutralized with 2N HCl, and then concentrated. The residue was extracted twice with AcOEt. Organic layer was washed by Brine, dried over anhydrous $MgSO_4$, and concentrated to give a solid. Crude product was recrystallized by Hexane/AcOEt to afford compound 183 (153 mg, 78%).

$^1$H NMR (300 MHz, DMSO-$d_6$) δ 7.16 (2H, s), 7.62(1H, dd, J=2.0, 8.5 Hz), 7.73 (1H, d, J=2.9 Hz), 7.82 (1H, s), 8.08-8.11 (3H, m), 8.60 (1H, s), 8.95 (1H, d, J=2.9 Hz), 13.2 (1H, br s), MS (M+H) 557. mp 228-2

Example 184

3-[2,6-Dichloro-4-(2,4-dichloro-benzenesulfonylamino)-phenoxy]-quinoline-8-carboxylic acid (184)

To a solution of 3-[2,6-Dichloro-4-(2-chloro-4-trifluoromethyl-benzenesulfonylamino)-phenoxy]-quinoline-8-carboxylic acid methyl ester (183) (402 mg, 0.7 mmol) in THF/MeOH=0.1 ml/0.3 ml was added 4N NaOH (0.2 ml, 0.77 mmol). The mixture was refluxed for 12 hr. After cooling to room temp. the reaction mixture was filtered to remove insoluble materials. The filtrate was concentrated and the residue was dissolved in aq $NH_4Cl$ and extracted twice with AcOEt. Organic layer was washed by Brine, and dried over anhydrous $MgSO_4$, and concentrated to afford compound 184 (197 mg, 50%) as a white solid.

$^1$H NMR (300 MHz, DMSO-$d_6$) δ 7.32 (2H, s), 7.70-7.81 (2H, m), 7.90 (1H, d, J=2.2 Hz), 7.96 (1H, d, J=2.2 Hz), 8.17-8.19 (1H, m), 8.22-8.24 (1H, m), 8.38-8.39 (1H, m), 9.11 (1H, d, J=2.2 Hz), 11.4 (1H, br s), 15.4 (1H, br s), MS (M+H) 557. mp 263-266° C.

Example 185

2,4-Dichloro-N-[3,5-dichloro-4-(6-methyl-quinoln-3-yloxy)-phenyl]-5-methyl-benzenesulfonamide (185)

To a solution of 3,5-Dichloro-4-(6-methyl-quinlin-3-yloxy)-phenylamine (339) (400 mg, 1.25 mmol) in Pyridine (0.12 ml, 1.48 mmol)-$CH_2Cl_2$ (4 ml) was added 2,4-Dichloro-5-methylbenzenesulfonyl chloride (325 mg, 1.25 mmol). The mixture was stirred at room temperature for 12 hr. The reaction mixture was concentrated and the residue was purified by column chromatography (Hexane/AcOEt=2/1, 80 g of silica gel) to provide compound (185) (453 mg, 66%) as a white solid.

$^1$H NMR (300 MHz, DMSO-$d_6$) δ 2.41 (3H, s), 2.44(3H, s), 7.31 (3H, s), 7.49 (1H, d, J=8.7 Hz), 7.61 (1H, s), 7.88-7.91 (2H, m), 8.19 (1H, s), 8.74 (1H, d, J=3.0 Hz), 11.3 (1H, br s), MS (M+H) 541. mp 228-230°.

Example 186

Part 1

Preparation of 3-chloro-5-fluoro-4-(quinolin-3-yloxy)nitrobenzene (186.1)

To a solution of 3,4-Difluoronitrobenzene 1.00 g in conc.$H_2SO_4$ (20 ml), was added portionwise $Cl_2O$ in $CCl_4$ (25 ml, prepared as described by Cady G. H. et. al in Inorg. Synth. Vol 5, p 156(1957)). The mixture was stirred at room temperature overnight. The mixture was poured into crashed ice and extracted with $Et_2O$ (30 ml×3). Combined ether layers were washed with 10% $Na_2SO_3$ and brine, and dried over $Na_2SO_4$. The solvent was concentrated to Ca. 10 ml (This solution contains 3-Chloro-4,5-difluoronitrobenzene). This solution was diluted with acetone (60 ml), and then 3-hydroxyquinoline 0.75 g and $K_2CO_3$ 2.2 g were added to this solution. The mixture was heated to reflux for 1.5 hr. After cooling the reaction mixture was filtered through a short celite pad. The filtrate was concentrated to give an oil, which was then purified by column chromatography (silica gel, AcOEt:Hexane=1:5) to provide the intermediate compound 186.1 (0.980 g) as a yellow oil.

Part 2

Preparation of 3-Chloro-5-fluoro-4-(quinolin-3-yloxy)phenylamine (186.2)

To a solution of 3-Chloro-5-fluoro-4-(quinolin-3-yloxy)nitrobenzene (186.1) (0.980 g) and $NH_4Cl$ (1.64 g) in EtOH (50 ml)-$H_2O$ (5 ml), was added iron powder (1.92 g). The mixture was heated to reflux for 1 hr. After cooling the reaction mixture was filtered through short celite pad. The filtrate was concentrated, diluted with sat. $NaHCO_3$ and extracted with AcOEt (30 ml×3). The combined organic layeres were washed with brine and dried over $Na_2SO_4$. Concentration of solvent afford crude product, which was purified by column chromatography (silica gel, AcOEt:Hexane=1:3) to provide aniline 186.2 (0.420 g) as a colorless solid.

Part 3

Preparation of N-[3-chloro-5-fluoro-4-(quinolin-3-yloxy)phenyl]-2,4-dichloro-5-methyl-benzenesulfonamide (186)

To a solution of 3-chloro-5-fluoro-4-(quinolin-3-yloxy)phenylamine (186.2) (0.420 g) in pyridine (2.2 ml), was added 2,4-dichloro-5-methylbenzenesulfonylchloride 0.360 g. The mixture was stirred at room for 1 hr. The reaction mixture was purified directly by column chromatography (silica gel, AcOEt:Hexane=1:3). The product was triturated by hexane to give title compound (0.522 g). (73%) as a solid.

NMR(300 MHz/$CDCl_3$) δ 2.43(3H, s), 7.05(1H, d, J=2.6 Hz), 7.09-7.11(1H, m), 7.21(1H, d, J=2.6 Hz), 7.36(1H, brs), 7.49-7.66(4H, m), 7.96(1H, s), 8.10(1H, d, J=8.2 Hz), 8.80 (1H, brs) MS (M+H) 511. mp 187° C.

Example 187

This illustrates the synthesis of 7-chloro-2-(2-fluoro-4-amino-benzyl)-benzoxazole 187.

To the nitro compound 149 (419 mg, 1.4 mmol) in ethyl acetate (10 mL) was added $SnCl_2 \cdot 2H_2O$ (1.2 g, 5.5 mmol). The reaction mixture was heated to reflux for 30 minutes. After allowing to cool to room temperature, the reaction mixture was poured into 13 mL of saturated 2N $KOH_{(aq)}$. The layers were separated, and the aqueous layer extracted 1×30 mL ethyl acetate. The combined organic layers were washed with saturated brine and dried over $Na_2SO_4$. After concentration, the yellow oil was purified by radial chromatography (2 mm silica gel layer Chromatatron plate, 3:2 hexanes:ethyl acetate). Eluant containing the desired product was concentrated to 194 mg of aniline 187.

$^1$H NMR ($d_6$-acetone) δ 7.58 (dd, 1H); 7.39-7.31 (m, 2H); 7.11 (t, 1H); 6.50-6.43 (m, 2H); 4.94 (bs, 2H); 4.21 (s, 2H). MS (M+H) 277.1.

Example 188

This Illustrates the Synthesis of Sulfonamide 188.

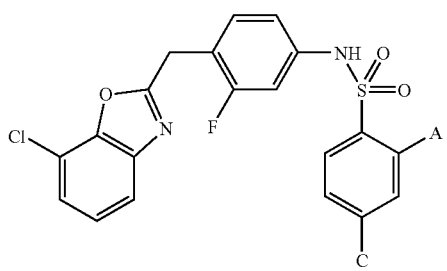

Example 188 A=C=Cl

Example 189 A=H; C=COMe

To aniline 187 (95 mg, 0.34 mmol) in acetone (1 mL) was added 2,6-lutidine (60 µL, 0.51 mmol) and 2,4-dichloro-benzenesulfonyl chloride (93 mg, 0.38 mmol, Maybridge Chemical Co.). After 16 hours, the reaction mixture was filtered through a 1 cm plug of silica gel. After concentration, the yellow oil was purified by radial chromatography (1 mm silica gel layer Chromatatron plate, 3:1 hexanes:ethyl acetate). Eluant containing the product was concentrated and the residue recrystallized from hot hexanes/ethyl acetate. Filtration and drying under vacuum yielded the sulphonamide 188 as light yellow crystals (65 mg).

$^1$H NMR ($d_6$-acetone) δ 9.70 (bs, 1H); 8.16 (d, 1H); 7.71 (d, 1H); 7.60-7.56 (m, 2H); 7.42-7.32 (m, 3H); 7.11-7.09 (m, 2H); 4.32 (s, 2H). MS (M–H) 482.9.

Example 189

This illustrates the synthesis of sulfonamide 189.

By the method of example 188, using the aniline 187 and 4-acetyl-benzenesulfonyl chloride compound 189 was obtained as light yellow crystals.

$^1$H NMR ($d_6$-acetone) δ 9.50 (bs, 1H); 8.11 (d, 2H); 8.11 (d, 2H); 7.98 (d, 2H); 7.57 (d, 1H); 7.42-7.32 (m, 3H); 7.12-7.06 (m, 2H); 4.33 (s, 2H); 2.61 (s, 3H). MS (M–H): 482.9.

Example 190

This illustrates the synthesis of compound 190.

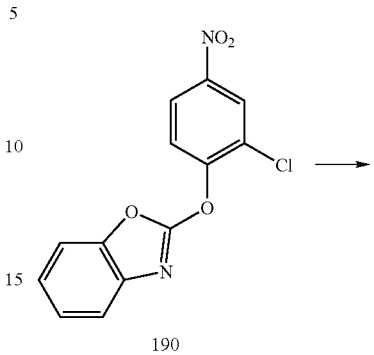

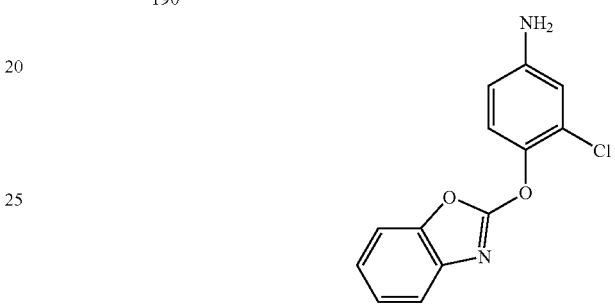

2-chloro-4-nitro-phenol (2 g, 11.5 mmol) was dissolved in DMF (5 mL) and treated with $Cs_2CO_3$ (3.7 g, 11.5 mmol). The reaction mixture was heated to 50° C. until gas evolution stopped. 2-chlorobenzoxazole (2.65 g, 17.3 mmol) was added, and then the reaction mixture was warmed to 75° C. After 5 hours, the heat was removed and the reaction mixture was poured into 150 mL of deionized water with vigorous stirring. The precipitate was collected by filtration and rinsed several times with distilled water.

The product was dried under a stream of air for 15 minutes, then under vacuum overnight to afford compound 190 as an off-white solid (3.4 g), homogeneous by TLC ($R_f$=0.55, 3:1 hexanes:ethyl acetate). MS (M+H) 291.0

Example 191

This illustrates the synthesis of compound 191. See above.

A round-bottomed flask was charged with 2.01 g (6.93 mmol) of compound 190, 50 mL of isopropyl alcohol, and 20 mL of THF. Then 0.5 mL of a 50/50 suspension of Raney Nickel in water was added. The reaction was then stirred under a hydrogen balloon at room temperature for 24 hours. Raney Nickel was removed by filtration through celite, and the solution was concentrated in vacuo. Recrystallization from ethanol and hexanes gave 1.01 g (60%) of aniline 191 as off-white needles. MS (M+H) 261.0.

Example 192

This illustrates the synthesis of compound 192. (See Table below)

A round-bottomed flask was charged with aniline 191 (144 mg, 0.55 mmol), 2,4-dichlorobenzenesulfonyl chloride (221 mg, 0.55 mmol), 2,6-lutidine (97 mg, 0.55 mmol), catalytic DMAP, and acetone (3.0 mL). The reaction was allowed to stir overnight. The reaction was then diluted with 20 mL of methylene chloride and washed with 10 mL of 1N HCl and 10 mL of brine. The organics were dried over $Na_2SO_4$ and concentrated to a clear oil. This oil was further purified using silica gel flash chromatography. The desired fractions were combined and concentrated to a stiff foam. The product was recrystallized from methylene chloride and hexanes to yield 165 mg (65%) of compound 192 as white crystals.

$^1$H NMR ($d_6$-DMSO) δ 11.21 (1H, s); 8.12 (1H, d, J=8.6 Hz); 7.92 (1H, d, J=2.1 Hz); 7.69-7.63 (3H, m); 7.48 (1H, dd, J=7.3, 4.3 Hz); 7.31-7.29 (3H, m); 7.18 (1H, dd, J=9.0, 2.6 Hz). MS (M−H) 467.0

The additional examples of Table 25 were prepared from aniline 191 and the corresponding sulfonyl chloride by the method of example 192.

TABLE 25

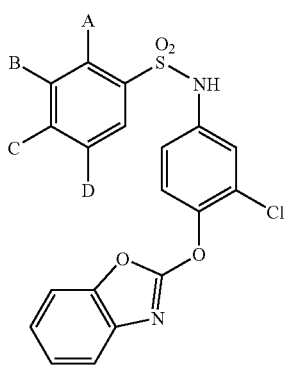

| Example | A | B | C | D | (M − H) |
|---|---|---|---|---|---|
| 192 | Cl | H | Cl | H | 467 |
| 193 | Cl | H | Cl | Me | 481 |
| 194 | Me | H | Cl | Me | — |
| 195 | Cl | H | CF$_3$ | H | 501 |
| 196 | H | H | —COMe | H | 441 |
| 197 | [2-chloro-5-pyridyl] | | | | 434 |

Example 193

$^1$H NMR ($d_6$-DMSO) δ 11.14 (1H, s); 8.14 (1H, s); 7.87 (1H, s); 7.65-7.61 (2H, m); 7.50-7.48 (1H, m); 7.32-7.28 (3H, m); 7.19 (1H, dd, J=8.9, 2.7 Hz); 2.40 (3H, s). MS (M−H) 481

Example 194

$^1$H NMR ($d_6$-DMSO) δ 10.92 (1H, s); 7.94 (1H, s); 7.65-7.60 (2H, m); 7.54 (1H, s); 7.49 (1H, dd, J=4.8,1.6 Hz); 7.31-7.27 (3H, m); 7.16 (1H, dd, J=8.9, 2.6 Hz); 2.56 (3H, s); 2.36 (3H, s).

Example 195

$^1$H NMR ($d_6$-DMSO) δ 11.36 (1H, s); 8.32 (1H, d); 8.18 (1H, s); 7.97 (1H, dd); 7.64 (2H, dd); 7.47 (1H, d); 7.31 (3H, m); 7.20 (1H, dd). MS (M−H) 501.

Example 196

$^1$H NMR (400 MHz) ($d_6$-DMSO) δ 10.96 (1H, s); 8.15 (2H, dd); 7.97 (2H, d); 7.62 (2H, d); 7.49 (1H, t); 7.31 (3H, m); 7.22 (1H, t); 2.62 (3H, s). MS (M−H) 441.0

Example 197

$^1$H NMR ($d_6$-DMSO) δ 11.04 (1H, s); 8.89 (1H, s); 8.34 (1H, dd); 8.05 (1H, d); 7.87 (1H, d); 7.67 (1H, dd); 7.52 (1H, t); 7.38 (1H, d); 7.25 (1H, t); 7.19 (1H, t); 2.62 (3H, s). MS (M−H) 434.0

Example 198

Preparation of 3-Chloro-4-(quinolin-3-yloxy)nitrobenzene (198)

To a solution of 3-hydroxyquinoline (1.00 g) and 3-chloro-4-fluoronitrobenzene (1.21 g) in Acetone (20 ml), was added $K_2CO_3$ (2.86 g). The mixture was refluxed for 1 hr. After cooling the reaction mixture was filtered through a short celite pad. The filtrate was concentrated to provide compound 198 (2.07 g, quant.) as a brown oil.

$^1$H NMR(300 MHz/CDCl$_3$) δ 7.02(1H, d, J=9.1 Hz), 7.61 (1H, m), 7.72-7.80(3H, m), 8.10-8.18(2H, m), 8.45(1H, d, J=2.7 Hz), 8.82(1H, d, J=2.8 Hz).

Example 199

Preparation of 3-Chloro-4-(quinolin-3-yloxy)phenylamine (199)

To a solution of nitrobenzene 198 (2.07 g) and NH$_4$Cl (1.84 g) in EtOH (40 ml)-H$_2$O (10 ml), was added iron powder (1.92 g). The mixture was heated to reflux for 1 hr. After cooling the reaction mixture was filtered through short celite pad. The filtrate was concentrated, diluted with sat. NaHCO$_3$ (30 ml) and extracted with AcOEt (30 ml). The combined organic layers were washed with brine (30 ml) and dried over Na$_2$SO$_4$. Concentration of the solvent afforded the aniline 199 (1.77 g, 95%) as a yellow solid.

$^1$H NMR(300 MHz/CDCl$_3$) δ 3.77(2H, brs), 6.63(1H, dd, J=2.7 Hz, J=8.6 Hz), 6.83(1H, d, J=2.7 Hz), 6.99(1H, d, J=8.6 Hz), 7.24(1H, d, J=2.8 Hz), 7.49(1H, m), 7.56-7.64(2H, m), 8.08(1H, m), 8.86(1H, J=2.8 Hz)

The structures for examples 200-208 are illustrated in Table 26.

TABLE 26

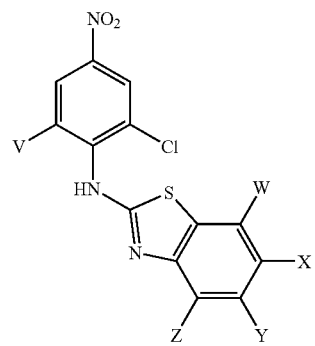

| EXAMPLE | V | W | X | Y | Z | MS(M − H) |
|---|---|---|---|---|---|---|
| 200 | Cl | H | Cl | H | H | 372 |
| 201 | H | H | H | H | H | 304 |
| 203 | H | Cl | H | H | Me | 352 |
| 204 | Cl | Cl | H | Cl | H | 406 |
| 205 | Cl | H | H | H | Me | 354 (M + H) |
| 206 | Cl | H | Me | H | H | 354 (M + H) |

TABLE 26-continued

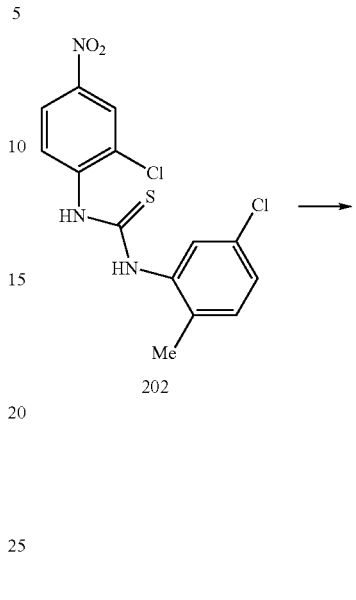

| EXAMPLE | V | W | X | Y | Z | MS(M − H) |
|---|---|---|---|---|---|---|
| 207 | Cl | Cl | H | H | H | 372 |
| 208 | Cl | H | —SO$_2$Me | H | H | 416 |

Example 200

This illustrates the synthesis of compound 200.

2-amino-6-chlorobenzothiazole (3.68 g, 20 mmol) and 1,2,3-trichloro-5-nitrobenzene (4.53 g, 20 mmol) were dissolved in anhydrous DMSO (10 mL). Solid K$_2$CO$_3$ (3.04 g, 22 mmol) was added and the reaction mixture heated to 150° C. for 4 hours. Let cool, then poured into 200 mL deionized water. A fine yellow solid precipitated which was collected by filtration after attempts to dissolve the product in ethyl acetate failed. The yellow solid was suspended in 100 mL of ethyl acetate and heated to reflux. After cooling to room temperature, filtration, rinsing with ethyl acetate followed by hexanes, and drying under vacuum provided the nitro compound 200 as a yellow powder. (1.06 g)

$^1$H NMR (d$_6$-DMSO) δ 8.37 (s, 2H); 7.76 (bs, 1H); 7.30 (dd, 1H); 7.23 (bs, 1H). MS (M−H) 372

Example 201

This illustrates the synthesis of compound 201.

To a solution of 2-chloro-4-nitro aniline (2 g) and potassium t-butoxide (12 mmol) in THF (18 mL) was added a solution of 2-chlorobenzothiazole (2.75 g) in THF (6 mL). The mixture was heated at reflux overnight then quenched into water (100 mL). The product is extracted with methylene chloride and purified by flash chromatography to afford compound 201 (300 mg) as a yellow solid.

$^1$H NMR (d6-acetone) δ 9.74 (br s, 1H), 9.214 (br d, 1H), 8.346 (m, 2H), 7.891 (d, J=8 Hz, 1H), 7.794 (d, J=8 Hz, 1H), 7.466 (t, J=7.2 Hz, 1H), 7.321 (t, J=7.2 Hz, 1H). MS (M−H) 304.

Example 202

This illustrates the synthesis of compound 202.

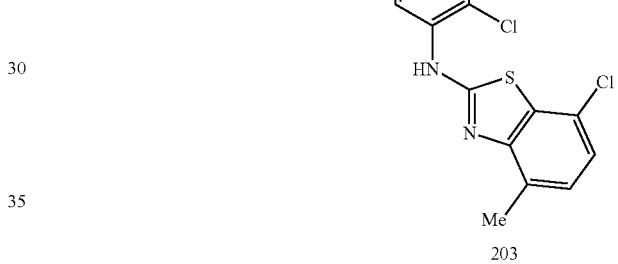

By the method of Abuzar et al, (Ind. J. Chem 20B, 230-233 (1981)) 2-chloro-4-nitro phenylisothiocyanate (Lancaster) (0.95 g) was coupled with 2-amino-4-chlorotoluene (0.69 g) in reluxing acetone to form the mixed thiourea 202 (1.5 g).

$^1$H NMR (DMSO) δ 10.021 (s, 1H), 9.789 (s, 1H), 8.373 (m, 1H), 8.197 (m, 2H), 7.441 (d, J=1.6 Hz, 1H), 7.315 (d, J=8.4 Hz, 1H), 7.268 (dd, J=8.4, 2. Hz, 1H), 2.237 (s, 3H). MS (M+H) 356. Anal. calcd.: 47.20% C, 3.11% H, 11.80% N; found: 47.24% C, 3.15% N, 11.69% N.

Example 203

This illustrates the synthesis of compound 203.

To a cool solution of thiourea 202 (0.63 g) in chloroform (6 mL) was added bromine (0.6 g) slowly. The mixture was then heated to reflux for 2 hours. On cooling, the solids were collected by filtration and then triturated with acetone to afford benzothiazole 203 as its HBR salt (0.5 g).

$^1$H NMR (DMSO) δ 8.989 (br d, J=8.4 Hz, 1H), 8.365 (d, J=2.4 Hz, 1H), 8.291 (dd, J=9.2, 2.8 Hz, 1H), 7.259 (m, 2H), 5.4 (br s), 2.557 (s, 3H). MS (M−H) 352. Anal. calcd.: for M+0.9HBr: 39.38% C, 2.34% H, 9.84% N; found: 39.44% C, 2.35% H, 9.66% N.

Example 204

This illustrates the synthesis of compound 204.

By the method of examples 202 and 203, 2,6-dichloro-4-nitrophenylisothiocyanate (GB1131780 (1966)) was coupled with 3,5-dichloroaniline to form the corresponding mixed thiourea which was cyclized with bromine to afford benzothiazole 204 suitable for use in the next reaction. MS (M−H) 406

Example 205

By the method of example 200, benzothiazole 205 was prepared in 78% yield as a yellow solid. MS (M+H) 354.

Example 206

By the method of example 200, benzothiazole 206 was prepared in 30% yield as a yellow solid. MS (M+H) 354

Example 207

This illustrates the synthesis of compound 207.

2,7-dichlorobenzothiazole (Example 73.2) (0.85 g, 4.2 mmol) and 2,6-dichloro-4-nitroaniline (2.1 g, 10.4 mmol) were dissolved in anhydrous DMSO (10 mL). Solid $Cs_2CO_3$ (4.1 g, 12.5 mmol) was added and the reaction mixture heated to 80° C. for 16 hours. Let cool, then poured into 200 mL DI water. Excess cesium carbonate was neutralized with acetic acid. The aqueous layer was extracted 2×100 mL of ethyl acetate. The combined organic layers were washed with saturated brine, dried over $MgSO_4$, filtered, and concentrated to a yellow-brown solid. The insolubility of this compound prevented purification, so the crude material was used directly in the next reaction.

$^1$H NMR (400 MHz) ($d_6$-acetone) δ 10.35 (bs, 1H); 8.36 (s, 2H); 7.37 (t, 1H); 7.30 (dd, 1H); 7.21 (dd, 1H). MS (M−H) 371.9.

Example 208

By the method of examples 202 and 203, 2,6-dichloro-4-nitrophenylisothiocyanate (GB1131780 (1966)) was coupled with methyl-(4-aminophenyl)-sulfone to form the corresponding mixed thiourea which was cyclized with bromine to afford benzothiazole 208 suitable for use in the next reaction.

$^1$H NMR (DMSO) δ 8.44 (s, 2H), 8.28 (br s, 2H), 7.82 (br d, 1H), 7.41 (br d, 1H), 3.19 (s, 3H). MS (M−H) 416.

Examples 209-216

Reduction of the nitro derivatives of Table 26 by the methods of example 32 or example 175 gave the corresponding anilines illustrated in Table 27.

The structures for examples 209-216 are illustrated in Table 27.

TABLE 27

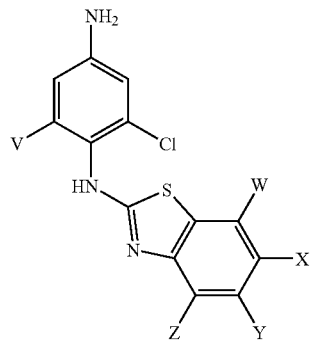

| EXAMPLE | V | W | X | Y | Z | MS(M + H) |
|---|---|---|---|---|---|---|
| 209 | Cl | H | Cl | H | H | 344 |
| 210 | H | H | H | H | H | 276 |
| 211 | H | Cl | H | H | Me | 324 |
| 212 | Cl | Cl | H | Cl | H | 378 |
| 213 | Cl | H | H | H | Me | 324 |
| 214 | Cl | H | Me | H | H | 324 |
| 215 | Cl | Cl | H | H | H | 344 |
| 216 | Cl | H | —SO$_2$Me | H | H | 388 |

Example 209

$^1$H NMR ($d_6$-acetone) δ 8.78 (s, 1H); 7.29 (d, 1H); 7.41 (d, 1H); 7.27 (d, 1H); 6.86 (s, 2H); 5.42 (s. 1H). MS (M+H) 344

Example 212

$^1$H NMR (DMSO) δ 10.09 (s, 1H), 7.48 (br s, 1H), 7.31 (d, J=1.8 Hz, 1H), 6.72 (s, 2H), 5.91 (br s, 2H). MS (M+H) 378

Example 215

Crude 207 was reduced with $SnCl_2.2H_2O$ according to the procedure of Example 32 to afford compound 215 as a greenish/gray solid after recrystallization from hot ethyl acetate/hexanes (1.14 g).

$^1$H NMR ($d_6$-acetone) δ 8.87 (bs, 1H); 7.40 (dd, 1H); 7.30 (t, 1H); 7.11 (d, 1H); 6.87 (s, 2H); 5.44 (bs, 2H). MS (M+H) 344.0

Example 216

$^1$H NMR (DMSO) δ 10.08 (s, 1H), 8.31 (s, 1H), 7.76 (d, J=8.4 Hz, 1H), 7.57 (d, J=8.4 Hz, 1H), 6.73 (s, 2H), 5.90 (s, 2H), 3.17 (s, 3H). MS (M−H) 388

Examples 217-238

Sulfonation of the anilines of Table 27 by the methods of example 3 or 192 provides the compounds illustrated in Table 28.

TABLE 28

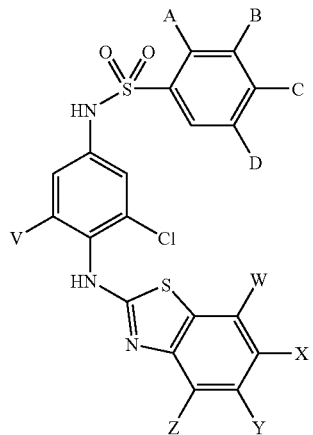

| Example # | A | B | C | D | V | W | X | Y | Z | MS(M − H) |
|---|---|---|---|---|---|---|---|---|---|---|
| 217 | Cl | H | Cl | Me | Cl | H | Cl | H | H | 564 |
| 218 | Cl | H | Cl | H | Cl | H | Cl | H | H | 550 |
| 219 | Cl | H | CF$_3$ | H | Cl | H | Cl | H | H | 584 |
| 220 | Cl | H | Cl | H | H | H | H | H | H | 482 |
| 221 | Cl | H | CF$_3$ | H | H | H | H | H | H | 516 |
| 222 | Cl | H | Cl | Me | H | H | H | H | H | 496 |
| 223 | Cl | H | Cl | H | Cl | H | Cl | H | Me | 530 |
| 224 | Cl | H | CF$_3$ | H | Cl | H | Cl | H | Me | 564 |
| 225 | Cl | H | Cl | H | Cl | Cl | H | Cl | H | 584 |
| 226 | Cl | H | CF$_3$ | H | Cl | Cl | H | Cl | H | 618 |
| 227 | Cl | H | Cl | Me | Cl | Cl | H | Cl | H | 598 |
| 228 | Cl | H | Cl | H | Cl | H | H | H | Me | 530 |
| 229 | Cl | H | CF$_3$ | H | Cl | H | H | H | Me | 564 |
| 230 | Cl | H | Cl | Me | Cl | H | H | H | Me | 544 |
| 231 | H | H | —COMe | H | Cl | H | H | H | Me | — |
| 232 | Cl | H | Cl | H | Cl | H | Me | H | H | 530 |
| 233 | Cl | H | CF$_3$ | H | Cl | H | Me | H | H | 564 |
| 234 | Cl | H | Cl | Me | Cl | H | Me | H | H | 544 |
| 235 | Cl | H | Cl | H | Cl | Cl | H | H | H | 550 |
| 236 | Cl | H | CF$_3$ | H | Cl | Cl | H | H | H | 584 |
| 237 | Cl | H | Cl | H | Cl | H | —SO$_2$Me | H | H | 594 |
| 238 | Cl | H | CF$_3$ | H | Cl | H | —SO$_2$Me | H | H | 628 |

Example 217

$^1$H NMR (d$_6$-acetone) δ 9.19 (bs, 1H); 8.51 (s, 1H); 7.74 (d, 1H); 7.72 (s, 1H); 7.43 (s, 2H); 7.37 (d, 1H); 7.28 (dd, 1H); 2.46 (s, 3H). MS (M–H) 563.9

Example 218

$^1$H NMR (d$_6$-acetone) δ 9.19 (bs, 1H); 8.22 (d, 1H); 7.78 (d, 1H); 7.74 (d, 1H); 7.67 (dd, 1H); 7.43 (s, 2H); 7.37 (d, 1H); 7.28 (dd, 1H). MS (M–H) 549.8

Example 219

$^1$H NMR (d$_6$-acetone) δ 10.05 (bs, 1H); 9.22 (bs, 1H); 8.45 (d, 1H); 8.06 (s, 1H); 7.98 (d, 1H); 7.73 (m, 1H); 7.45 (s, 2H); 7.36 (d, 1H); 7.28 (dt, 1H). MS (M–H) 583.8.

Example 223

$^1$H NMR (DMSO) δ 10.96 (1H, s), 10.11 (1H, s), 8.12-8.22 (1H, broad), 8.06 (1H, d, 8.6), 7.90 (1H, d, J=2.1 Hz), 7.65 (1H, dd, J=8.6, 2.1 Hz), 7.23 (1H, d, J=3.5 Hz), 7.10-7.20 (3H, m), 2.44 (3H, s). MS (M–H) 529.8

Example 224

$^1$H NMR (DMSO) δ 11.11 (1H, s), 10.11 (1H, s), 8.27 (1H, d, J=8.0 Hz), 8.16 (2H, s), 7.94 (1H, d, J=8.6 Hz), 7.10-7.26 (4H, m), 2.43 (3H, s). MS (M–H) 563.9. mp 192.6° C.

Example 225

$^1$H NMR (DMSO) δ 11.49 (s, 1H), 10.44 (s, 1H), 8.164 (d, J=8.4 Hz, 1H) 7.95 (d, J=2 Hz, 1H), 7.71 (dd, J=8.4, 2 Hz, 1H), 7.50 (br s, 1H), 7.35 (d, J=1.6 Hz, 1H), 7.25 (s, 2H). MS (M–H) 584.

Example 226

$^1$H NMR(DMSO) δ 11.59 (s, 1H), 10.40 (s, 1H), 8.368 (d, J=8.4 Hz, 1H), 8.20 (br s, 1H), 8.00 (br d, J=8.4 Hz, 1H), 7.48 (br s, 1H), 7.344 (t, J=1.6 Hz, 1H), 7.274 (d, J=1.6 Hz, 2H). MS (M–H) 618.

Example 227

$^1$H NMR (DMSO) δ 11.37 (s, 1H), 10.40 (s, 1H), 8.19 (br s, 1H), 7.90 (m, 1H), 7.53 (br s, 1H), 7.35 (br s, 1H), 7.25 (br s, 2H), 2.415 (s, 3H). MS (M–H) 598.

Example 228

¹H NMR (d₆-DMSO) δ 11.44 (1H, broad s); 9.96 (1H, broad s); 8.33 (1H, d); 8.19 (1H, s); 7.99 (1H, dd); 7.43 (1H, broad s); 7.26 (2H, s); 7.07 (1H, d); 6.97 (1H, t); 2.35 (3H, s). MS (M−H) 529.9.

Example 229

¹H NMR(d₆-DMSO) δ 11.26 (1H, broad s); 9.96 (1H, broad s); 8.12 (1H, d); 7.93 (1H, d); 7.69 (1H, dd); 7.43 (1H, broad s); 7.23 (2H, s); 7.08 (1H, d); 6.97 (1H, t); 2.36 (3H, s). MS (M−H) 564.

Example 230

¹H NMR (d₆-DMSO) δ 11.23 (1H, broad s); 9.96 (1H, broad s); 8.14 (1H, s); 7.88 (1H, s); 7.43 (1H, broad s); 7.24 (2H, s); 7.08 (1H, d); 6.97 (1H, t); 2.40 (3H, s); 2.36 (3H, s). MS (M−H) 543.9.

Example 231

¹NMR (d₆-DMSO) δ 11.02 (1H, broad s); 9.96 (1H, broad s); 8.16 (2H, d); 7.97 (2H, d); 7.43 (1H, broad s); 7.26 (1H, s); 7.07 (1H, d); 6.97 (1H, t); 2.62 (3H, s); 2.36 (3H, s).

Example 232

¹H NMR (d₆-DMSO) δ 11.28 (1H, broad s); 9.79 (1H, broad s); 8.13 (1H, d); 7.93 (2H, d); 7.70 (1H, dd); 7.44 (1H, broad s); 7.21 (3H, s); 7.05 (1H, d); 2.30 (3H, s). MS (M−H) 529.9.

Example 233

¹H NMR (d₆-DMSO) δ 11.43 (1H, broad s); 9.79 (1H, broad s); 8.34 (1H, d); 8.19 (1H, s); 7.99 (1H, d); 7.44 (1H, broad s); 7.24 (3H, s); 7.04 (1H, d); 2.30 (3H, s). MS (M−H) 564.

Example 234

¹H NMR (d₆-DMSO) δ 11.22 (1H, broad s); 9.79 (1H, broad s); 8.15 (1H, s); 7.89 (1H, s); 7.44 (1H, broad s); 7.23 (3H, s); 7.04 (1H, d); 2.41 (3H, s); 2.31 (3H, s). MS (M−H) 543.9.

Example 235

¹H NMR (d₆-acetone) δ 9.92 (bs, 1H); 9.35 (bs, 1H); 8.23 (d, 1H); 7.78 (d, 1H); 7.67 (dd, 1H); 7.45 (s, 2H); 7.36-7.29 (m, 2H); 7.16 (dd, 1H). MS (M−H) 549.8.

Example 236

¹H NMR (d₆-acetone) δ 8.45 (d, 1H); 8.06 (s, 1H); 7.97 (d, 1H); 7.46 (s, 2H); 7.33-7.29 (m, 2H); 7.16 (dd, 1H). MS (M−H) 583.8.

Example 237

¹H NMR (DMSO) δ 11.43 (br s, 1H), 10.40 (br s, 1H), 8.33 (br s, 1H), 8.16 (d, J=8 Hz, 1H), 7.94 (d, J=2 Hz, 1H), 7.753 (dd, J=8.2, 2 Hz, 1H), 7.71 (dd, J=8.4, 2 Hz, 1H), 7.55 (br s, 1H), 7.265 (s, 2H), 3.22 (s, 3H). MS (M−H) 594.

Example 238

¹H NMR (DMSO) δ 11.55 (br s, 1H), 10.40 (br s, 1H), 8.38 (m, 2H), 8.22 (br s, 1H), 8.02 (br d, 1H), 7.77 (dd, J=8.4, 2 Hz, 1H), 7.55 (br s, 1H), 7.295 (s, 2H), 3.19 (s, 3H). MS (M−H) 628.

TABLE 29

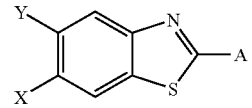

| Example # | A | X | Y | yield |
| --- | --- | --- | --- | --- |
| 239 | SH | H | CF₃ | 92% |
| 240 | SH | H | CO₂H | 66% |
| 241 | SH | CN | H | 97% |
| 243 | SH | H | CN | 49% |
| 245 | SH | H | Me | 53% |
| 250 | Cl | H | Cl | 96% |

Example 239

2-Mercapto-5-trifluoromethyl-benzothiazole (239)

In analogy to the procedure of Chaudhuri, N. *Synth. Commun.* 1996, 26, 20, 3783, O-ethylxanthic acid, potassium salt (Lancaster, 7.5 g, 46.9 mmol) was added to a solution of 2-bromo-5-trifluoromethylphenylamine (Aldrich, 5.0 g, 20.8 mmol) in N,N-dimethylformamide (DMF, 30 mL). The mixture was heated to reflux for 4 hours. After cooling to room temperature, the mixture was poured into ice water and acidified with 2N HCl. The solid product was collected by filtration. Recrystalization from CHCl₃/Hexanes gave 239 (4.5 g, 92%) as a white solid.

¹H NMR (400 MHz, DMSO-d₆) δ 14.00 (s, 1H), 7.94 (d, J=8.1 Hz, 1H), 7.62 (dd, J=8.4, 1.0 Hz, 1H), 7.48 (d, J=1.0 Hz, 1H). MS (M−H) 234.

Example 240

2-Mercapto-benzothiazol-5-carboxylic acid (240)

2-Mercapto-benzothiazol-5-carboxylic acid (240) (3.5 g, 66%) was synthesized from 4-chloro-3-nitro-benzoic acid, obtained from Fluka, and potassium dithiocarbonate O-ethyl ester, obtained from Lancaster, according to the procedure of Chaudhuri, N. *Synth. Commun.* 1996, 26, 20, 3783.

¹H NMR (400 MHz, DMSO-d₆) δ 14.0 (s, 1H), 13.3 (bs, 1H), 7.85-7.79 (m, 3H).

Example 241

2-Mercapto-benzothiazole-6-carbonitrile (241)

The title compound was prepared using the method of example 239, starting with 4-amino-3-chloro-benzonitrile (Lancaster, 5.0 g, 32.7 mmol), O-ethylxanthic acid, potassium salt (Lancaster, 11.8 g, 73.7 mmol) in DMF (40 mL). The mercaptobenzothiazole (241) (6.1 g, 97%) was obtained as a pale brown solid.

¹H NMR (DMSO-d₆) δ 14.10 (s, 1H), 8.22 (d, J=1.3 Hz, 1H), 7.82 (dd, J=8.4, 1.5 Hz, 1H), 7.40 (d, J=8.5 Hz, 1H). MS (M−H) 191.

Example 242

3-Amino-4-chloro-benzonitrile (242)

The title compound was prepared using the method of example 32, starting with 4-chloro-3-nitro-benzonitrile (Fluka, 11.0 g, 60 mmol), tin chloride dihydrate (Aldrich, 67.8 g, 300 mmol). 9.0 g (98%) of crude compound 242 was obtained as a yellowish solid.

$^1$H NMR (DMSO-$d_6$) δ 7.39 (d, J=8.1 Hz, 1H), 7.10 (d, J=2.0 Hz, 1H), 6.93 (dd, J=8.2, 2.0 Hz, 1H), 5.88 (s, 2H). MS (M–H) 151.

Example 243

2-Mercapto-benzothiazole-5-carbonitrile (243)

The title compound was prepared using the method of example 239, starting with 3-amino-4-chloro-benzonitrile (242) (9.0 g, 59.0 mmol), O-ethylxanthic acid, potassium salt (Lancaster, 21.23 g, 132.7 mmol) in DMF (90 mL). 5.6 g (49%) of compound 243 was obtained as a pale brown solid.

$^1$H NMR (DMSO-$d_6$) δ 14.10 (br s, 1H), 7.90 (d, J=8.3 Hz, 1H), 7.70 (dd, J=8.3, 1.1 Hz, 1H), 7.60 (br s, 1H). MS (M–H) 191.

Example 244

2-Bromo-5-methyl-phenylamine (244)

The title compound was prepared using the method of example 32, starting with 1-bromo-4-methyl-2-nitro-benzene (Lancaster, 10.1 g, 46.7 mmol), tin chloride dihydrate (Aldrich, 52.8 g, 233 mmol). 8.2 g (94%) of crude compound 244 was obtained as a pale brown oil.

$^1$H NMR (DMSO-$d_6$) δ 7.18 (d, J=8.1 Hz, 1H), 6.60 (d, J=2.1 Hz, 1H), 6.93 (dd, J=8.1, 1.8 Hz, 1H), 5.34 (s, 2H), 2.26 (s, 3H). MS (M+H)186.

Example 245

2-Mercapto-5-Methyl-benzothiazole (245)

The title compound was prepared using the method of example 239, starting with 2-bromo-5-methyl-phenylamine (244) (4.48 g, 24.0 mmol), O-ethylxanthic acid, potassium salt (Lancaster, 8.70 g, 54 mmol) in DMF (35 mL). The mercaptobenzothiazole 245 was obtained as an pale brown solid (2.31 g, 53%).

$^1$H NMR (DMSO-$d_6$) δ 13.70 (br s, 1H), 7.56 (d, J=8.6 Hz, 1H), 7.15-7.10 (m, 2H), 2.38 (s, 3H). MS (M–H) 180.

Example 246 & 247

2,3-Dichloro-5-nitrobenzoic acid (246)

2,3-Dichlorobenzoic acid, obtained from Aldrich, (40 g, 0.21 mole) was added portion wise to a −20° C. concentrated $H_2SO_4$, obtained from Acros, (233 mL) solution which was fitted with a mechanical overhead stirrer. During the addition process, a separate flask containing concentrated $H_2SO_4$ (50 mL) was cooled to 0° C. and fuming $HNO_3$, obtained from Acros, (16.6 mL) was slowly added. This solution was then added dropwise to the 2,3-Dichlorobenzoic acid solution at a rate which kept the reaction mixture at or slightly below −15° C. After the addition was complete the resulting solution was allowed to warm to 10° C. over 3 hours. The crude solid material was filtered through a fitted filter funnel, washed with cold $H_2O$ (200 mL), and dried under a stream of air followed by high vacuum to yield 21.7 g (44%) of product (246) which contained 4% of the undesired regioisomer (2,3-Dichloro-6-nitrobenzoic acid 247) based on $^1$H NMR analysis. The filtrate was slowly poured over ice and additional solid precipitated. This solid was observed to be a 3:1 mixture of 2,3-dichloro-6-nitrobenzoic acid (247) to 2,3-dichloro-5-nitrobenzoic acid (246) based on $^1$H NMR analysis.

2,3-Dichloro-5-nitrobenzoic acid (246): $^1$H NMR (DMSO-$d_6$) δ 8.63 (d, J=2.7 Hz, 1H), 8.47 (d, J=2.7 Hz, 1H). 2,3-Dichloro-6-nitrobenzoic acid: (247). $^1$H NMR (DMSO-$d_6$) δ 8.22 (d, J=9.0 Hz, 1H), 8.02 (d, J=9.0 Hz, 1H).

Example 248

1-(2,3-Dichloro-5-nitro-phenyl)-ethanone (248)

To thionyl chloride, obtained from Aldrich, (125 mL) at 0° C. was slowly added 2,3-Dichloro-5-nitrobenzoic acid (246) (21.7 g, 91.9 mmol). The ice bath was taken away and the resulting solution was heated to reflux for 17 hours (note: acid completely dissolves upon heating). After cooling to ambient temperature, the excess thionyl chloride was removed under vacuum and the resulting acid chloride was allowed to stand under high vacuum for 15 h and used in the next step without further purification. To a 1M solution of NaH, 60% oil dispersion obtained from Aldrich, (11.39 g, 285 mmol) in DMF at 0° C. was slowly added diethylmalonate, obtained form Aldrich, (14.65 mL, 96.5 mmol) dropwise and the resulting solution was allowed to stir for 30 minutes. The acid chloride was dissolved in DMF (184 mL) and slowly added via cannula to the reaction mixture. The resulting solution was then allowed to stir for 16 h as ambient temperature was reached followed by recooling to 0° C. and slowly quenching with excess 2M aqueous HCl (200 mL). To the crude reaction was added $H_2O$ (500 mL) and EtOAc (500 mL). The aqueous layer was extracted three times with EtOAc (500 mL), the organic layers were combined, washed four times with saturated aqueous brine (500 mL), dried over $Na_2SO_4$, and concentrated under vacuum to yield an oil which was used in the next step without further purification. The resulting product was dissolved in 111 mL of a 7.7/5/1 AcOH/$H_2O$/conc. $H_2SO_4$, solution and heated to reflux for 22 hours. The AcOH was removed under vacuum followed by EtOAc addition (200 mL). The solution was neutralized using 2M aqueous NaOH, extracted 3 times with EtOAc (200 mL). The combined organic layers were washed twice with saturated aqueous brine (200 mL), dried over $Na_2SO_4$, and concentrated under reduced pressure. The crude material was purified by column chromatography (30% $CH_2Cl_2$ in hexane) to yield 17.6 g (82%) of ketone 248 as a light brown solid. $^1$H NMR (DMSO-$d_6$) δ 8.61 (d, J=2.6 Hz, 1H), 8.48 (d, J=2.6 Hz, 1H), 2.65 (s, 3H).

Example 249

2-Methoxy-4-nitrobenzenethiol (249)

2-Methoxy-4-nitrobenzenethiol (249) was prepared according to the method of Price and Stacy, *J. Amer. Chem. Soc.* 68, 498-500 (1946)) in 67% yield from 1-chloro-2-methoxy-4-nitro-benzene, obtained from Aldrich.

$^1$H NMR (DMSO-$d_6$) δ 7.8 (bd, J=8.4 Hz, 1H), 7.73 (bs, 1H), 7.62 (bd, J=8.4 Hz, 1H), 5.8 (bs, 1H), 3.95 (s, 3H). MS (M–H) 184.

Example 250

2,5-Dichloro-benzenethiazole (250)

5-Chloro-benzenethiazole-2-thiol, obtained from Aldrich, (2 g, 9.9 mmol) was added slowly to sulfuryl chloride, obtained from Aldrich, (20 mL) and stirred for 1 h followed by heating to 50° C. for 15 minutes. The mixture was cooled, poured slowly over ice water and stirred for 30 minutes. The product precipitated out of solution as a yellow solid and was collected by vacuum filtration and dried under a stream of air followed by high vacuum to give 1.92 g (96%) of compound 250.

$^1$H NMR (400 MHz, DMSO-d$_6$) δ 8.18 (d, J=8.7 Hz, 1H), 8.1 (d, J=2.0, 1H), 7.59 (dd, J=8.7, 2.1 Hz, 1H).

TABLE 30

Table 30 illustrates the structures of examples 251-264.

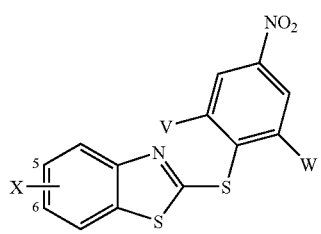

| # | X | V | W | Yield |
|---|---|---|---|---|
| 251 | 5-Cl | Cl | —COMe | 52% |
| 252 | 5-CF$_3$ | Cl | H | 92% |
| 253 | 5-CO$_2$H | Cl | H | 66% |
| 254 | 5-CO$_2$Me | Cl | H | 100% |
| 255 | 5-CO$_2$H | Cl | Cl | 100% |
| 256 | 5-CO$_2$Me | Cl | Cl | 100% |
| 257 | 5-Cl | H | —OMe | 75% |
| 258 | 5-CF$_3$ | Cl | Cl | 99% |
| 259 | 5-CF$_3$ | Cl | —COMe | 75% |
| 260 | 6-CN | Cl | Cl | 99% |
| 261 | 6-CN | Cl | H | 93% |
| 262 | 5-CN | Cl | Cl | 99% |
| 263 | 5-CN | Cl | H | 92% |
| 264 | 5-Me | Cl | —COMe | 98% |

Example 251

1-[3-Chloro-2-(5-chloro-benzothiazol-2-ylsulfanyl)-5-nitro-phenyl]-ethanone (251)

To a 0.55M solution of 5-chloro-2-mercaptobenzothiazole, obtained from Aldrich, (5.55 g, 27.5 mmol) in DMF at ambient temperature was added NaH, 60% oil dispersion obtained from Aldrich, (1.2 g, 30.0 mmol) portionwise followed by 1-(2,3-Dichloro-5-nitro-phenyl)-ethanone (248) (5.83 g, 25 mmol). The reaction solution turned from bright orange to deep red upon acetophenone addition and was heated to 60° C. for 1 hour. The mixture was allowed to cool for a couple of minutes and the product was precipitated out of solution by the slow addition of H$_2$O (250 mL). After 1 h of stirring the product was collect by vacuum filtration using a buchner funnel, dried under a stream of air for 3 h, and triterated with a 1:1 MeOH/CH$_2$Cl$_2$ solution (200 mL) to yield 5.2 g (52%) of 251 as an orange solid. An additonal 3.77 g (39%) could be isolated by purifying the mother liquor using column chromatography (dry load,100% CH$_2$Cl$_2$).

$^1$H NMR (DMSO-d$_6$) δ 8.68 (d, J=2.5 Hz, 1H), 8.6 (d, J=2.4 Hz, 1H), 8.05 (d, =8.6 Hz, 1H), 7.95 (d, J=2.0 Hz, 1H), 7.56 (dd, J=8.6, 2.0 Hz, 1H), 2.65 (s, 3H).

Example 252

2-(2-Chloro-4-nitro-phenylsulfanyl)-5-trifluoromethyl-benzothiazole (252)

2-(2-Chloro-4-nitro-phenylsulfanyl)-5-trifluoromethyl-benzothiazole (252) was prepared (92%) from 2-chloro-1-fluoro-4-nitrobenzene, obtained from Aldrich, and 5-trifluoromethyl-benzothiazol-2-thiol (239) in a similar manner as described in example 251.

$^1$NMR (DMSO-d$_6$) δ 8.58 (d, J=2.4 Hz, 1H), 8.38-8.32 (m, 2H), 8.05 (d, =8.6 Hz, 1H), 8.28 (dd, J=8.7, 2.5 Hz, 1H), 8.09 (d, J=8.7 Hz, 1H), 7.8 (bd, J=9.9 Hz, 1H).

Example 253

2-(2-chloro-4-nitro-phenylsulfanyl)-benzothiazol-5-carboxylic acid (253)

2-(2-chloro-4-nitro-phenylsulfanyl)-benzothiazol-5-carboxylic acid was prepared (66%) from 2-mercapto-benzothiazol-5-carboxylic acid (240) and 2-chloro-1-fluoro-4-nitrobenzene, obtained from Aldrich, in a similar manner as described in example 251.

$^1$H NMR (DMSO-d$_6$) δ 8.56 (d, J=2.4 Hz, 1H), 8.42 (bs, 1H), 8.27 (dd, =8.7, 2.4 Hz, 1H), 8.28 (d, J=8.4 Hz, 1H), 8.17 (d, J=8.7 Hz, 1H), 8.0 (dd, J=8.4, 1.4 Hz, 1H). MS (M–H) 365.

Example 254

2-(2-Chloro-4-nitro-phenylsulfanyl)-benzothiazole-5-carboxylic acid methyl ester (254)

To a 0.25M solution of 2-(2-chloro-4-nitro-phenylsulfanyl)-benzothiazol-5-carboxylic acid (253), (1.38 g, 3.8 mmol) in 10% MeOH in THF was added a 2M solution of (trimethylsilyl)diazomethane in hexane, obtained from Aldrich, (2.1 mL, 4.18 mmol) and the resulting solution was allowed to stir for 18 hours. The crude reaction mixture was concentrated under vacuum to yield 1.4 g (100%) of ester 254 which was taken on without further purification.

$^1$H NMR (DMSO-d$_6$) δ 8.6 (d, J=2.5 Hz, 1H), 8.45 (d, J=1.4 Hz, 1H), 8.28 (dd, =8.7, 2.5 Hz, 1H), 8.24 (d, J=8.5 Hz, 1H), 8.1 (d, J=8.7 Hz, 1H), 8.0 (dd, J=8.4, 1.4 Hz, 1H), 3.9 (s, 3H).

Example 255

2-(2,6-Dichloro-4-nitro-phenylsulfanyl)-benzothiazole-5-carboxylic acid (255)

2-(2,6-Dichloro-4-nitro-phenylsulfanyl)-benzothiazole-5-carboxylic acid (255) was prepared (100%) from 2-mercapto-benzothiazol-5-carboxylic acid (240) and 1,2,3-trichloro-5-nitrobenzene, obtained from Aldrich, in a similar manner as described in example 251.

¹H NMR (DMSO-d₆) δ 11.2 (bs, 1H), 8.6 (s, 2H), 8.31 (d, J=1.4 Hz, 1H), 8.13 (d, J=8.4 Hz, 1H), 7.94 (dd, J=8.5, 1.4 Hz, 1H). MS (M−H) 399

Example 256

2-(2,6-Dichloro-4-nitro-phenylsulfanyl)-benzothiazole-5-carboxylic acid methyl ester (256)

2-(2,6-Dichloro-4-nitro-phenylsulfanyl)-benzothiazole-5-carboxylic acid methyl ester (256) was prepared (100%) from 2-(2,6-dichloro-4-nitro-phenylsulfanyl)-benzothiazole-5-carboxylic acid 255 in a similar manner as described in example 254.

¹H NMR (400 MHz, DMSO-d₆) δ 8.6 (s, 2H), 8.33 (d, J=1.6 Hz, 1H), 8.16 (d, J=8.5 Hz, 1H), 7.95 (dd, J=8.4, 1.6 Hz, 1H), 3.9 (s, 3H).

Example 257

5-Chloro-2-(2-methoxy-4-nitro-phenylsulfanyl)-benzothiazole (257)

5-Chloro-2-(2-methoxy-4-nitro-phenylsulfanyl)-benzothiazole (257) was prepared (75%) from 2-methoxy-4-nitrobenzenethiol (249) and 2,5-dichlorobenzothiazole (250), in a similar manner as described in example 251.

¹H NMR (DMSO-d₆) δ 8.05 (bd, J=8.6 Hz, 1H), 8.03 (d, J=2.0, 1H), 7.99-7.94 (m, 3H), 7.48 (dd, J=8.6, 2.1 Hz, 1H), 3.95 (s, 3H).

Example 258

2-(2,6-Dichloro-4-nitro-phenylsulfanyl)-5-trifluoromethyl-benzothiazole (258)

To a solution of 2-mercapto-5-trifluoromethyl-benzothiazole (239) (470 mg, 2.0 mmol) in DMF (20 mL) was added NaH (Aldrich, 60% suspension in hexanes, 80 mg, 2.0 mmol). After the resulting mixture was stirred at ambient temperature for 20 minutes, was added 1,2,3-trichloro-5-nitrobenzene (Acros, 452 mg, 2.0 mmol). The mixture was then heated at 60° C. for 4 hours. After cooled to room temperature, the mixture was poured to water and stirred for 1 hour. The solid product was collected by vacuum filtration to give 258 as a pale yellow solid (840 mg, 99%) which was used in the next reaction without further purification.

¹H NMR (DMSO-d₆) δ 8.61 (s, 2H), 8.27 (d, J=8.4 Hz, 1H), 7.21 (br s, 1H), 7.74 (dd, J=8.4, 1.5 Hz, 1H). MS (M+H) 425.

Example 259

1-[3-Chloro-5-nitro-2-(5-trifluoromethyl-benzothiazol-2-ylsulfanyl)-phenyl]-ethanone (259)

The title compound was prepared using the method of example 258, starting with 5-trifluoromethyl-benzothiazole-2-thiol (239) (470 mg, 2.0 mmol), 1-(2,3-dichloro-5-nitrophenyl)-ethanone (248) (466 mg, 2.0 mmol) and NaH (Aldrich, 60% suspension, 80 mg, 2.0 mmol) in DMF (20 mL). Compound 259 (750 mg, 87%) was obtained as a yellow solid.

¹H NMR (DMSO-d₆) δ 8.68 (d, J=2.6 Hz, 1H), 8.62 (d, J=2.5 Hz, 1H), 8.27 (d, J=8.4 Hz, 1H), 8.20 (br s, 1H), 7.74 (dd, J=8.5, 1.7 Hz, 1H), 2.65 (s, 3H). MS (M+H) 433.

Example 260

2-(2,6-Dichloro-4-nitro-phenylsulfanyl)-benzothiazole-6-carbonitrile (260)

The title compound was prepared using the method of example 258, starting with 2-mercapto-benzothiazole-6-carbonitrile (241) (960 mg, 5.0 mmol), 1,2,3-trichloro-5-nitrobenzene (Acros, 1.13 g, 5.0 mmol) and NaH (Aldrich, 60% suspension, 200 mg, 5.0 mmol) in DMF (25 mL). Compound 260 (1.9 g, 99%) was obtained as a yellow solid.

¹H NMR (DMSO-d₆) δ 8.61 (s, 2H), 8.58 (d, J=1.8 Hz, 1H), 7.99 (d, J=8.5 Hz, 1H), 7.88 (dd, J=8.5, 1.8 Hz, 1H).

Example 261

2-(2-Chloro-4-nitro-phenylsulfanyl)-benzothiazole-6-carbonitrile (261)

The title compound was prepared using the method of example 258, starting with 2-mercapto-benzothiazole-6-carbonitrile (241) (960 mg, 5.0 mmol), 2-chloro-1-fluoro-4-nitrobenzene (Aldrich, 878 mg, 5.0 mmol) and NaH (Aldrich, 60% suspension, 200 mg, 5.0 mmol) in DMF (25 mL). Compound 261 (1.62 g, 93%) was obtained as a yellow solid.

¹H NMR (DMSO-d₆) δ 8.62 (d, J=1.5 Hz, 1H), 8.56 (d, J=2.4 Hz, 1H), 8.29 (dd, J=8.6, 2.4 Hz, 1H), 8.16 (d, J=8.6 Hz, 1H), 8.06 (d, J=8.6 Hz, 1H), 7.91 (dd, J=8.5, 1.6 Hz, 1H). MS (M+H) 348.

Example 262

2-(2,6-Dichloro-4-nitro-phenylsulfanyl)-benzothiazole-5-carbonitrile (262)

The title compound was prepared using the method of example 258, starting with 2-mercapto-benzothiazole-5-carbonitrile (243) (960 mg, 5.0 mmol), 1,2,3-trichloro-5-nitrobenzene (Acros, 1.13 g, 5.0 mmol) and NaH (Aldrich, 60% suspension, 200 mg, 5.0 mmol) in DMF (25 mL). Compound 262 (1.9 was 99%) was obtained as a yellow solid.

¹H NMR (DMSO-d₆) δ 8.62 (s, 2H), 8.38 (d, J=1.2 Hz, 1H), 8.24 (d, J=8.4 Hz, 1H), 7.88 (dd, J=8.4, 1.5 Hz, 1H).

Example 263

2-(2-Chloro-4-nitro-phenylsulfanyl)-benzothiazole-5-carbonitrile (263)

The title compound was prepared using the method of example 258, starting with 2-mercapto-benzothiazole-5-carbonitrile (243) (960 mg, 5.0 mmol), 2-chloro-1-fluoro-4-nitrobenzene (Aldrich, 878 mg, 5.0 mmol) and NaH (Aldrich, 60% suspension, 200 mg, 5.0 mmol) in DMF (25 mL). Compound 263 (1.60 g, 92%) was obtained as a yellow solid.

¹H NMR (400 MHz, DMSO-d₆) δ 8.56 (d, J=2.4 Hz, 1H), 8.49 (d, J=1.2 Hz, 1H), 8.29 (d, J=8.4 Hz, 1H), 8.29 (dd, J=8.7, 2.5 Hz, 1H), 8.12 (d, J=8.7 Hz, 1H), 7.85 (dd, J=8.5, 1.5 Hz, 1H). MS (M+H) 348.

Example 264

1-[3-Chloro-2-(5-methyl-benzothiazol-2-ylsulfanyl)-5-nitro-phenyl]-ethanone (264)

The title compound was prepared using the method of example 258, starting with 5-methyl-benzothiazole-2-thiol (245) (1.90 g, 10.5 mmol), 1-(2,3-dichloro-5-nitro-phenyl)-ethanone (248) (2.45 g, 10.5 mmol) and NaH (Aldrich, 60% suspension, 420 mg, 10.5 mmol) in DMF (20 mL). Compound 264 (3.87 g, 98%) was obtained as a yellow solid.

$^1$H NMR (400 MHz, DMSO-$d_6$) δ 8.65 (d, J=2.3 Hz, 1H), 8.58 (d, J=2.5 Hz, 1H), 7.87 (d, J=8.3 Hz, 1H), 7.67 (br s, 1H), 7.24 (dd, J=8.2, 1.5 Hz, 1H), 2.65 (s, 3H), 2.41 (s, 3H). MS (M+H) 379.

Examples 265-276: Reduction of the compounds of Table 30 provides the compounds illustrated in Table 31.

TABLE 31

Table 31 illustrates the structures of examples 265-276

| # | X | Y | V | W | Yield |
|---|---|---|---|---|---|
| 265 | H | Cl | Cl | COMe | 83% |
| 266 | H | CF$_3$ | Cl | H | 97% |
| 267 | H | CO$_2$Me | Cl | H | 96% |
| 268 | H | CO$_2$Me | Cl | Cl | 93% |
| 269 | H | Cl | H | OMe | 100% |
| 270 | H | CF$_3$ | Cl | Cl | 96% |
| 271 | H | CF$_3$ | Cl | COMe | 100% |
| 272 | CN | H | Cl | Cl | 98% |
| 273 | CN | H | Cl | H | 93% |
| 274 | H | CN | Cl | Cl | 80% |
| 275 | H | CN | Cl | H | 93% |
| 276 | H | Me | Cl | COMe | 68% |

Example 265

1-[5-Amino-3-chloro-2-(5-chloro-benzothiazol-2-ylsulfanyl)-phenyl]-ethanone (265)

To a 0.14M solution of 1-[3-Chloro-2-(5-chloro-benzothiazol-2-ylsulfanyl)-5-nitro-phenyl]-ethanone (251) (4.08 g, 10.26 mmol) in a 2:2:1 solution of EtOH, obtained from gold shield, THF, obtained from Aldrich, H$_2$O was added NH$_4^+$Cl$^-$, obtained from Aldrich, (2.74 g, 51.29 mmol) followed by iron(0) powder, obtained from Aldrich, (2.86 g, 51.29 mmol). The resulting solution was heated to reflux for 2.5 h with vigorous stirring. TLC and mass spectral analysis showed starting material and hydroxyl amine intermediate so an additional 5 Eq. of both NH$_4^+$Cl$^-$ and iron powder were subsequently added and the reaction mixture was allowed to continue to reflux for an additional 1.75 hours. The hot solution was immediately filtered through a plug of celite and the celite was washed with copious amounts of EtOAc. The organic layer was concentrated under vacuum, resuspended in EtOAc (100 mL) and NaHCO$_3$ (100 mL), and extracted 3 times with EtOAc (100 mL). The organic layer was washed twice with saturated aqueous brine (100 mL), dried over Na$_2$SO$_4$, concentrated under vacuum, and purified by column chromatography (10-50% EtOAc in hexane) to yield compound 265 (3.14 g, 83%) as a yellow solid.

$^1$H NMR (DMSO-$d_6$) δ 7.95 (d, J=8.6 Hz, 1H), 7.89 (d, J=2.0 Hz, 1H), 7.39 (dd, J=8.6, 2.1 Hz, 1H), 6.95 (d, J=2.4 Hz, 1H), 6.72 (d, J=2.4 Hz, 1H), 6.41 (s, 2H), 2.45 (s, 3H). MS (M+H) 369.

Example 266

3-Chloro-4-(5-trifluoromethyl-benzothiazol-2-ylsulfanyl)-phenyl amine (266)

3-Chloro-4-(5-trifluoromethyl-benzothiazol-2-ylsulfanyl)-phenylamine (266) was prepared (97%) from 2-(2-Chloro-4-nitro-phenylsulfanyl)-5-trifluoromethyl-benzothiazole (252), in a similar manner as described in example 90.

$^1$H NMR (DMSO-$d_6$) δ 8.2-8.12 (m, 2H), 7.65 (dd, J=8.5, 1.7 Hz, 1H), 7.52 (d, J=8.5 Hz, 1H), 6.9 (d, J=2.4 Hz, 1H), 6.7 (dd, J=8.5, 2.4 Hz, 1H), 6.25 (bs, 2H).). MS (M−H) 359.

Example 267

2-(4-Amino-2-chloro-phenylsulfanyl)-benzothiazole-5-carboxylic acid methyl ester (267)

2-(4-Amino-2-chloro-phenylsulfanyl)-benzothiazole-5-carboxylic acid methyl ester (267) was prepared (96%) from 2-(2-Chloro-4-nitro-phenylsulfanyl)-benzothiazole-5-carboxylic acid methyl ester (254) by the method of example 90.

$^1$H NMR (DMSO-$d_6$) δ 8.3 (d, J=1.6 Hz, 1H), 8.05 (d, J=8.4 Hz, 1H), 7.88 (dd, =8.4, 1.6 Hz, 1H), 7.55 (d, J=8.5 Hz, 1H), 6.89 (d, J=2.4 Hz, 1H), 6.65 (dd, J=8.5, 2.4 Hz, 1H), 3.9 (s, 3H). MS (M−H) 349.

Example 268

2-(4-Amino-2,6-dichloro-phenylsulfanyl)-benzothiazole-5-carboxylic acid methyl ester (268)

2-(4-Amino-2,6-dichloro-phenylsulfanyl)-benzothiazole-5-carboxylic acid methyl ester (268) was prepared (93%) from 2-(2,6-Dichloro-4-nitro-phenylsulfanyl)-benzothiazole-5-carboxylic acid methyl ester (256) in a similar manner as described in example 90.

$^1$H NMR (DMSO-$d_6$) δ 8.34 (d, J=1.2 Hz, 1H), 8.09 (d, J=8.4 Hz, 1H), 7.93 (dd, J=8.4, 1.6 Hz, 1H), 6.9 (s, 2H), 6.5 (s, 2H), 3.9 (s, 3H). MS (M−H) 383.

Example 269

4-(5-Chloro-benzothiazol-2-ylsulfanyl)-3-methoxy-phenylamine (269)

4-(5-Chloro-benzothiazol-2-ylsulfanyl)-3-methoxy-phenylamine (269) was prepared (100%) from 5-chloro-2-(2-methoxy-4-nitro-phenylsulfanyl)-benzothiazole (257), by the method of example 265.

$^1$H NMR (400 MHz, DMSO-$d_6$) δ 7.9 (d, J=8.5 Hz, 1H), 7.85 (d, J=2.0, 1H), 7.34 (dd, J=8.5, 2.0 Hz, 1H), 7.3 (d, J=8.3 Hz, 1H), 6.39 (d, J=2.0 Hz, 1H), 6.29 (dd, J=8.3, 2.1 Hz, 1H), 5.93 (s, 2H), 3.7 (s, 3H). MS (M+H) 323.

Example 270

3,5-Dichloro-4-(5-trifluoromethyl-benzothiazol-2-ylsulfanyl)-phenylamine (270)

To a solution of 2-(2,6-dichloro-4-nitro-phenylsulfanyl)-5-trifluoromethyl-benzothiazole (258) (840 mg, 1.98 mmol) in EtOAc (20 mL) was added tin chloride dihydrate (Aldrich, 2.15 g, 9.52 mmol) and the resulting mixture was heated to reflux for 3 hours. After cooled to room temperature, to the mixture was added excess of 4N aqueous NaOH solution and the resulting mixture was stirred for 20 minutes. The mixture was filtered through Celite pad and washed with EtOAc. The organic layer was separated, washed twice with a brine solution, dried over $Na_2SO_4$, and concentrated under vacuum to give compound 270 (755 mg, 96%) product as a pale yellow solid, which was used in the next reaction without further purification.

$^1$H NMR (DMSO-$d_6$) δ 8.20-8.15 (m, 2H), 7.66 (dd, J=8.4, 1.7 Hz, 1H), 6.88 (s, 2H), 6.50 (s, 2H). MS (M+H) 395.

Example 271

1-[5-Amino-3-chloro-2-(5-trifluoromethyl-benzothiazol-2-ylsulfanyl)-phenyl]-ethanone (271)

The title compound was prepared using the method of example 270, starting with 1-[3-chloro-5-nitro-2-(5-trifluoromethyl-benzothiazol-2-ylsulfanyl)-phenyl]-ethanone (259) (750 mg, 1.67 mmol), tin chloride dihydrate (Aldrich, 1.89 g, 8.37 mmol). Compound 271 (755 mg, 100%) was obtained as a yellowish solid.

$^1$H NMR (DMSO-$d_6$) δ 8.20-8.13 (m, 2H), 7.66 (dd, J=8.4, 1.0 Hz, 1H), 6.96 (d, J=2.4 Hz, 1H), 6.75 (d, J=2.4 Hz, 1H), 6.43 (s, 2H), 2.48 (s, 3H). MS (M+H) 403.

Example 272

2-(4-Amino-2,6-dichloro-phenylsulfanyl)-benzothiazole-6-carbonitrile (272)

The title compound was prepared using the method of example 270, starting with 2-(2,6-dichloro-4-nitro-phenylsulfanyl)-benzothiazole-6-carbonitrile (260) (1.9 g, 4.97 mmol), tin chloride dihydrate (Aldrich, 5.62 g, 24.9 mmol). Compound 272 (1.72 g, 98%) was obtained as a yellowish solid.

$^1$H NMR (400 MHz, DMSO-$d_6$) δ 8.48 (d, J=1.5 Hz,1H), 7.97 (d, J=8.7 Hz, 1H), 7.86 (dd, J=8.5, 1.7 Hz, 1H), 6.88 (s, 2H), 6.53 (s, 2H). MS (M+H) 352.

Example 273

2-(4-Amino-2-chloro-phenylsulfanyl)-benzothiazole-6-carbonitrile (273)

The title compound was prepared using the method of example 270, starting with 2-(2-chloro-4-nitro-phenylsulfanyl)-benzothiazole-6-carbonitrile (261) (1.6 g, 4.6 mmol), tin chloride dihydrate (Aldrich, 5.21 g, 23.1 mmol). Compound 273 (1.36 g, 93%) was obtained as a yellowish solid. MS (M+H) 318.

Example 274

2-(4-Amino-2,6-dichloro-phenylsulfanyl)-benzothiazole-5-carbonitrile (274)

The title compound was prepared using the method of example 270, starting with 2-(2,6-dichloro-4-nitro-phenylsulfanyl)-benzothiazole-5-carbonitrile (262) (1.9 g, 4.97 mmol), tin chloride dihydrate (Aldrich, 5.62 g, 24.9 mmol). Compound 274 (1.40 g, 80%) was obtained as a yellowish solid.

$^1$H NMR (DMSO-$d_6$) δ 8.35 (d, J=1.4 Hz, 1H), 8.16 (d, J=8.5 Hz, 1H), 7.73 (dd, J=8.4, 1.5 Hz, 1H), 6.88 (s, 2H), 6.50 (s, 2H). MS (M+H) 352.

Example 275

2-(4-Amino-2-chloro-phenylsulfanyl)-benzothiazole-5-carbonitrile (275)

The title compound was prepared using the method of example 270, starting with 2-(2-chloro-4-nitro-phenylsulfanyl)-benzothiazole-5-carbonitrile (263) (1.59 g, 4.58 mmol), tin chloride dihydrate (Aldrich, 5.18 g, 22.9 mmol). Compound 275 (1.35 g, 93%) was obtained as a yellowish solid.

$^1$H NMR (DMSO-$d_6$) δ 8.32 (d, J=1.4 Hz, 1H), 8.13 (d, J=8.1 Hz, 1H), 7.71 (dd, J=8.3, 1.5 Hz, 1H), 7.54 (d, J=8.5 Hz, 1H), 6.88 (d, J=2.4 Hz, 1H), 6.65 (dd, J=8.4, 2.4 Hz, 1H). MS (M+H) 318.

Example 276

1-[5-Amino-3-chloro-2-(5-methyl-benzothiazol-2-ylsulfanyl)-phenyl]-ethanone (276)

To a solution of 1-[3-chloro-5-nitro-2-(5-methyl-benzothiazol-2-ylsulfanyl)-phenyl]-ethanone (264) (3.87 g, 10.2 mmol) in 2:2:1 of EtOH/THF/$H_2O$, was added ammonium chloride (Aldrich 2.74 g, 51.2 mmol) and iron powder (Aldrich, 2.87 g, 51.2 mmol). The mixture was refluxed for 3 hours. The mixture was filtered through Celite pad while it was hot, washed the Celite pad with EtOAc. The filtrate was diluted with saturated aqueous $NaHCO_3$ solution and was extracted 3× with EtOAc (150 mL). The organic layers were combined and washed twice with a brine solution (100 mL), dried over $Na_2SO_4$, and concentrated under vacuum. The crude solid was chromatographed (0-15% EtOAc in $CH_2Cl_2$) to yield 2.42 g (68%) of compound 276 as a pale yellow solid.

$^1$H NMR (DMSO-$d_6$) δ 8.10 (d, J=8.1 Hz, 1H), 7.62 (d, J=1.1 Hz, 1H), 7.16 (dd, J=8.1, 1.2 Hz, 1H), 6.94 (d, J=2.4 Hz, 1H), 6.69 (d, J=2.5 Hz, 1H), 6.38 (s, 2H), 2.46 (s, 3H), 2.40 (s, 3H). MS (M+H) 349.

Examples 277-307: The compounds illustrated in Table 32 were prepared by sulfonylation of the anilines of Table 31 by the method of Example 277 unless otherwise specified.

TABLE 32

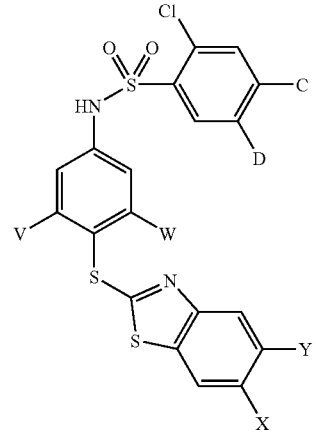

| Example # | C | D | V | W | X | Y | MS (M − H) | Yield |
|---|---|---|---|---|---|---|---|---|
| 277 | $CF_3$ | H | COMe | Cl | H | Cl | 609 | 72% |
| 278 | Cl | H | COMe | Cl | H | Cl | 589 | 73% |

TABLE 32-continued

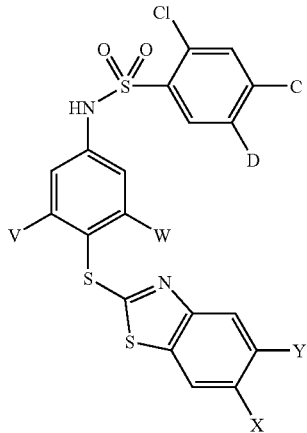

| Example # | C | D | V | W | X | Y | MS (M−H) | Yield |
|---|---|---|---|---|---|---|---|---|
| 279 | Cl | Me | COMe | Cl | H | Cl | 589 | 73% |
| 280 | Cl | H | H | Cl | H | $CF_3$ | 567 | 68% |
| 281 | $CF_3$ | H | H | Cl | H | $CF_3$ | 601 | 70% |
| 282 | Cl | H | H | Cl | H | $CO_2Me$ | 557 | 68% |
| 283 | Cl | H | Cl | Cl | H | $CO_2Me$ | 557 | 68% |
| 284 | $CF_3$ | H | H | Cl | $CONH_2$ | H | 576 | 14% |
| 285 | $CF_3$ | H | Cl | Cl | $CONH_2$ | H | 610 | 55% |
| 286 | $CF_3$ | H | H | Cl | $CN_4H$ | H | 635 | 67% |
| 287 | $CF_3$ | H | Cl | Cl | $CN_4H$ | H | 635 | 65% |
| 288 | $CF_3$ | H | H | OMe | H | Cl | 563 | 72% |
| 289 | Cl | H | Cl | Cl | H | $CF_3$ | 601 | 61% |
| 290 | $CF_3$ | H | Cl | Cl | H | $CF_3$ | 635 | 76% |
| 291 | Cl | H | COMe | Cl | H | $CF_3$ | 609 | 32% |
| 292 | $CF_3$ | H | COMe | Cl | H | $CF_3$ | 643 | 29% |
| 293 | Cl | H | Cl | Cl | CN | H | 558 | 71% |
| 294 | $CF_3$ | H | Cl | Cl | CN | H | 592 | 83% |
| 295 | Cl | H | H | Cl | CN | H | 524 | 88% |
| 296 | $CF_3$ | H | H | Cl | CN | H | 558 | 64% |
| 297 | Cl | H | Cl | Cl | H | CN | 558 | 66% |
| 298 | $CF_3$ | H | Cl | Cl | H | CN | 592 | 72% |
| 299 | Cl | H | H | Cl | H | CN | 524 | 58% |
| 300 | $CF_3$ | H | H | Cl | N | CN | 558 | 58% |
| 301 | Cl | H | Cl | Cl | H | $CN_4H$ | 601 | 77% |
| 302 | $CF_3$ | H | Cl | Cl | H | $CN_4H$ | 635 | 82% |
| 303 | Cl | H | Cl | Cl | H | $CONH_2$ | 601 | 77% |
| 304 | Cl | H | H | Cl | H | $CN_4H$ | 567 | 78% |
| 305 | $CF_3$ | H | H | Cl | H | $CN_4H$ | 601 | 83% |
| 306 | $CF_3$ | H | COMe | Cl | H | Me | 589 | 73% |
| 307 | Cl | Me | COMe | Cl | H | Me | 569 | 74% |

Example 277

N-[3-Acetyl-5-chloro-4-(5-chloro-benzothiazol-2-ylsulfanyl)-phenyl]-2-chloro-4-trifluoromethyl-benzenesulfonamide (277)

To a 1M solution of 1-[5-Amino-3-chloro-2-(5-chloro-benzothiazol-2-ylsulfanyl)-phenyl]-ethanone, (265) (4.12 g, 11.19 mmol) in pyridine, obtained from Aldrich, was added 2-chloro-4-trifluoromethyl-benzenesulfonyl chloride (3.75 g, 13.43 mmol) and heated to 90° C. for 1.5 hours. The crude reaction mixture was concentrated under vacuum, partitioned between 2M aqueous HCl (100 mL) and EtOAc (100 mL), and extracted 3 times with EtOAc (100 mL). The combined organic layers were washed twice with saturated aqueous brine (100 mL), dried over $Na_2SO_4$, concentrated under vacuum, purified by column chromatography (0-5% $Et_2O$ in $CH_2Cl_2$), and triturated with $CH_2Cl_2$/hexane mixture with 0.5 mL of MeOH added to yield compound 277 (4.9 g, 72%) as an off white solid.

$^1$H NMR (400 MHz, DMSO-$d_6$) δ 11.9 (s, 1H), 8.43 (d, J=8.2 Hz, 1H), 8.23 (s, 1H), 8.01 (bd, J=7.2 Hz, 1H), 7.95 (d, J=8.6 Hz, 1H), 7.9 (d, J=2.1 Hz, 1H), 7.48 (d, J=2.4 Hz, 1H), 7.42 (dd, J=8.6, 2.1 Hz, 1H), 7.31 (d, J=2.4 Hz, 1H), 2.45 (s, 3H). MS (EI): m/z 609 (38, M−H), 610 (10, M−H), 611 (50, M−H), 612 (12, M−H), 613 (20, M−H), 614 (5, M−H), 615 (3, M−H).

Example 278

N-[3-Acety-5-chloro-4-(5-chloro-benzothiazol-2-ylsulfanyl)-phenyl]-2,4-dichloro-benzenesulfonamide (278) By the Method of Example 93

$^1$H NMR (DMSO-$d_6$) δ 11.8 (s, 1H), 8.24 (d, J=8.6 Hz, 1H), 8.1-7.95 (m, 2H), 7.91 (d, J=2.0 Hz, 1H), 7.71 (dd, J=8.6, 2.1 Hz, 1H), 7.45 (d, J=2.4 Hz, 1H), 7.42 (dd, J=8.6, 2.1 Hz, 1H), 7.29 (d, J=2.4 Hz, 1H), 2.45 (s, 3H). MS (M−H) 575.

Example 279

N-[3-Acetyl-5-chloro-4-(5-chloro-benzothiazol-2-ylsulfanyl)-phenyl]-2,4-dichloro-5-methyl-benzene-sulfonamide (279)

$^1$H NMR (DMSO-$d_6$) δ 11.8 (s, 1H), 8.3 (s, 1H), 7.98 (d, J=8.6 Hz, 1H), 7.93-7.9 (m, 2H), 7.46 (d, J=2.4 Hz, 1H), 7.42 (dd, J=8.6, 2.1 Hz, 1H), 7.3 (d, J=2.4 Hz, 1H), 2.45 (s, 3H), 2.4 (s, 3H). MS (M−H) 589.

Example 280

2,4-Dichloro-N-[3-chloro-4-(5-trifluoromethyl-benzothiazol-2-ylsulfanyl)-phenyl]-benzenesulfonamide (280)

$^1$H NMR (400 MHz, DMSO-$d_6$) δ 11.6 (s, 1H), 8.23-8.16 (m, 3H), 7.96 (bs, 1H), 7.88 (bd, J=8.6 Hz, 1H), 7.75-7.67 (m, 2H), 7.4 (bs, 1H), 7.23 (bd, J=10.7 Hz, 1H). MS M−H) 567.

Example 281

2-Chloro-N-[3-chloro-4-(5-trifluoromethyl-benzothiazol-2-ylsulfanyl)-phenyl]-4-trifluoromethyl-benzenesulfonamide (281)

$^1$H NMR (400 MHz, DMSO-$d_6$) δ 11.8 (s, 1H), 8.4 (d, J=8.3 Hz, 1H), 8.23 (bs, 1H), 7.98-7.94 (m, 2H), 8.03 (bd, J=8.4 Hz, 1H), 7.9 (d, J=8.6 Hz, 1H), 7.69 (bd, J=10.1 Hz, 1H), 7.44 (d, J=2.4 Hz, 1H), 7.25 (dd, J=8.5, 2.4 Hz, 1H). MS (M−H) 601.

Example 282

2-[2-Chloro-4-(2,4-dichloro-benzenesulfonylamino)-phenylsulfanyl]-benzothiazole-5-carboxylic acid methyl ester (282)

$^1$H NMR (DMSO-$d_6$) δ 11.5 (s, 1H), 8.32 (d, J=1.5 Hz, 1H), 8.19 (d, J=8.6 Hz, 1H), 8.08 (d, =8.4 Hz, 1H), 7.96 (d, J=2.0 Hz, 1H), 7.92 (dd, J=9.1, 1.6 Hz, 1H), 7.88 (d, J=8.6 Hz, 1H), 7.73 (dd, J=8.6, 2.1 Hz, 1H), 7.4 (d, J=2.2 Hz, 1H), 7.22 (dd, J=8.2, 2.0 Hz, 1H), 3.9 (s, 3H). MS (M−H) 557.

Example 283

2-[2,6-Dichloro-4-(2,4-dichloro-benzenesulfonylamino)-phenylsulfanyl]-benzothiazole-5-carboxylic acid methyl ester (283) By the Method of Example 93

$^1$H NMR (DMSO-d$_6$) δ 11.9 (s, 1H), 8.32 (d, J=0.9 Hz, 1H), 8.22 (d, J=8.6 Hz, 1H), 8.09 (d, =8.4 Hz, 1H), 8.0 (d, J=1.9 Hz, 1H), 7.92 (dd, J=8.4, 1.6 Hz, 1H), 7.75 (dd, J=8.6, 2.1 Hz, 1H), 7.4 (s, 2H), 3.9 (s, 3H). MS (M−H) 591.

Example 284

2-[2-Chloro-4-(2-chloro-4-trifluoromethyl-benzenesulfonylamino)-phenylsulfanyl]-benzothiazole-6-carboxylic acid amide (284)

2-[2-Chloro-4-(2-chloro-4-trifluoromethyl-benzenesulfonylamino)-phenylsulfanyl]-benzothiazole-6-carboxylic acid amide (284) was prepared (14%) from 2-chloro-N-[3-chloro-4-(6-cyano-benzothiazol-2-ylsulfanyl)-phenyl]-4-trifluoromethyl-benzenesulfonamide (296) by the method of example 303.

$^1$H NMR (DMSO-d$_6$) δ 11.8 (s, 1H), 8.42 (d, J=1.3 Hz, 1H), 8.38 (d, J=8.5 Hz, 1H), 8.21 (bs, 1H), 8.05-7.99 (m, 2H), 7.94 (dd, J=8.6, 1.5 Hz, 1H), 7.89-7.83 (m, 2H), 7.45 (s, 1H), 7.42 (d, J=1.9 Hz, 1H), 7.24 (dd, J=8.5, 2.1 Hz, 1H). MS (M−H) 576.

Example 285

2-[2,6-Dichloro-4-(2-chloro-4-trifluoromethyl-benzensulfonylamino)-phenylsulfanyl]-benzothiazole-6-carboxylic acid amide (285)

2-[2,6-Dichloro-4-(2-chloro-4-trifluoromethyl-benzensulfonylamino)-phenylsulfanyl]-benzothiazole-6-carboxylic acid amide (285) was prepared (55%) from 2-chloro-N-[3,5-dichloro-4-(6-cyano-benzothiazol-2-ylsulfanyl)-phenyl]-4-trifluoromethyl-benzenesulfonamide (294), by the method of example 303.

$^1$H NMR (DMSO-d$_6$) δ 12.0 (bs, 1H), 8.48-8.4 (m, 2H), 8.23 (bs, 1H), 8.05-8.0 (m, 2H), 7.95 (dd, J=8.5, 1.7 Hz, 1H), 7.85 (d, J=8.5 Hz, 1H), 7.48 (s, 1H), 7.4 (s, 2H). MS (M−H) 610.

Example 286

2-Chloro-N-{3-chloro-4-[6-(1H-tetrazol-5-yl)-benzothiazol-2-ylsulfanyl]-phenyl}-4-trifluoromethyl-benzenesulfonamide 2-Chloro-N-{3-chloro-4-[6-(1H-tetrazol-5-yl)-benzothiazol-2-ylsulfanyl]-phenyl}-4-trifluoromethyl-benzenesulfonamide (286) was prepared (67%) from 2-chloro-N-[3-chloro-4-(6-cyano-benzothiazol-2-ylsulfanyl)-phenyl]-4-trifluoromethyl-benzenesulfonamide (296)), by the method of example 301.

$^1$H NMR (DMSO-d$_6$) δ 8.62 (bs, 1H), 8.36 (d, J=8.5 Hz, 1H), 8.19 (bs, 1H), 8.08 (d, J=8.1 Hz, 1H), 8.04-7.95 (m, 2H), 7.84 (d, J=8.6 Hz, 1H), 7.38 (d, J=2.0 Hz, 1H), 7.2 (dd, J=7.9, 1.8 Hz, 1H). MS (M−H) 601.

Example 287

2-Chloro-N-{3,5-dichloro-4-[6-(1H-tetrazol-5-yl)-benzothiazol-2-ylsulfanyl]-phenyl}-4-trifluoromethyl-benzenesulfonamide (287)

2-Chloro-N-{3,5-dichloro-4-[6-(1H-tetrazol-5-yl)-benzothiazol-2-ylsulfanyl]phenyl}-4-trifluoromethyl-benzenesulfonamide (287) was prepared (65%) from 2-chloro-N-[3,5-dichloro-4-(6-cyano-benzothiazol-2-ylsulfanyl)-phenyl]-4-trifluoromethyl-benzenesulfonamide (294) by the method of example 301.

$^1$H NMR (DMSO-d$_6$) δ 8.65 (bs, 1H), 8.44 (d, J=8.4 Hz, 1H), 8.24 (bs, 1H), 8.09 (d, J=8.6 Hz, 1H), 8.06-7.98 (m, 2H), 7.4 (bs, 2H). MS (M−H) 635.

Example 288

2-Chloro-N-[4-(5-chloro-benzothiazol-2-ylsulfanyl)-3-methoxy-phenyl]-4-trifluoromethyl-benzenesulfonamide (288) By the Method of Example 93

$^1$H NMR (DMSO-d$_6$) δ 11.5 (s, 1H), 8.4 (d, J=8.3 Hz, 1H), 8.2 (bs, 1H), 8.01 (d, J=8.3, 1H), 7.89 (d, J=8.5 Hz, 1H), 7.87 (d, J=2.1 Hz, 1H), 7.63 (d, J=8.4 Hz, 1H), 7.38 (dd, J=8.6, 2.0 Hz, 1H), 6.96 (d, J=2.0 Hz, 1H), 6.83 (dd, J=8.4, 2.1 Hz, 1H), 3.8 (s, 3H). MS (M−H) 563.

Example 289

2,4-Dichloro-N-[3,5-dichloro-4-(5-trifluoromethyl-benzothiazol-2-ylsulfanyl)-phenyl]-benzenesulfonamide (289)

$^1$H NMR (DMSO-d$_6$) δ 11.90 (s, 1H), 8.25-8.15 (m, 3H), 7.98 (d, J=2.0 Hz, 1H), 7.76-7.67 (m, 2H), 7.38 (s, 2H). MS (M−H) 601

Example 290

2-Chloro-N-[3,5-dichloro-4-(5-trifluoromethyl-benzothiazol-2-ylsulfanyl)-phenyl]-4-trifluoromethyl-benzenesulfonamide (290)

$^1$H NMR (DMSO-d$_6$) δ 11.90 (br s, 1H), 8.43 (d, J=8.4 Hz, 1H), 8.26-8.15 (m, 3H), 8.03 (dd, J=8.4, 1.7 Hz, 1H), 7.68 (dd, J=8.6, 1.6 Hz, 1H), 7.40 (s, 2H). MS (M−H) 635.

Example 291

N-[3-Acetyl-5-chloro-4-(5-trifluoromethyl-benzothiazol-2-ylsulfanyl)-phenyl]-2,4-dichloro-benzenesulfonamide (291)

$^1$H NMR (DMSO-d$_6$) δ 11.80 (br s, 1H), 8.25 (d, J=8.6 Hz, 1H), 8.22-8.15 (m, 2H), 7.97 (d, J=2.1 Hz, 1H), 7.72 (dd, J=8.6, 2.1 Hz, 1H), 7.69 (dd, J=8.6, 1.6 Hz, 1H), 7.46 (d, J=2.4 Hz, 1H), 7.31 (d, J=2.4 Hz, 1H), 2.47 (s, 3H). MS (M−H) 609.

Example 292

N-[3-Acetyl-5-chloro-4-(5-trifluoromethyl-benzothiazol-2-ylsulfanyl)-phenyl]-2-chloro-4-trifluoromethyl-benzenesulfonamide (292)

$^1$H NMR (DMSO-d$_6$) δ 11.90 (br s, 1H), 8.42 (d, J=8.1 Hz, 1H), 8.23-8.17 (m, 3H), 8.01 (dd, J=8.5, 1.4 Hz, 1H), 7.65

(dd, J=8.5, 1.5 Hz, 1H), 7.44 (d, J=2.4 Hz, 1H), 7.36 (d, J=2.4 Hz, 1H), 2.48 (s, 3H). MS (M–H) 643.

Example 293

2,4-Dichloro-N-[3,5-dichloro-4-(6-cyano-benzothiazol-2-ylsulfanyl)-phenyl]-benzenesulfonamide (293)

$^1$H NMR (DMSO-$d_6$) δ 11.90 (br s, 1H), 8.49 (d, J=1.1 Hz, 1H), 8.23 (d, J=8.6 Hz, 1H), 7.97 (d, J=2.0 Hz, 1H), 7.96 (d, J=8.5 Hz, 1H), 7.86 (dd, J=8.5, 1.6 Hz, 1H), 7.74 (dd, J=8.6, 2.0 Hz, 1H), 7.38 (s, 2H). MS (M–H) 558.

Example 294

2-Chloro-N-[3,5-dichloro-4-(6-cyano-benzothiazol-2-ylsulfanyl)-phenyl]-4-trifluoromethyl-benzenesulfonamide (294)

$^1$H NMR (DMSO-$d_6$) δ 11.90 (br s, 1H), 8.49 (d, J=1.5 Hz, 1H), 8.43 (d, J=8.1 Hz, 1H), 8.24 (br s, 1H), 8.03 (dd, J=8.2, 1.0 Hz, 1H), 7.97 (d, J=8.5 Hz, 1H), 7.87 (dd, J=8.5, 1.7 Hz, 1H), 7.40 (s, 2H). MS (M–H) 592.

Example 295

2,4-Dichloro-N-[3-chloro-4-(6-cyano-benzothiazol-2-ylsulfanyl)-phenyl]-benzenesulfonamide (295)

$^1$H NMR (DMSO-$d_6$) δ 11.60 (br s, 1H), 8.49 (d, J=1.8 Hz, 1H), 8.18 (d, J=8.6 Hz, 1H), 8.00-7.94 (m, 2H), 7.90-7.84 (m, 2H), 7.72 (dd, J=8.6, 2.0 Hz, 1H), 7.41 (d, J=2.3 Hz, 1H), 7.23 (dd, J=8.5, 2.4 Hz, 1H). MS (M–H) 524.

Example 296

2-Chloro-N-[3-chloro-4-(6-cyano-benzothiazol-2-ylsulfanyl)-phenyl]-4-trifluoromethyl-benzenesulfonamide (296)

$^1$H NMR (DMSO-$d_6$) δ 11.78 (br s, 1H), 8.48 (br s, 1H), 8.39 (d, J=8.0 Hz, 1H), 8.22 (br s, 1H), 8.02 (br d, J=8.4 Hz, 1H), 7.97 (d, J=8.6 Hz, 1H), 7.90 (d, J=8.6 Hz, 1H), 7.86 (dd, J=8.5, 1.5 Hz, 1H), 7.43 (d, J=2.3 Hz, 1H), 7.25 (dd, J=8.5, 2.4 Hz, 1H). MS (M–H) 558.

Example 297

2,4-Dichloro-N-[3,5-dichloro-4-(5-cyano-benzothiazol-2-ylsulfanyl)-phenyl]-benzenesulfonamide (297)

$^1$H NMR (DMSO-$d_6$) δ 11.90 (br s, 1H), 8.36 (d, J=1.1 Hz, 1H), 8.23 (d, J=8.5 Hz, 1H), 8.16 (d, J=8.2 Hz, 1H), 7.98 (d, J=2.0 Hz, 1H), 7.77 (dd, J=8.5, 1.5 Hz, 1H), 7.73 (dd, J=8.4, 2.0 Hz, 1H), 7.38 (s, 2H). MS (M–H) 558.

Example 298

2-Chloro-N-[3,5-dichloro-4-(5-cyano-benzothiazol-2-ylsulfanyl)-phenyl]-4-trifluoromethyl-benzenesulfonamide (298)

$^1$H NMR (DMSO-$d_6$) δ 11.98 (br s, 1H), 8.43 (d, J=8.3 Hz, 1H), 8.35 (d, J=1.5 Hz, 1H), 8.23 (br s, 1H), 8.15 (d, J=8.2 Hz, 1H), 8.03 (dd, J=8.4, 1.0 Hz, 1H), 7.76 (dd, J=8.4, 1.4 Hz, 1H), 7.40 (s, 2H). MS (M–H) 592.

Example 299

2,4-Dichloro-N-[3-chloro-4-(5-cyano-benzothiazol-2-ylsulfanyl)-phenyl]-benzenesulfonamide $^1$H NMR (DMSO-$d_6$) δ 11.60 (br s, 1H), 8.36 (d, J=1.5 Hz, 1H), 8.18 (d, J=8.6 Hz, 1H), 8.15 (d, J=8.3 Hz, 1H), 7.96 (d, J=2.0 Hz, 1H), 7.88 (d, J=8.6 Hz, 1H), 7.75 (dd, J=8.4, 1.5 Hz, 1H), 7.72 (dd, J=8.5, 2.0 Hz, 1H), 7.40 (d, J=2.4 Hz, 1H), 7.23 (dd, J=8.5, 2.4 Hz, 1H). MS (M–H) 524.

Example 300

2-Chloro-N-[3-chloro-4-(5-cyano-benzothiazol-2-ylsulfanyl)-phenyl]-4-trifluoromethyl-benzenesulfonamide (300)

$^1$H NMR (DMSO-$d_6$) δ 11.70 (br s, 1H), 8.39 (d, J=8.4 Hz, 1H), 8.35 (d, J=1.4 Hz, 1H), 8.21 (br s, 1H), 8.13 (d, J=8.4 Hz, 1H), 8.03 (dd, J=8.5, 1.5 Hz, 1H), 7.88 (d, J=8.6 Hz, 1H), 7.75 (dd, J=8.4, 1.6 Hz, 1H), 7.43 (d, J=2.4 Hz, 1H), 7.24 (dd, J=8.5, 2.4 Hz, 1H). MS (M–H) 558.

Example 301

2,4-Dichloro-N-{3,5-dichloro-4-[5-(1H-tetrazol-5-yl)-benzothiazol-2-ylsulfanyl]-phenyl}-benzenesulfonamide (301)

To a solution of 2,4-dichloro-N-[3,5-dichloro-4-(5-cyano-benzothiazol-2-ylsulfanyl)-phenyl]-benzenesulfonamide (297) (250 mg, 0.45 mmol) in toluene (5 mL), was added azidotrimethylsilane (Aldrich, 0.12 mL, 0.90 mmol) and dibutyltin oxide (Aldrich, 11 mg, 0.045 mmol). The resulting mixture was heated at 90° C. overnight (15 hours). A 1M aqueous solution of HCl (50 mL) and ice was added and the crude reaction mixture was extracted 3× with EtOAc (50 mL). The organic layers were combined and washed twice with a brine solution (100 mL), dried over $Na_2SO_4$, and concentrated under vacuum. The crude solid was chromatographed (20% EtOAc in $CH_2Cl_2$, then 10% MeOH in $CH_2Cl_2$) to yield 209 mg (77%) of product as a white solid.

$^1$H NMR (DMSO-$d_6$) δ 8.44 (d, J=1.7 Hz, 1H), 8.21 (d, J=8.6 Hz, 1H), 8.16 (d, J=8.4 Hz, 1H), 8.01 (dd, J=8.4, 1.7 Hz, 1H), 7.96 (d, J=2.0 Hz, 1H), 7.72 (dd, J=8.6, 2.0 Hz, 1H), 7.38 (s, 2H). MS (M–H) 601.

Example 302

2-Chloro-N-{3,5-dichloro-4-[5-(1H-tetrazol-5-yl)-benzothiazol-2-ylsulfanyl]-phenyl}-4-trifluoromethyl-benzenesulfonamide (302)

The title compound was prepared by the method of example 301.

$^1$H NMR (DMSO-$d_6$) δ 8.44 (d, J=1.5 Hz, 1H), 8.42 (d, J=8.4 Hz, 1H), 8.23 (d, J=1.3 Hz, 1H), 8.15 (d, J=8.4 Hz, 1H), 8.02 (dd, J=8.4, 1.4 Hz, 1H), 7.40 (s, 2H). MS (M–H) 635.

Example 303

2-[2,6-Dichloro-4-(2,4-dichloro-benzenesulfonylamino)-phenylsulfanyl]-benzothiazole-5-carboxylic acid amide (303)

To a solution of 2,4-dichloro-N-[3,5-dichloro-4-(5-cyano-benzothiazol-2-ylsulfanyl)-phenyl]-benzenesulfonamide (297) (250 mg, 0.45 mmol) in tert-butanol (10 mL), was added KOH (EM Science Product, 126 mg, 2.25 mmol). The resulting mixture was refluxed for 1 hour. After cooling to room temperature, a 1M aqueous solution of HCl (50 mL) was added and the crude reaction mixture was extracted 3× with EtOAc (50 mL). The organic layers were combined and washed twice with a brine solution (100 mL), dried over $Na_2SO_4$, and concentrated under vacuum. The crude solid was chromatographed (20% EtOAc in $CH_2Cl_2$, then 10% MeOH in $CH_2Cl_2$) to yield 207 mg (80%) of compound 303 as a white solid.

$^1$H NMR (DMSO-$d_6$) δ 11.80 (s, 1H), 8.33 (br s, 1H), 8.22 (dd, J=8.5, 1.9 Hz, 1H), 8.08 (br s, 1H), 8.03-7.96 (m, 2H), 7.85 (m, 1H), 7.74 (m, 1H), 7.47 (br s, 1H), 7.38 (s, 2H). MS (M–H) 578.

Example 304

2,4-Dichloro-N-{3-chloro-4-[5-(1H-tetrazol-5-yl)-benzothiazol-2-ylsulfanyl]-phenyl}-benzenesulfonamide (304) The Title Compound was Prepared by the Method of Example 301

$^1$H NMR (DMSO-$d_6$) δ 8.44 (d, J=1.5 Hz, 1H), 8.17 (d, J=8.6 Hz, 1H), 8.14 (d, J=8.4 Hz, 1H), 8.01 (dd, J=8.4, 1.6 Hz, 1H), 7.95 (d, J=2.1 Hz, 1H), 7.87 (d, J=8.6 Hz, 1H), 7.71 (dd, J=8.6, 2.1 Hz, 1H), 7.39 (d, J=2.4 Hz, 1H), 7.21 (dd, J=8.6, 2.4 Hz, 1H). MS (M–H) 567.

Example 305

2-Chloro-N-{3-chloro-4-[5-(1H-tetrazol-5-yl)-benzothiazol-2-ylsulfanyl]-phenyl}-4-trifluoromethyl-benzenesulfonamide (305)

The title compound was prepared by the method of example 301.

$^1$H NMR (DMSO-$d_6$) δ 8.43 (d, J=1.5 Hz, 1H), 8.36 (d, J=8.4 Hz, 1H), 8.17 (d, J=1.4 Hz, 1H), 8.12 (d, J=8.4 Hz, 1H), 8.03-7.96 (m, 2H), 7.85 (d, J=8.6 Hz, 1H), 7.40 (d, J=2.4 Hz, 1H), 7.20 (dd, J=8.6, 2.4 Hz, 1H). MS (M–H) 601.

Example 306

N-[3-Acetyl-5-chloro-4-(5-methyl-benzothiazol-2-ylsulfanyl)-phenyl]-2-chloro-4-trifluoromethyl-benzenesulfonamide (306)

$^1$H NMR (DMSO-$d_6$) δ 11.90 (br s, 1H), 8.43 (d, J=8.1 Hz, 1H), 8.23 (d, J=1.2 Hz, 1H), 8.01 (dd, J=8.4, 1.1 Hz, 1H), 7.78 (d, J=8.2 Hz, 1H), 7.62 (s, 1H), 7.46 (d, J=2.4 Hz, 1H), 7.29 (d, J=2.4 Hz, 1H), 7.19 (dd, J=8.5, 1.2 Hz, 1H), 2.47 (s, 3H), 2.40 (s, 3H). MS (M–H) 589.

Example 307

N-[3-Acetyl-5-chloro-4-(5-methyl-benzothiazol-2-ylsulfanyl)-phenyl]-2,4-dichloro-5-methyl-benzenesulfonamide (307)

$^1$H NMR (DMSO-$d_6$) δ 11.70 (br s, 1H), 8.28 (s, 1H), 7.92 (s, 1H), 7.80 (d, J=8.1 Hz, 1H), 7.64 (s, 1H), 7.45 (d, J=2.3 Hz, 1H), 7.29 (d, J=2.3 Hz, 1H), 7.19 (dd, J=8.2, 1.5 Hz, 1H), 2.48-2.38 (m, 9H). MS (M–H) 569.

Example 308

3-Hydroxy-6-methylquinoline (308)

A solution of 3-Amino-6-methylquinoline [(1.21 g, 7.65 mmol), prepared according to J. Chem. Soc. 2024-2027 (1948) Morley, J. S.; Simpson, J. C. E.] in 6N $H_2SO_4$ (25 ml) was cooled in an ice bath. To the solution $NaNO_2$ (560 mg, 8.10 mmol) in water (2 ml) was added and stirred for 30 min at 0 degrees. Separately 5% $H_2SO_4$ was refluxed and above Diazo reaction mixture was added to this refluxing solution. After 30 min the reaction mixture was cooled to room temperature, and was neutralized by 6N NaOH. The resulting insoluble material was collected by filtration. This solid was recrystallized by $CHCl_3$/AcOEt to afford compound (308) (348 mg, 29%).

$^1$H NMR (300 MHz, DMSO-$d_6$) δ 7.34 (1H, dd, J=1.9, 8.6 Hz), 7.42(1H, d, J=2.8 Hz), 7.55 (1H, s), 7.79 (1H, d, J=8.6 Hz), 8.50 (1H, d, J=2.8 Hz).

Example 309

3-(2,6-Dichloro-4-nitro-phenoxy)-6-methyl-quinoline (309)

To a solution of 3-Hydroxy-6-methylquinoline (308) (348 mg, 2.19 mmol) in DMF (3.5 ml), was added NaH (60% oil suspension, 90 mg, 2.25 mmol) in one portion at room temperature. After 5 min 3,4,5-Trichloronitrobenzene (509 mg, 2.25 mmol) in DMF (2 ml) was added and the reaction mixture was heated at 50 degrees with stirring for 2 hr. After cooling to room temperature. Ice/water was added to the reaction mixture, which was then acidified with 2N HCl and extracted twice with AcOEt. Organic layer was washed with Brine, dried over anhydrous $MgSO_4$, and concentrated. Crude residue was purified by column chromatography (Hexane/AcOEt=4/1, 80 g of silica gel) to afford compound 309 (510 mg, 67%).

$^1$H NMR (300 MHz, DMSO-$d_6$) δ 7.52-7.57(2H,m), 7.61 (1H, s), 7.94(1H, d, J=8.6 Hz), 8.63 (2H, s), 8.86 (1H, d, J=2.9 Hz).

Example 310

3-(2,6-Dichloro-4-nitro-phenoxy)-quinoline-6-carboxylic acid (310)

A solution of 3-(2,6-Dichloro-4-nitro-phenoxy)-6-methyl-quinoline (309) (510 mg, 1.46 mmol) and chromium (VI) oxide (292 mg, 2.92 mmol) in c $H_2SO_4$/$H_2O$=2.4 ml/4.7 ml was heated at 100 degrees while three 292 mg portions of chromic anhydride were added eight hour intervals. After 32 hr heating was stopped and allowed to stand for over night. Insoluble material was collected by filtration, and this solid was washed with water twice to afford compound (310) (443 mg, 80%).

$^1$H NMR (300 MHz, DMSO-$d_6$) δ 7.94 (1H, d, J=3.0 Hz), 8.14(2H, s), 8.56 (1H, s), 8.65 (2H, s), 9.09 (1H, d, J=3.0 Hz).

Example 311

3-(2,6-Dichloro-4-nitro-phenoxy)-quinoline-6-carboxylic acid methyl ester (311)

To a solution of 3-(2,6-Dichloro-4-nitro-phenoxy)-quinoline-6-carboxylic acid (310) (443 mg, 0.93 mmol) in dry THF (20 ml) was added CH$_2$N$_2$ in Et$_2$O solution [Prepared from Nitrosomethylurea (1.65 g) and 50% KOH (5 ml)]. This mixture was stirred at room temperature for 1 hr. AcOH (1 ml) was added to the reaction mixture, which was then concentrated. Sat NaHCO$_3$ was added to the residue, which was extracted twice with AcOEt. Organic layer was washed by Brine, dried over anhydrous MgSO$_4$, and concentrated to afford compound 311 (415 mg).

$^1$H NMR (300 MHz, DMSO-d$_6$) δ 3.89 (3H, s), 5.75(2H, br s), 6.76 (2H, s), 7.73 (1H, d, J=2.9 Hz), 8.09 (2H, s), 8.67 (1H, s), 8.94 (1H, d, J=2.9 Hz).

Example 312

3-(4-Amino-2,6-dichloro-phenoxy)-quinoline-6-carboxylic acid methyl ester (312)

To a solution of 3-(2,6-Dichloro-4-nitro-phenoxy)-quinoline-6-carboxylic acid methyl ester (311) (0.93 mmol) and NH$_4$Cl (283 mg, 5.3 mmol) in EtOH/THF/water (8 ml/16 ml/1 ml) was added Iron powder (296 mg, 5.3 mmol). The reaction mixture was refluxed for 4 hr. Insoluble materials were removed by Celite pad, which was washed by THF, acetone and then EtOH. The filtrate was concentrated, and sat NaHCO$_3$ was added and extracted twice with AcOEt. Organic layer was washed by brine, dried over anhydrous MgSO$_4$, and concentrated to afford compound 312 (372 mg, over weight).

$^1$H NMR (300 MHz, DMSO-d$_6$) δ 3.89 (3H, s), 5.75(2H,s), 6.76 (2H, s), 7.73 (1H, d, J=2.9 Hz), 8.09 (2H, s), 8.67 (1H, s), 8.94 (1H, d, J=2.9 Hz).

Example 313

3-Hydroxy-8-quinolinecarboxylic acid methyl ester (313)

To the mixture of 8-Quinoline carboxylic acid (500 mg, 2.89 mmol) in THF (80 ml) was added CH$_2$N$_2$ in Et$_2$O sol. [Prepared from Nitrosomethylurea (1.65 g) and 50% KOH (5 ml)] at room temperature. The reaction mixture was stirred for 12 hr and then concentrated to give the intermediate ester.

$^1$H NMR (300 MHz, DMSO-d$_6$) δ 3.92 (3H, s), 7.60-7.70 (2H, m), 7.93-7.96(1H, m), 8.14-8.17 (1H, m), 8.44-8.48(1H, m), 8.97-8.99(1H, m)

To a solution of the intermediate 8-Quinolinecarboxylic acid methyl ester (2.89 mmol) in AcOH (4 ml) was added 30% H$_2$O$_2$ (0.6 ml). The reaction mixture was heated at 85 degrees for 7.5 hr. The reaction mixture was treated with sat NaHCO$_3$, and extracted six times with CHCl$_3$. Organic layer was dried over anhydrous MgSO$_4$, and concentrated. Crude residue was triturated with CHCl$_3$/Toluene to provide compound 313 (256 mg, 44%, in 2 steps).

$^1$H NMR (300 MHz, DMSO-d$_6$) δ 3.89 (3H, s), 7.52(1H, d, J=6.9 Hz), 7.57 (1H, d, J=1.5 Hz), 7.66 (1H, dd, J=1.5, 6.9 Hz), 7.95 (1H, dd, J=1.5, 8.1 Hz), 8.63 (1H, d, J=2.7 Hz), 10.5 (1H, br s).

Example 314

3-(2,6-Dichloro-4-nitro-phenoxy)-quinoline-8-carboxylic acid methyl ester (314)

To a solution of 3-Hydroxy-8-quinolinecarboxylic acid methyl ester (313) (256 mg, 1.26 mmol) and 3,4,5-Trichloronitrobenzene (294 mg, 1.30 mmol) in Acetone (40 ml) was added K$_2$CO$_3$ (870 mg, 6.30 mmol). This mixture was refluxed for 3.5 hr. The reaction mixture was cooled to room temperature and insoluble materials were removed by Celite filtration. The filtrate was concentrated and the residue was purified by column chromatography. (Hexane/AcOEt=4/1, 80 g of silica gel) to afford compound 314.

$^1$H NMR (300 MHz, DMSO-d$_6$) δ 3.92 (3H, s), 7.67(1H, dd, J=7.3 Hz), 7.79 (1H, d, J=2.9 Hz), 7.88 (1H, dd, J=1.5, 7.3 Hz), 9.05 (1H, d, J=2.9 Hz).

Example 315

3-(4-Amino-2,6-dichloro-phenoxy)-quinoline-8-carboxylic acid methyl ester (315)

To a solution of 3-(2,6-Dichloro-4-nitro-phenoxy)-quinoline-8-carboxylic acid methyl ester (314) (1.26 mmol) and NH$_4$Cl (370 mg, 6.91 mmol) in EtOH/THF/H$_2$O=8 ml/4 ml/2 ml was added Iron powder (386 mg, 6.91 mmol). The reaction mixture was refluxed for 3.5 hr. After cooling to room temperature and insoluble materials were filtered by Celite filtration. The filtrate was concentrated and sat NaHCO$_3$ was added to the residue, which was extracted twice with AcOEt. Organic layer was washed by Brine, dried over MgSO$_4$, and concentrated. Crude residue was purified by column chromatography (Hexane/AcOEt=2/1, 80 g of silica gel) to afford compound 315 (543 mg).

$^1$H NMR (300 MHz, DMSO-d$_6$) δ 3.91(3H, s), 5.77(2H, br s), 6.78 (2H, s), 7.50 (1H, d, J=3.0 Hz), 7.61 (1H, dd, J=8.1 Hz), 7.81 (1H, dd, J=1.4, 6.4 Hz), 8.08 (1H, dd, J=1.4 Hz, 6.4 Hz), 8.93 (1H, d, J=3.0 Hz).

TABLE 33

| Example # | V | X | Y | Z |
|---|---|---|---|---|
| 316 | H | Cl | H | Cl |
| 317 | H | F | F | H |
| 318 | H | F | H | F |
| 319 | Cl | Me | Me | H |

Example 316

3-chloro-4-(3,5-dichloro-phenylsulfanyl)-phenylamine (316)

A solution of potassium t-butoxide (1M in THF) (13 ml) was added via syringe to a solution of 3,5 dichlorothiophenol (2.37 g) and 3-chloro-4-fluoro-nitrobenzene (2.3 g) in THF (20 mL). The exothermic reaction was allowed to stir until it cooled to room temperature. It was poured into water. The resulting solid was collected by filtration and rinsed quickly with ether to leave the intermediate nitro compound. (3.5 g).

This was dissolved in ethyl acetate at reflux. Tin (II) chloride dihydrate (2.3 g) was added in portions as a solid and the reflux continued for 2 hr. After cooling, the mixture was diluted in ethyl acetate, quenched with KOH (0.5 N, 500 mL) and extracted with ethyl acetate 3×. The organic layer was washed with water, dried over magnesium sulfate and concentrated to afford the aniline (316) (2.9 g) as a light tan solid useable in subsequent reactions. Mp 157-160° C.

$^1$H NMR (DMSO) δ 7.36 (d, J=8.4 Hz, 1H), 7.341 (t, J=2 Hz, 1H), 6.91 (m, 2H), 6.831 (d, J=2.4 Hz, 1H), 6.602 (dd, J=8.4, 2.8 Hz, 1H), 6.01 (br s, 2H).

Examples 317 and 318

3,4 difluorothiophenol and 3,5-difluorothiophenol were prepared by the method of D. K. Kim et al (J. Med. Chem. 40, 2363-2373 (1997) and converted by the method of example 316 to the corresponding anilines.

Example 317

3-chloro-4-(3,5-difluoro-phenylsulfanyl)-phenylamine (317)

$^1$H NMR (DMSO) δ 7.361 (d, J=8.4 Hz, 1H), 6.983 (m, 1H), 6.84 (d, J=2.4 Hz, 1H) 6.61 (m, 3H), 6.02 (s, 2H).

Example 318

3-chloro-4-(3,4-difluoro-phenylsulfanyl)-phenylamine (318)

$^1$H NMR (acetone) δ 7.377 (d, J=8.4 Hz, 1H), 7.258 (dt J=10.4, 8.4 Hz, 1H), 6.97 (m, 1H) 6.94 (m, 2H), 6.714 (dd, 8.4, 2.5 Hz, 1H), 5.42 (s, 2H).

Example 319

3,5-Dichloro-4-(3,4-dimethyl-phenylsulfanyl)-phenylamine (319)

A mixture of 3,4-dimethylthiophenol (1.38 g, 10 mmol), 3,4,5-trichoronitrobenzene 2.49 g, 11 mmol) and $K_2CO_3$ (4.15 g, 30 mmol) in acetone (15 ml) was refluxed for 2 hr. After reaction mixture was concentrated, crude product was purified by column chromatography (H/A=9/1, 180 g of silica gel) to afford a yellow oil. Unpurified crude 3,5-Dichloro-4-(3,4-dimethyl-phenylsulfanyl)-nitrobenzene was dissolved in $CH_2Cl_2$/AcOEt (5 ml/20 ml). To the solution was added $SnCl_2/2H_2O$ (9.03 g, 40 mmol) and the reaction mixture was stirred at room temperature for 12 hr. 30% NaOH was added to the reaction mixture, which was extracted twice with AcOEt. Organic layer was washed by water, dried over $MgSO_4$ and concentrated to give 2.86 g (96% 2 steps) of compound 319 as a white solid.

$^1$H NMR (300 MHz,DMSO-$d_6$) δ 2.14(6H, s), 6.11(2H, br s), 6.66(1H, dd, J=1.8, 8.1 Hz), 6.77(2H, s), 6.82(1H, d, J=1.8 Hz), 7.02(1H, d, J=8.1 Hz).

TABLE 34

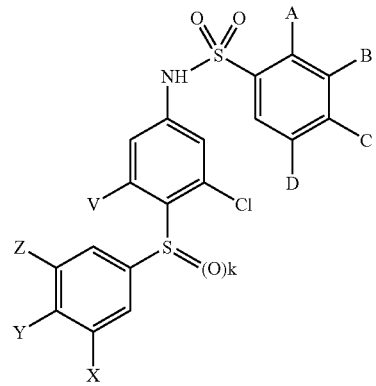

| EXAMPLE # | k | A | B | C | D | V | X | Y | Z | MS (M − H) |
|---|---|---|---|---|---|---|---|---|---|---|
| 320 | 0 | Cl | H | Cl | H | H | Cl | H | Cl | 509.9 |
| 321 | 1 | Cl | H | Cl | H | H | Cl | H | Cl | 525.8 |
| 322 | 2 | Cl | H | Cl | H | H | Cl | H | Cl | 541.8 |
| 323 | 0 | Cl | H | Cl | H | H | F | H | F | 478 |
| 324 | 1 | Cl | H | Cl | H | H | F | H | F | |
| 325 | 2 | Cl | H | Cl | H | H | F | H | F | 509.9 |
| 326 | 0 | Cl | H | $CF_3$ | H | H | F | H | F | 512 |
| 327 | 1 | Cl | H | $CF_3$ | H | H | F | H | F | 461 |
| 328 | 2 | Cl | H | $CF_3$ | H | H | F | H | F | 544 |
| 329 | 0 | Cl | H | Cl | Me | H | F | H | F | 491.9 |
| 330 | 1 | Cl | H | Cl | Me | H | F | H | F | |
| 331 | 2 | Cl | H | Cl | Me | H | F | H | F | 523.8 |
| 332 | 0 | Cl | H | Cl | H | H | F | F | H | |
| 333 | 1 | Cl | H | Cl | H | H | F | F | H | 493.9 |
| 334 | 2 | Cl | H | Cl | H | H | F | F | H | 509.9 |
| 335 | 0 | Cl | H | $CF_3$ | H | H | F | F | H | 512 |
| 336 | 1 | Cl | H | $CF_3$ | H | H | F | F | H | 493.9 |
| 337 | 2 | Cl | H | $CF_3$ | H | H | F | F | H | 544 |
| 338 | 0 | Cl | H | $CF_3$ | H | Cl | Me | Me | H | 540 |

Examples 320-337

The anilines of Table 33 were sulfonylated by the method of example 3 and then oxidized to the corresponding sulfoxide by the method of example 103 or sulfone by the method of example 104 to provide the examples 320-337 illustrated in Table 34.

Example 324

$^1$H NMR (DMSO) δ 11.5 (br s, 1H), 8.12 (d, J=8.8 Hz, 1H), 7.88 (d, J=2 Hz, 1H), 7.748 (d, J=8 Hz, 1H), 7.661 (dd, J=8.8, 2 Hz, 1H), 7.476 (m, 1H), 7.42 (m, 2H), 7.28 (dd, J=8.4, 2 Hz, 1H) 7.17 (br s, 1H).

Example 330

$^1$H NMR (acetone) δ 10.1 (br s, 1H), 8.147 (s, 1H), 7.80 (d, 1H), 7.648 (s, 1H), 7.49 (m, 1H), 7.40 (m, 2H), 7.15 (d, 1H), 2.433 (s, 3H).

Example 332

$^1$H NMR (acetone) δ 9.80 (br s, 1H), 8.162 (d, J=8.4 Hz, 1H), 7.735 (d, J=2 Hz, 1H), 7.615 (dd, J=8.4, 2.1 Hz, 1H), 7.436 (d, J=2.2 Hz, 1H), 7.358 (dt, J=10.5, 8.4 Hz, 1H), 7.292 (ddd, 1H), 7.224 (dd, J=8.4, 2.3 Hz, 1H), 7.176 (d, J=8.4 Hz, 1H), 7.16 (m, 1H).

Example 338

2-Chloro-N-[3,5-dichloro-4-(3,4-dimethyl-phenyl-sulfanyl)-phenyl]-4-trifluoromethyl-benzenesulfonamide (338)

A solution of aniline 319 (860 mg, 2.68 mmol) and 3-chloro-4-trifluoromethylbenzene-sulfonylchloride (658 mg, 2.68 mmol) in pyridine (10 ml) was stirred at room temperature for 2-hr. Water was added to the reaction mixture, which was then acidified by 2N HCl. Reaction mixture was extracted twice with AcOEt. Organic layer was washed by Brine, dried over $MgSO_4$ and concentrated. Crude residue was purified by column chromatography (H/A=4/1, 80 g of silica gel) to afford compound 317 (591 mg, 41%) as a white solid.

$^1$H NMR (400 MHz, DMSO-$d_6$) δ 2.11(3H,s), 2.13(3H,s), 6.78(1H,dd, J=2.1,8.3 Hz), 6.81(1H,s), 7.01(1H,d, J=8.3 Hz), 7.30(2H, s), 7.98(2H,dd, J=2.1,8.3 Hz), 8.18(1H,s), 8.35(1H, d, J=8.3 Hz), 11.6(1H, br s), mp 156-158° C. MS (M+H) 540.

Example 339

3,5-Dichloro-4-(6-methyl-quinolin-3-yloxy)-phenylamine (339)

To a solution of 3-(2,6-Dichloro-4-nitro-phenoxy)-6-methyl-quinoline (309) (1.30 g, 3.71 mmol) and $NH_4Cl$ (992 mg, 18.55 mmol) in EtOH/THF/$H_2O$=12 ml/12 ml/3 ml, was added Iron Powder (1.04 g, 18.55 mmol). The mixture was refluxed for 4 hr. Insoluble materials were removed by Celite filtration. The filtrate was concentrated and sat $NaHCO_3$ was added to the residue, which was then extracted twice with AcOEt. Organic layer was washed with Brine, dried over anhydrous $MgSO_4$, and concentrated to afford compound 339 (1.18 g, 98%).

$^1$H NMR (300 MHz, DMSO-$d_6$) δ 2.44 (3H, s), 5.75 (2H, br s), 6.77 (2H, s), 7.27 (1H, d, J=2.8 Hz), 7.48 (1H, d, J=8.6 Hz), 7.67 (1H, s), 7.89 (1H, d, J=8.6 Hz), 8.74 (1H, d, J=2.8 Hz)

Example 340

2-Mercapto-4-methyl-benzothiazole (340)

The title compound was prepared using the method of example 239, starting with 2-bromo-4-methyl-phenylamine (Acros) (27.9 g), O-ethylxanthic acid, potassium salt (Lancaster, 54 g) in DMF (250 mL). The mercaptobenzothiazole 340 was obtained as an pale brown solid (27 g). Recrystalization from $CHCl_3$ gave pinkish white crystals (20 g).

$^1$H NMR (DMSO-$d_6$) δ 7.499 (br s, 1H), 7.223 (d, J=8 Hz, 1H), 7.198(d, J=8 Hz, 1H), 2.342 (s, 3H).

Example 341

Compound 341 was prepared by the method of example 84.1 by coupling thiol 340 (9.3 g) with 1,2,3,-trichloro-5-nitrobenzene (11.3 g) in DMF using NaH as base. Trituration with ether gave 341 (12.4 g) as a yellow solid.

$^1$H NMR (DMSO-$d_6$) δ 8.577 (s, 2H), 7.795 (br s, 1H), 7.736 (d, J=8.4 Hz, 1H), 7.303 (d, J=8.4 Hz, 1H), 2.405 (s, 3H).

Example 342

Reduction of compound 341 (12.4 g) with SnCl2 by the method of example 32 gave after trituration with methylene chloride, aniline 342 (9 g) as a solid.

$^1$H NMR (DMSO-$d_6$) δ 7.709 (br s, 1H), 7.699 (d, J=8 Hz, 1H), 7.262 (d, J=8 Hz, 1H), 6.859 (s, 2H), 6.45 (s, 2H), 2.384 (s, 3H).

Example 344

Compound 344 was prepared by the method of example 84.1 by coupling thiol 245 (2.01 g) with 1,2,3,-trichloro-5-nitrobenzene (2.51 g) in DMF using NaH as base. Recrystalization with ether/hexane gave compound 344 (3.2 g) as a yellow solid. Mp 116-118° C.

Example 345

Reduction of compound 344 (3.01 g) with SnCl2 by the method of example 32 gave aniline 345 (2.8 g) as a solid.

$^1$H NMR (DMSO-$d_6$) δ 7.772 (d, J=8.0 Hz, 1H), 7.630 (br s, 1H), 7.155 (br d, J=8 Hz, 1H), 6.855 (s, 2H), 6.442 (s, 2H), 2.409 (s, 3H). MS (M+H) 341 Anal. calcd.: 49.27% C, 2.95% H, 8.21% N; found. 49.39% C, 3.16% H, 7.98% N.

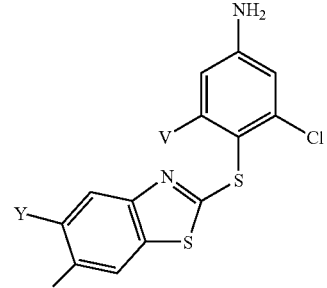

Example 342: X=Me, Y=H
Example 345: X=H, Y=Me

Examples 346-351

Sulfonylation of anilines 342 or 345 by the method of example 3 gave the sulfonamides of Table 35.

TABLE 35

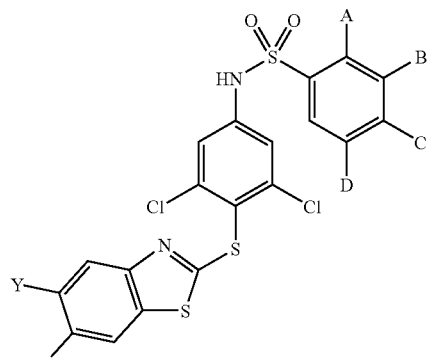

| Example # | A | B | C | D | X | Y | MS (M − H) |
|---|---|---|---|---|---|---|---|
| 346 | Cl | H | $CF_3$ | H | Me | H | 581 |
| 347 | $CF_3$ | H | Cl | H | Me | H | 581 |
| 348 | Cl | H | Cl | Me | Me | H | 561 |
| 349 | Cl | H | $CF_3$ | H | H | Me | 581 |

TABLE 35-continued

| Example # | A | B | C | D | X | Y | MS (M − H) |
|---|---|---|---|---|---|---|---|
| 350 | Cl | H | Cl | Me | H | Me | 561 |
| 351 | Cl | H | Me | H | H | Me | 527 |

Example 346

¹H NMR (DMSO-d₆) δ 11.90 (s, 1H), 8.416 (d, J=8.0 Hz, 1H), 8.228 (br s, 1H), 8.024 (br d, J=8 Hz, 1H), 7.690 (m, 2H), 7.383 (s, 2H), 7.265 (br d, J=8 Hz, 1H), 2.379 (s, 3H). MS (M−H) 580.8.

Example 347

¹H NMR(d₆-DMSO) δ 11.70-12.00 (1H, broad), 8.22 (1H, d, J=8.6 Hz), 8.17 (1H, s), 8.08 (1H, d, J=8.5 Hz), 7.68-7.75 (2H, m), 7.39 (2H, s), 7.28 (1H, d, J=8.2 Hz), 2.39 (3H, s). MS (M−H) 580.8. mp 227.0° C. Anal. calcd.: C 43.20; H, 2.07; N 4.80; found C, 43.23; H, 1.97; N 4.91.

Example 348

¹H NMR (DMSO-d₆) δ 11.71 (br s, 1H), 8.237 (br s, 1H), 7.915 (s, 1H), 7.708 (s, 1H), 7.698 (d, J=8 Hz, 1H), 7.365 (s, 2H), 7.266 (dd, J=8, 1.6 Hz, 1H), 2.414 (s, 3H), 2.380 (s, 3H). MS (M−H) 560.8.

Example 349

¹H NMR (DMSO-d₆) δ 11.94 (br s, 1H), 8.416 (d, J=8.4 Hz, 1H), 8.231 (d, J=1.6 Hz, 1H), 8.024 (dd, J=8.4, 1.6 Hz, 1H), 7.767 (d, J=8 Hz, 1H), 7.628 (s, 1H), 7.382 (s, 2H), 7.185 (dd, J=8.4, 1.6 Hz, 1H), 2.398 (s, 3H). MS (M−H) 580.8.

Example 350

¹H NMR (DMSO-d6) δ 11.725 (br s, 1H), 8.236 (br s, 1H), 7.918 (s, 1H), 7.785 (d, J=8 Hz, 1H), 7.637 (s, 1H), 7.363 (s, 2H), 7.183 (d, J=8 Hz, 1H), 2.408 (s, 6H). MS (M−H) 560.9.

Example 351

¹H NMR (d₆-DMSO) δ 11.67 (1H, s), 8.12 (1H, d, J=8.1 Hz), 7.80 (1H, d, J=8.2 Hz), 7.58-7.68 (2H, m), 7.46 (1H, d, J=8.1 Hz), 7.35 (2H, s), 7.20 (1H, d, J=8.2 Hz), 2.40 (6H, s). MS: (M−H) 526.8. mp 112.8° C. Anal. calcd.: 47.60% C, 2.85% H, 5.29% N; found 47.28% C, 2.98% H, 5.28% N.

Example 352

Aniline 342 was converted according to the method of example 34 to afford the corresponding sulfonyl chloride 352 as a white solid.

¹H NMR (CDCl₃) δ 8.131 (s, 2H), 7.786 (d, J=8.4 Hz, 1H), 7.567 (br s, 1H), 7.28 (br d, J=8 Hz, 1H), 2.482 (s, 3H).

Example 353

Coupling of compound 352 (85 mg) with 3,4-dichloroaniline (42 mg) by the method of example 3 gave the sulfonamide 353 (76 mg) as a white solid.

¹H NMR (d₆-DMSO) δ 11.01 (1H, s), 8.04 (1H, s), 7.76 (1H, s), 7.72 (1H, d, J=8.5 Hz), 7.62 (1H, d, J=8.7 Hz), 7.34 (1H, s), 7.29 (1H, d, J=7.6 Hz), 7.13-7.23 (1H, m), 2.40 (3H, s). MS (M−H) 546.8. mp 181.0° C. Anal. calcd.: 43.65% C, 2.20% H, 5.09% N; found 43.10% C, 2.21% H, 4.81% N.

Example 354

Coupling of compound 352 (85 mg) with 2,4-dichloroaniline (42 mg) by the method of example 3 gave after recrystalization from methanol water, the sulfonamide 354 (38 mg) as a white solid.

¹H NMR (d₆-DMSO) δ 10.72 (1H, s), 7.96 (2H, s), 7.79 (1H, s), 7.72-7.77 (2H, m), 7.47 (1H, dd, J=8.7, 2.4 Hz), 7.33 (1H, d, J=8.6 Hz), 7.31 (1H, d, J=8.6 Hz), 2.41 (3H, s). MS (M+H) 548.9. mp 160.7° C. Anal. calcd.: 43.65% C, 2.20% H, 5.09% N; found 43.83% C, 2.19% H, 5.10% N.

The following examples illustrate the synthesis of compounds 355-358.

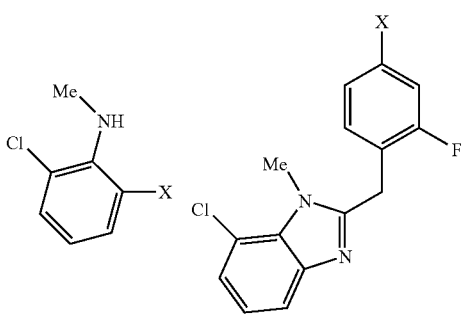

355 X=NO2  357 X=NO2
356 X=NH2  358 X=NH2

Example 355

2,3-dichloronitrobenzene (6.15 g, 32 mmol), methylamine hydrochloride (2.38 g, 35 mmol), triethylamine (9.8 mL, 71 mmol), and DMF (16 mL) were combined in a 100 mL round-bottomed flask and heated to 90° C. overnight. The reaction was then cooled to room temperature and dumped over 600 mL of ice-water. The resulting orange solid was collected by filtration and dried at the pump. Recrystallization from hot hexanes yielded 3.2 g (53%) of compound 355 as bright orange crystals.

$^1$H NMR (($d_6$-DMSO) δ 7.75 (1H, dd); 7.62 (1H, dd); 6.76 (1H, t); 6.63 (1H, broad s); 2.75 (3H, t).

Example 356

A round-bottomed flask was charged with 3.8 g (20 mmol) of compound 355, 22.9 g (102 mmol) of tin dichloride dihydrate, and 125 mL of EtOAc. This was heated to 75° C. for 3.0 hours. The reaction was cooled to room temperature, diluted with 300 mL of EtOAc and washed with 250 mL of 2N aqueous KOH solution followed by 200 mL of brine. The organics were dried over sodium sulfate and concentrated to a white amorphous solid 355 (2.9 g, 90%) that was used without further purification (turned brown upon standing in air).

$^1$H NMR ($d_6$-DMSO) δ 6.68 (1H, t); 6.56 (2H, m); 4.98 (2H, broad s); 3.76 (1H, broad s); 2.59 (3H, t).

Example 359

$^1$H NMR ($d_6$-DMSO) δ 11.01 (1H, s); 8.07 (1H, d); 7.87 (1H, d); 7.63 (1H,

Example 357

A round-bottomed flask was charged with 356 (1.0 g, 6.4 mmol), 4-nitro-2-flourophenyl acetic acid (148) (1.4 g, 7.0 mmol), and 4N aqueous HCl (13 mL). This was refluxed overnight. The reaction was then cooled and basified with saturated aqueous sodium bicarbonate. The organics were extracted with methylene chloride, dried over Na$_2$SO$_4$, and concentrated to a pink solid. This was recrystallized from methylene chloride and hexanes to yield compound 357 (1.4 g, 75%) as fluffy crystals.

$^1$H NMR (400 MHz) ($d_6$-DMSO) δ 8.16 (1H, dd); 8.08 (1H, dd); 7.62 (1H, t); 7.49 (1H, dd); 7.23 (1H, dd); 7.13 (1H, t); 4.48 (2H, s); 4.08 (3H, s).

Example 358

Nitro compound 357 (1.3 g, 4.0 mmol) was reduced by the method of example 356 to give the aniline 358 (1.0 g, 86%) as off-white crystals. MS (M+H) 290.1.

Example 359-361

Aniline 358 was coupled with various sulfonyl chlorides by the method of example 192 to give the sulfonamides illustrated in Table 35

TABLE 36

| # | A | B | C | D | yield | (M−H) |
|---|---|---|---|---|-------|-------|
| 359 | Cl | H | Cl | H | 36% | 496 |
| 360 | H | H | —COMe | H | 50% | 470 |
| 361 | Me | H | Cl | Me | 60% | |
| 362 | Cl | H | Cl | Me | 496% | |

Example 359

$^1$H NMR ($d_6$-DMSO) δ 11.01 (1H, s); 8.07 (1H, d); 7.87 (1H, d); 7.63 (1H, dd); 7.49 (1H, d); 7.22 (1H, d); 7.15 (2H, m); 6.89 (2H, m); 4.21 (2H, s); 3.99 (3H, s). MS (M−H) 496.0.

Example 360

$^1$H NMR ($d_6$-DMSO) δ 10.78 (1H, s); 8.12 (2H, d); 7.94 (2H, d); 7.51 (1H, d); 7.26 (1H, d); 7.17 (2H, t); 6.97 (2H, m); 4.24 (2H, s); 4.01 (3H, s). MS (M−H) 470.1.

Example 361

$^1$H NMR ($d_6$-DMSO) δ 10.75 (1H, s); 7.91 (1H, s); 7.51 (2H, m); 7.26 (1H, d); 7.16 (2H, dd); 6.88 (2H, t); 4.24 (2H, s); 4.01 (3H, s); 2.54 (3H, s); 2.34 (3H, s).

Example 362

$^1$H NMR ($d_6$-DMSO) δ 10.97 (1H, s); 8.10 (1H, s); 7.83 (1H, s); 7.52 (1H, d); 7.27 (1H, d); 7.17 (2H, t); 6.94 (2H, m); 4.24 (2H, s); 4.01 (3H, s); 2.38 (3H, s).

Example 363

This illustrates the preparation of 2,6-dichloro-benzothiazole (363).

2-Amino-6-chlorobenzothiazole (15.7 g, 85 mmol) in H$_3$PO4 (85%) (470 ml) was heated to 100 degrees and dissolved. Then clear solution was cooled and vigorously stirred by mechanical stirrer. NaNO$_2$ (17.6 g, 255 mmol) in water (30 ml) was added slowly keeps the temperature below 0 degrees. Separately a solution of CuSO$_4$/5H$_2$O (85 g), NaCl (107 g) in water (350 ml) was cooled to −5 degrees and stirred by mechanical stirrer. After Potassium Iodide Starch paper's color was disappeared Diazonium solution was keeping cold and added slowly to the copper chloride solution with vigorous stirring. The reaction Mixture was allowed to warm to room temperature. After 1-hour water (1 L) and ether (1 L) were added to the reaction mixture and extracted twice. Organic layer was washed by water and dried over anhydrous $MgSO_4$ and concentrated. Crude residue was purified by silica gel chromatography (H/A=4/1, 180 g of silica gel) to provide title compound 363 (7.46 g, 48%).

Example 364

This illustrates the preparation of 3,5-dichloro-4-(6-chloro-benzothiazol-2-yloxy)-phenylamine.

To the solution of 4-amino-2,6-dichloro phenol (6 g, 26.5 mmol) and 2,6-dichlorobenzothiazole (363) (6 g, 29.4 mmol, 1.1 eq) in DMSO (25 ml), was added $K_2CO_3$ (11 g, 80 mmol, 3.0 eq). The mixture was stirred and heated to 160 degree. After 5.5-hr water (20 ml) was added to the reaction mixture, which was neutralized with 2N HCl, and was extracted with AcOEt three times. And the organic layer was washed with Brine and was dried over anhydrous $MgSO_4$, and then concentrated. Crude residue was purified by column chromatography ($CHCl_3$/Acetone=9/1, 180 g of silica gel) to afford 3,5-Dichloro-4-(6-chloro-benzothiazol-2-yloxy)-phenylamine (364) as a black solid (4.52 g, 49%).

$^1$H NMR (300 MHz,DMSO-$d_6$) δ 5.86(2H,br s), 6.74(2H, s), 7.48(1H,dd, J=2.1,5.7 Hz), 7.70(1H,d, 8.7 Hz), 8.10(1H,d, 2.1 Hz).

Example 365

This illustrates the preparation of 2-Chloro-N-[3,5-dichloro-4-(6-chloro-benzothiazol-2-yloxy)-phenyl]-4-trifluoromethyl-benzenesulfonamide (365).

A solution of 3,5-dichloro-4-(6-chloro-benzothiazol-2-yloxy) -phenylamine (364) (2.0 g, 5.79 mmol) and 3-chloro-4-trifluoromethylbenzenesulfonylchloride (1.7 g, 6.08 mmol) in pyridine (10 ml) was stirred at room temperature. After 3-hr water was added to the reaction mixture, which was then acidify by 2N HCl. Reaction mixture was extracted twice with AcOEt. Organic layer was washed by brine, dried over $MgSO_4$ and concentrated. Crude residue was purified by column chromatography (H/A=4/1, 80 g of silica gel) to afford title compound 365 (2.11 g, 65%) as a white solid. mp 82-84° C.

$^1$H NMR (400 MHz,DMSO-$d_6$) δ 7.32(2H,s), 7.46(1H,dd, J=2.2,8.7 Hz), 7.67(1H,d, J=8.7 Hz), 8.00(1H,d, 8.0 Hz), 8.14(1H,d, J=2.2 Hz), 8.20(1H,s), 8.38(1H,d, J=8.3 Hz), 11.6 (1H,br s). MS (M+H) 586.

Example 366

This illustrates the preparation of 2,4-Dichloro-N-[3,5-dichloro-4-(6-chloro-benzothiazol-2-yloxy)-phenyl]benzenesulfonamide (366).

A solution of 3,5-dichloro-4-(6-chloro-benzothiazol-2-yloxy) -phenylamine (364) (2.0 g, 5.79 mmol) and 2,4-dichloro benzenesulfonylchloride (1.5 g, 6.08 mmol) in pyridine (10 ml) was stirred at room temperature for 12-hr. Water was added to the reaction mixture, which was then acidified by 2N HCl. Reaction mixture was extracted twice with AcOEt. Organic layer was washed by Brine, dried over $MgSO_4$ and concentrated. Crude residue was purified by column chromatography (H/A=4/1, 80 g of silica gel) to afford title compound (366) (1.49 g, 46%) as a white solid. mp 73-75° C.

$^1$H NMR (300 MHz,DMSO-$d_6$) δ 7.29 (2H, s), 7.46 (1H, dd, J=2.2, 8.8 Hz), 7.69 (1H, d, J=8.8 Hz), 7.71 (1H, dd, J=2.2, 8.4 Hz), 7.95 (1H, d, J=2.2 Hz), 8.14 (1H, d, J=2.2 Hz), 8.18 (1H, d, J=8.4 Hz), 11.5 (1H, br s). MS (M+H) 553.

Example 367

This illustrates the preparation of 3,5-Dichloro-4-(6-methoxybenzothiazol-2-yloxy)phenylamine (367).

To a solution of 2-chloro-6-methoxybenzothiazole (prepared as described by Weinstock et. al., J. Med. Chem. 30: p 1166 (1987)) and 4-Amino-2,6-dichlorophenol 1.3 g (available from Tokyo Chemical Industry Co., Ltd.) in DMSO (9 ml), was added $K_2CO_3$ 3.12 g. The mixture was heated at 150 degree for 3 hr. The reaction mixture was purified by column chromatography (silica gel, AcOEt:Hexane=1:2) to provide the aniline 367 (1.43 g, 56%). mp 158-160° C.

NMR(300 MHz/$CDCl_3$) δ 3.84(3H, s), 3.85(2H, brs), 6.69 (2H, s) 6.97(1H, dd, J=2.6 Hz, J=8.9 Hz), 7.18(1H, d, J=2.6 Hz), 7.61(1H, d, J=8.9 Hz).

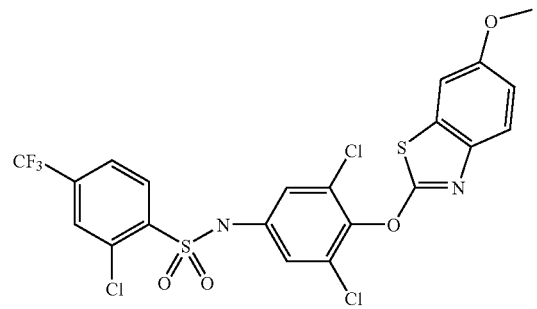

Example 368

This illustrates the preparation of 2-Chloro-N-[3,5-dichloro-4-(6-methoxybenzothol-2-yloxy)-phenyl]-4-trifluoromethyl-benzenesulfonamide (368). To a solution of 3,5-dichloro-4-(6-methoxybenzothiazol-2-yloxy)phenylamine (367) (1.40 g) in pyridine (5 ml), was added 2-Chloro-4-trifluorobenzenesulfonamide 1.15 g. The mixture was stirred at room temperature for 2 hr. The reaction mixture was purified directly by column chromatography (silica gel, AcOEt: Hexane=1:3). The product was triturated by hexane to give the title compound 368 (1.97 g, 82%) as a colorless powder. mp 164-165° C.

NMR (300 MHz/DMSO-d6) δ 3.79(3H, s), 7.00(1H, dd, J=2.9 Hz, J=8.8 Hz), 7.31(2H, s), 7.55(1H, d, J=8.8 Hz), 7.58(1H, d, J=2.9 Hz), 8.00(1H, dd, J=1.5 Hz, J=8.1 Hz), 8.20 (1H, d, J=1.5 Hz), 8.37(1H, d, J=8.1 Hz), 11.59(1H, brs). MS (M+H) 583.

Examples 369-370

The examples illustrated in Table 37, were prepared from aniline 75 and the corresponding sulfonyl chlorides by the method of procedure 3. The compounds were purified by chromatography on silica gel.

TABLE 37

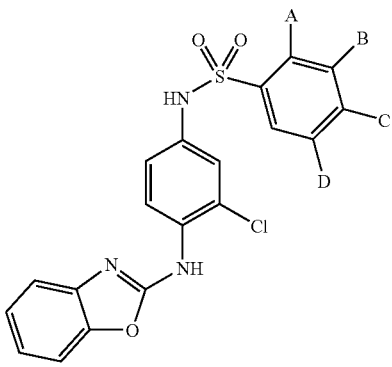

| Example # | A | B | C | D | MS (M – H) |
|---|---|---|---|---|---|
| 369 | Cl | H | Cl | H | 466 |
| 370 | H | Cl | Cl | H | 466 |
| 371 | Me | H | Cl | Me | 460 |
| 372 | Cl | H | Cl | Me | 480 |

Example 369

$^1$H NMR (d6-acetone) δ 9.54 (br s, 1H), 8.82 (br s, 1H), 8.446 (d, J=8.8 Hz, 1H), 8.129 (d, J=8.4 Hz, 1H), 7.763 (d, J=2 Hz, 1H), 7.602 (dd, J=8.4, 2 Hz, 1H), 7.428 (m, 2H), 7.327 (dd, J=9.2, 2.4 Hz, 1H), 7.252 (td, J=7.6, 1.2 Hz, 1H), 7.17 (td, J=8, 1.2 Hz, 1H). MS (M–H) 466.0.

Example 370

$^1$H NMR (d6-DMSO) δ 10.643 (br s, 1H), 9.954 (br s, 1H), 7.983 (d, J=2 Hz, 1H), 7.934 (br d, J=8 Hz, 1H), 7.885 (d, J=8.4 Hz, 1H), 7.717 (dd, J=8.4, 2.4 Hz, 1H), 7.454 (d, J=8 Hz, 1H), 7.360 (br d, J=7.6 Hz, 1H), 7.226 (d, J=2 Hz, 1H), 7.194 (t, J=8 Hz, 1H), 7.142 (dd, J=8.8, 2 Hz, 1H), 7.106 (t, J=8 Hz, 1H). MS (M–H) 466.0.

Example 371

$^1$H NMR (d6-acetone) δ 9.31 (br s, 1H), 8.80 (br s, 1H), 8.403 (d, J=8 Hz, 1H), 7.928 (s, 1H), 7.45-7.35 (m, 4H), 7.3-7.2 (m, 2H), 7.164 (br t, J=8 Hz, 1H), 2.64 (s, 3H), 2.387 (s, 3H). MS (M–H) 460.0.

Example 372

$^1$H NMR (d6-acetone) δ 9.48 (br s, 1H), 8.82 (br s, 1H), 8.064 (s, 1H), 7.707 (s, 1H), 7.45-7.40 (m, 4H), 7.335 (dd, J=8.8, 2 HZ, 1H), 7.252 (td, J=7.6, 1.2 Hz, 1H), 7.19 (td, J=8, 1.2 Hz, 1H) 2.425 (s, 3H). MS (M–H) 479.9.

Example 373

Using methods similar to Lehmann, et al., ibid., selected compounds exhibited the following IC$_{50}$ values in a PPARγ ligand binding assay utilizing [$^3$H]-BRL 49653 as the radio-ligand. IC$_{50}$ values are defined as the concentration of test compounds required to reduce by 50% the specific binding of [$^3$H]-BRL 49653 and are represented by (+) <30 μM; (++) <10 μM; (+++) <1 μM.

TABLE 38

| Compound | IC$_{50}$(μM) |
|---|---|
| 4.1 | +++ |
| 16.1 | +++ |
| 27.3 | ++ |
| 27.5 | ++ |
| 49.1 | +++ |
| 50.1 | +++ |
| 72.2 | ++ |
| 72.3 | +++ |
| 72.4 | ++ |
| 73.4 | +++ |
| 73.5 | +++ |
| 73.6 | +++ |
| 73.7 | +++ |
| 73.8 | +++ |
| 73.9 | +++ |
| 79.5 | +++ |
| 86 | +++ |
| 87.3 | +++ |
| 95 | +++ |
| 97 | +++ |
| 108.4 | +++ |
| 158 | +++ |
| 160 | +++ |
| 178 | +++ |
| 179 | +++ |
| 219 | +++ |
| 233 | +++ |
| 290 | +++ |
| 292 | +++ |
| 349 | +++ |
| 364 | ++ |
| 365 | ++ |
| 368 | +++ |

Example 374

Selected compounds were administered to KK-Ay mice as a 0.018% (30 mg/kg) dietary admixture in powdered diet and evaluated for anti-diabetic efficacy as described (T. Shibata, K. Matsui, K. Nagao, H. Shinkai, F. Yonemori and K. Wakitani 1999; *European Journal of Pharmacology* 364:211-219). The change in serum glucose levels compared to untreated control animals is exemplified in Table 39.

TABLE 39

| Example # | KKAy Glucose |
|---|---|
| 87.3 | ++ |
| 178 | ++ |
| 179 | ++ |
| 219 | + |
| 233 | – |
| 364 | + |
| 365 | ++ |

(–) <10%;
(+) 10% to 20%;
(++) glucose lowering >20%.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A compound having the formula:

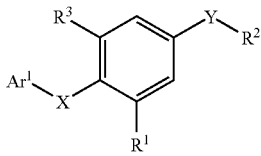

(Ii)

wherein
Ar¹ is unsubstituted 3-quinolinyl;
X is —O—;
Y is —NH—S(O)$_2$—;
R¹ is halogen;
R² is a phenyl group having from 0 to 3 substituents, wherein the substituent is halogen; and
R³ is halogen;
or a pharmaceutically acceptable salt of the compound.

2. A composition comprising a pharmaceutically acceptable excipient and a compound having the formula:

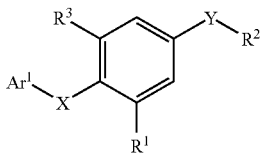

(Ii)

wherein
Ar¹ is unsubstituted 3-quinolinyl;
X is —O—;
Y is —NH—S(O)$_2$—;
R¹ is halogen;
R² is a phenyl group having from 0 to 3 substituents, wherein the substituent is halogen; and
R³ is halogen;
or a pharmaceutically acceptable salt of the compound.

3. A method for treating a condition mediated by PPARγ in a host, said method comprising administering to said host an efficacious amount of a compound having the formula:

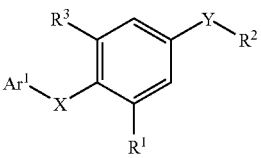

(Ii)

wherein
Ar¹ is unsubstituted 3-quinolinyl;
X is —O—;
Y is —NH—S(O)$_2$—;
R¹ is halogen;
R² is a phenyl group having from 0 to 3 substituents, wherein the substituent is halogen; and
R³ is halogen;
or a pharmaceutically acceptable salt of the compound.

4. A method in accordance with claim 3, wherein said condition is selected from the group consisting of non-insulin-dependent diabetes mellitus, obesity, hypercholesterolemia, hyperlipidemia, hyperlipoproteinemia, and inflammatory conditions.

* * * * *